US008501178B2

(12) United States Patent
Mi et al.

(10) Patent No.: US 8,501,178 B2
(45) Date of Patent: Aug. 6, 2013

(54) USE OF DR6 AND P75 ANTAGONISTS TO PROMOTE SURVIVAL OF CELLS OF THE NERVOUS SYSTEM

(75) Inventors: Sha Mi, Belmont, MA (US); Kenneth J. Rhodes, Belmont, MA (US); R. Blake Pepinsky, Arlington, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 13/131,231

(22) PCT Filed: Nov. 24, 2009

(86) PCT No.: PCT/US2009/065755
§ 371 (c)(1),
(2), (4) Date: Feb. 2, 2012

(87) PCT Pub. No.: WO2010/062904
PCT Pub. Date: Jun. 3, 2010

(65) Prior Publication Data
US 2012/0141456 A1 Jun. 7, 2012

Related U.S. Application Data

(60) Provisional application No. 61/117,917, filed on Nov. 25, 2008.

(51) Int. Cl.
*A61K 39/00* (2006.01)
*A61K 39/395* (2006.01)
(52) U.S. Cl.
USPC .................. 424/139.1; 424/130.1; 424/184.1
(58) Field of Classification Search
None
See application file for complete search history.

(56) References Cited

U.S. PATENT DOCUMENTS

| 5,213,962 A | 5/1993 | Van Nostrand et al. |
| 5,218,100 A | 6/1993 | Müller-Hill et al. |
| 5,270,165 A | 12/1993 | Van Nostrand et al. |

(Continued)

FOREIGN PATENT DOCUMENTS

| EP | 0 276 723 B1 | 8/1988 |
| EP | 0 417 563 B1 | 3/1991 |

(Continued)

OTHER PUBLICATIONS

Popko 2011 "Downregulating DR6 to drive remyelination" Nature Medicine 17:779-780.*

(Continued)

*Primary Examiner* — Jeffrey Stucker
*Assistant Examiner* — Adam M Weidner
(74) *Attorney, Agent, or Firm* — Sterne, Kessler, Goldstein & Fox P.L.L.C.

(57) ABSTRACT

The present invention relates to Death Receptor-6 (DR6) proteins which are members of the tumor necrosis factor (TNF) receptor family, and have now been shown to be important for regulating apoptosis in cells of the nervous system. In addition, it has been discovered that p75 is a ligand for DR6. As a result, this invention relates to methods for inhibiting the interaction of DR6 and p75 using DR6 and/or p75 antagonists. In addition, the methods described herein include methods of promoting survival of cells of the nervous system using DR6 antagonists, optionally in combination with p75 antagonists, and methods of treating neurodegenerative conditions by the administration of a DR6 antagonists, optionally in combination with a p75 antagonist.

18 Claims, 36 Drawing Sheets

U.S. PATENT DOCUMENTS

Figure 1B:
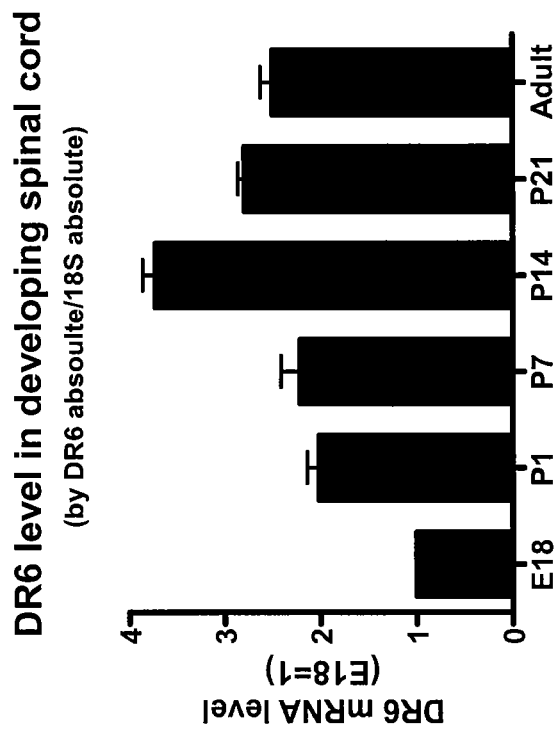

| | | | |
|---|---|---|---|
| 5,427,931 | A | 6/1995 | Van Nostrand et al. |
| 5,610,279 | A | 3/1997 | Brockhaus et al. |
| 5,705,401 | A | 1/1998 | Masters et al. |
| 5,716,805 | A | 2/1998 | Srinivasan et al. |
| 5,721,130 | A | 2/1998 | Seubert et al. |
| 5,981,208 | A | 11/1999 | Tamburini et al. |
| 6,013,476 | A | 1/2000 | Deen et al. |
| 6,194,151 | B1 | 2/2001 | Busfield |
| 6,358,508 | B1 | 3/2002 | Ni et al. |
| 6,423,494 | B1 | 7/2002 | Jin et al. |
| 6,660,839 | B1 | 12/2003 | Deen et al. |
| 6,667,390 | B2 | 12/2003 | Ni et al. |
| 6,916,907 | B1 | 7/2005 | Yang et al. |
| 6,919,078 | B2 | 7/2005 | Ni et al. |
| 6,949,358 | B1 | 9/2005 | Ni et al. |
| 7,049,422 | B2 | 5/2006 | Deen et al. |
| 7,241,570 | B2 | 7/2007 | Prescott et al. |
| 7,645,449 | B2 | 1/2010 | Stassi et al. |
| 7,776,560 | B2 | 8/2010 | Ni et al. |
| 2002/0164684 | A1 | 11/2002 | Ni et al. |
| 2002/0168359 | A1 | 11/2002 | Ni et al. |
| 2003/0108551 | A1 | 6/2003 | Nicolau et al. |
| 2003/0232756 | A1 | 12/2003 | Brezillion et al. |
| 2004/0043022 | A1 | 3/2004 | Heuer et al. |
| 2004/0110178 | A1 | 6/2004 | Prescott et al. |
| 2005/0069540 | A1 | 3/2005 | Liu et al. |
| 2005/0186287 | A1 | 8/2005 | Beyreuther et al. |
| 2005/0208050 | A1 | 9/2005 | Multhaup et al. |
| 2007/0077623 | A1 | 4/2007 | Ashkenazi et al. |
| 2008/0206762 | A1 | 8/2008 | Ferrer Abizanda et al. |
| 2008/0233132 | A1 | 9/2008 | Miller et al. |
| 2009/0131327 | A1 | 5/2009 | Doherty et al. |
| 2010/0099609 | A1 | 4/2010 | John et al. |
| 2010/0203044 | A1 | 8/2010 | Nikolaev et al. |
| 2011/0110942 | A1 | 5/2011 | Kallop et al. |

FOREIGN PATENT DOCUMENTS

| | | |
|---|---|---|
| EP | 0 564 946 A1 | 10/1993 |
| EP | 0 783 104 A1 | 7/1997 |
| EP | 1 961 766 A1 | 8/2008 |
| KR | 10-2008-0034874 A | 4/2008 |
| WO | WO 90/05138 A1 | 5/1990 |
| WO | WO 92/00521 A1 | 1/1992 |
| WO | WO 93/08829 A1 | 5/1993 |
| WO | WO 93/21526 A1 | 10/1993 |
| WO | WO 94/04690 A1 | 3/1994 |
| WO | WO 94/10308 A1 | 5/1994 |
| WO | WO 97/01633 A1 | 1/1997 |
| WO | WO 97/25428 A1 | 7/1997 |
| WO | WO 97/37228 A1 | 10/1997 |
| WO | WO 98/18921 A1 | 5/1998 |
| WO | WO 98/28426 A2 | 7/1998 |
| WO | WO 98/46751 A1 | 10/1998 |
| WO | WO 98/56892 A1 | 12/1998 |
| WO | WO 99/06066 A2 | 2/1999 |
| WO | WO 99/14328 A2 | 3/1999 |
| WO | WO 99/43839 A1 | 9/1999 |
| WO | WO 00/51632 A2 | 9/2000 |
| WO | WO 00/63250 A1 | 10/2000 |
| WO | WO 01/85209 A2 | 11/2001 |
| WO | WO/02/02641 * | 1/2002 |
| WO | WO 02/48898 A1 | 6/2002 |
| WO | WO 03/040183 A2 | 5/2003 |
| WO | WO/03/048328 * | 6/2003 |
| WO | WO 03/051290 A2 | 6/2003 |
| WO | WO/03/095493 * | 11/2003 |
| WO | WO 2004/013172 A2 | 2/2004 |
| WO | WO 2004/071528 A1 | 8/2004 |
| WO | WO 2004/076682 A2 | 9/2004 |
| WO | WO 2005/028511 A2 | 3/2005 |
| WO | WO 2005/044293 A2 | 5/2005 |
| WO | WO 2005/082939 A2 | 9/2005 |
| WO | WO 2006/081171 A1 | 8/2006 |
| WO | WO 2006/134185 A1 | 12/2006 |
| WO | WO 2007/002633 A2 | 1/2007 |
| WO | WO 2007/062852 A2 | 6/2007 |
| WO | WO 2007/064972 A2 | 6/2007 |
| WO | WO 2008/008463 A2 | 1/2008 |
| WO | WO 2008/013573 A1 | 1/2008 |
| WO | WO 2008/027017 A1 | 3/2008 |
| WO | WO/2008/080045 * | 7/2008 |
| WO | WO 2008/080045 A2 | 7/2008 |
| WO | WO 2009/152463 A2 | 12/2009 |
| WO | WO 2010/046332 A1 | 4/2010 |
| WO | WO 2010/062904 A2 | 6/2010 |
| WO | WO 2010/096470 A2 | 8/2010 |

OTHER PUBLICATIONS

Genway Product Catalog #18-793-313951. Accessed from "http://legacy.genwaybio.com/product_info.php?products_id=313951" on Mar. 22, 2013.*

Abel, T., and Maniatis, T., "Action of leucine zippers," *Nature* 341:24-25, Nature Publishing Group, England (1989).

Anderson, D.M., et al., "A homologue of the TNF receptor and its ligand enhance T-cell growth and dendritic-cell function," *Nature* 390: 175-179, Macmillan Publishers Ltd, England (1997).

Armitage, R.J. et al, "Molecular and biological characterization of a murine ligand for CD40," *Nature* 357:80-82, Nature Publishing Group, England (1992).

Ashkenazi, A., and Chamow, S.M., "Immunoadhesins as research tools and therapeutic agents," *Current Opinion in immunology* 9:195-200, Current Biology Ltd, England (1997).

Ashkenazi, A., and Dixit, V., "Apoptosis control by death and decoy receptors," *Current Opinion in Cell Biology* 11:255-260, Elsevier Science Ltd, England (1999).

Ashkenazi, A., and Dixit, V.M., "Death Receptors: Signaling and Modulation," *Science* 281:1305-1308, American Association for the Advancement of Science, United States (1998).

Ashkenazi, A., "Targeting death and decoy receptors of the tumour-necrosis factor superfamily," *Nature Reviews Cancer* 2:420-430, Nature Publishing Group, England (2002).

Baloyannis, S.J., "Dendritic pathology in Alzheimer's disease," *Journal of the Neurological Sciences* 283:153-157, Elsevier B.V., Netherlands (Mar. 2009).

Benn, S.C., and Wolf, C.J., "Adult Neuron Survival Strategies—Slamming on the Brakes," *Nature Reviews Neuroscience* 5:686-700, Nature Publishing Group, England (2004).

Bittner et al., "γ-Secretase Inhibition Reduces Spine Density in Vivo via an Amyloid Precursor Protein-Dependent Pathway," *The Journal of Neuroscience* 29:10405-10409, Society for Neuroscience, United States (Aug. 2009).

Bond, J.P., et al., "Assemblies of Alzheimer's peptides Aβ25-35 and Aβ31-35: reverse-turn conformation and side-chain interactions revealed by X-ray diffraction," *Journal of Structural Biology* 141:156-170, Elsevier Science, United States (2003).

Bossen, C., et al., "Interactions of Tumor Necrosis Factor (TNF) and TNF Receptor Family Members in the Mouse and Human," *Journal of Biolocial Chemistry* 281(20):13964-13971, The American Society for Biochemistry and Molecular Biology, Inc., United States (2006).

Brockhaus, M., et al., "Identification of Two Types of Tumor Necrosis Factor Receptors on Human Cell Lines by Monoclonal Antibodies," *Proc. Natl. Acad Sci. USA* 87:3127-3131, National Academy of Sciences, United States (1990).

Brodbeck, J., et al., "Rosiglitazone increases dendritic spine density and rescues spine loss caused by apolipoprotein E4 in primary cortical neurons," *Proc. Natl. Acad. Sci. USA* 105:1343-1346, National Academy of Sciences, United States (Jan. 2008).

Brodeur, B.R., et al., "Mouse-Human Myeloma Partners for the Production of Heterohybridomas," in *Monoclonal Antibody Production Techniques and Applications*, Schook, L.B., ed., pp. 51-63, Marcel Dekker, Inc., New York, United States (1987).

Browning, J.L. et a l., "Lymphotoxin β, a Novel Member of the TNF Family That Forms a Heteromeric Complex with Lymphotoxin on the Cell Surface," *Cell* 72:847-856, Cell Press, United States (1993).

Chicheportiche, Y., et al., "TWEAK, a New Secreted Ligand in the Tumor Necrosis Factor Family That Weakly Induces Apoptosis," *The Journal of Biological Chemistry* 272:32401-32410, The American Society for Biochemistry and Molecular Biology, Inc., United States (1997).

Clackson, T., et al., "Making antibody fragments using phage display libraries," *Nature 352*:624-628, Nature Publishing Group, England (1991).

Coulson, E.J., "Does the p75 neurotrophin receptor mediate Aβ-induced toxicity in Alzheimer's disease?," *J. Neurochem. 98*:654-660, International Society for Neurochemistry, Switzerland (2006).

Darnay, B.G., and Aggarwal, B.B., "Signal transduction by tumour necrosis factor and tumour necrosis factor related ligands and their receptors," *Ann Rheum Dis 58*:2-13, BMJ Publishing Group Ltd & European League Against Rheumatism, England (1999).

Dealtry, G.B., et al., "DNA fragmentation and cytotoxicity caused by tumor necrosis factor is enhanced by interferon-γ" *Eur. J. Immunol. 17*:689-693, VCH Verlagsgesellschaft mbH, Germany (1987).

Deckwerth, T.L. et al.,"BAX Is Required for Neuronal Death after Trophic Factor Deprivation and during Development," *Neuron 17*:401-411, Cell Press, United States (1996).

Degli-Esposti, M.A., et al., "Cloning and Characterization of TRAIL-R3, a Novel Member of the Emerging TRAIL Receptor Family," *J. Exp. Med. 186*:1165-1170, The Rockefeller University Press, United States (1997).

Esch, F.S., et al., "Cleavage of Amyloid B Peptide During Constitutive Processing of Its Precursor," *Science 248*:1122-1124, American Association for the Advancement of Science, United States (1990).

Evan, G.I., et al., "Isolation of Monoclonal Antibodies Specific for Human c-*myc* Proto-Oncogene Product," *Molecular and Cellular Biology 5*:3610-3616, American Society for Microbiology, United States (1985).

Ferri, A., et al., "Inhibiting Axon Degeneration and Synapse Loss Attenuates Apoptosis and Disease Progression in a Mouse Model of Motoneuron Disease," *Current Biology13*:669-673, Elsevier Science Ltd., England (2003).

Ferri, A., et al., "Progressive and selective degeneration of motoneurons in a mouse model of SMA," *NeuroReport 15*:275-280, Lippincott Williams & Wilkins, United States (2004).

Field, J., et al., "Purification of a RAS-Responsive Adenylyl Cyclase Complex from *Saccharomyces cerevisiae* by Use of an Epitope Addition Method," *Molecular and Cellular Biology 8*:2159-2165, American Society for Microbiology, United States (1988).

Finckh, U., et al, "Novel mutations and repeated findings of mutations in familial Alzheimer disease," *Neurogenetics 6*:85-89, Springer-Verlag, Germany (2005).

Finn, J.T., et al., "Evidence That Wallerian Degeneration and Localized Axon Degeneration Induced by Local Neurotrophin Deprivation Do Not Involve Caspases," *J. Neurosci. 20*:1333-1341, Society for Neuroscience, United States (2000).

Fleming, S.M., et al., "Genetic Mouse Models of Parkinsonism: Strengths and Limitations," *NeuroRx®: The Journal of the American Society for Experimental NeuroTherapeutics 2*:495-503, The American Society for Experimental NeuroTherapeutics, Inc., United States (2005).

Goate, A., et al., "Segregation of a missense mutation in the amyloid precursor protein gene with familial Alzheimer's disease," *Nature 349*:704-706, Nature Publishing Group, England (1991).

Golstein, P., "Cell Death: TRAIL and its receptors," *Current Biology 7*:R750-R753, Current Biology Ltd, England (1997).

Goodwin, R., et al., "Molecular Cloning and Expression of the Type 1 and Type 2 Murine Receptors for Tumor Necrosis Factor," *Molecular and Cellular Biology 11*:3020-3026, American Society for Microbiology, United States (1991).

Graham, R.K., et al., "Cleavage at the Caspase-6 Site Is Required for Neuronal Dysfunction and Degeneration Due to Mutant Huntingtin," *Cell 125*:1179-1191, Elsevier Inc., United States (2006).

Gray, N.W., et al., "Rapid Redistribution of Synaptic PSD-95 in the Neocortex in Vivo," *PLOS Biology 4*:2065-2075, Public Library of Science, United States (2006).

Gruss, H.-J., and Dower, S.K., "Tumor Necrosis Factor Ligand Superfamily: Involvement in the Pathology of Malignant Lymphomas," *Blood 85*:3378-3404, The American Society of Hematology, United States (1995).

Guo, H., et al.," Active Caspase-6 and Caspase-6-Cleaved Tau in Neuropil Threads, Neuritic Plaques, and Neurofibrillary Tangles of Alzheimer's Disease," *American Journal of Pathology 165*: 523-531, American Society for Investigative Pathology, United States (2004).

Gurney, M.E., et al., "Motor Neuron Degeneration in Mice That Express a Human Cu, Zn Superoxide Dismutase Mutation," *Science 264*:1772-1775, American Association for the Advancement of Science, United States (1994).

Haak-Frendscho, M., et al., "Inhibition of TNF by a TNF Receptor Immunoadhesin Comparison to an Anti-TNF Monoclonal Antibody," *Journal of Immunology 152*:1347-1353, The American Association of Immunologists, United States (1994).

Haass, C., et al., "Processing of Processing of β-Amyloid Precursor Protein in Microglia and Astrocytes Favors an Internal Localization over Constitutive Secretion," *The Journal of Neuroscience 11*:3783-3793, Society for Neuroscience, United States (1991).

Hahne, M., et al.,"APRIL, a New Ligand of the Tumor Necrosis Factor Family, Stimulates Tumor Cell Growth," *J. Exp. Med. 188*: 1185-1190, The Rockefeller University Press, United States (1998).

Hamburger, V., et al., "Neuronal Death in the Spinal Ganglia of the Chick Embryo and its Reduction by Nerve Growth Factor," *The Journal of Neuroscience 1*:60-71, Society for Neuroscience, United States (1981).

Henderson, C.E., et al., "Neurotrophins promote motor neuron survival and are present in embryonic limb bud," *Nature 363*:266-270, Nature Publishing Group, England (1993).

Hesse, L., et al.,"The βA4 amyloid precursor protein binding to copper," *FEBS Letters 349*:109-116, Federation of European Biochemical Societies, Netherlands (1994).

Hilbich, C., et al.,"Amyloid-like Properties of Peptides Flanking the Epitope of Amyloid Precursor Protein-specific Monoclonal Antibody 22C11," *The Journal of Biological Chemistry 268*:26571-26577, The American Society for Biochemistry and Molecular Biology, Inc., United States (1993).

Hohmann, H.-P., et al, "Two Different Cell Types Have Different Major Receptors for Human Tumor Necrosis Factor (TNFα)" *The Journal of Biological Chemistry 264*:14927-14934, The American Society for Biochemistry and Molecular Biology, Inc., United States (1989).

Hopp, T.P., et al.,"A Short Polypeptide Marker Sequence Useful for Recombinant Protein Identification and Purification," *Bio/Technology 6*:1204-1210, Nature Publishing Group, England (1988).

Hoppe, H.-J., et al.,"A parallel three stranded α-helical bundle at the nucleation site of collagen triple-helix formation," *FEBS Letters 344*:191-195, Federation of European Biochemical Societies, Netherlands (1994).

Horowitz, P.M., et al., "Early N-terminal changes and caspase-6 cleavage of Tau in Alzheimer's disease," *J. Neurosci. 24*:7895-7902, Society for Neuroscience, United States (2004).

Hsiao, K., et al., "Correlative Memory Deficits, Aβ Elevation, and Amyloid Plaques in Transgenic Mice," *Science 274*:99-102, American Association for the Advancement of Science, United States (1996).

Iliades, P., et al., "Triabodies: single chain Fv fragments without a linker form trivalent trimers," *FEBS Letters 409*:437-441, Federation of European Biochemical Societies, Netherlands (1997).

Jakobovits, A., et al.,"Analysis of homozygous mutant chimeric mice: Deletion of the immunoglobulin heavy-chain joining region blocks B-cell development and antibody production," *Proc. Natl. Acad. Sci. USA 90*:2551-2555, National Academy of Sciences, United States (1993).

Jakobovits, A., et al., "Germ-line transmission and expression of a human-derived yeast artificial chromosome," *Nature 362*: 255-258, Nature Group Publishing, England (1993).

Janus, C., et al., "Aβ peptide immunization reduces behavioral impairment and plaques in a model of Alzheimer's disease," *Nature 408*:979-982, Macmillan Magazines Ltd, England (2000).

Jin, L.-W., et al., "Peptides Containing the RERMS Sequence of Amyloid β/A4 Protein Precursor Bind Cell Surface and Promote Neurite Extension," *The Journal of Neuroscience 14*:5461-5470, Society for Neuroscience, United States (1994).

Joachim, C., et al., "Antibodies to Non-beta Regions of the Beta-amyloid Precursor Protein Detect a Subset of Senile Plaques," *American Journal of Pathology 138*:373-384, American Association of Pathologies, United States (1991).

Johnson, K.S., and Chiswell, D.J., "Human antibody engineering," *Current Opinion in Structural Biology* 3:564-571, Current Biology Ltd, England (1993).

Johnson, D., et al., "Expression and Structure of the Human NGF Receptor," *Cell* 47:545-554, Cell Press, United States (1986).

Jones, P.T., et al., "Replacing the complementarity-determining regions in a human antibody with those from a mouse," *Nature* 321:522-525, Nature Publishing Group, England (1986).

Kang, J., et al., "The precursor of Alzheimer's disease amyloid A4 protein resembles a cell-surface receptor," *Nature* 325:733-736, Nature Publishing Group, England (1987).

Kitaguchi, N., et al., "Novel precursor of Alzheimer's disease amyloid protein shows protease inhibitory activity," *Nature* 331:530-532, Nature Publishing Group (1988).

Knowles, J.K., et al., "The p75 Neurotrophin Receptor Promotes Amyloid-β(1-42)-Induced Neuritic Dystrophy in Vitro and in Vivo," *The Journal of Neuroscience* 29(34):10627-10637, Society for Neuroscience, United States (Aug. 2009).

Köhler, G., and Milstein, C., "Continuous cultures of fused cells secreting antibody of predefined specificity," *Nature* 256: 495-497, Nature Publishing Group, England (1975).

Kortt, A.A., et al., "Single-chain Fv fragments of anti-neuraminidase antibody NC10 containing five- and ten-residue linkers form dimers and with zero-residue linker a trimer," *Protein Engineering* 10:423-433, Oxford University Press, England (1997).

Kozbor, D., et al., "A Human Hybrid Myeloma for Production of Human Monoclonal Antibodies," *The Journal of Immunology* 133: 3001-3005, The American Association of Immunologists, United States (1984).

Kuida, K., et al., "Decreased apoptosis in the brain and premature lethality in CPP32-deficient mice," *Nature* 384:368-372, Nature Publishing Group, England (1996).

Landschulz, W.H., et al., "The Leucine Zipper: A Hypothetical Structure Common to a New Class of DNA Binding Proteins," *Science* 240:1759-1764, American Association for the Advancement of Science, United States (1988).

Lavrik, I., et al., "Death receptor signaling," *Journal of Cell Science* 118:265-267, The Company of Biologists Ltd, England (2005).

Levine, M.S., et al., "Gepetic mouse models of Huntington's and Parkinson's diseases: illuminating but imperfect," *TRENDS in Neurosciences* 27:691-697, Elsevier Ltd., England (2004).

Lewis, M., et al., "Cloning and expression of cDNAs for two distinct murine tumor necrosis factor receptors demonstrate one receptor is species specific." *Proc. Natl. Acad. Sci. USA* 88:2830-2834, National Academy of Sciences, United States (1991).

Lim, G.P., et al., "A Diet Enriched with the Omega-3 Fatty Acid Docosahexaenoic Acid Reduces Amyloid Burden in an Aged Alzheimer Mouse Model," *The Journal of Neuroscience* 25(12):3032-3040, Society for Neuroscience, United States (2005).

Liu, J., et al., "Enhanced CD4+ T cell Proliferation and Th2 Cytokine Production in DR6-Deficient Mice," *Immunity* 15:23-34, Cell Press, United States (2001).

Locksley, R.M., et al., "The TNF and TNF Receptor Superfamilies: Integrating Mammalian Biology," *Cell* 104:487-501, Cell Press, United States (2001).

Loetscher, H., et al., "Molecular Cloning and Expression of the Human 55 kd Tumor Necrosis Factor Receptor," *Cell* 61:351-359, Cell Press, United States (1990).

Mallet, S., et al., "Characterization of the MRC OX40 antigen of activated CD4 positive T lymphocytes—a molecule related to nerve growth factor receptor," *The EMBO Journal* 9:1063-1068, Oxford University Press, England (1990).

Marks, J.D., et al., "By-Passing Immunization: Building High Affinity Human Antibodies by Chain Shuffling," *Bio/Technology* 10:779-783, Nature Publishing Group, England (1992).

Marks, J.D., et al., "By-passing Immunization: Human Antibodies From V-gene Libraries Displayed on Phage," *J Mol Biol.* 222: 581-597. Academic Press Limited, England (1991).

Marsters, S.A., et al., "A novel receptor for Apo2L/TRAIL contains a truncated death domain," *Current Biology* 7:1003-1006, Current Biology Ltd, England (1997).

Marsters, S.A., et al., "Identification of a ligand for the death-domain-containing receptor Apo3," *Current Biology* 8:525-528, Current Biology Ltd, England (1998).

Martin, G.A., et al., "GAP Domains Responsible for Ras p21-Dependent Inhibition of Muscarinic Atrial K+ Channel Currents," *Science* 255:192-194, American Association for the Advancement of Science, United States (1992).

McCafferty, J., et al., "Phage antibodies: filamentous phage displaying antibody variable domains," *Nature* 348:552-554, Nature Publishing Group, England (1990).

McGowan, E., et al.,"A decade of modeling Alzheimer's diseases in transgenic mice," *TRENDS in Genetics* 22:281-289, Elsevier Ltd, England (2006).

Mi, S., et al., "Death receptor 6 negatively regulates oligodendrocyte survival, maturation and myelination," *Nature Medicine* 17(7):816-822, Nature America, Inc., United States (2011).

Mi, S., et al., "LINGO-1 is a component of the Nogo-66 receptor/p75 signaling complex," *Nature Neuroscience* 7:221-228, Nature Publishing Group, England (2004).

Mi, S., et al., "LINGO-1 negatively regulates myelination by oligodendrocytes," *Nature Neuroscience* 8:745-751, Nature Publishing Group, England (2005).

Milstein, C., and Cuello, A.C., "Hybrid hybridomas and their use in immunohistochemistry," *Nature* 305:537-540, Nature Publishing Group, England (1983).

Minkeviciene, R., et al., "Memantine Improves Spatial Learning in a Transgenic Mouse Model of Alzheimer's Disease," *The Journal of Pharmacology and Experimental Therapetics* 311:677-682, The American Society for Pharmacology and Experimental Therapeutics, United States (2004).

Moechars, D., et al., "Premature death in transgenic mice that overexpress a mutant amyloid precursor protein is preceded by severe neurodegeneration and apoptosis," *Neuroscience* 91:819-830, Elsevier Science Ltd, England (1999).

Moore, P.A., et al., "BLyS: Member of the Tumor Necrosis Factor Family and B Lymphocyte Stimulator," *Science* 285: 260-263, American Association for the Advancement of Science, United States (1999).

Morgan, D., et al.,"Aβ peptide vaccination prevents memory loss in an animal model of Alzheimer's disease," *Nature* 408:982-985, Macmillan Magazines Ltd, England (2000).

Mouri, A., et al., "Oral vaccination with a viral vector containing Aβ cDNA attenuates age-related Aβ accumulation and memory deficits without causing inflammation in a mouse Alzheimer model," *The FASEB Journal* 21:2135-2148, The Federation of American Societies for Experimental Biology, United States (2007).

Mukhopadhyay, A., et al., "Identification and Characterization of a Novel Cytokine, THANK, a TNF Homologue That Activates Apoptosis, Nuclear Factor-κB, and c-Jun NH2-Terminal Kinase," The Journal of Biological Chemistry 274:15978-15981, The American Society for Biochemistry and Molecular Biology, United States (1999).

Nagasaka, Y., et al., "A unique gene expression signature discriminates familiar Alzheimer's disease mutation carriers from their wild-type siblings," *PNAS* 102:14854-14859, National Academy of Sciences, United States (2005).

Neve, R.L., et al., "Expression of the Alzheimer Amyloid Precursor Gene Transcripts in the Human Brain," *Neuron* 1:669-677, Cell Press, United States (1988).

Nicholson, D.W., "Neuroscience: Good and bad cell death," *Nature* 457:970-971, Nature Publishing Group, England (Feb. 2009).

Nikolaev, A., et al., "APP binds DR6 to trigger axon pruning and neuron death via distinct caspases," *Nature* 457:981-990, Macmillan Publishers Limited., England (Feb. 2009).

Nocentini, G., et al., "A new member of the tumor necrosis factorynerve growth factor receptor family inhibits T cell receptor-induced apoptosis," *Proc. Natl. Acad. Sci. USA* 94:6216-6221, The National Academy of Sciences, United States (1997).

O'Leary, D.D.M., et al., "Topographic Targeting Errors in the Retinocollicular Projection and Their Elimination by Selective Ganglion Cell Death," *The Journal of Neuroscience* 6:3692-3705, Society of Neuroscience, United States (1986).

Ohsawa, I., et al., "The Amino-Terminal Region of Amyloid Precursor Protein Is Responsible for Neurite Outgrowth in Rat Neocortical Explant Culture," *Biochemical and Biophysical Research Communications* 236:59-65, Academic Press, United States (1997).

Oppenheim, R.W., "Cell death during development of the nervous system," *Annu. Rev. Neurosci.* 14:453-501, Annual Reviews Inc., United States (1991).

Paborsky, L.R., et al., "Mammalian cell transient expression of tissue factor for the production of antigen," *Protein Engineering* 3:547-553, Oxford University Press, England (1990).

Paganetti, P., et al., "β-site specific intrabodies to decrease and prevent generation of Alzheimer's Aβ peptide," *The Journal of Cell Biology* 168(6):863-868, The Rockefeller University Press, United States (2005).

Palmert, M.R., et al.,"Antisera to an Amino-Terminal Peptide Detect the Amyloid Protein Precursor of Alzheimer's Disease and Recognize Senile Plaques," *Biochemical and Biophysical Research Communications* 156:432-437, Academic Press, Inc., United States (1988).

Pan, G., et al.,"An Antagonist Decoy Receptor and a Death-Domain Containing Receptor for TRAIL," *Science* 277:815-818, American Association for the Advancement of Science, United States (1997).

Pan, G., et al., "Identification and functional characterization of DR6, a novel death domain-containing TNF receptor," *FEBS Letters* 431:351-356, Federation of European Biochemical Societies, England (1998).

Pan, G., et al., "The Receptor for the Cytotoxic Ligand TRAIL," *Science* 276:111-113, American Association for the Advancement of Science, United States (1997).

Pitti, R.M. et al., "Induction of Apoptosis by Apo-2 Ligand, a New Member of the Tumor Necrosis Factor Cytokine Family," *The Journal of Biological Chemistry* 271:12687-12690, The American Society for Biochemistry and Molecular Biology, Inc., United States (1996).

Ponomarev, S.Y., and Audie, J., "Computational prediction and analysis of the DR6-NAPP interaction," *Proteins* 79:1376-1395, Wiley-Liss, Inc., United States (2011).

Ponte, P., et al.,"A new A4 amyloid mRNA contains a domain homologous to serine proteinase inhibitors," *Nature* 331:525-527, Nature Publishing Group, England (1988).

Portelius, E., et al., "Identification of novel N-terminal fragments of amyloid precursor protein in cerebrospinal fluid," *Experimental Neurology* 223:351-358, Elsevier Inc., United States (Jun. 2010).

Price, D.L., et al., "Genetic Neurodegenerative Diseases: The Human Illness and Transgenic Models," *Science* 282:1079-1083, American Association for the Advancement of Science, United States (1998).

Priller, C., et al., "Synapse Formation and Function Is Modulated by the Amyloid Precursor Protein," *J. Neurosci.* 26:7212-7221, Society for Neuroscience, United States (2006).

Quast, T., et al., "sAPP as a regulator of dendrite motility and melanine release in epidermal melanocytes and melanoma cells," *The FASEB Journal* 17:1739-1741, The Federation of American Societies for Experimental Biology, United States (2003).

Radeke, M.J., et al., "Gene transfer and molecular cloning of the rat nerve growth factor receptor," *Nature* 325:593-597, Nature Publishing Group, England (1987).

Rakover, I., et al., "Immunotherapy against APP β-Secretase Cleavage Site Improves Cognitive Function and Reduces Neuroinflammation in Tg2576 Mice without a Significant Effect on Brain Aβ levels," *Neurodegenerative Dis* 4:392-402, Karger AG, Switzerland (2007).

Raux, G., et al., "Molecular diagnosis of autosomal dominant early onset Alzheimer's disease: an update," *J. Med. Genet.* 42:793-795, BMJ Group, England (2005).

Riechmann, L., et al., "Reshaping human antibodies for therapy," *Nature* 332:323-327, Nature Publishing Group, England (1988).

Roberson, E.D., and Mucke, L., "100 Years and Counting: Prospects for Defeating Alzheimer's Disease," *Science* 314:781-784, American Association for the Advancement of Science, United States (2006).

Rohn, T.T., et al.,"A Monoclonal Antibody to Amyloid Precursor Protein Induces Neuronal Apoptosis," *Journal of Neurochemistry* 74:2331-2342, International Society for Neurochemistry, Lippincott Williams & Wilkins, Inc., United States (2000).

Rossjohn, J., et al., "Crystal structure of the N-terminal, growth factor-like domain of Alzheimer amyloid precursor protein," *Nature Structural Biology* 6:327-331, Nature American Inc, United States (1999).

Sandbrink, R., et al., "APP Gene Family Alternative Splicing Generates Functionally Related Isoforms," *Annals New York Academy of Sciences* 777:281-287, New York Academy of Sciences, United States (1996).

Schall, T.J., et al., "Molecular Cloning and Expression of a Receptor for Human Tumor Necrosis Factor," *Cell* 61:361-370, Cell Press, United States (1990).

Scheuner, D., et al., "Secreted amyloid β-protein similar to that in the senile plaques of Alzheimer's disease is increased in vivo by the presenilin 1 and 2 and *APP* mutations linked to familial Alzheimer's disease," *Nature Medicine* 2:864-870, Nature Publishing Group, England (1996).

Schmid, D.S., et al., "DNA fragmentation: Manifestation of target cell destruction mediated by cytotoxic T-cell lines, lymphotoxin-secreting helper T-cell clones, and cell-free lymphotoxin-containing supernatant," *Proc. Natl. Acad. Sci. USA* 83:1881-1885, National Academy of Sciences, United States (1986).

Schmidt, C.S., et al., "Resistance to Myelin Oligodendrocyte Glycoprotein-Induced Experimental Autoimmune Encephalomyelitis by Death Receptor 6-Deficient Mice," *The Journal of Immunology* 175:2286-2292, The American Association of Immunologists, Inc., United States (2005).

Schmitt, F.A., et al, "The Severe Impairment Battery: Concurrent Validity and the Assessment of Longitudinal Change in Alzheimer's Disease," *Alzheimer Disease and Associated Disorders* 11(Suppl. 2):S51-S56, Lippincott-Raven Publishers, United States (1997).

Schneider, P., et al., "BAFF, A Novel Ligand of the Tumor Necrosis Factor Family, Stimulates B Cell Growth," *J. Exp. Med.* 189:1747-1756, The Rockefeller University Press, United States (1999).

Selkoe, D.J., "Amyloid β-Protein and the Genetics of Alzheimer's Disease," *The Journal of Biological Chemistry* 271: 18295-18298, The American Society for Biochemistry and Molecular Biology, Inc., United States (1996).

Seubert, P., et al., "Secretion of β-amyloid precursor protein cleaved at the amino terminus of the β-amyloid peptide," *Nature* 361:260-263, Nature Publishing Group, England (1993).

Sheridan, J.P., et al., "Control of TRAIL-Induced Apoptosis by a Family of Signaling and Decoy Receptors," *Science* 277:818-821, American Association for the Advancement of Science, United States (1997).

Shu, H.-B., et al., "TALL-1 is a novel member of the TNF family that is down-regulated by mitogens," *Journal of Leukocyte Biology* 65:680-683, Society for Leukocyte Biology, United States (1999).

Sisodia, S.S., et al., "Evidence that β-Amyloid Protein in Alzheimer's Disease is Not Derived by Normal Processing," *Science* 248:492-495, American Association for the Advancement of Science, United States (1990).

Skinner, R.H., et al., "Use or the Glu-Glu-Pne C-terminal Epitope for Rapid Purification of the Catalytic Domain of Normal and Mutant ras GTPase-activating Proteins," *The Journal of Biological Chemistry* 266:14163-14166, The American Society for Biochemistry and Molecular Biology, Inc., United States (1991).

Smith, C.A., et al.,"A Receptor for Tumor Necrosis Factor Defines an Unusual Family of Cellular and Viral Proteins," *Science* 248:1019-1023, American Association for the Advancement of Science, United States (1990).

Smith, D.L., et al., "Reversal of long-term dendritic spine alterations in Alzheimer disease models," *PNAS* 106:16877-16882, National Academy of Sciences, United States (Sep. 2009).

Sotthibundhu, A., et al.,"β-Arnyloidl-42 Induces Neuronal Death through the p75 Neurotrophin Receptor" *The Journal of Neuroscience* 28(15):3941-3946, Society for Neuroscience, United States (Apr. 2008).

Spires, T.L., et al., "Dendritic Spine Abnormalities in Amyloid Precursor Protein Transgenic Mice Demonstrated by Gene Transfer and Intravital Multiphoton Microscopy," *J. Neurosci.* 25:7278-7287, Society for Neurscience, United States (2005).

Stamenkovic, I., et al., "A B-lymphocyte activation molecule related to the nerve growth factor receptor and induced by cytokines in carcinomas," *The EMBO Journal* 8:1403-1410, Oxford University Press, England (1989).

Stamenkovic, I., et al., "The B Lymphocyte Adhesion Molecule CD22 Interacts with Leukocyte Common Antigen CD45R0 on T Cells and α2-6 Sialyltransferase, CD75, on B Cells," *Cell* 66:1133-1144, Cell Press, United States (1991).

Suresh, M.R., et al., "Bispecific Monoclonal Antibodies from Hybrid Hybridomas," *Methods in Enzymology* 121:210-228, Academic Press, Inc., United States (1986).

Suzuki, N., et al.,"An Increased Percentage of Long Amyloid β Protein Secretea by Familial Amyloid β Protein Precursor ((βAPP717) Mutants," *Science* 264:1336-1340, American Association for the Advancement of Science, United States (1994).

Tanzi, R.E., et al.,"Amyloid βProtein Gene: cDNA, mRNA Distribution, and Genetic Linkage Near the Alzheimer Locus," *Science* 235:880-884, American Association for the Advancement of Science, United States (1987).

Tanzi, R.E., et al., "Protease inhibitor domain encoded by an amyloid protein precursor mRNA associated with Alzheimer's disease," *Nature* 331:528-530, Nature Publishing Group, England (1988).

Tokuda, E., et al., "Dysequilibrium between caspases and their inhibitors in a mouse model for amyotrophic lateral sclerosis," *Brain Research* 1148:234-242, Elsevier B.V., Netherlands (2007).

Town, T., et al., "CD40 signaling and Alzheimer's disease pathogenesis," *Neurochemistry International* 39:371-380, Elsevier Science Ltd., England (2001).

Traunecker, A., et al., "Bispecific single chain molecules (Janusins) target cytotoxic lymphocytes on HIV infected cells," *The EMBO Journal* 10:3655-3659, Oxford University Press, England (1991).

Tsai, J., et al., "Fibrillar amyloid deposition leads to local synaptic abnormalities and breakage of neuronal branches," *Nature Neuroscience* 7:1181-1183, Nature Publishing Group, England (2004).

Tsuda, E., et al., "Isolation of a Novel Cytokine from Human Fibroblasts That Specifically Inhibits Osteociastogenesis," *Biochemical and Biophysical Research Communications* 234:137-142, Academic Press, United States (1997).

Turner, R.S., et al.,"Amyloids β40 and β42 Are Generated Intracellularly in Cultured Human Neurons and Their Secretion Increases with Maturation," *The Journal of Biological Chemistry* 271:8966-8970, The American Society for Biochemistry and Molecular Biology, Inc., United States (1996).

Turner, B.J., et al., "Effect of p75 Neurotrophin Receptor Antagonist on Disease Progression in Transgenic Amyotrophic Lateral Sclerosis Mice," *Journal of Neuroscience* 78:193-199, Wiley-Liss, Inc., United States (2004).

Van Nostrand, W.E., et al., "Protease nexin-II, a potent antichymotrypsin, shows identity to amyloid β-protein precursor," *Nature* 341:546-549, Nature Publishing Group, England (1989).

Venkataraman, C., et al., "Death receptor 6 regulates the development of pulmonary eosinophilla and airway inflammation in a mouse model of asthma," *Immunology Letters* 106:42-47, Elsevier B.V., Netherlands (2006).

Verhoeyen, M., et al., "Reshaping Human Antibodies: Grafting an Antilysozyme Activity," *Science* 239:1534-1536, American Association for the Advancement of Science, United States (Mar. 1988).

Von Bülow, G.-U., and Bram, R.J., "NF-AT Activation Induced by a CAML-Interacting Member of the Tumor Necrosis Factor Receptor Superfamily," *Science* 278:138-141, American Association for the Advancement of Science, United States (1997).

Wajant, H., "Death receptors," *Essays in Biochemistry* 39:53-71, The Biochemical Society, England (2003).

Wallach, D., "TNF Ligand and TNF/NGF Receptor Families," *Cytokine Reference*:377-411, Academic Press Inc., United States (2000).

Wang, H., and Tessier-Lavigne, M., "En *passant* neurotrophic action of an intermediate axonal target in the developing mammalian CNS," *Nature* 401:765-769, Macmillan Magazines Ltd, England (1999).

Wang, H., et al., "Nortriptyline delays disease onset in models of chronic neurodegeneration," *European Journal of Neuroscience* 26:633-641, Federation of European Neuroscience, Blackwell Publishing Ltd, England (2007).

Wang, K.C., et al., "p75 interacts with the Nogo receptor as a co-receptor for Nogo, MAG and Omgp," *Nature* 420:74-78, Nature Publishing Group, England (2002).

Ware, C.F., "The TNF Superfamily," *Cytokine & Growth Factor Reviews* 14:181-184, Elsevier Science Ltd, England (2003).

Waterhouse, P., et al., "Combinatorial infection and in vivo recombination: a strategy for making large phage antibody repertoires," *Nucleic Acids Research* 21:2265-2266, Oxford University Press, England (1993).

Weidemann, A., et al., "Identification, Biogenesis, and Localization of Precursors of Alzheimer's Disease A4 Amyloid Protein," *Cell* 57:115-126, Cell Press, United States (1989).

Wiley, S.R., et al., "Identification and Characterization of a New Member of the TNF Family that Induces Apoptosis," *Immunity* 3:673-682, Cell Press, United States (1995).

Wong, P.C., et al., "Genetically engineered mouse models of neurodegenerative diseases," *Nature Neuroscience* 5:633-639, Nature Publishing Group, England (2002).

Yaar, M., et al., "Amyloid β Binds Trimers as Well as Monomers of the 75-kDa Neurotrophin Receptor and Activates Receptor Signaling," *The Journal of Biological Chemistry* 277(10):7720-7725, American Society for Biochemistry and Molecular Biology, United States (2002).

Yaar, M., et al., "Binding of β-Amyloid to the p75 Neurotrophin Receptor Induces Apoptosis," *The Journal of Clinical Investigation* 100(9):2333-2340, American Society for Clinical Investigation, United States (1997).

Yuen, E.C., et al., "Nerve growth factor and the neurotrophic factor hypothesis," *Brain & Development* 18:362-368, Elsevier Science B.V., Netherlands (1996).

Zagrebelsky, M., et al., "The p75 Neurotrophin Receptor Negatively Modulates Dendrite Complexity and Spine Density in Hippocampal Neurons," *The Journal of Neuroscience* 25(43):9989-9999, Society for Neuroscience, United States (2005).

Zhao, H., et al., "Impaired c-Jun Amino Terminal Kinase Activity and T Cell Differentiation in Death Receptor 6-deficient Mice," *J. Exp. Med.* 194:1441-1448, The Rockefeller University Press, United States (2001).

NCBI Entrez, GenBank Report, Accession No. P05067, Entry Date Apr. 1993.

International Preliminary Report on Patentability for International Patent Application No. PCT/US2007/088521, European Patent Office, Netherlands, mailed on Jul. 16, 2008.

International Search Report and Written Opinion for International Patent Application No. PCT/US2009/065755, ISA/US, Commissioner for Patents, United States, mailed on Nov. 4, 2010.

\* cited by examiner

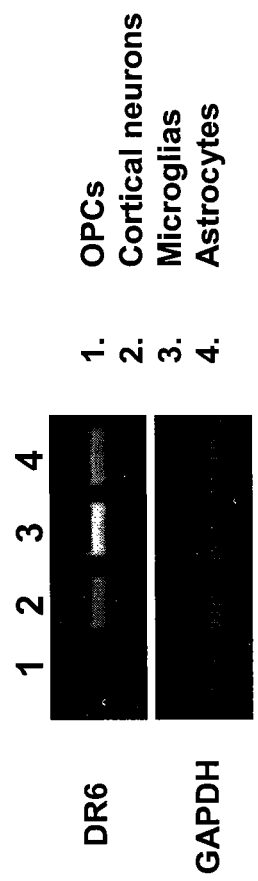

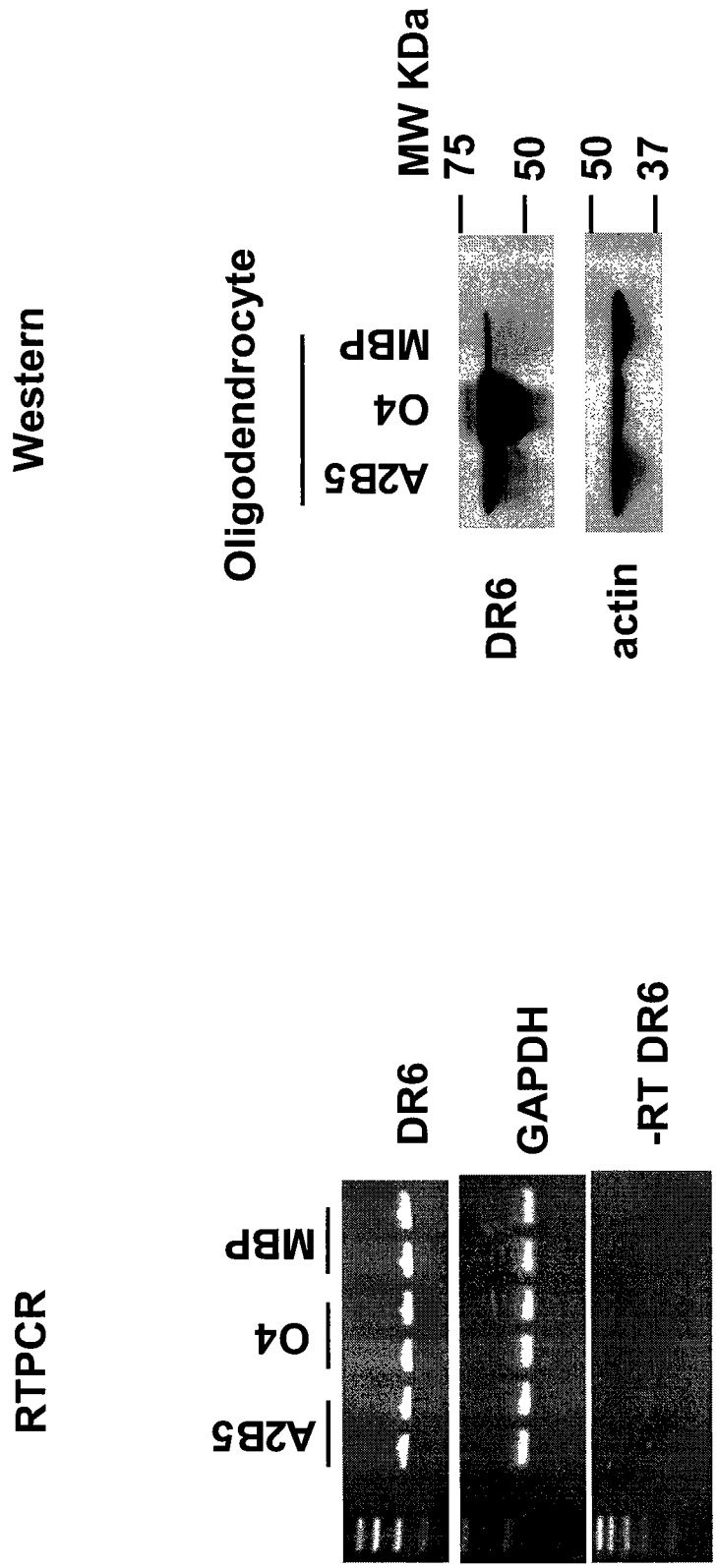

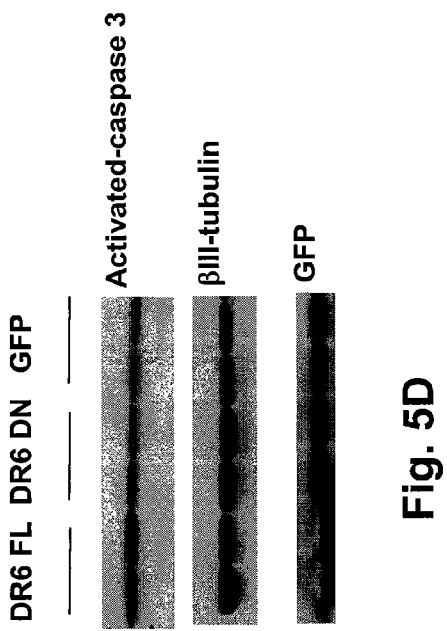
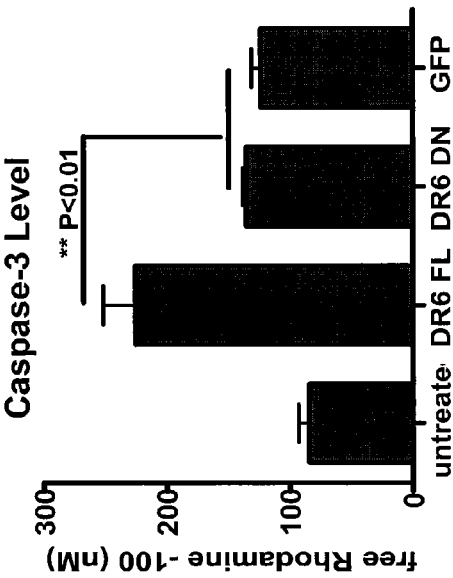
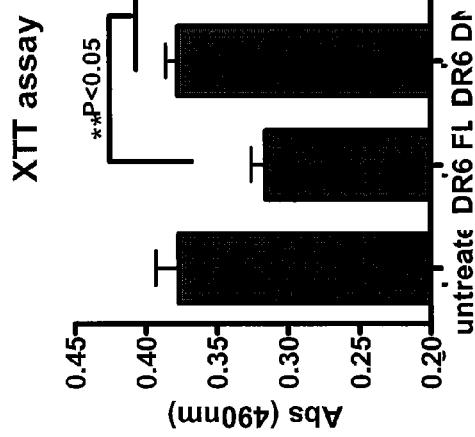
Fig. 5B
Fig. 5C
Fig. 5D

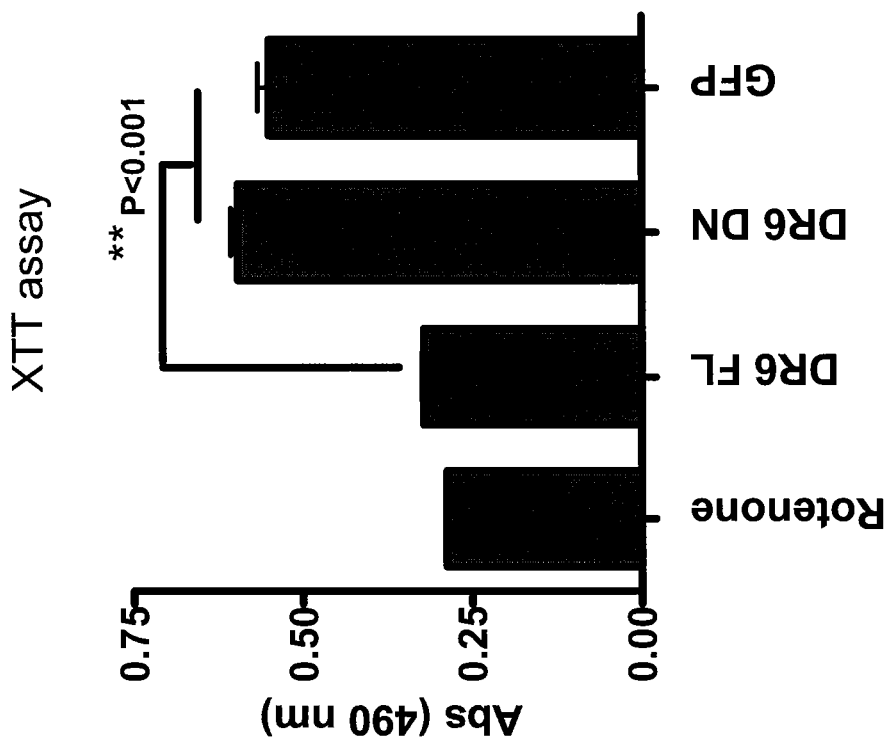
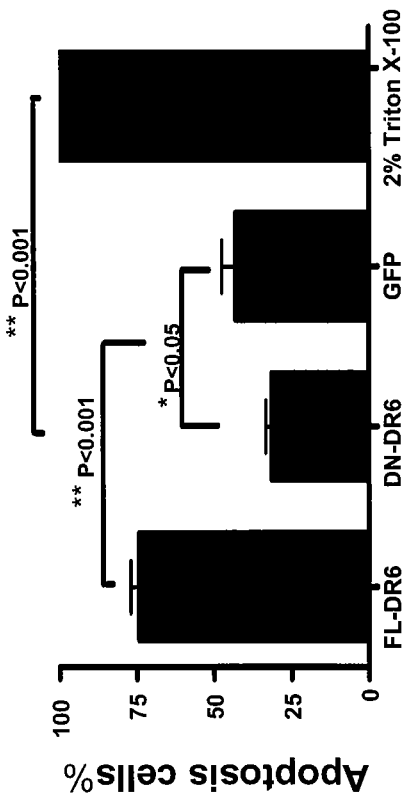
Fig. 6A
Fig. 6B

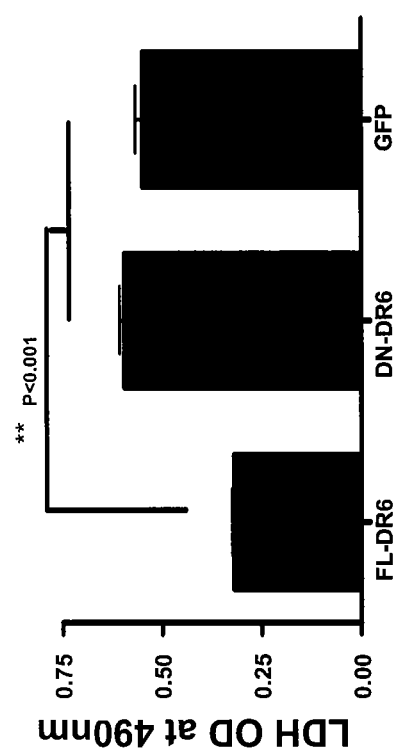

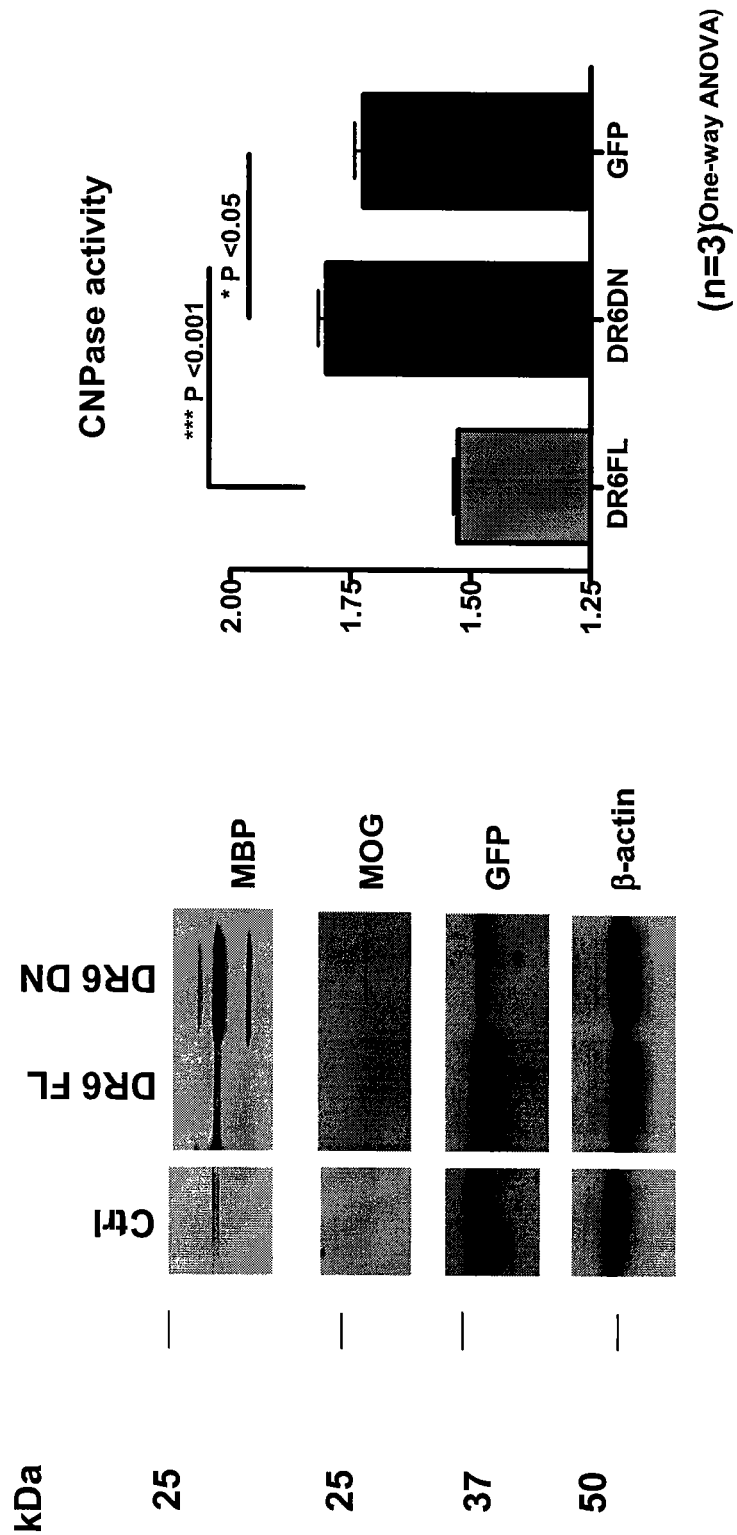

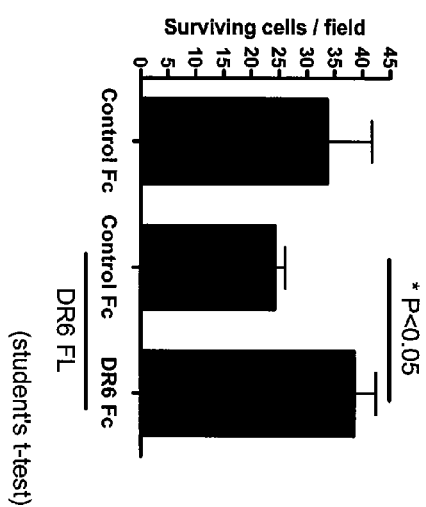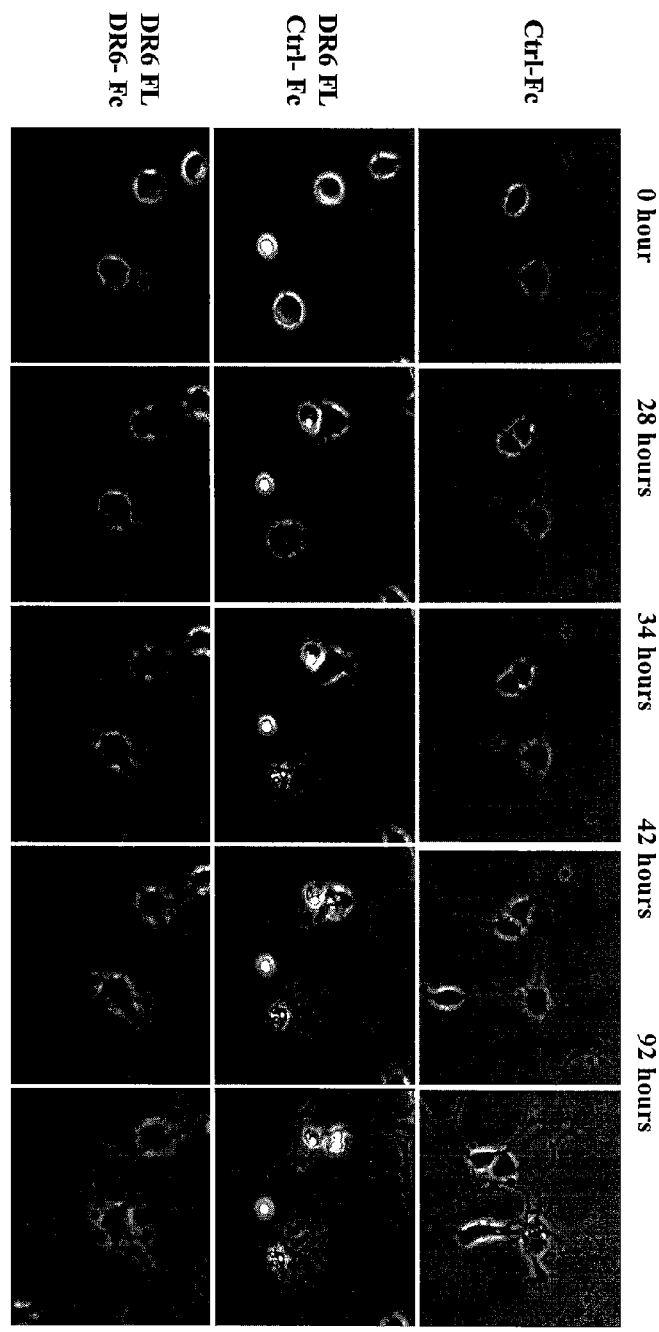

Fig. 10B
Fig. 10A
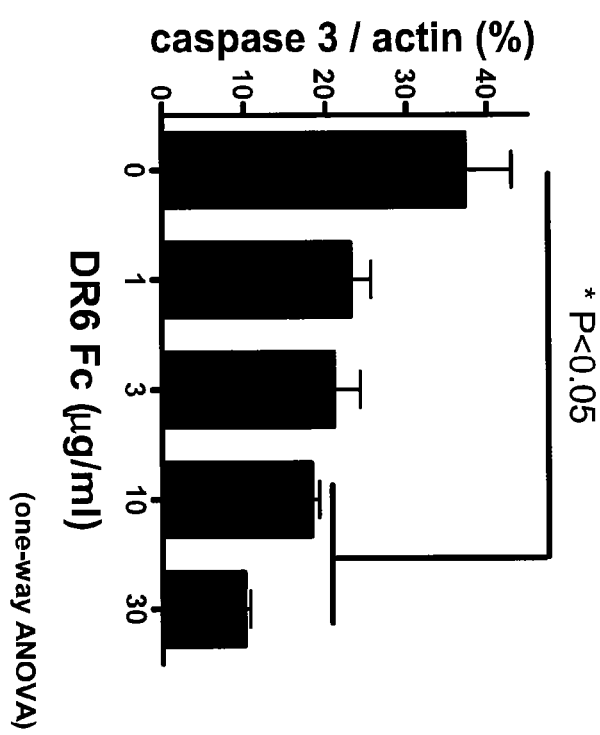
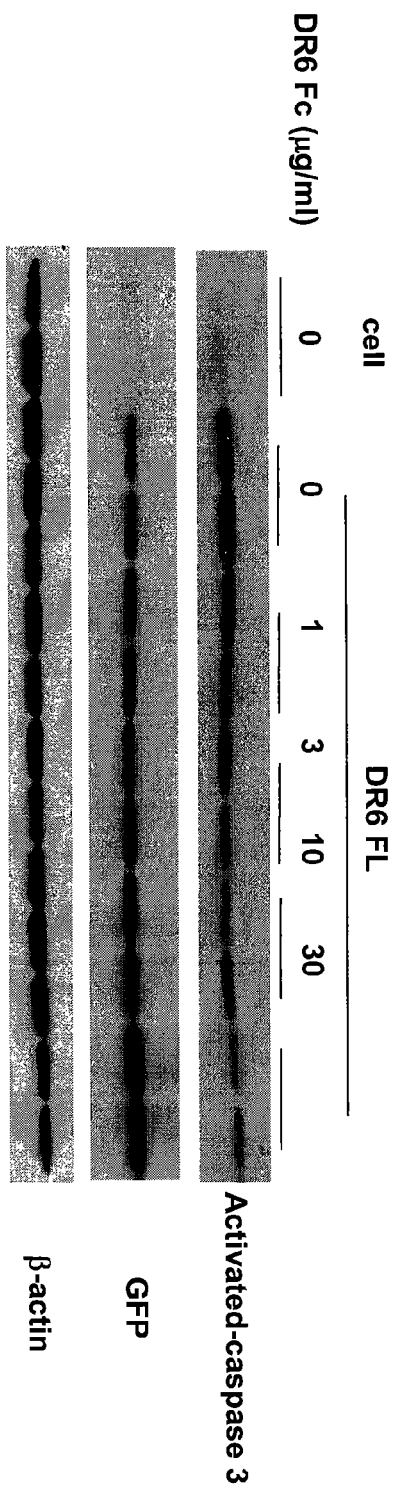

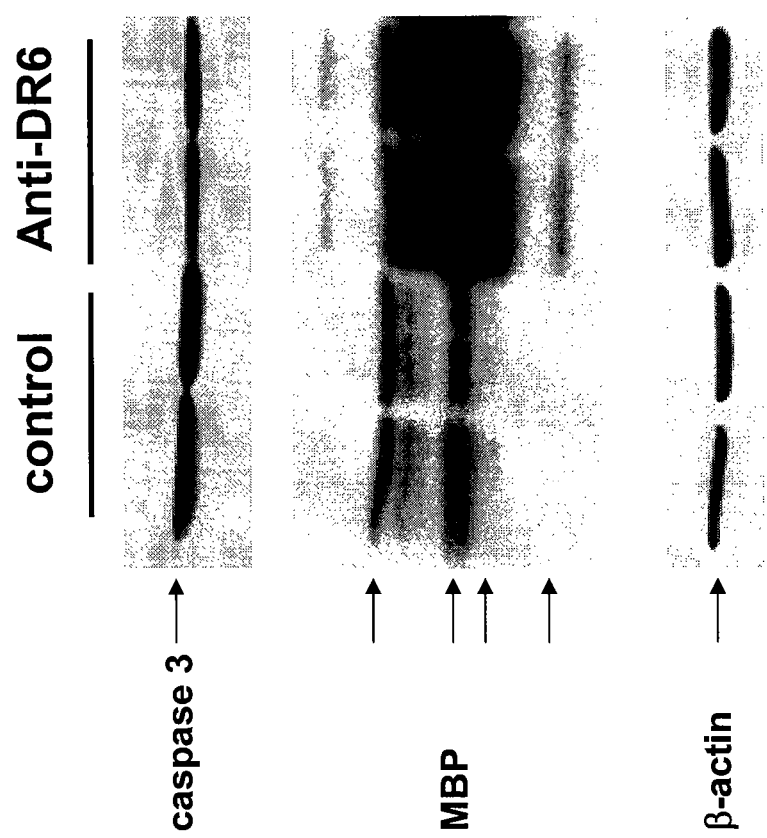

Fig. 16A
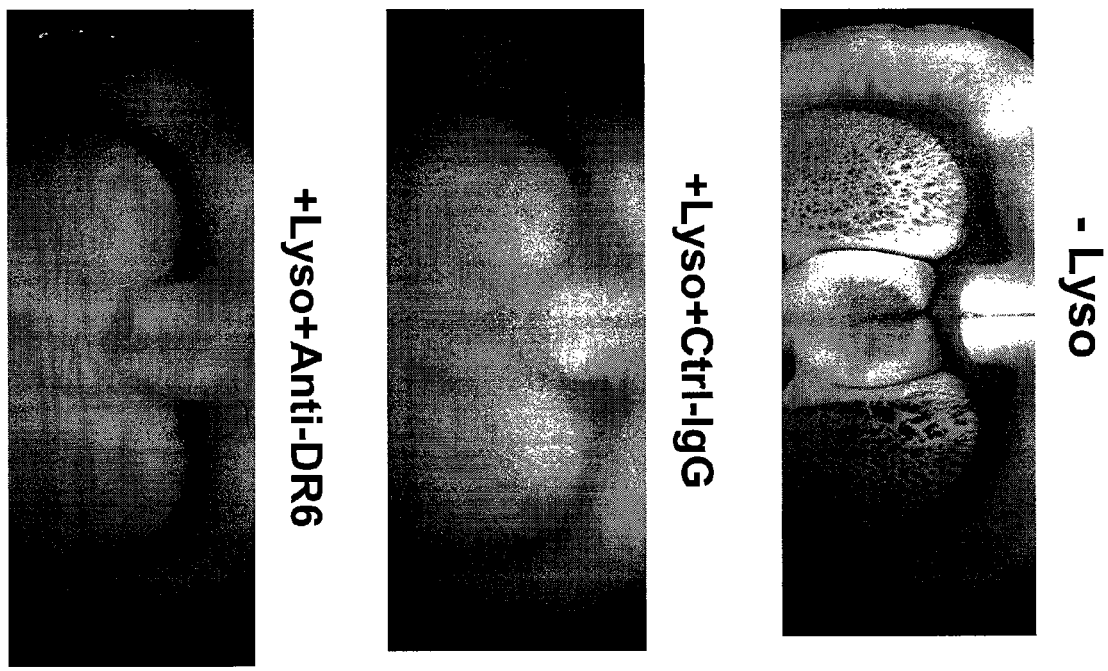
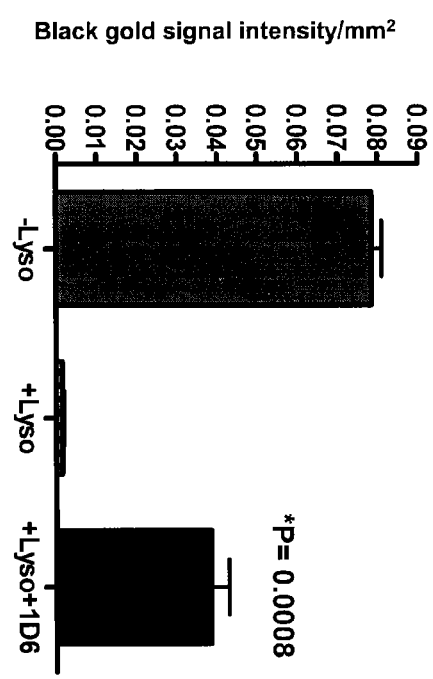
Fig. 16B

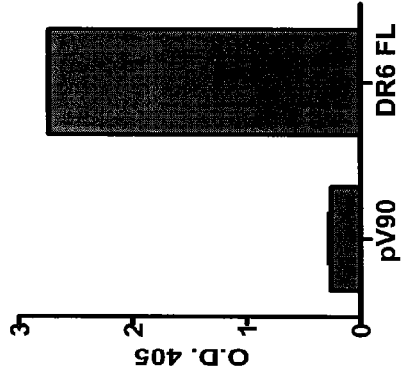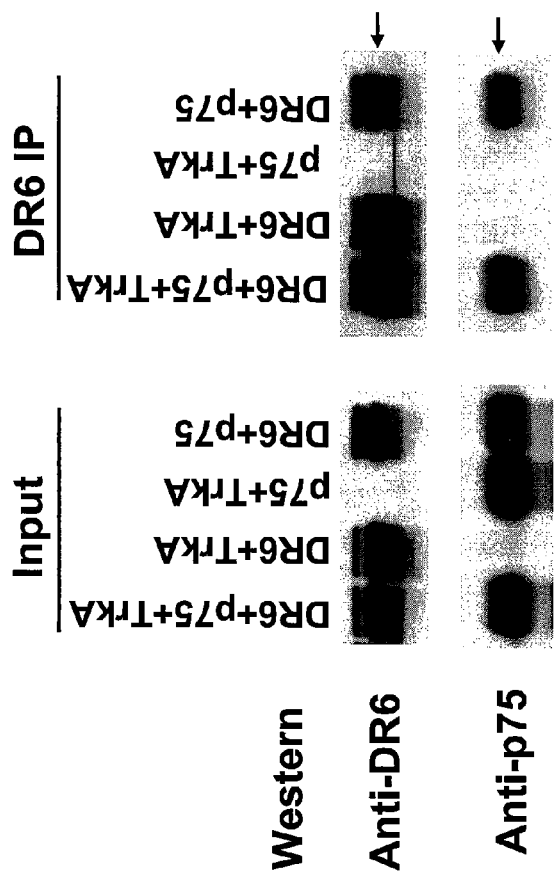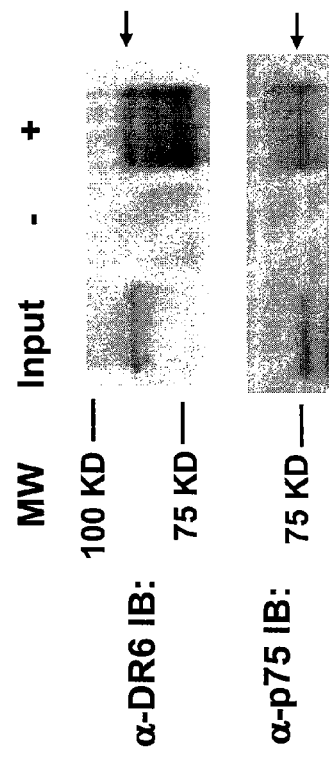

USE OF DR6 AND P75 ANTAGONISTS TO PROMOTE SURVIVAL OF CELLS OF THE NERVOUS SYSTEM

CROSS-REFERENCE TO RELATED APPLICATIONS

This is a U.S. National Phase of International Appl. No. PCT/US2009/065755, filed Nov. 24, 2009, which claims the benefit of U.S. Provisional Appl. No. 61/117,917, filed Nov. 25, 2008, each of which is hereby incorporated by reference in its entirety.

REFERENCE TO A SEQUENCE LISTING SUBMITTED ELECTRONICALLY VIA EFS-WEB

The content of the electronically submitted sequence listing (Name: sequencelisting.ascii.txt, Size: 115,276 bytes; and Date of Creation: May 25, 2011) is herein incorporated by reference in its entirety.

BACKGROUND OF THE INVENTION

1. Field of the Invention

This invention relates to neurobiology, neurology and pharmacology. More particularly, it relates to methods for promoting survival of cells of the nervous system using Death Receptor-6 (DR6) antagonists, optionally in combination with p75 antagonists. The invention also relates to methods of treating neurodegenerative conditions by the administration of a DR6 antagonist, optionally in combination with a p75 antagonist. The invention also relates to methods of preventing the interaction of DR6 and p75 using DR6 and/or p75 antagonists.

2. Background

Apoptosis (i.e. programmed cell death) has been shown to play an important role in numerous diseases of the nervous system including both acute and chronic injuries. For example, the role of apoptosis has been demonstrated in Alzheimer's disease, Parkinson's disease, Huntington's disease, motor neuron disease (e.g. amyotrophic lateral sclerosis, which is also called ALS or Lou Gehrig's disease), multiple sclerosis, neuronal trauma and cerebral ischemia (e.g. stroke).

Many studies have been directed to understanding the molecular mechanisms of apoptosis, and these studies have led to the discovery of a family of receptors called the death receptors. Eight death receptors, which are characterized by a cytoplasmic death domain, have been identified thus far. The death receptors have been grouped into two different families. Members of the first family recruit a death inducing signaling complex (DISC), which promotes apoptotic signaling. Members of the second family recruit a different set of molecules to transduce apoptotic signals. Interestingly, members of the second family also transduce cell survival signals.

Death receptor 6 (DR6) is a member of the second family of death receptors. DR6 is widely expressed, but appears to function differently in different cell types. DR6 mRNA has been observed in heart, brain, placental, pancreas, lymph node, thymus and prostate tissues. Lower levels have been observed in other cell types including skeletal muscle, kidney and testes, but little or no expression has previously been observed in adult liver or any lines of hematopoeitic origin. Interestingly, it has been observed that DR6 is capable of inducing apoptosis in only a subset of cells tested. For example, overexpression of DR6 in HeLa S3 cervical carcinoma cells resulted in apoptosis in a death-domain-dependent manner (Pan et al. *FEBS* 431:351-356 (1998)). In addition, Nikoleav et al. (*Nature* 457:981-990 (2009)) have shown that beta-amyloid precursor protein (APP) is a DR6 ligand and suggested that the binding of an APP fragment to DR6 triggers degeneration of neuronal cell bodies and axons. In contrast, DR6 did not induce cell death in MCF7 (a human breast adenocarcinoma line) cells (Pan et al. *FEBS* 431:351-356 (1998)). The characteristics that differentiate a cell's response to DR6 expression and signaling have not yet been identified.

Drugs that can specifically modulate apoptosis may be useful for treating diseases involving neuronal cell death, for example, because neurons may have less capacity to regenerate than other cell types. However, currently available anti-apoptotic drugs have low specificity and selectivity and as a result, produce undesirable side effects. Such side effects might be reduced or avoided by for example, targeting anti-apoptotic drugs specifically to the desired site of action. Alternatively, characterization of death receptors such as DR6 that specifically act in a particular subset of cell types has the potential to provide a more specific therapeutic effect.

BRIEF SUMMARY OF THE INVENTION

The present invention is based on the discovery that DR6 is specifically able to induce apoptosis in cells of the nervous system and that p75 is a ligand for DR6. It has also been discovered that antagonists of DR6 and p75, including anti-DR6 antibodies, are able to inhibit the interaction of DR6 and p75 and to inhibit death of cells of the nervous system. Accordingly, antagonists of DR6 and/or p75 can be useful for therapy in which modulation of DR6 expression or activity is advantageous.

Based on the discoveries described herein, an isolated antibody or antigen-binding fragment thereof that can specifically bind to a DR6 polypeptide, such that the antibody promotes survival of cells of the nervous system is described. Also described is an isolated antibody or antigen-binding fragment thereof that specifically binds to DR6, wherein the antibody promotes proliferation, differentiation or survival of oligodendrocytes. DR6 antibodies also include an isolated antibody or antigen-binding fragment thereof which specifically binds to DR6, wherein the antibody promotes myelination. In some embodiments, the DR6 antibody inhibits binding of DR6 to p75. In some embodiments, the DR6 antibody inhibits binding of DR6 to p75 but does not inhibit binding of DR6 to beta-amyloid precursor protein (APP).

In some embodiments, the DR6 antibody is an isolated antibody or antigen-binding fragment thereof that specifically binds to the same DR6 epitope as a reference monoclonal Fab antibody fragment selected from the group consisting of M50-H01, M51-H09, M53-E04, M53-F04, M62-B02, M63-E10, M66-B03, M67-G02, M72-F03, and M73-C04 or a reference monoclonal antibody selected from the group consisting of 1P1D6.3, 1P2F2.1, and 1P5D10.2.

In some embodiments, the DR6 antibody an isolated antibody or antigen-binding fragment thereof which specifically binds to DR6, wherein said antibody or fragment thereof competitively inhibits a reference monoclonal Fab antibody fragment selected from the group consisting of M50-H01, M51-H09, M53-E04, M53-F04, M62-B02, M63-E10, M66-B03, M67-G02, M72-F03, and M73-C04 or a reference monoclonal antibody selected from the group consisting of 1P1D6.3, 1P2F2.1, and 1P5D10.2 from binding to DR6.

In some embodiments, the DR6 antibody is an isolated antibody or antigen-binding fragment thereof that specifically binds to DR6, wherein said antibody or fragment thereof is comprises an antigen binding domain identical to that of a monoclonal Fab antibody fragment selected from the group consisting of M50-H01, M51-H09, M53-E04, M53-F04, M62-B02, M63-E10, M66-B03, M67-G02, M72-F03, and M73-C04 or a reference monoclonal antibody selected from the group consisting of 1P1D6.3, 1P2F2.1, and 1P5D10.2.

In some embodiments, the DR6 antibody is an isolated antibody or fragment thereof that specifically binds to DR6, wherein the heavy chain variable region (VH) of said antibody or fragment thereof comprises an amino acid sequence at least 90% identical to a reference amino acid sequence selected from the group consisting of: SEQ ID NO:7, SEQ ID NO:17, SEQ ID NO:27, SEQ ID NO:37, SEQ ID NO:47, SEQ ID NO:57, SEQ ID NO:67, SEQ ID NO:77, SEQ ID NO:87, SEQ ID NO: 97, SEQ ID NO:107, SEQ ID NO:117, and SEQ ID NO:127.

In some embodiments, the DR6 antibody is an isolated antibody or fragment thereof that specifically binds to DR6, wherein the light chain variable region (VL) of said antibody or fragment thereof comprises an amino acid sequence at least 90% identical to a reference amino acid sequence selected from the group consisting of SEQ ID NO:12, SEQ ID NO:22, SEQ ID NO:32, SEQ ID NO:42, SEQ ID NO:52, SEQ ID NO:62, SEQ ID NO:72, SEQ ID NO:82, SEQ ID NO:92, SEQ ID NO:102 SEQ ID NO:112, SEQ ID NO:122, and SEQ ID NO:132.

In some embodiments, the DR6 antibody is an isolated antibody or fragment thereof that specifically binds to DR6, wherein the VH of said antibody or fragment thereof comprises an amino acid sequence identical, except for 20 or fewer conservative amino acid substitutions, to a reference amino acid sequence selected from the group consisting of: SEQ ID NO:7, SEQ ID NO:17, SEQ ID NO:27, SEQ ID NO:37, SEQ ID NO:47, SEQ ID NO:57, SEQ ID NO:67, SEQ ID NO:77, SEQ ID NO:87, SEQ ID NO: 97, SEQ ID NO:107, SEQ ID NO:117, and SEQ ID NO:127.

In some embodiments, the DR6 antibody is an isolated antibody or fragment thereof that specifically binds to DR6, wherein the VL of said antibody or fragment thereof comprises an amino acid sequence identical, except for 20 or fewer conservative amino acid substitutions, to a reference amino acid sequence selected from the group consisting of: SEQ ID NO:12, SEQ ID NO:22, SEQ ID NO:32, SEQ ID NO:42, SEQ ID NO:52, SEQ ID NO:62, SEQ ID NO:72, SEQ ID NO:82, SEQ ID NO:92, SEQ ID NO:102 SEQ ID NO:112, SEQ ID NO:122, and SEQ ID NO:132.

In some embodiments, the DR6 antibody is an isolated antibody or fragment thereof that specifically binds to DR6, wherein the VL of said antibody or fragment thereof comprises an amino acid sequence selected from the group consisting of: SEQ ID NO:7, SEQ ID NO:17, SEQ ED NO:27, SEQ ID NO:37, SEQ ID NO:47, SEQ ID NO:57, SEQ ID NO:67, SEQ ID NO:77, SEQ ID NO:87, SEQ ID NO: 97, SEQ ID NO:107, SEQ ID NO:117, and SEQ ID NO:127.

In some embodiments, the DR6 antibody is an isolated antibody or fragment thereof that specifically binds to DR6, wherein the VL of said antibody or fragment thereof comprises an amino acid sequence selected from the group consisting of: SEQ ID NO:12, SEQ ID NO:22, SEQ ID NO:32, SEQ ID NO:42, SEQ ID NO:52, SEQ ID NO:62, SEQ ID NO:72, SEQ ID NO:82, SEQ ID NO:92, SEQ ID NO:102 SEQ ID NO:112, SEQ ID NO:122, and SEQ ID NO:132.

In some embodiments, the DR6 antibody is an isolated antibody or fragment thereof that specifically binds to DR6, wherein the VH and VL of said antibody or fragment thereof comprise, respectively, amino acid sequences at least 90% identical to reference amino acid sequences selected from the group consisting of: SEQ ID NO:7 and SEQ ID NO:12; SEQ ID NO:17 and SEQ ID NO:22; SEQ ID NO:27 and SEQ ID NO:32; SEQ ID NO:37 and SEQ ID NO:42; SEQ ID NO:47 and SEQ ID NO:52; SEQ ID NO:57 and SEQ ID NO:62; SEQ ID NO:67 and SEQ ID NO:72; SEQ ID NO:77 and SEQ ID NO:82; SEQ ID NO:87 and SEQ ID NO:92; SEQ ID NO:97 and SEQ ID NO:102; SEQ ID NO:107 and SEQ ID NO:112; SEQ ID N0117 and SEQ ID NO:122; and SEQ ID NO:127 and SEQ ID NO:132.

In some embodiments, the DR6 antibody is an isolated antibody or fragment thereof that specifically binds to DR6, wherein the VH and VL of said antibody or fragment thereof comprise, respectively, amino acid sequences identical, except for 20 or fewer conservative amino acid substitutions each, to reference amino acid sequences selected from the group consisting of: SEQ ID NO:7 and SEQ ID NO:12; SEQ ID NO:17 and SEQ ID NO:22; SEQ ID NO:27 and SEQ ID NO:32; SEQ ID NO:37 and SEQ ID NO:42; SEQ ID NO:47 and SEQ ID NO:52; SEQ ID NO:57 and SEQ ID NO:62; SEQ ID NO:67 and SEQ ID NO:72; SEQ ID NO:77 and SEQ ID NO:82; SEQ ID NO:87 and SEQ ID NO:92; SEQ ID NO:97 and SEQ ID NO:102; SEQ ID NO:107 and SEQ ID NO:112; SEQ ID N0117 and SEQ ID NO:122; and SEQ ID NO:127 and SEQ ID NO:132.

In some embodiments, the DR6 antibody is an isolated antibody or fragment thereof that specifically binds to DR6, wherein the VH and VL of said antibody or fragment thereof comprise, respectively, amino acid sequences selected from the group consisting of: SEQ ID NO:7 and SEQ ID NO:12; SEQ ID NO:17 and SEQ ID NO:22; SEQ ID NO:27 and SEQ ID NO:32; SEQ ID NO:37 and SEQ ID NO:42; SEQ ID NO:47 and SEQ ID NO:52; SEQ ID NO:57 and SEQ ID NO:62; SEQ ID NO:67 and SEQ ID NO:72; SEQ ID NO:77 and SEQ ID NO:82; SEQ ID NO:87 and SEQ ID NO:92; SEQ ID NO:97 and SEQ ID NO:102; SEQ ID NO:107 and SEQ ID NO:112; SEQ ID N0117 and SEQ ID NO:122; and SEQ ID NO:127 and SEQ ID NO:132.

In some embodiments, the DR6 antibody is an isolated antibody or fragment thereof that specifically binds to DR6, wherein the VH of said antibody or fragment thereof comprises a Kabat heavy chain complementarity determining region-1 (VH-CDR1) amino acid sequence identical, except for two or fewer amino acid substitutions, to a reference VH-CDR1 amino acid sequence selected from the group consisting of: SEQ ID NO: 8, SEQ ID NO: 18, SEQ ID NO: 28, SEQ ID NO: 38, SEQ ID NO: 48, SEQ ID NO: 58, SEQ ID NO: 68, SEQ ID NO: 78, SEQ ID NO: 88, SEQ ID NO: 98, SEQ ID NO: 108 SEQ ID NO: 118, and SEQ ID NO: 128. In one embodiment, the VH-CDR1 amino acid sequence is selected from the group consisting of: SEQ ID NO: 8, SEQ ID NO: 18, SEQ ID NO: 28, SEQ ID NO: 38, SEQ ID NO: 48, SEQ ID NO: 58, SEQ ID NO: 68, SEQ ID NO: 78, SEQ ID NO: 88, SEQ ID NO: 98, SEQ ID NO: 108 SEQ ID NO: 118, and SEQ ID NO: 128.

In some embodiments, the DR6 antibody is an isolated antibody or fragment thereof that specifically binds to DR6, wherein the VH of said antibody or fragment thereof comprises a Kabat heavy chain complementarity determining region-2 (VH-CDR2) amino acid sequence identical, except for four or fewer amino acid substitutions, to a reference VH-CDR2 amino acid sequence selected from the group consisting of: SEQ ID NO: 9, SEQ ID NO: 19, SEQ ID NO: 29, SEQ ID NO: 39, SEQ ID NO: 49, SEQ ID NO: 59, SEQ ID NO: 69, SEQ ID NO: 79, SEQ ID NO: 89, SEQ ID NO: 99, SEQ ID NO: 109, SEQ ID NO: 119 and SEQ ID NO: 129. In one embodiment, the VH-CDR2 amino acid sequence is selected from the group consisting of: SEQ ID NO: 9, SEQ ID NO: 19, SEQ ID NO: 29, SEQ ID NO: 39, SEQ ID NO: 49, SEQ ID NO: 59, SEQ ID NO: 69, SEQ ID NO: 79, SEQ ID NO: 89, SEQ ID NO: 99, SEQ ID NO: 109, SEQ ID NO: 119 and SEQ ID NO: 129.

In some embodiments, the DR6 antibody is an isolated antibody or fragment thereof that specifically binds to DR6, wherein the VH of said antibody or fragment thereof comprises a Kabat heavy chain complementarity determining region-3 (VH-CDR3) amino acid sequence identical, except for four or fewer amino acid substitutions, to a reference VH-CDR3 amino acid sequence selected from the group consisting of: SEQ ID NO: 10, SEQ ID NO: 20, SEQ ID NO: 30, SEQ ID NO: 40, SEQ ID NO: 40, SEQ ID NO: 60, SEQ ID NO: 70, SEQ ID NO: 80, SEQ ID NO: 90, SEQ ID NO: 100, SEQ ID NO: 110, SEQ ID NO: 120 and SEQ ID NO:130. In one embodiment, the VH-CDR3 amino acid sequence is selected from the group consisting of: SEQ ID NO: 10, SEQ ID NO: 20, SEQ ID NO: 30, SEQ ID NO: 40, SEQ ID NO: 40, SEQ ID NO: 60, SEQ ID NO: 70, SEQ ID NO: 80, SEQ ID NO: 90, SEQ ID NO: 100, SEQ ID NO: 110, SEQ ID NO: 120 and SEQ ID NO:130.

In some embodiments, the DR6 antibody is an isolated antibody or fragment thereof that specifically binds to DR6, wherein the VL of said antibody or fragment thereof comprises a Kabat light chain complementarity determining region-1 (VL-CDR1) amino acid sequence identical, except for four or fewer amino acid substitutions, to a reference VL-CDR1 amino acid sequence selected from the group consisting of: SEQ ID NO: 13, SEQ ID NO: 23, SEQ ID NO: 33, SEQ ID NO: 43, SEQ ID NO: 53, SEQ ID NO: 63, SEQ ID NO: 73, SEQ ID NO: 83, SEQ ID NO: 93, SEQ ID NO: 103, SEQ ID NO: 113, SEQ ID NO: 123 and SEQ ID NO: 133. In one embodiment, the VL-CDR1 amino acid sequence is selected from the group consisting of: SEQ ID NO: 13, SEQ ID NO: 23, SEQ ID NO: 33, SEQ ID NO: 43, SEQ ID NO: 53, SEQ ID NO: 63, SEQ ID NO: 73, SEQ ID NO: 83, SEQ ID NO: 93, SEQ ID NO: 103, SEQ ID NO: 113, SEQ ID NO: 123 and SEQ ID NO: 133.

In some embodiments, the DR6 antibody is an isolated antibody or fragment thereof that specifically binds to DR6, wherein the VL of said antibody or fragment thereof comprises a Kabat light chain complementarity determining region-2 (VL-CDR2) amino acid sequence identical, except for two or fewer amino acid substitutions, to a reference VL-CDR2 amino acid sequence selected from the group consisting of: SEQ ID NO: 14, SEQ ID NO: 24, SEQ ID NO: 34, SEQ ID NO: 44, SEQ ID NO: 54, SEQ ID NO: 64, SEQ ID NO: 74, SEQ ID NO: 84, SEQ ID NO: 94, SEQ ID NO: 104, SEQ ID NO: 114, SEQ ID NO: 124, and SEQ ID NO: 134. In one embodiment, the VL-CDR2 amino acid sequence is selected from the group consisting of: SEQ ID NO: 14, SEQ ID NO: 24, SEQ ID NO: 34, SEQ ID NO: 44, SEQ ID NO: 54, SEQ ID NO: 64, SEQ ID NO: 74, SEQ ID NO: 84, SEQ ID NO: 94, SEQ ID NO: 104, SEQ ID NO: 114, SEQ ID NO: 124, and SEQ ID NO: 134.

In some embodiments, the DR6 antibody is an isolated antibody or fragment thereof that specifically binds to DR6, wherein the VL of said antibody or fragment thereof comprises a Kabat light chain complementarity determining region-3 (VL-CDR3) amino acid sequence identical, except for four or fewer amino acid substitutions, to a reference VL-CDR3 amino acid sequence selected from the group consisting of: SEQ ID NO: 15, SEQ ID NO: 25, SEQ ID NO: 35, SEQ ID NO: 45, SEQ ID NO: 55, SEQ ID NO: 65, SEQ ID NO: 75, SEQ ID NO: 85, SEQ ID NO: 95, SEQ ID NO: 105, SEQ ID NO: 115, SEQ ID NO: 125, and SEQ ID NO: 135. In one embodiment, the VL-CDR3 amino acid sequence is selected from the group consisting of: SEQ ID NO: 15, SEQ ID NO: 25, SEQ ID NO: 35, SEQ ID NO: 45, SEQ ID NO: 55, SEQ ID NO: 65, SEQ ID NO: 75, SEQ ID NO: 85, SEQ ID NO: 95, SEQ ID NO: 105, SEQ ID NO: 115, SEQ ID NO: 125, and SEQ ID NO: 135.

In some embodiments, the DR6 antibody is an isolated antibody or fragment thereof that specifically binds to DR6, wherein the VH of said antibody or fragment thereof comprises VH-CDR1, VH-CDR2, and VH-CDR3 amino acid sequences selected from the group consisting of: SEQ ID NOs: 8, 9, and 10; SEQ ID NOs: 18, 19, and 20; SEQ ID NOs: 28, 29, and 30; SEQ ID NOs: 38, 39, and 40; SEQ ID NOs: 48, 49, and 50; SEQ ID NOs: 58, 59, and 60; SEQ ID NOs: 68, 69, and 70; SEQ ID NOs: 78, 79, and 80; SEQ ID NOs: 88, 89, and 90; SEQ ID NOs: 98, 99, and 100; SEQ ID NOs: 108, 109, and 110; SEQ ID NOs: 118, 119, and 120; and SEQ ID NOs: 128, 129, and 130, except for one, two, three, or four amino acid substitutions in at least one of said VH-CDRs.

In some embodiments, the DR6 antibody is an isolated antibody or fragment thereof that specifically binds to DR6, wherein the VH of said antibody or fragment thereof comprises VH-CDR1, VH-CDR2, and VH-CDR3 amino acid sequences selected from the group consisting of: SEQ ID NOs: 8, 9, and 10; SEQ ID NOs: 18, 19, and 20; SEQ ID NOs: 28, 29, and 30; SEQ ID NOs: 38, 39, and 40; SEQ ID NOs: 48, 49, and 50; SEQ ID NOs: 58, 59, and 60; SEQ ID NOs: 68, 69, and 70; SEQ ID NOs: 78, 79, and 80; SEQ ID NOs: 88, 89, and 90; SEQ ID NOs: 98, 99, and 100; SEQ ID NOs: 108, 109, and 110; SEQ ID NOs: 118, 119, and 120; and SEQ ID NOs: 128, 129, and 130.

In some embodiments, the DR6 antibody is an isolated antibody or fragment thereof that specifically binds to DR6, wherein the VL of said antibody or fragment thereof comprises VL-CDR1, VL-CDR2, and VL-CDR3 amino acid sequences selected from the group consisting of: SEQ ID NOs: 13, 14, and 15; SEQ ID NOs: 23, 24, and 25; SEQ ID NOs: 33, 34, and 35; SEQ ID NOs: 43, 44, and 45; SEQ ID NOs: 53, 54, and 55; SEQ ID NOs: 63, 64, and 65; SEQ ID NOs: 73, 74, and 75; SEQ ID NOs: 83, 84, and 85; SEQ ID NOs: 93, 94, and 95; SEQ ID NOs: 103, 104, and 105; SEQ ID NOs: 113, 114, and 115; SEQ ID NOs: 123, 124, and 125; and SEQ ID NOs: 133, 134, and 135, except for one, two, three, or four amino acid substitutions in at least one of said VL-CDRs.

In some embodiments, the DR6 antibody is an isolated antibody or fragment thereof that specifically binds to DR6, wherein the VL of said antibody or fragment thereof comprises VL-CDR1, VL-CDR2, and VL-CDR3 amino acid sequences selected from the group consisting of: SEQ ID NOs: 13, 14, and 15; SEQ ID NOs: 23, 24, and 25; SEQ ID NOs: 33, 34, and 35; SEQ ID NOs: 43, 44, and 45; SEQ ID NOs: 53, 54, and 55; SEQ ID NOs: 63, 64, and 65; SEQ ID NOs: 73, 74, and 75; SEQ ID NOs: 83, 84, and 85; SEQ ID NOs: 93, 94, and 95; SEQ ID NOs: 103, 104, and 105; SEQ ID NOs: 113, 114, and 115; SEQ ID NOs: 123, 124, and 125; and SEQ ID NOs: 133, 134, and 135.

In various embodiments of the above-described antibodies or fragments thereof, the VH framework regions and/or VL framework regions are human, except for five or fewer amino acid substitutions.

In some embodiments, the above-described antibodies or fragments thereof bind to a linear epitope or a non-linear conformation epitope In some embodiments, the above-described antibodies or fragments thereof are multivalent, and comprise at least two heavy chains and at least two light chains.

In some embodiments, the above-described antibodies or fragments thereof are multispecific. In further embodiments, the above-described antibodies or fragments thereof are bispecific.

In various embodiments of the above-described antibodies or fragments thereof, the heavy and light chain variable domains are murine. In further embodiments, the heavy and light chain variable domains are from a monoclonal antibody selected from the group consisting of 1P1D6.3, 1P2F2.1, and 1P5D10.2.

In various embodiments of the above-described antibodies or fragments thereof, the heavy and light chain variable domains are fully human. In further embodiments, the heavy and light chain variable domains are from a monoclonal Fab antibody fragment selected from the group consisting of M50-H01, M51-H09, M53-E04, M53-F04, M62-B02, M63-E10, M66-B03, M67-G02, M72-F03, and M73-C04.

In various embodiments, the above-described antibodies or fragments thereof are humanized.

In various embodiments, the above-described antibodies or fragments thereof are chimeric.

In various embodiments, the above-described antibodies or fragments thereof are primatized.

In various embodiments, the above-described antibodies or fragments thereof are fully human.

In certain embodiments, the above-described antibodies or fragments thereof are Fab fragments, Fab' fragments, $F(ab)_2$ fragments, or Fv fragments. In certain embodiments, the above-described antibodies are single chain antibodies. In certain embodiments, the antibodies or fragments thereof are conjugated to a polymer. In certain embodiments, the polymer is a polyalkylene glycol. In further embodiments, the polyalkylene gycol is polyethylene glycol (PEG).

In certain embodiments, the above-described antibodies or fragments thereof comprise light chain constant regions selected from the group consisting of a human kappa constant region and a human lambda constant region.

In certain embodiments, the above-described antibodies or fragments thereof comprise a heavy chain constant region or fragment thereof. In further embodiments, the heavy chain constant region or fragment thereof is selected from the group consisting of human IgG4, IgG4 agly, IgG1, and IgG1agly.

In some embodiments, the above-described antibodies or fragments thereof specifically bind to a DR6 polypeptide or fragment thereof, or a DR6 variant polypeptide, with an affinity characterized by a dissociation constant ($K_D$) which is less than the $K_D$ for said reference monoclonal antibody. In further embodiments, the dissociation constant ($K_D$) is no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In some embodiments, the above-described antibodies or fragments thereof preferentially bind to a human DR6 polypeptide or fragment thereof, relative to a murine DR6 polypeptide or fragment thereof.

In addition, the methods described herein relate generally to methods of promoting survival and preventing apoptosis of cells of the nervous system. In certain embodiments, the methods include a method of promoting survival of cells of the nervous system comprising contacting said cells with a DR6 antagonist. In some particular embodiments, the cells of the nervous system cells are cells of the central nervous system, such as brain cells, spinal cord cells, or cell lines derived from such cells. In some embodiments, the cells of the central nervous system are cortical neurons, oligodendrocytes, microglia or astrocytes, or cell lines derived from such cells. In some embodiments the cells of the nervous system are neurons, for example cortical neurons, motor neurons and dorsal root ganglion (DRG) neurons or cell lines derived from such cells. In some embodiments the cells are glial cells including microglia and macroglia or cell lines derived from such cells. Examples of macroglial cells include astrocytes, oligodendrocytes, ependymocytes and radial glial cells. In some embodiments, the cells are precursors of these cells such as oligodendrocyte precursor cells or cell lines derived from such cells. In some embodiments, the cells of the nervous system are peripheral nervous system cells. In some embodiments, the peripheral nervous system cells are dorsal root ganglion neurons, schwann cells, or cell lines derived from such cells.

The methods described herein also provide a method of promoting oligodendrocyte proliferation, differentiation or survival comprising contacting oligodendrocyte cells or oligodendrocyte precursor cells with a DR6 antagonist. In some embodiments, the method is a method of treating a condition associated with oligodendrocyte death or lack of differentiation, comprising administering a therapeutically effective amount of a DR6 antagonist.

The methods described herein also provide a method of promoting myelination comprising contacting a mixture of neuronal cells and oligodendrocyte cells or oligodendrocyte precursor cells with a DR6 antagonist. In some embodiments, the method is a method of treating a condition associated with dysmyelination or demyelination comprising administering a therapeutically effective amount of a DR6 antagonist.

The method also relates generally to methods of treating conditions associated with death of cells of the nervous system. In another embodiment, the method is a method of treating a condition associated with death of cells of the nervous system comprising administering an effective amount of a DR6 antagonist to a mammal in need thereof. In some particular embodiments the condition associated with death of cells of the nervous system can be Alzheimer's disease, Parkinson's disease, Huntington's disease, motor neuron disease (e.g. amyotrophic lateral sclerosis, which is also called ALS or Lou Gehrig's disease), multiple sclerosis, neuronal trauma or cerebral ischemia (e.g. stroke). In some particular embodiments, the condition is neuropathic pain.

The methods described herein also include methods of inhibiting the binding of DR6 to p75 comprising contacting a DR6 polypeptide and/or p75 polypeptide with a DR6 antagonist under conditions wherein binding of DR6 to p75 is inhibited.

In various embodiments of the above methods, the DR6 antagonist can be any molecule which interferes with the ability of DR6 to negatively regulate survival of cells of the nervous system. In certain embodiments, the DR6 antagonist is selected from the group consisting of a soluble DR6 polypeptide, a DR6 antagonist compound, a DR6 antagonist antibody or fragment thereof, a DR6 antagonist polynucleotide (e.g. RNA interference), a DR6 aptamer, or a combination of two or more DR6 antagonists.

In certain embodiments, the DR6 antagonist polypeptide is a soluble DR6 polypeptide. Certain soluble DR6 polypeptides as described herein include, but are not limited to soluble DR6 polypeptides which comprise the DR6 extracellular domain or one or more of the DR6 TNFR-like cysteine-rich motifs. In some embodiments, the soluble DR6 polypeptide lacks one or more of a DR6 TNFR-like cysteine-rich motif, a transmembrane domain, a death domain or a cytoplasmic domain. In some embodiments, the DR6 antagonist polypeptide comprises amino acids 1 to 349 of SEQ ID NO:2 (DR6); 40 to 349 of SEQ ID NO:2; or 41 to 349 of SEQ ID NO:2.

In some embodiments, the soluble DR6 antagonist is a fusion polypeptide comprising a non-DR6-heterologous polypeptide. In some embodiments, the non-DR6 heterologous polypeptide is selected from the group consisting of an immunoglobulin polypeptide or fragment thereof, a serum albumin polypeptide, a targeting polypeptide, a reporter polypeptide, and a purification-facilitating polypeptide. In some embodiments, the antibody Ig polypeptide is a hinge and an Fc polypeptide.

In alternative embodiments the DR6 antagonist is an antibody or fragment thereof as described above. In other embodiments, the DR6 antagonist is an antibody or fragment thereof which binds to a DR6 polypeptide comprising one or more of the following domains (i) a DR6 extracellular domain, and (ii) a DR6 TNFR-like cysteine-rich motif. Additionally, the DR6 antagonist antibody or fragment thereof can specifically bind to an epitope within a polypeptide comprising a DR6 polypeptide as described herein. The DR6 antagonist can also be an antigen-binding fragment of such antibodies or a combination of two or more antibodies or fragments thereof.

In other embodiments, the DR6 antagonist is a DR6 antagonist polynucleotide such as an antisense polynucleotide, an aptamer, a ribozyme, a small interfering RNA (siRNA), or a small-hairpin RNA (shRNA).

In additional embodiments, the DR6 antagonist is a DR6 aptamer. A DR6 aptamer is a small polypeptide or a polynucleotide which binds DR6 and promotes nervous system cell survival or prevents cell apoptosis.

In some embodiments of the above methods, the DR6 antagonist is administered to a subject by a method comprising (a) introducing into a nervous system cell a polynucleotide that encodes the DR6 antagonist through operable association with an expression control sequence; and (b) allowing expression of said DR6 antagonist. In some embodiments the nervous system cells are in a mammal and said introducing comprises (a) administering to said mammal a polynucleotide which encodes a DR6 antagonist through operable association with an expression control sequence. In some embodiments, the cultured host cell is derived from the mammal to be treated. In certain embodiments, the polynucleotide is introduced into the host cell or nervous system cell via transfection, electroporation, viral transduction or direct microinjection.

In certain embodiments the DR6 antagonist is a polynucleotide that can be administered to a mammal, at or near the site of the disease, disorder or injury. In some embodiments, the polynucleotide is administered as an expression vector. In certain embodiments, the vector is a viral vector which is selected from the group consisting of an adenoviral vector, an alphavirus vector, an enterovirus vector, a pestivirus vector, a lentiviral vector, a baculoviral vector, a herpesvirus vector (e.g. an Epstein Barr viral vector, or a herpes simplex viral vector) a papovaviral vector, a poxvirus vector (e.g. a vaccinia viral vector) and a parvovirus. In some embodiments, the vector is administered by a route selected from the group consisting of topical administration, intraocular administration, and parenteral administration (e.g. intravenous, intraarterial, intramuscular, intracardiac, subcutaneous, intradermal, intrathecal, intraperitoneal).

According to the methods described herein, the DR6 antagonist can be used in combination with a p75 antagonist. The p75 antagonist can be used simultaneously or sequentially.

The methods described herein also include methods of inhibiting the binding of DR6 to p75 comprising contacting a p75 polypeptide and/or DR6 polypeptide with a p75 antagonist under conditions wherein binding of DR6 to p75 is inhibited. The p75 antagonist can be (i) a p75 antagonist compound; (ii) p75 antagonist polypeptide; (iii) a p75 antagonist antibody or fragment thereof; (iv) a p75 antagonist polynucleotide; (v) a p75 aptamer; or (vi) a combination of two or more of said p75 antagonists.

BRIEF DESCRIPTION OF THE DRAWINGS/FIGURES

Figure 1A:
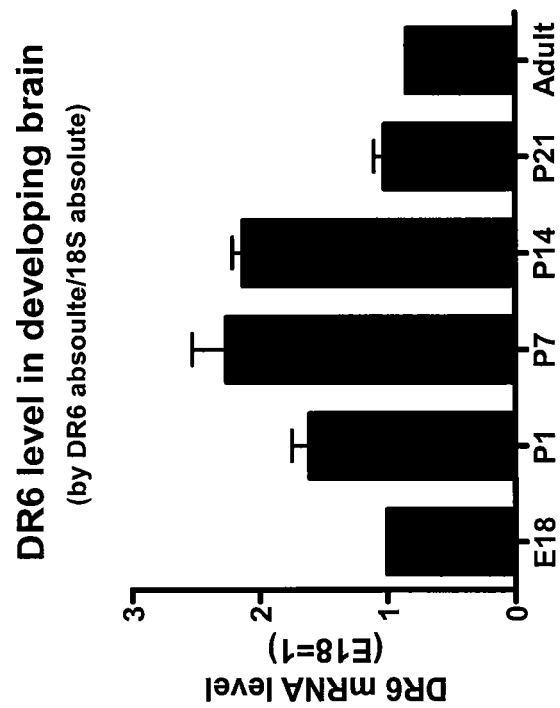
Figure 1C:
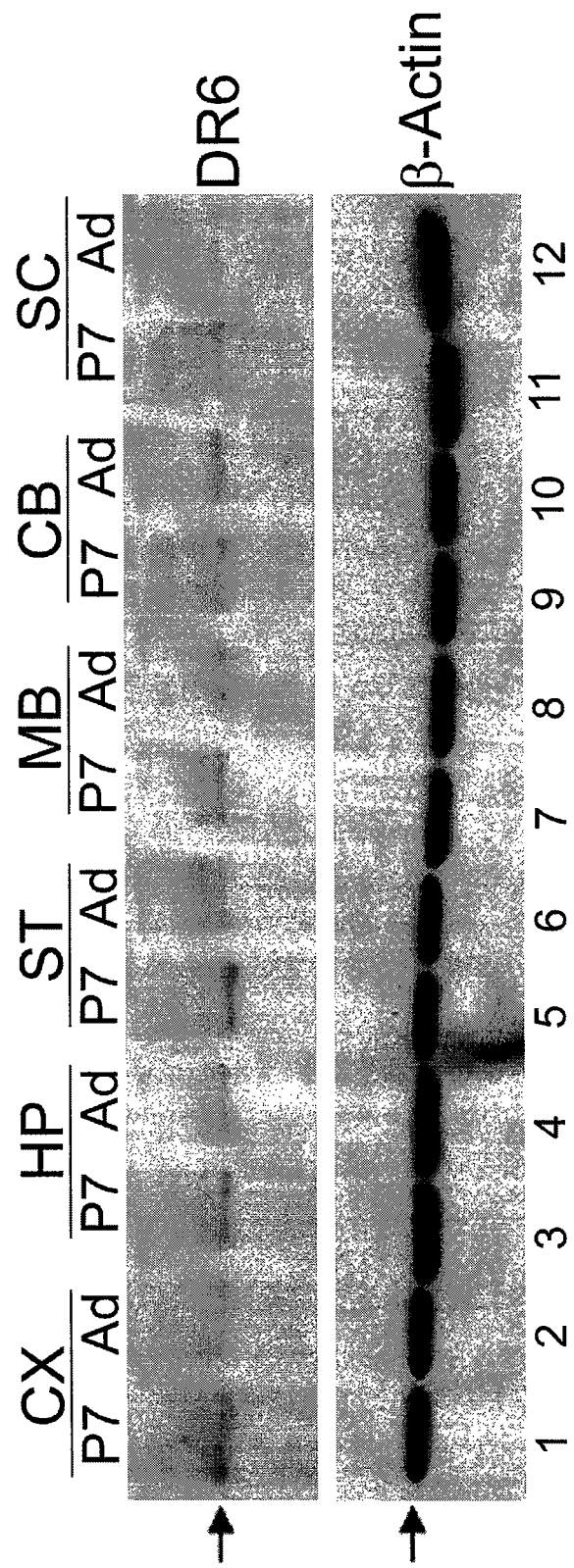

FIGS. 1A-D—DR6 is regulated during development and expressed in the CNS. Graphs displaying results of DR6 quantitative PCR. DR6 mRNA levels from E18, P1, P7, P14, P21 and adult rat brain (FIG. 1A) and spinal cord (FIG. 1B) are expressed as a ratio of the DR6 mRNA level/DR6 mRNA level at E18. Protein expression in the cortex (CX), hippocampus (HP), striatum (ST), mid brain (MB), cerebellum (CB) and spinal cord (SC) based on Western blot using anti-DR6 antibody (FIG. 1C). RT-PCR of DR6 and GAPDH from lysates of oligodendrocyte precursor cells (OPCs), cortical neurons, microglias and astrocytes (FIG. 1D).

FIGS. 2A-B—DR6 is expressed in oligodendrocytes. RT-PCR of DR6 and glyceraldehyde 3-phosphate dehydrogenase (GAPDH) from lysates of A2B5, O4 and MBP positive oligodendrocytes (FIG. 2A). The DR6 RT-PCR was performed without RT enzyme as a negative control (-RT DR6). Western blot showing expression of DR6 in A2B5, O4, and MBP-positive oligodendrocytes (FIG. 2B).

Figure 3:
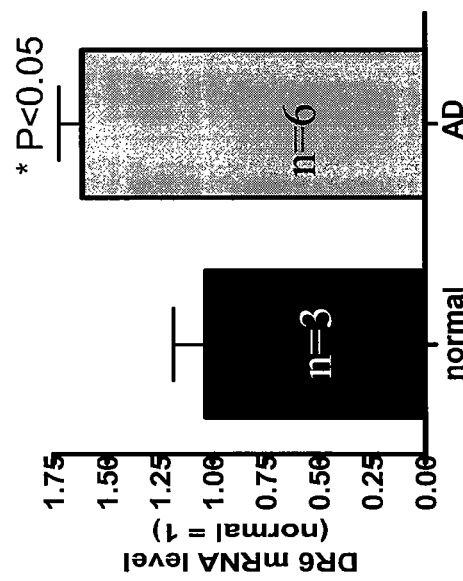

FIG. 3—DR6 is regulated in Alzheimer's disease. Graph displaying quantitative PCR of DR6 mRNA levels in Alzheimer's disease brains and control brains. Levels are expressed as a ratio of Alzheimer's Disease brain mRNA level/average control brain mRNA level.

Figure 4:
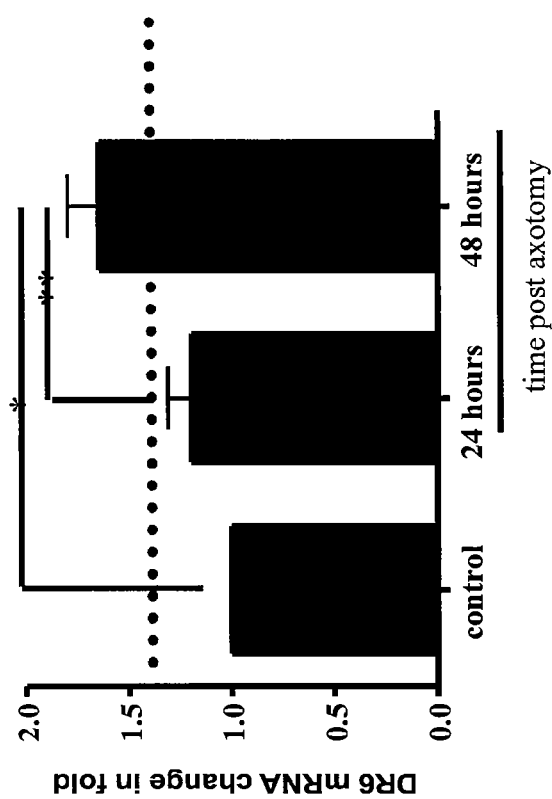

FIG. 4—DR6 is regulated in response to neuronal injury. Graph displaying quantitative PCR of DR6 mRNA levels in control neurons and neurons subjected to axotomy. DR6 mRNA levels are expressed as a ratio of the mRNA level in axotomy sample/mRNA level in control sample.

Figure 5A:
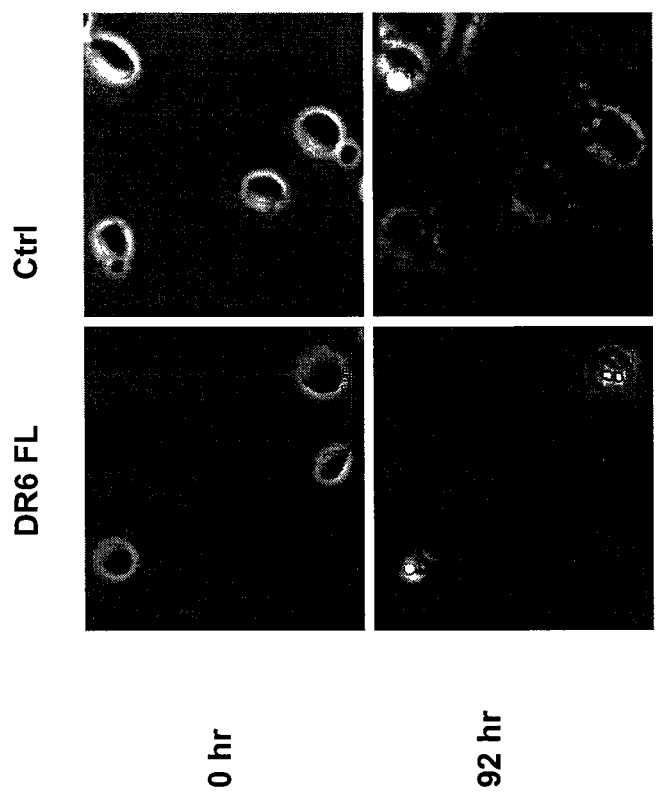

FIGS. 5A-D—Overexpression of DR6 induces neuronal death. Images of cortical neurons infected with lentivirus expressing FL-DR6 and control cortical neurons (FIG. 5A). Graph displaying absorbance measured in an XTT assay for cell viability performed on untreated cells, cells infected with full-length DR6 (DR6-FL) lentivirus, dominant negative DR6 (DR6-DN) lentivirus and GFP lentivirus (FIG. 5B). Graph displaying free rhodamine measured in an assay for caspase-3 activity in untreated cells, DR6-FL, DR6-DN and GFP lentivirus infected cells (FIG. 5C). Western blots of DR6-FL, DR6-DN and GFP lentivirus infected cells probed with anti-activated caspase-3, anti-βIII-tubulin and anti-GFP antibodies (FIG. 5D).

FIGS. 6A-B—Overexpression of DR6 induces death of OPCs. Graph depicting percent cytotoxicity on cells infected with DR6-FL, DR6-DN or GFP lentivirus (FIG. 6A). Graph depicting absorbance as measured in an XTT assay on cells treated with rotenone and cells infected with DR6-FL, DR6-DN or GFP lentivirus (FIG. 6B). Graph depicting absorbance measured in an LDH assay for cell viability in cells infected with DR6-FL, DR6-DN or GFP lentivirus (FIG. 6C).

FIGS. 7A-B—Blocking DR6 signaling pathway promotes oligodendrocyte survival and differentiation. Western blots of cell lysates from DR6 FL and DR6 DN infected oligodendrocytes probed with anti-MBP, anti-MOG, anti-GFP and anti- β-actin antibodies (FIG. 7A). An ELISA measuring the level of CNPase in DR6 FL and DR6 DN infected oligodendrocytes (FIG. 7B).

FIGS. 8A-B—Soluble DR6 blocks full-length DR6 from inducing neuronal cell death. Time lapse images of cultured E18 cerebral cortical neurons that were treated with control human Fc (top panels), infected with FL-DR6 and treated with control human-Fc (middle panels) and infected with FL-DR6 and treated with DR6-Fc (bottom panels) (FIG. 8A). Graph depicting number of surviving cells after treatment with DR6-Fc or control Fc (FIG. 8B).

Figure 9B:
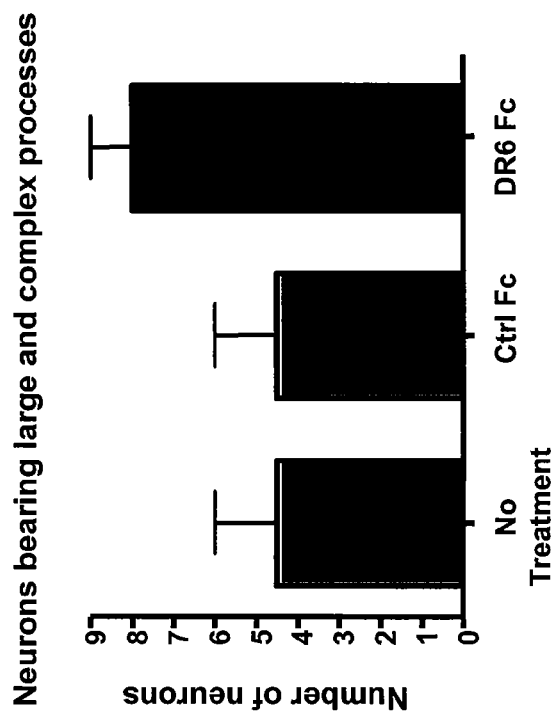
Figure 9A:
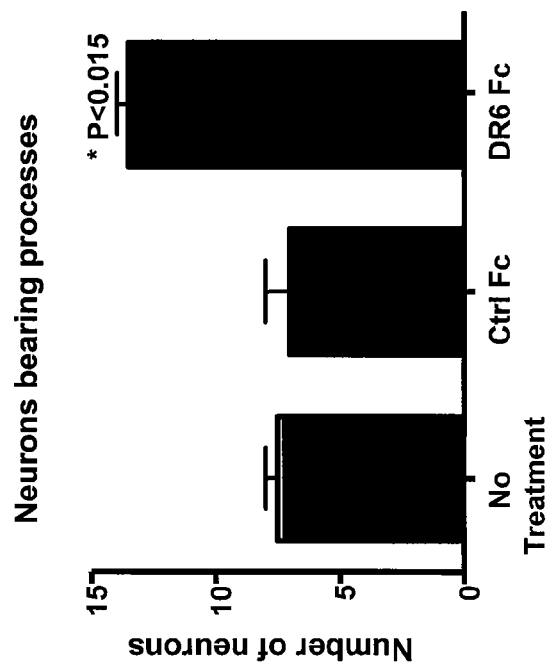

FIGS. 9A-B—Soluble DR6 promotes aged DRG neuron survival and neurite outgrowth in neurons expressing DR6-FL. Graph depicting neurons bearing processes after treatment with DR6-Fc, control Fc, or no treatment (FIG. 9A). Graph depicting neurons bearing large and complex processes after treatment with DR6-Fc, control Fc, or no treatment (FIG. 9B).

FIGS. 10A-B—DR6-induced neuronal death is inhibited by DR6-Fc. Western blots of untreated and DR6-FL lentivirus infected cells incubated in media containing of 0, 1, 3, or 30 µg/ml of recombinant soluble DR6 (DR6 Fc) probed with anti-activated caspase-3, anti-GFP and anti-β-actin antibodies (FIG. 10A). Graph depicting level of activated caspase-3 in cultures treated with DR6-Fc (FIG. 10B).

Figure 11A:
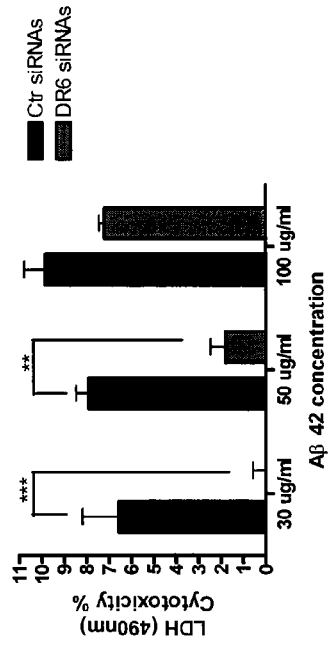
Figure 11B:
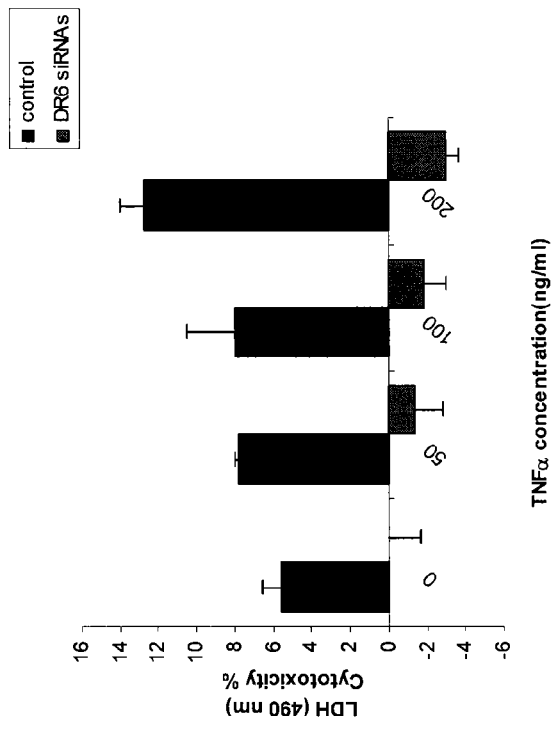
Figure 11C:
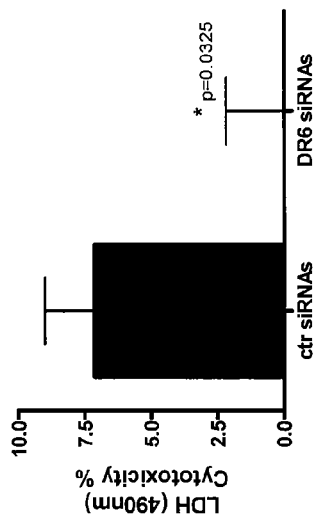
Figure 11D:
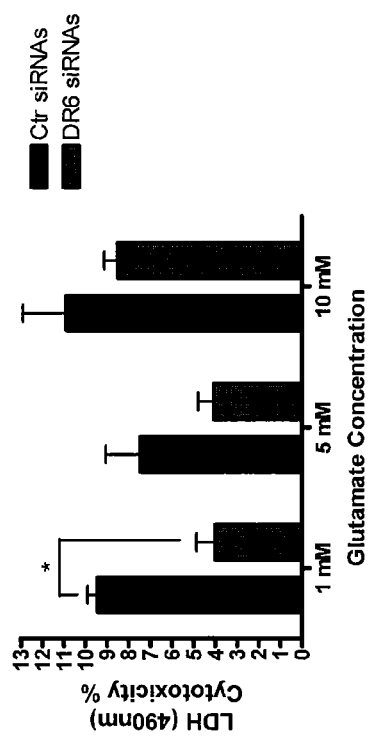

FIGS. 11A-D—DR6 RNAi promotes neuron survival. Graphs depicting percent cytotoxicity as measured in an LDH assay on cells treated with DR6 or control siRNAs (FIG. 11A). Graphs depicting percent cytotoxicity as measured in an XTT assay on cells exposed to DR6 or control siRNAs and treated with increasing concentrations of Abeta42 (FIG. 11B), glutamate (FIG. 11C) or TNF alpha (FIG. 11D).

Figure 12B:
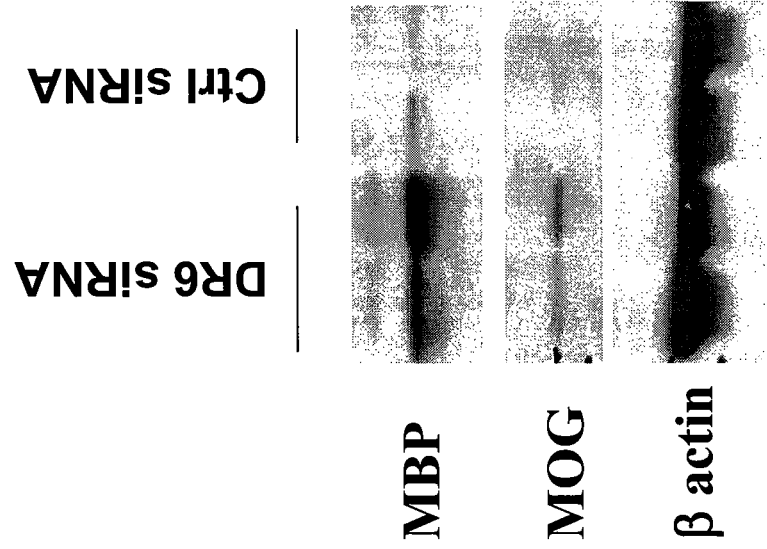
Figure 12A:
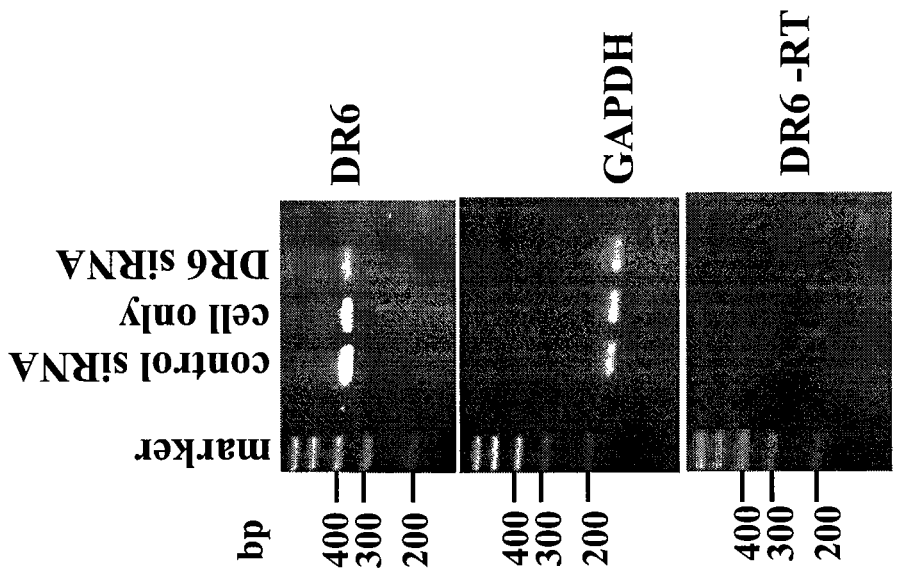

FIGS. 12A-B—DR6 siRNA promotes oligodendrocyte differentiation. RT-PCR of DR6 and GAPDH from lysates of oligodendrocytes treated with control siRNA or DR6 siRNA (FIG. 12A). The DR6 RT-PCR reaction was also performed without the RT enzyme as a negative control (DR6-RT). Western blots of DR6 siRNA or control siRNA treated cells probed with anti-MBP, anti-MOG and anti-β-actin antibodies (FIG. 12B).

Figure 13A:
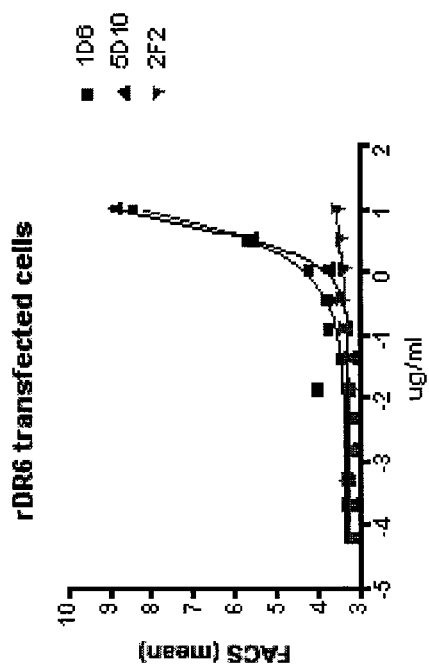
Figure 13B:
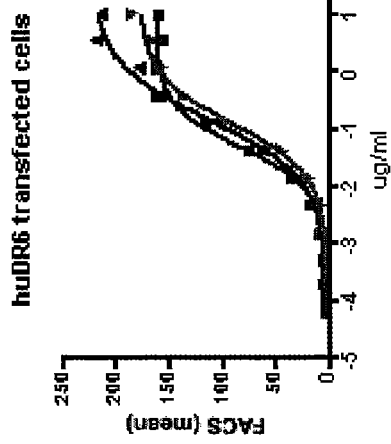
Figure 13C:
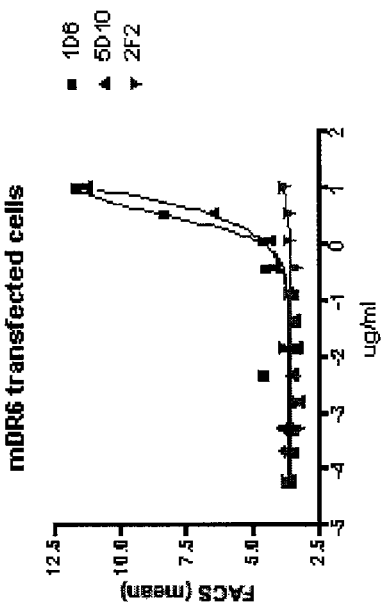

FIGS. 13A-C—Anti-DR6 antibodies bind to rat, mouse and human DR6. Graphs depict FACS analysis performed to assess the ability of anti-DR6 antibodies (1D10, 2F2 and 5D10) to bind to DR6 produced from 293T cells transfected with rat (FIG. 13A), human (FIG. 13B) or mouse DR6 (FIG. 13C).

Figure 14B:
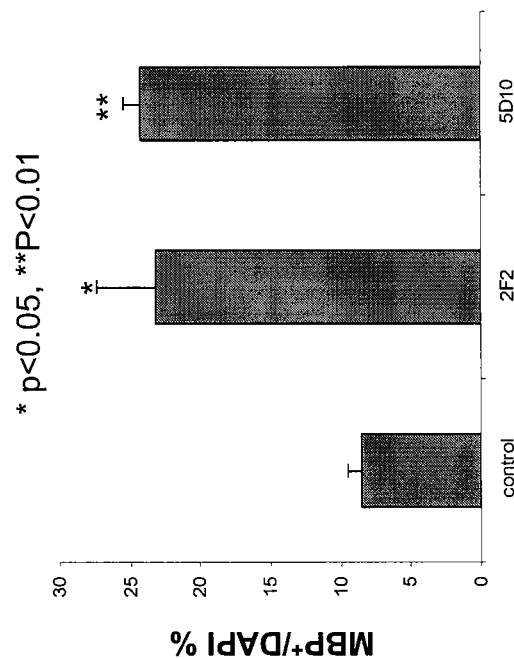
Figure 14A:
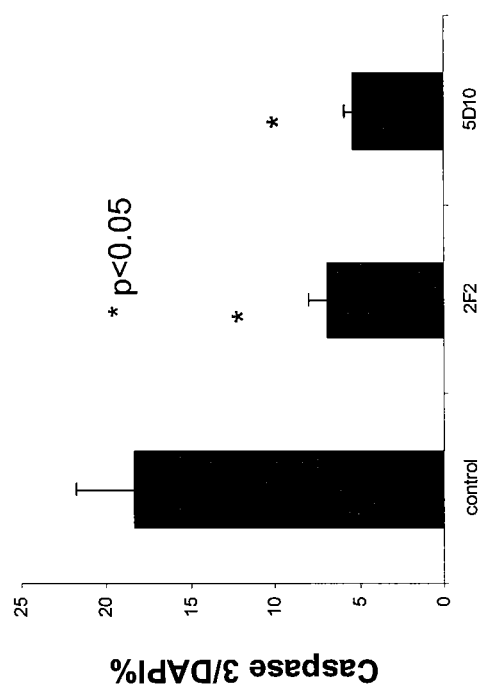

FIGS. 14A-C—Blocking DR6 by anti-DR6 antibodies promotes oligodendrocyte differentiation and inhibits apoptosis. Graph depicting percent caspase 3 activity in oligodendrocyte cultures treated with anti-DR6 antibodies. (FIG. 14A). Graph depicting percent MBP+ cells in oligodendrocyte cultures treated with anti-DR6 antibodies. (FIG. 14B). Western blot of cell cultures treated with anti-DR6 antibody and probed with rabbit anti-cleaved caspase-3 (1:1000, Cell Signaling), mouse anti-MBP antibody (SMI 94 and SMI 99, 1:4000, Convance) and rabbit anti-β-actin antibodies (1:2000, Sigma) (FIG. 14C).

Figure 15:
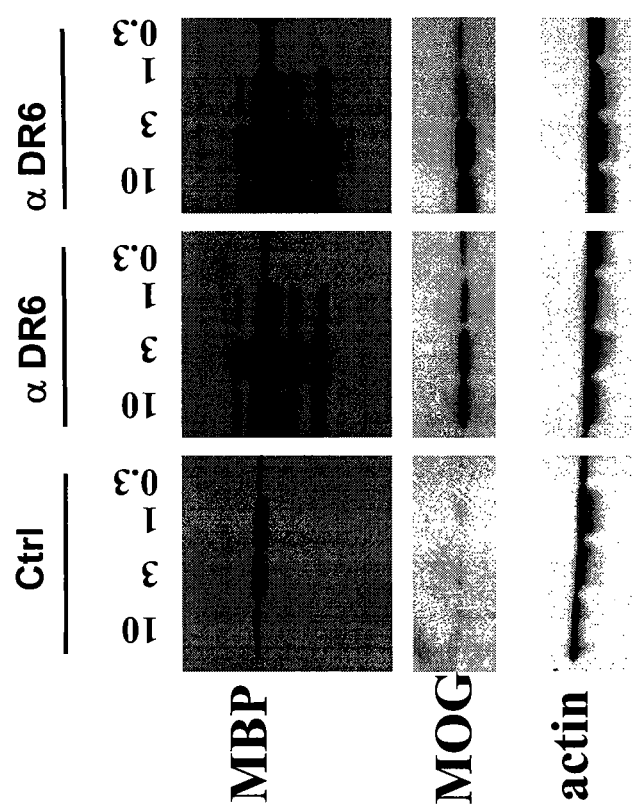

FIG. 15—Blocking DR6 by anti-DR6 antibodies promotes oligodendrocyte/DRG myelination in co-culture. Western blot of co-cultures of oligodendrocytes and DRG neurons treated with anti-DR6 antibody and probed with mouse anti-MBP antibody (SMI 94 and SMI 99, 1:4000, Convance), mouse anti-MOG antibody (1:500) and rabbit anti-β-actin antibodies (1:2000, Sigma).

FIG. 16A-B—Blocking DR6 by anti-DR6 antibodies promote remyelination in rat brain slice culture. Images of p17 brain slices no treatment and after treatment with bioactive lipid lysophosphatidylcholine (LPC) and anti-DR6 antibody (FIG. 16A). Graph depicting black gold staining intensity after no treatment and treatment with bioactive lipid lysophosphatidylcholine (LPC) and anti-DR6 antibody (FIG. 16B).

Figure 17A:
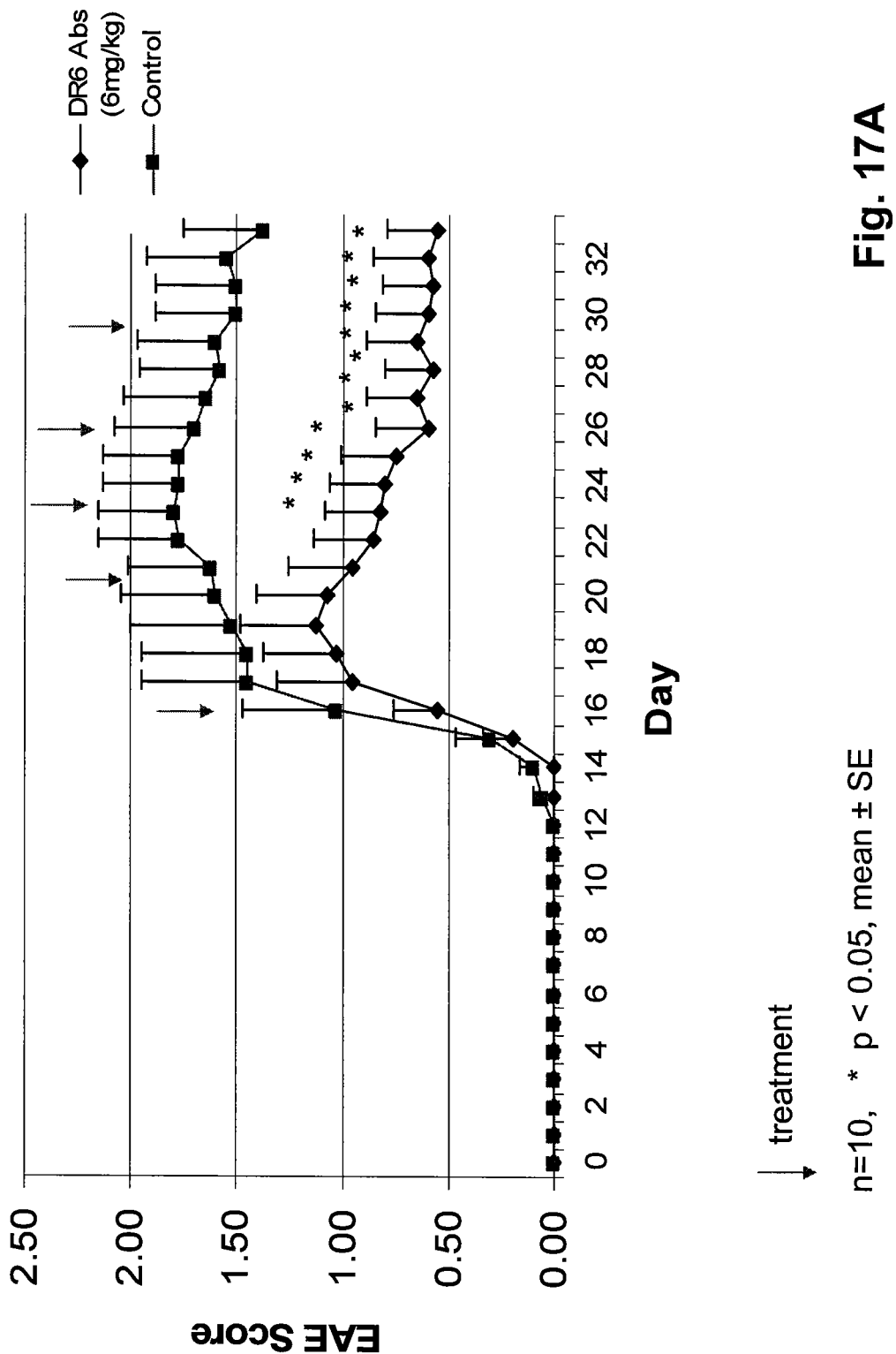
Figure 17B:
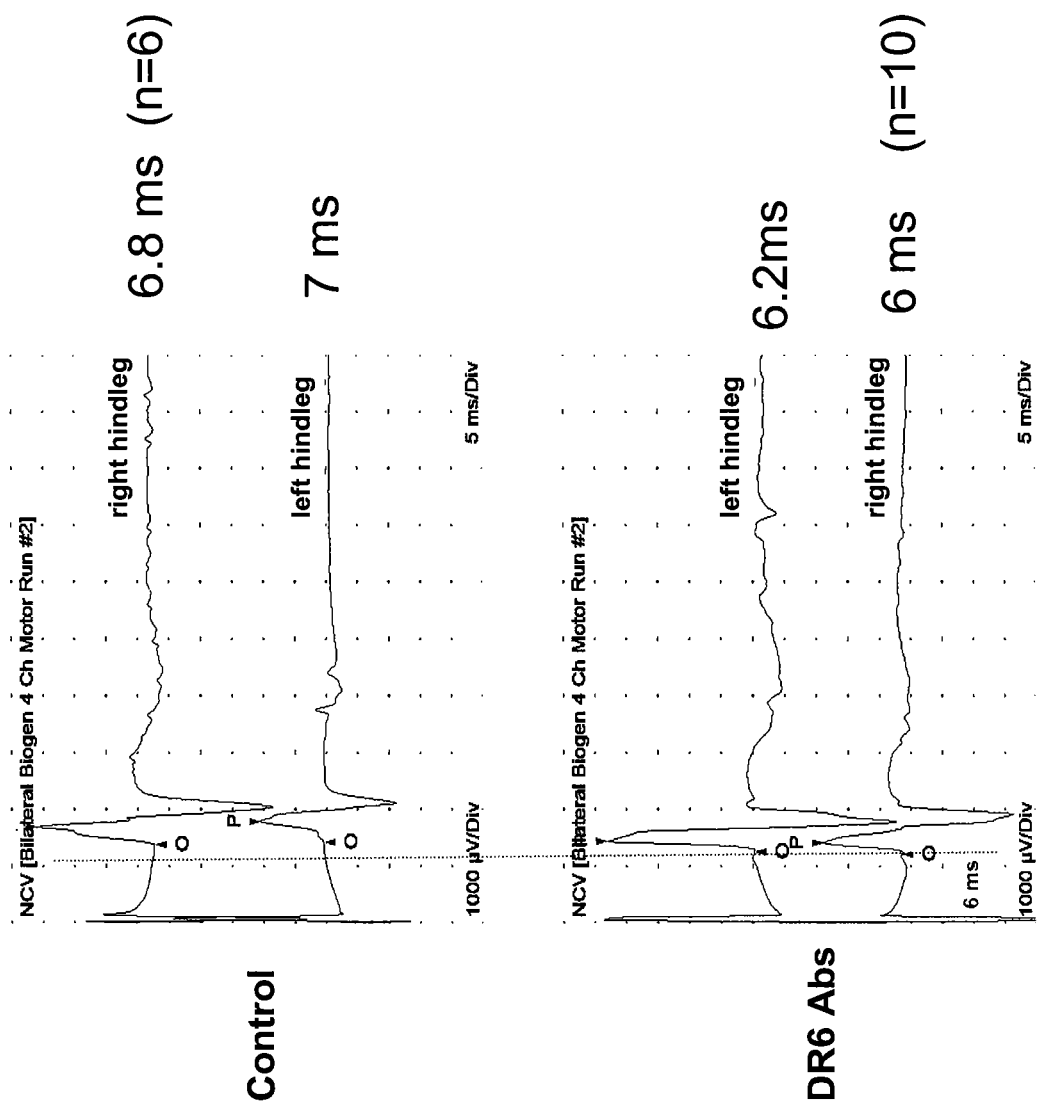

FIGS. 17A-B—Anti-DR6 antibodies promote functional recovery in rat EAE model. Graph depicting EAE scores (measured as a functional recovery of the EAE disease) in MOG induced EAE rats treated with anti-DR6 antibody beginning at day 14 of MOG injection and occurring twice a week for 2 weeks. EAE score was measured as functional recovery of the EAE disease. Graphs depicting nerve conduction velocities in rat EAE model treated with control or anti-DR6 antibody.

Figure 18B:
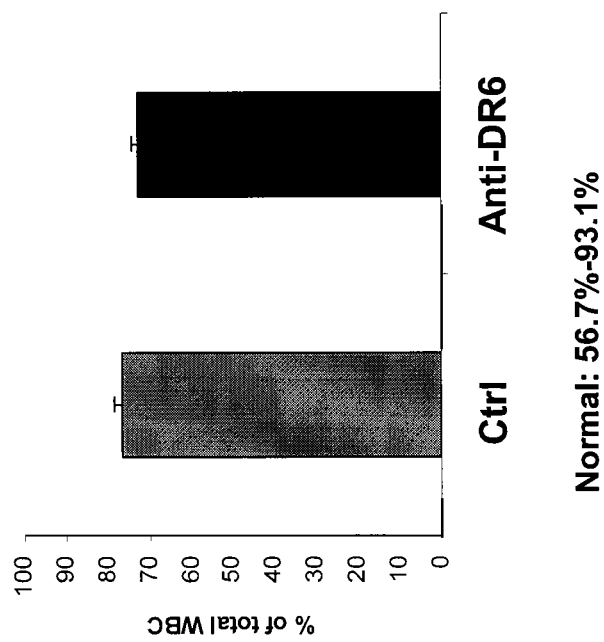
Figure 18A:
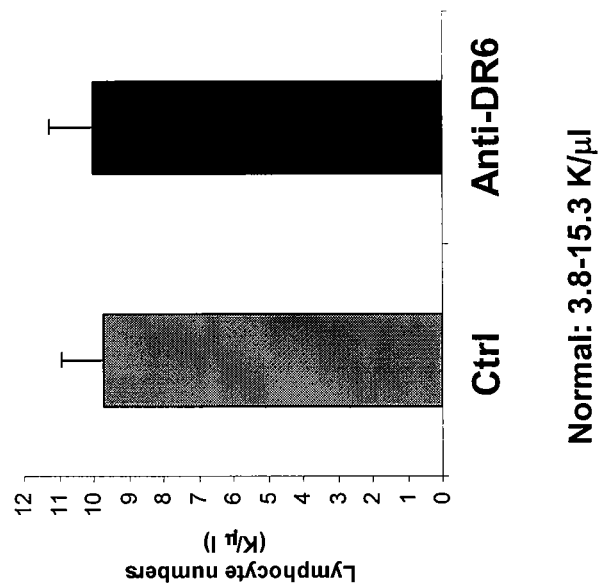

FIGS. 18A-B—Lymphocyte and whole blood cell numbers are not affected by anti-DR6 antibody treatment in EAE rats. Graphs depicting total lymphocyte number (FIG. 18A) and whole blood cell number (FIG. 18B) determined at the end of EAE study (day 32).

Figure 19:
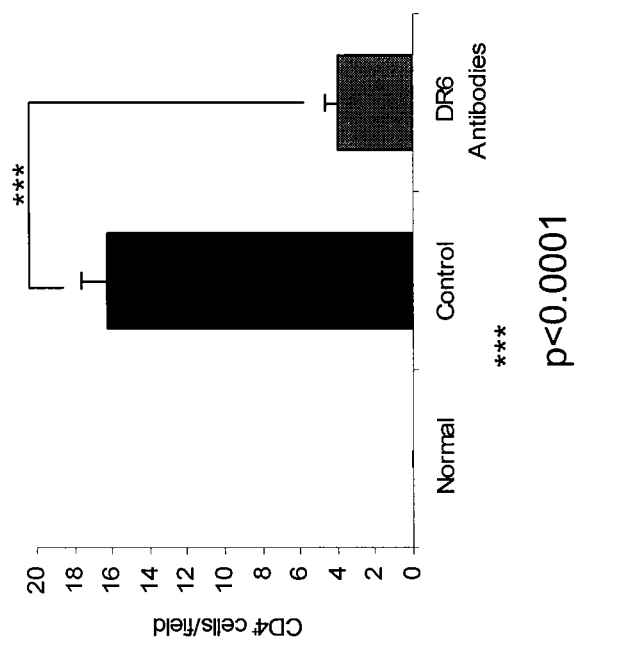

FIG. 19—DR6 antibodies inhibit T-cell infiltration into spinal cord in EAE rats. Graph depicting results of IHC staining of spinal cord tissue using an anti-CD4 antibody to visualize T cell infiltration in the EAE mice. Stainings were performed at the end of the EAE study.

Figures 20A, 20B, 20C:
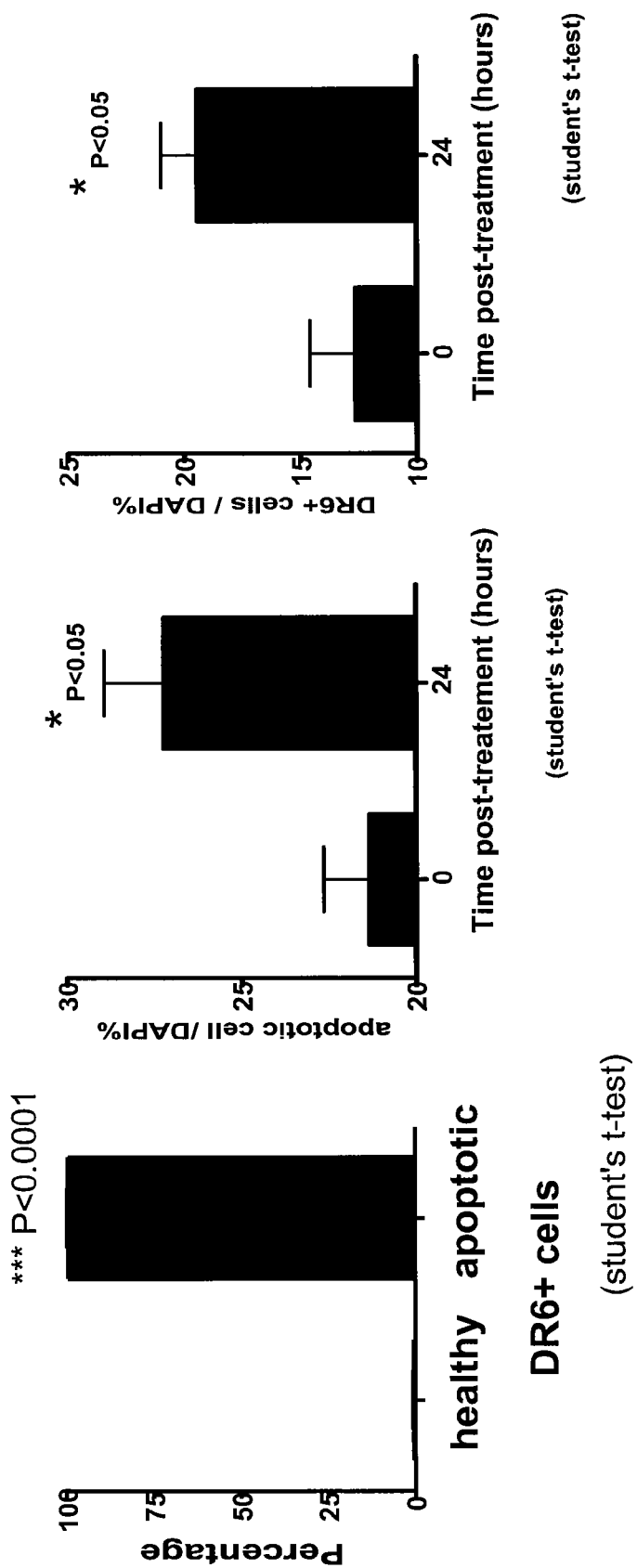

FIG. 20A-C—TNFα promotes neuron death and upregulates DR6. Graph depicting percent apoptotic cells after treatment with TNFα (FIG. 20A). Graph depicting % apoptotic cells versus total number of cells (DAPI+) after treatment with TNFα (FIG. 20B). Graph depicting % DR6+ cells versus total number of cells (DAPI+) after treatment with TNFα (FIG. 20C).

Figure 21B:
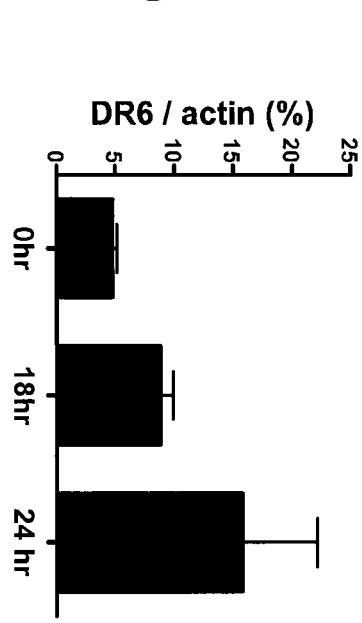
Figure 21A:
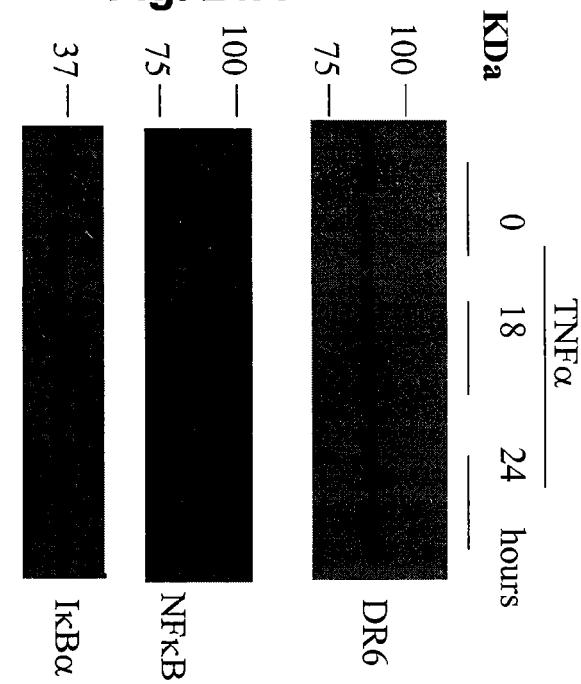
Figure 21D:
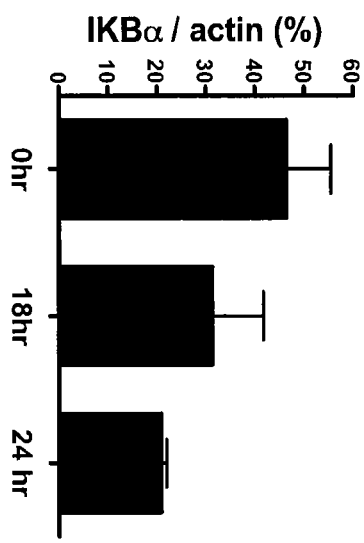
Figure 21C:
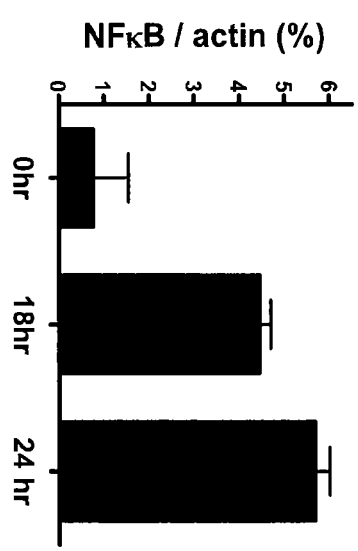

FIGS. 21A-D—TNFα upregulates DR6 and induces neuron death through NFkB signaling. Western blot of cortical neurons treated with TNFα for 18 and 24 hours and probed with anti-DR6, anti-NFκB, anti-IκBα, and anti-β-actin antibodies (FIG. 21A). Graph depicting quantitative amount of DR6 after treatment with TNFα (FIG. 21B). Graph depicting quantitative amount of NFκB after treatment with TNFα (FIG. 21C). Graph depicting quantitative amount of IκBα after treatment with TNFα (FIG. 21D).

Figure 22A:
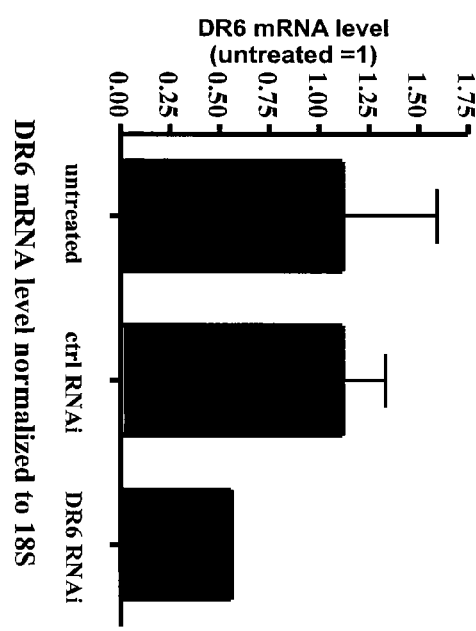
Figure 22B:
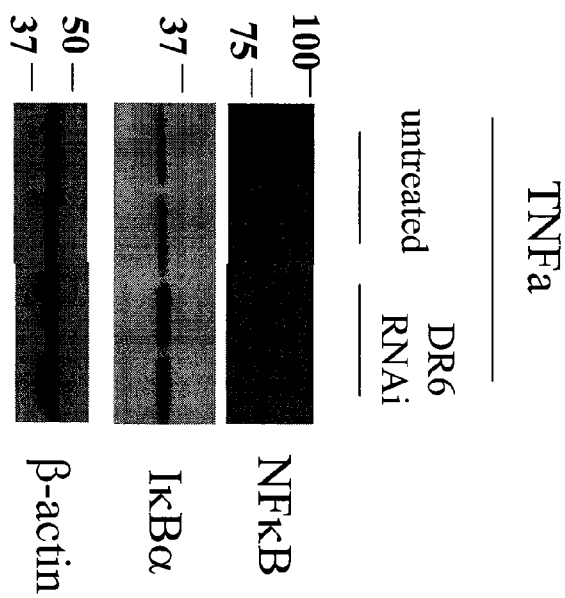
Figure 22C:
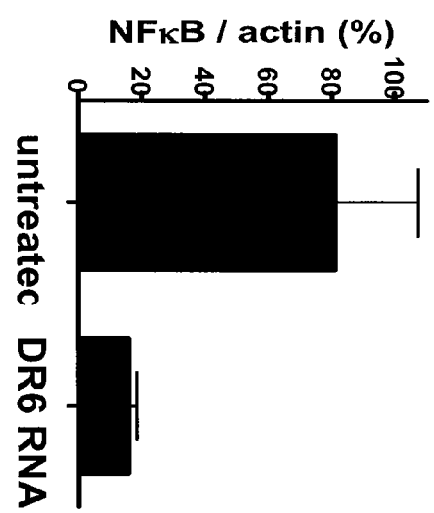
Figure 22D:
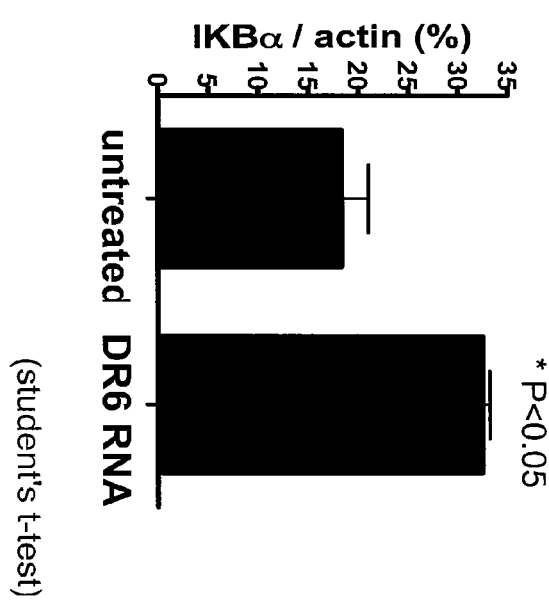

FIG. 22A-D—DR6 RNAi decreases NFκB expression in neurons. Graph depicting DR6 mRNA level after no treatment and treatment with DR6 RNAi and control RNAi (FIG. 22A). Western blot of cortical neurons treated with TNFα, and further treated with DR6 RNAi and probed with anti-NFκB, anti-IκBα, and anti-β-actin antibodies (FIG. 22B). Graph depicting quantitative amount of NFκB after no treatment and treatment with DR6 RNAi (FIG. 22C). Graph depicting quantitative amount of IκBα after no treatment and treatment with DR6 RNAi (FIG. 22D).

Figures 23A, 23B:
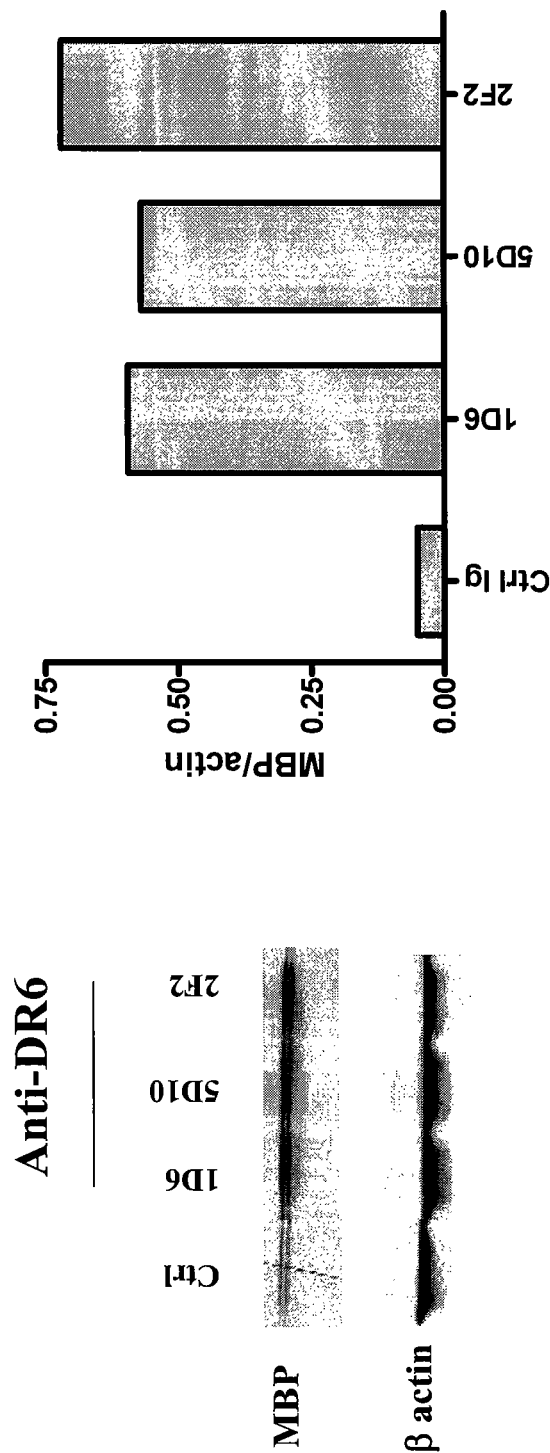

FIG. 23A-B—Anti-DR6 antibodies promote schwann cell myelination. Western blot showing MBP and beta-actin levels in schwann cell and DRG neuron co-cultures after treatment with anti-DR6 or control antibodies (FIG. 23A). Bar graph depicting quantitation of MBP levels as compared to beta-actin levels in the co-cultures (FIG. 23B).

Figure 24:
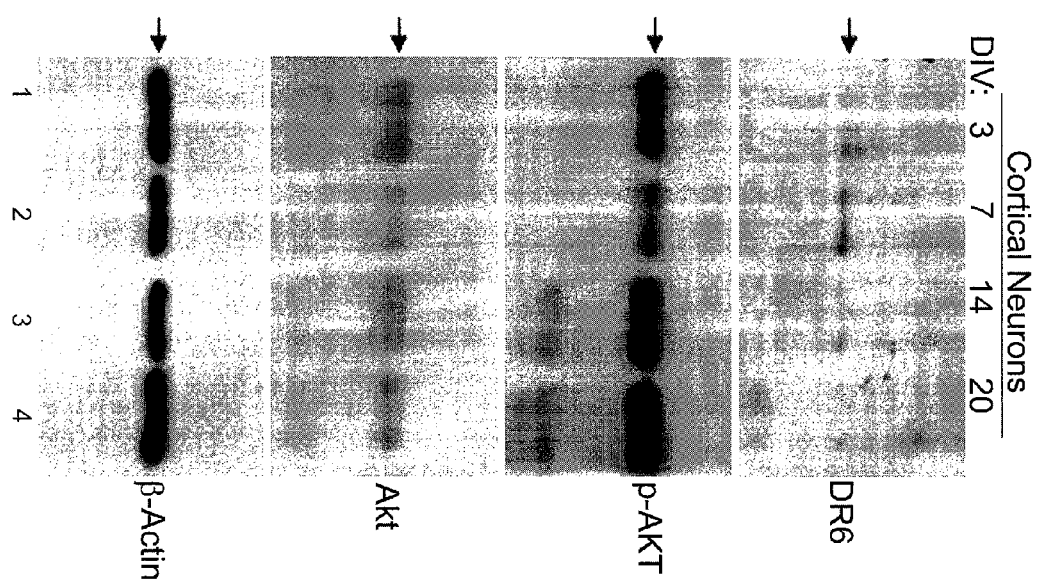

FIG. 24—Levels of DR6 and phosphorylated-AKT are inversely related. Western blot showing DR6, p-AKT, AKT and β-actin levels in cultured rat cortical neurons.

FIG. 25—DR6 and p75 interact. Western blots showing DR6 and p75 protein levels that result from immunoprecipitation of DR6 from cells recombinantly expressing combinations of DR6, p'75, and TrkA (negative control) proteins (FIG. 25A). Bar graph depicting quantification of binding of p75 to the surface of cells recombinantly expressing DR6 or pV90 (negative control) (FIG. 25C). Western blots showing DR6 and p75 protein levels the result from immunopreciptation of DR6 from human fetal spinal cord isolates (FIG. 25B).

Figure 26:

FIG. 26—DR6 and p75 are co-expressed in mouse brain. Bar graph showing quantification of DR6 and p75 mRNA levels in various regions of the mouse brain.

Figure 27A:
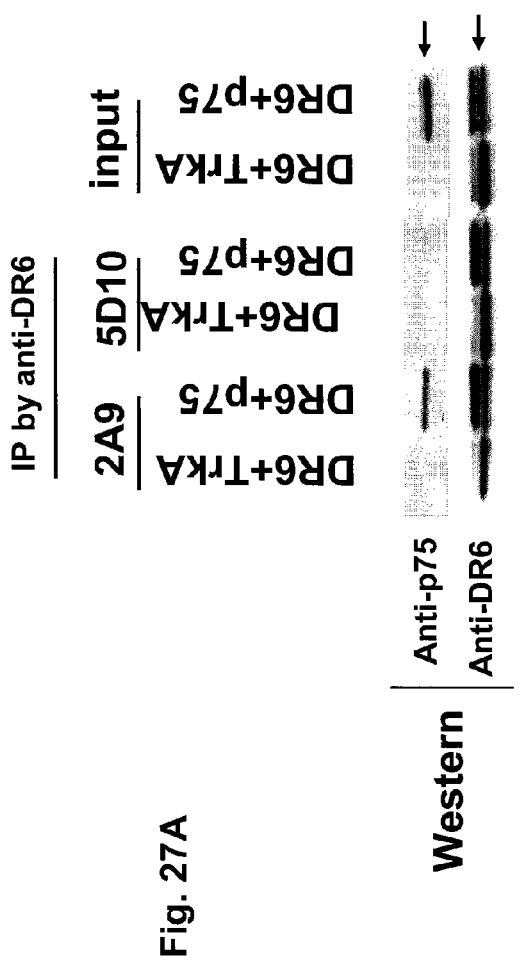
Figure 27B:
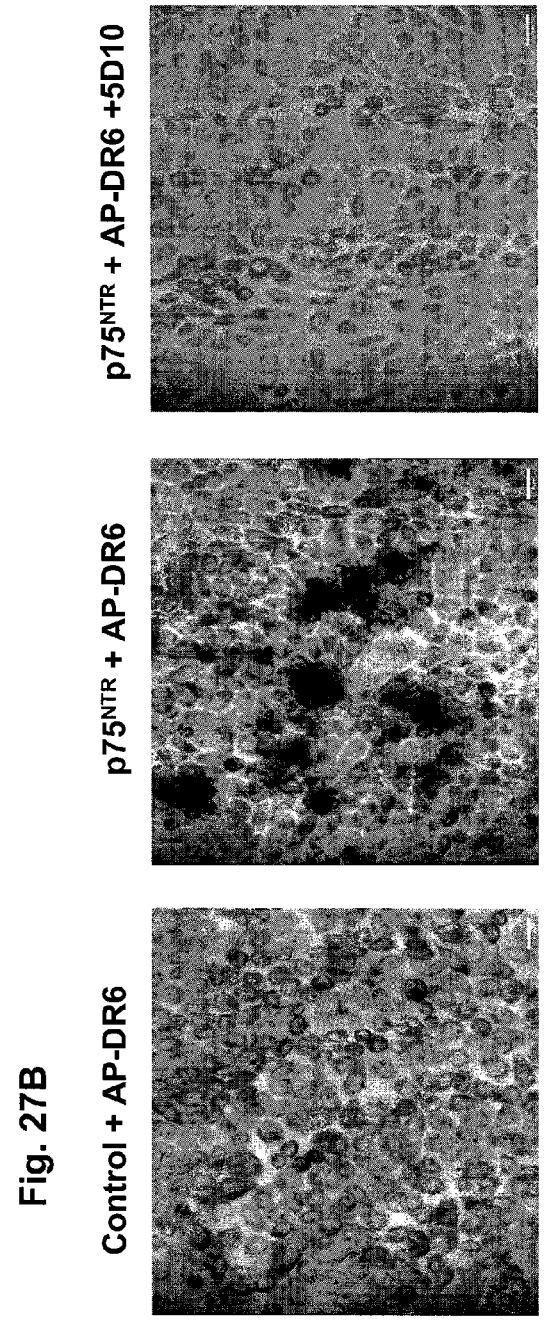

FIG. 27—DR6 antibody 5D10 blocks the interaction of DR6 and p75. Western blot showing p75 and DR6 proteins that immunoprecipitate with anti-DR6 antibodies 2A9 and 5D10 (FIG. 27A). Image showing CHO cells transfected with a control vector or a vector encoding p75 and exposed to either alkaline phosphatase-DR6 alone, or alkaline phosphatase-DR6 in combination with an anti-DR6 antibody (FIG. 27B).

Figure 28B:
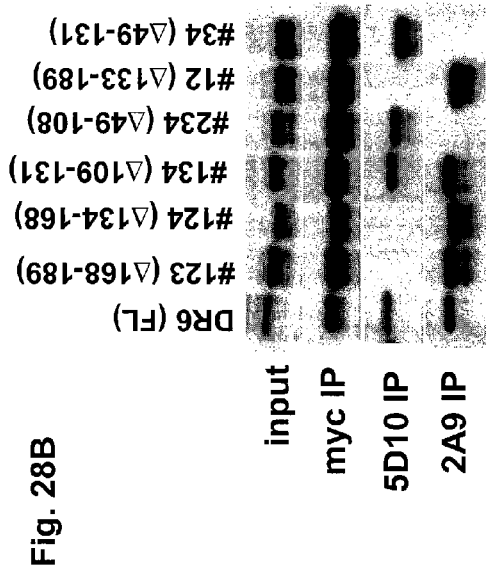
Figure 28A:
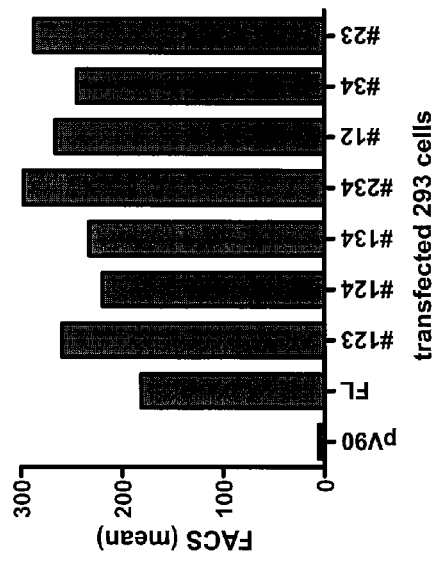
Figure 28C:
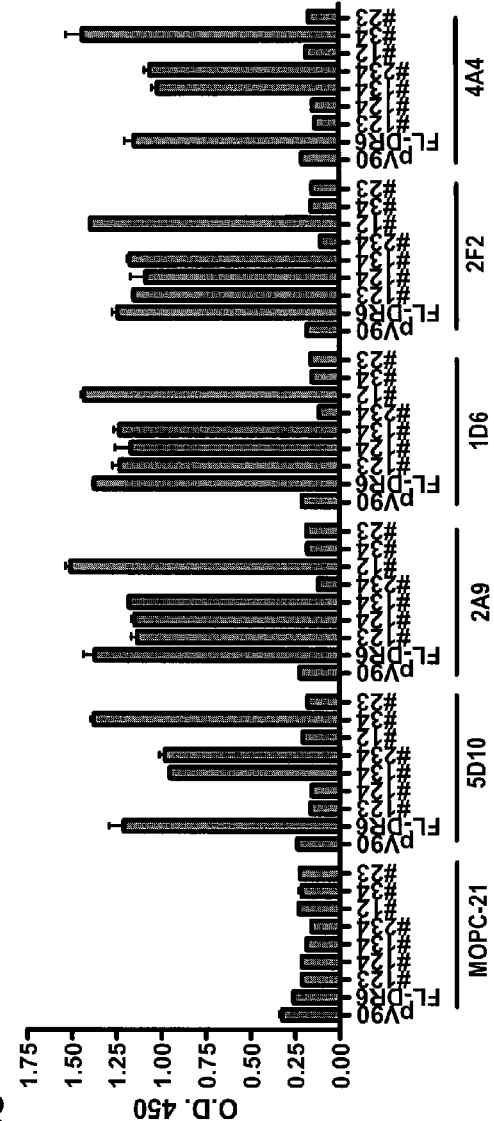

FIG. 28—Antibodies that block the DR6-p75 interaction bind to the Cys3/Cys4 domain of DR6. Bar graph showing level of expression of recombinant DR6 deletion mutants (FIG. 28A). Western blot showing amounts of myc-DR6 fusion proteins that immunoprecipitate using an anti-myc antibody (positive control), anti-DR6 antibody 5D10, and anti-DR6 antibody 2A9 (FIG. 28B). Bar graph showing quantitation of interaction of DR6 deletion proteins with anti-DR6 antibodies 5D10, 2A9, 1D6, 2F2, and A4A (FIG. 28C). MOPC-21 indicates a mouse monoclonal control antibody.

Figure 29:
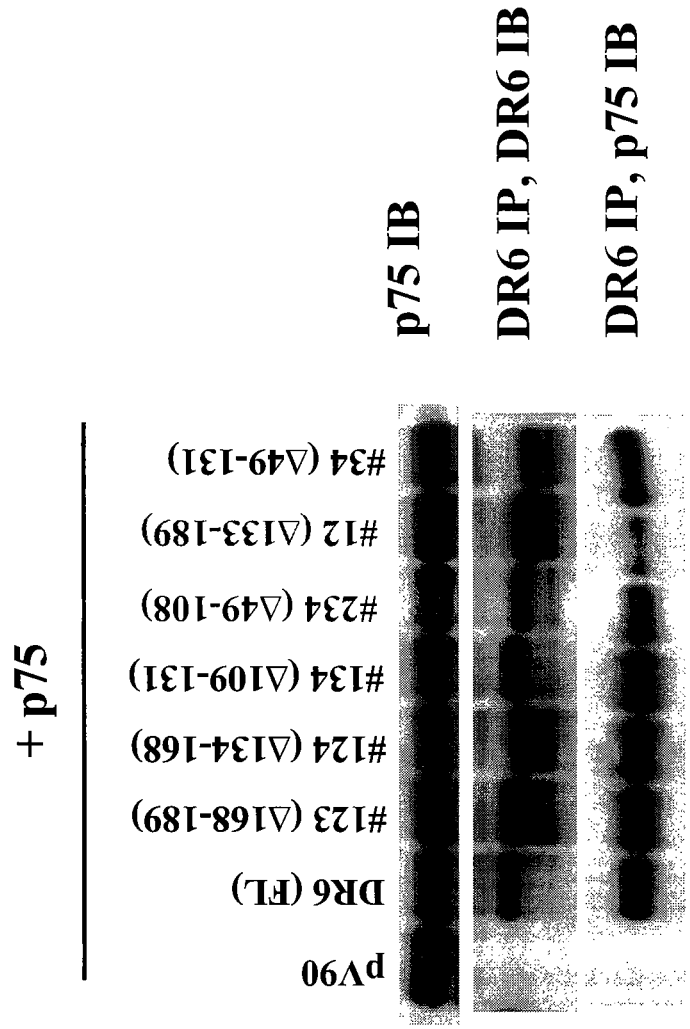

FIG. 29—The Cys3/Cys4 region of DR6 is important for binding to p75. Western blot showing the amounts of DR6 deletion protein and p75 protein that immunprepitate with DR6.

Figure 30:
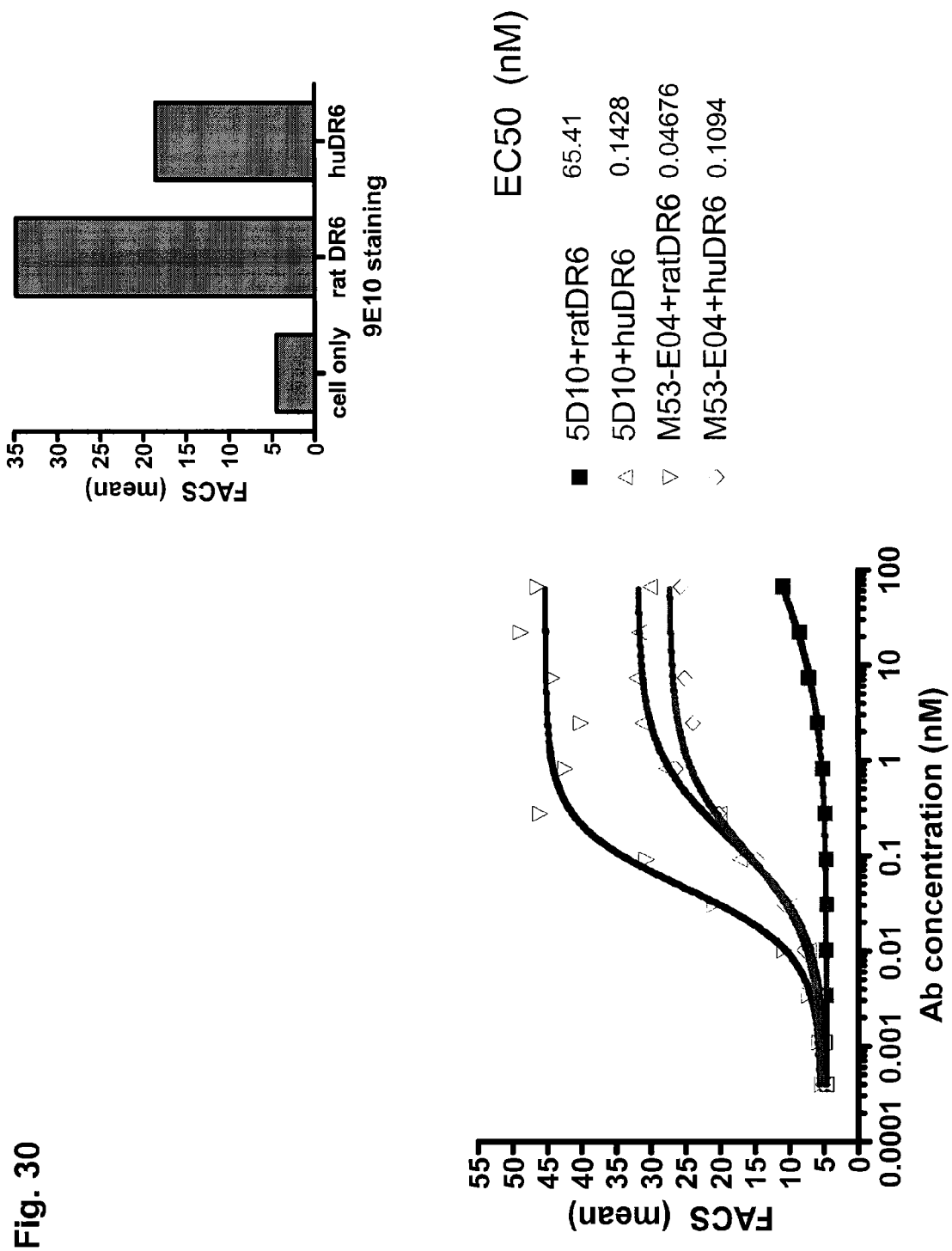

FIG. 30—Anti-DR6 antibodies 5D10 and M53E04 bind to human DR6. Graphs depict FACS analysis performed to assess the ability of anti-DR6 antibodies to bind to human and rat DR6. Anti-myc antibody 9E10 staining results show human and rat DR6 protein expression.

Figure 31:
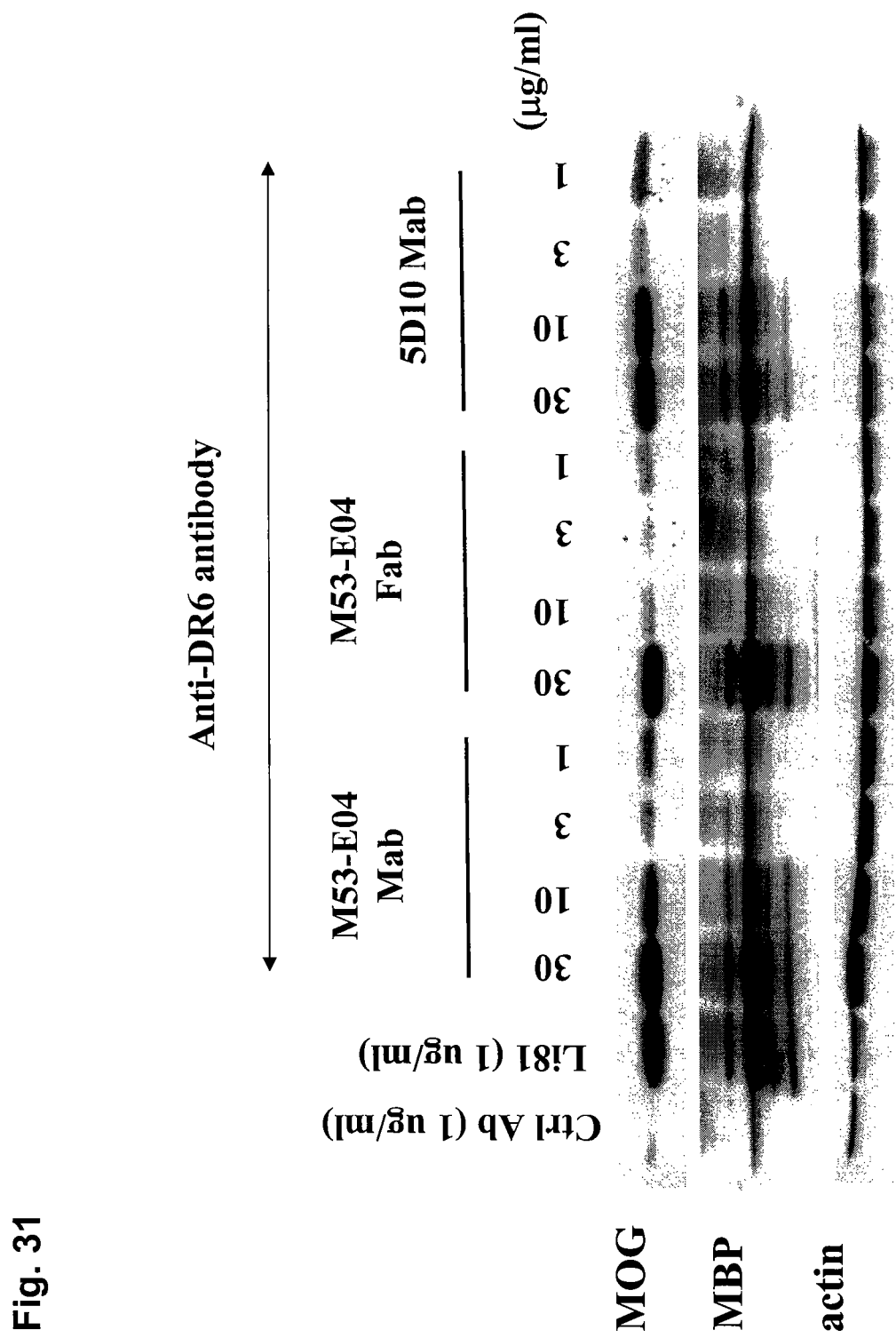

FIG. 31—Blocking DR6 by anti-DR6 antibodies promotes oligodendrocyte/DRG myelination in co-culture. Western blot of co-cultures of oligodendrocytes and DRG neurons treated with anti-DR6 antibodies (M53E04 and 5D10), an anti-LINGO-1 antibody (Li81), and a control antibody and probed with anti-MBP antibody, anti-MOG antibody, and anti-β-actin antibody.

DETAILED DESCRIPTION OF THE INVENTION

Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the methods described herein, suitable methods and materials are described below. The materials, methods and examples are illustrative only and are not intended to be limiting. Other features and advantages of the antibodies and methods described herein will be apparent from the detailed description and from the claims.

In order to further define this invention, the following terms and definitions are provided.

It is to be noted that the term "a" or "an" entity, refers to one or more of that entity; for example, "an immunoglobulin molecule," is understood to represent one or more immunoglobulin molecules. As such, the terms "a" (or "an"), "one or more," and "at least one" can be used interchangeably herein.

Throughout this specification and claims, the word "comprise," or variations such as "comprises" or "comprising," indicate the inclusion of any recited integer or group of integers but not the exclusion of any other integer or group of integers.

As used herein, the term "consists of," or variations such as "consist of" or "consisting of," as used throughout the specification and claims, indicate the inclusion of any recited integer or group of integers, but that no additional integer or group of integers can be added to the specified method, structure or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition.

As used herein, a "therapeutically effective amount" refers to an amount effective, at dosages and for periods of time necessary, to achieve a desired therapeutic result. A therapeutic result can be, e.g., lessening of symptoms, prolonged survival, improved mobility, or the like. A "therapeutically effective amount" can achieve any one of the desired therapeutic results or any combination of multiple desired therapeutic results A therapeutic result need not be a "cure".

As used herein, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, a "polynucleotide" can contain the nucleotide sequence of the full length cDNA sequence, including the untranslated 5' and 3' sequences, the coding sequences, as well as fragments, epitopes, domains, and variants of the nucleic acid sequence. The polynucleotide can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotides can be composed of triple-stranded regions comprising RNA or DNA or both RNA and DNA. polynucleotides can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

A polypeptide can be composed of amino acids joined to each other by peptide bonds or modified peptide bonds, i.e., peptide isosteres, and can contain amino acids other than the 20 gene-encoded amino acids (e.g. non-naturally occurring amino acids). The polypeptides described herein can be modified by either natural processes, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini. It will be appreciated that the same type of modification can be present in the same or varying degrees at several sites in a given polypeptide. Also, a given polypeptide can contain many types of modifications. Polypeptides can be branched, for example, as a result of ubiquitination, and they can be cyclic, with or without branching. Cyclic, branched, and branched cyclic polypeptides can result from posttranslation natural processes or can be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure And Molecular Properties, 2nd Ed., T. E. Creighton, W.H. Freeman and Company, New York (1993); Posttranslational Covalent Modification of Proteins, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992).)

The terms "fragment," "variant," "derivative" and "analog" when referring to a Death Receptor-6 (DR6) antagonist include any antagonist molecules which promote nervous system cell survival. Soluble DR6 polypeptides can include DR6 proteolytic fragments, deletion fragments and in particular, fragments which more easily reach the site of action when delivered to an animal. Polypeptide fragments further include any portion of the polypeptide which comprises an antigenic or immunogenic epitope of the native polypeptide, including linear as well as three-dimensional epitopes. Soluble DR6 polypeptides can comprise variant DR6 regions, including fragments as described above, and also polypeptides with altered amino acid sequences due to amino acid substitutions, deletions, or insertions. Variants can occur naturally, such as an allelic variant. By an "allelic variant" is intended alternate forms of a gene occupying a given locus on a chromosome of an organism. Genes II, Lewin, B., ed., John Wiley & Sons, New York (1985). Non-naturally occurring variants can be produced using art-known mutagenesis techniques. Soluble DR6 polypeptides can comprise conservative or non-conservative amino acid substitutions, deletions or additions. DR6 antagonists can also include derivative molecules. For example, soluble DR6 polypeptides can include DR6 regions which have been altered so as to exhibit additional features not found on the native polypeptide. Examples include fusion proteins and protein conjugates.

A "polypeptide fragment" refers to a short amino acid sequence of a DR6 polypeptide. Protein fragments can be "free-standing," or comprised within a larger polypeptide of which the fragment forms a part of region. Representative examples of polypeptide fragments, include, for example, fragments comprising about 5 amino acids, about 10 amino acids, about 15 amino acids, about 20 amino acids, about 30 amino acids, about 40 amino acids, about 50 amino acids, about 60 amino acids, about 70 amino acids, about 80 amino acids, about 90 amino acids, and about 100 amino acids in length.

As used herein, the term "antigen binding molecule" ("ABM") refers in its broadest sense to a molecule that specifically binds an antigenic determinant. It is understood by those of skill in the art that fragments of mature antibodies can bind specifically to an antigen. Accordingly, an antigen binding molecule, as the term is used herein, includes, but is not limited to, fragments of mature antibodies that bind specifically to a target antigen. An ABM need not contain a constant region. If one or more constant region(s) is present, in particular embodiments, the constant region is substantially identical to human immunoglobulin constant regions, e.g., at least about 85-90%, or about 95% or more identical. The ABMs can be glycoengineered to enhance antibody dependent cellular cytotoxicity.

Antibody or Immunoglobulin. In one embodiment, the DR6 antagonists for use in the treatment methods disclosed herein are "antibody" or "immunoglobulin" molecules, or immunospecific fragments thereof, e.g., naturally occurring antibody or immunoglobulin molecules or engineered antibody molecules or fragments that bind antigen in a manner similar to antibody molecules. The terms "antibody" and "immunoglobulin" are used interchangeably herein. As used herein, the term antibody or immunoglobulin is intended to include whole antibody molecules, including monoclonal, polyclonal and multispecific (e.g., bispecific) antibodies as well as antibody fragments having the Fc region and retaining binding specificity, and fusion proteins that include a region equivalent to the Fc region of an immunoglobulin and that retain binding specificity. Also encompassed are antibody fragments that retain binding specificity including, but not limited to, VH fragments, VL fragments, Fab fragments, F(ab')$_2$ fragments, scFv fragments, Fv fragments, minibodies, diabodies, triabodies, and tetrabodies (see, e.g., Hudson and Souriau, *Nature Med.* 9: 129-134 (2003)). Also encompassed are humanized, primatized and chimeric antibodies.

As will be discussed in more detail below, the term "immunoglobulin" comprises five broad classes of polypeptides that can be distinguished biochemically. Although all five classes are clearly useful in the methods described, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain ($C_H1$, $C_H2$ or $C_H3$) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the $C_H3$ and $C_L$ domains actually comprise the carboxy-terminus of the heavy and light chain, respectively.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε)) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention.

As indicated above, the variable region allows the antibody to selectively recognize and specifically bind epitopes on antigens. That is, the $V_L$ domain and $V_H$ domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the $V_H$ and $V_L$ chains. In some instances, e.g., certain immunoglobulin molecules derived from camelid species or engineered based on camelid immunoglobulins, a complete immunoglobulin molecule can consist of heavy chains only, with no light chains. See, e.g., Hamers Casterman et al., *Nature* 363:446 448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, *J. Mol. Biol.*, 196: 901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR DEFINITIONS[1]

|  | Kabat | Chothia |
| --- | --- | --- |
| $V_H$ CDR1 | 31-35 | 26-32 |
| $V_H$ CDR2 | 50-65 | 52-58 |
| $V_H$ CDR3 | 95-102 | 95-102 |
| $V_L$ CDR1 | 24-34 | 26-32 |
| $V_L$ CDR2 | 50-56 | 50-52 |
| $V_L$ CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in a C35 antibody or antigen-binding fragment, variant, or derivative thereof of are according to the Kabat numbering system.

In camelid species, however, the heavy chain variable region, referred to as $V_HH$, forms the entire CDR. The main differences between camelid $V_HH$ variable regions and those derived from conventional antibodies ($V_H$) include (a) more hydrophobic amino acids in the light chain contact surface of $V_H$ as compared to the corresponding region in $V_HH$, (b) a longer CDR3 in $V_HH$, and (c) the frequent occurrence of a disulfide bond between CDR1 and CDR3 in $V_HH$.

In one embodiment, an antigen binding molecule comprises at least one heavy or light chain CDR of an antibody molecule. In another embodiment, an antigen binding molecule comprises at least two CDRs from one or more antibody molecules. In another embodiment, an antigen binding molecule comprises at least three CDRs from one or more antibody molecules. In another embodiment, an antigen binding molecule comprises at least four CDRs from one or more antibody molecules. In another embodiment, an antigen binding molecule comprises at least five CDRs from one or more antibody molecules. In another embodiment, an antigen binding molecule comprises at least six CDRs from one or more antibody molecules. Exemplary antibody molecules comprising at least one CDR that can be included in the subject antigen binding molecules are known in the art and exemplary molecules are described herein.

Antibodies or immunospecific fragments thereof for use in the methods described herein include, but are not limited to, polyclonal, monoclonal, multispecific, human, humanized, primatized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to binding molecules disclosed herein). ScFv molecules are known in the art and are described, e.g., in U.S. Pat. No. 5,892,019. Immunoglobulin or antibody molecules can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass of immunoglobulin molecule.

Antibody fragments, including single-chain antibodies, can comprise the variable region(s) alone or in combination with the entirety or a portion of the following: hinge region, $C_H1$, $C_H2$, and $C_H3$ domains. Antigen-binding fragments can also comprise any combination of variable region(s) with a hinge region, $C_H1$, $C_H2$, and $C_H3$ domains. Antibodies or immunospecific fragments thereof for use in the diagnostic and therapeutic methods disclosed herein can be from any animal origin including birds and mammals. In certain embodiments, the antibodies are human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain. A polypeptide comprising a heavy chain portion comprises at least one of: a $C_H1$ domain, a hinge (e.g., upper, middle, and/or lower hinge region) domain, a $C_H2$ domain, a $C_H3$ domain, or a variant or fragment thereof. For example, a binding polypeptide can comprise a polypeptide chain comprising a $C_H1$ domain; a polypeptide chain comprising a $C_H1$ domain, at least a portion of a hinge domain, and a $C_H2$ domain; a polypeptide chain comprising a $C_H1$ domain and a $C_H3$ domain; a polypeptide chain comprising a $C_H1$ domain, at least a portion of a hinge domain, and a $C_H3$ domain, or a polypeptide chain comprising a $C_H1$ domain, at least a portion of a hinge domain, a $C_H2$ domain, and a $C_H3$ domain. In another embodiment, a polypeptide comprises a polypeptide chain comprising a $C_H3$ domain. Further, a binding polypeptide can lack at least a portion of a $C_H2$ domain (e.g., all or part of a $C_H2$ domain). As set forth above, it will be understood by one of ordinary skill in the art that these domains (e.g., the heavy chain portions) can be modified such that they vary in amino acid sequence from the naturally occurring immunoglobulin molecule.

In certain embodiments, DR6 antagonist antibodies or immunospecific fragments thereof for use in the treatment methods disclosed herein, the heavy chain portions of one polypeptide chain of a multimer are identical to those on a second polypeptide chain of the multimer. Alternatively, heavy chain portion-containing monomers for use in the methods described herein are not identical. For example, each monomer can comprise a different target binding site, forming, for example, a bispecific antibody.

The heavy chain portions of a binding polypeptide for use in the diagnostic and treatment methods disclosed herein can be derived from different immunoglobulin molecules. For example, a heavy chain portion of a polypeptide can comprise a $C_H1$ domain derived from an $IgG_1$ molecule and a hinge region derived from an $IgG_3$ molecule. In another example, a heavy chain portion can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain portion" includes amino acid sequences derived from an immunoglobulin light chain. Typically, the light chain portion comprises at least one of a $V_L$ or $C_L$ domain.

An isolated nucleic acid molecule encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations can be introduced by standard techniques, such as site-directed mutagenesis and PCR-mediated mutagenesis. For example, conservative amino acid substitutions are made at one or more non-essential amino acid residues.

Antibodies or immunospecific fragments thereof for use in the treatment methods disclosed herein can also be described or specified in terms of their binding affinity to a polypeptide. For example, binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

Antibodies or immunospecific fragments thereof for use in the treatment methods disclosed herein act as antagonists of DR6 as described herein. For example, an antibody for use in the methods described herein can function as an antagonist, blocking or inhibiting the suppressive activity of the DR6 polypeptide.

As used herein, the term "chimeric antibody" will be held to mean any antibody wherein the immunoreactive region or site is obtained or derived from a first species and the constant region (which can be intact, partial or modified) is obtained from a second species. In certain embodiments the target binding region or site will be from a non-human source (e.g. mouse or primate) and the constant region is human.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs can be derived from an antibody of the same class or even subclass as the antibody from which the framework regions are derived, it is envisaged that the CDRs will be derived from an antibody of different class and/or an antibody from a different species. An engineered antibody in which one or more "donor" CDRs from a non-human antibody of known specificity is grafted into a human heavy or light chain framework region is referred to herein as a "humanized antibody." In some cases it is not necessary to replace all of the CDRs with the complete CDRs from the donor variable region to transfer the antigen binding capacity of one variable domain to another. Rather, in some cases, it is only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein, the term humanized is used to refer to an antigen-binding molecule derived from a non-human antigen-binding molecule, for example, a murine antibody, that retains or substantially retains the antigen-binding properties of the parent molecule but which is less immunogenic in humans. This can be achieved by various methods including (a) grafting the entire non-human variable domains onto human constant regions to generate chimeric antibodies, (b) grafting only the non-human CDRs onto human framework and constant regions with or without retention of critical framework residues (e.g., those that are important for retaining good antigen binding affinity or antibody functions), or (c) transplanting the entire non-human variable domains, but "cloaking" them with a human-like section by replacement of surface residues. Such methods are disclosed in Jones et al., Morrison et al., *Proc. Natl. Acad. Sci.*, 81:6851-6855 (1984); Morrison and Oi, *Adv. Immunol.*, 44:65-92 (1988); Verhoeyen et al., *Science*, 239:1534-1536 (1988); Padlan, *Molec. Immun.*, 28:489-498 (1991); Padlan, *Molec. Immun.*, 31(3): 169-217 (1994), all of which are incorporated by reference in their entirety herein. There are generally 3 complementarity determining regions, or CDRs, (CDR1, CDR2 and CDR3) in each of the heavy and light chain variable domains of an antibody, which are flanked by four framework subregions (i.e., FR1, FR2, FR3, and FR4) in each of the heavy and light chain variable domains of an antibody: FR1-CDR1-FR2-CDR2-FR3-CDR3-FR4. A discussion of humanized antibodies can be found, inter alia, in U.S. Pat. No. 6,632,927, and in published U.S. Application No. 2003/0175269, both of which are incorporated herein by reference in their entirety.

As used herein, the terms "linked," "fused" or "fusion" are used interchangeably. These terms refer to the joining together of two or more elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two ore more segments that correspond to polypeptides encoded by the original ORFs (which segments are not normally so joined in nature.) Although the reading frame is thus made continuous throughout the fused segments, the segments can be physically or spatially separated by, for example, in-frame linker sequence.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product and the translation of such mRNA into polypeptide(s). If the final desired product is biochemical, expression includes the creation of that biochemical and any precursors.

By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; bears; and so on. In certain embodiments, the mammal is a human subject.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene can be endogenous or exogenous to the organism, present integrated into a chromosome or present in a transfection vector that is not integrated into the genome. The expression of the gene is either completely or partially inhibited. RNAi can also be considered to inhibit the function of a target RNA; the function of the target RNA can be complete or partial.

Death Receptor-6 (DR6/TNFRSF21)

It has been discovered that DR6 is expressed in cells of the nervous system including neurons and oligodendrocyte precursor cells and that DR6 can induce cell death in these cells.

DR6 is a polypeptide consisting of 655 amino acids. In certain embodiments, the human polypeptide is encoded by an mRNA comprising the nucleotides of SEQ ID NO:1 (Accession Number: NM_014452). In certain embodiments, the human DR6 polypeptide sequence comprises the amino acids of SEQ ID NO:2 (Accession Number: O75509). Mouse DR6 is also a 655 amino acid polypeptide. In certain embodiments, mouse DR6 is encoded by an mRNA comprising the nucleotides of SEQ ID NO:3 (Accession Number: NM_178589). In certain embodiments, the mouse DR6 polypeptide sequence comprises the amino acid sequence of SEQ ID NO:4 (Accession Number: NP_848704).

Table 2 lists DR6 domains and other regions according to the amino acid residue number based on the sequence of SEQ ID NO:2. As one of skill in the art will appreciate, the beginning and ending residues of the domains listed below can vary depending upon the computer modeling program used, the method used for determining the domain, minor sequence variations etc.

TABLE 2

| Domain or Region | Beginning Residue | Ending Residue |
|---|---|---|
| Signal Sequence | 1 | 40 or 41 |
| Extracellular Domain | 41 or 42 | 349 or 350 |
| TNFR-like Cysteine-Rich Motif-1 | 50 | 88 |
| TNFR-like Cysteine-Rich Motif-2 | 90 | 131 |
| TNFR-like Cysteine-Rich Motif-3 | 133 | 167 |

TABLE 2-continued

| Domain or Region | Beginning Residue | Ending Residue |
|---|---|---|
| TNFR-like Cysteine-Rich Motif-4 | 170 | 211 |
| Transmembrane | 350 or 351 | 367-370 |
| Cytoplasmic | 368-371 | 655 |
| Death Domain | 415 | 498 |
| Leucine Zipper Motif | 497 | 526 |

P75/TNR16

It has also been discovered that p75 neurotrophin receptor is a ligand for DR6. P75, also known as tumor necrosis factor receptor superfamily member 16 (TNR16 or TNFRSF16) or nerve growth factor receptor (NGFR), is a polypeptide consisting of 427 amino acids. The human polypeptide sequence is Accession Number NP_002498 (SEQ ID NO: 165) and the nucleic acid sequence is Accession Number NM_002507 (SEQ ID NO: 166). The p75 protein, like the DR6 protein, includes an extracellular region containing four TNFR Cysteine-Rich motifs, a transmembrane region, and an intracellular region containing a death domain. It has previously been shown that p75 is a low affinity receptor which can bind to NGF, BDNF, NT-3, and NT-4. Mi et al. *Nat. Neuroscience* 7:221-228 (2004). In addition, p75 is a component of the LINGO-1/Nogo-66 receptor signaling pathway and can mediate survival and death of neuronal cells. Id.

Methods of Using Antagonists of DR6 and p75

In one embodiment, the method is a method for promoting survival of cells of the nervous system comprising contacting said cells with a DR6 antagonist. Another embodiment provides methods for promoting oligodendrocyte proliferation, differentiation or survival comprising contacting oligodendrocyte cells or oligodendrocyte precursor cells with a DR6 antagonist. Another embodiment provides methods for promoting myelination comprising contacting a mixture of neuronal cells and oligodendrocytes or oligodendrocyte precursor cells with a DR6 antagonist. Yet another embodiment provides methods of inhibiting the binding of DR6 and p75 comprising contacing a DR6 polypeptide and/or a p75 polypeptide with a DR6 antagonist under conditions wherein binding of DR6 to p75 is inhibited. Similarly, the methods described herein also include methods of inhibiting the binding of DR6 to p75 comprising contacting a DR6 polypeptide and/or a p75 polypeptide with a p75 antagonist.

A DR6 antagonist can be a DR6 antagonist polypeptide, a DR6 antagonist compound, a DR6 antibody, a DR6 antagonist polynucleotide, a DR6 aptamer or a combination of two or more DR6 antagonists. Additional embodiments include methods for treating a condition associated with death of cells of the nervous system comprising administering a therapeutically effective amount of a DR6 antagonist.

A p75 antagonist can be a p75 antagonist polypeptide, a p75 antagonist compound, a p75 antibody, a p75 antagonist polynucleotide, a p75 aptamer, or a combination of two or more p75 antagonists. Additional embodiments include methods for treating a condition associated with death of cells of nervous system comprising administering a therapeutically effective amount of a DR6 antagonist in combination with a p75 antagonist.

In some particular embodiments the condition associated with death of nervous system cells can be Alzheimer's disease, Parkinson's disease, Huntington's disease, motor neuron disease (e.g. amyotrophic lateral sclerosis, which is also called ALS or Lou Gehrig's disease), multiple sclerosis, neuronal trauma or cerebral ischemia (e.g. stroke). Another embodiment provides methods for treating a disease of neuronal degeneration comprising administering a therapeutically effective amount of a DR6 antagonist.

Cells of the nervous system include both cells of the central nervous system (or "CNS cells" and cells of the peripheral nervous system (or "PNS cells). CNS cells include cells in the brain and cells in the spinal cord, as well as cell lines derived from such cells. PNS cells include, for example, dorsal root ganglion neurons, schwann cells, motor neurons and cell lines derived from such cells. Cells of the nervous system include neurons such as cortical neurons, motor neurons, dorsal root ganglion (DRG) neurons and cell lines derived from such cells. Cells of the nervous also include neuronal support cells or glial cells including microglia and macroglia as well as cell lines derived from such cells. Examples of macroglial cells include astrocytes, oligodendrocytes, ependymocytes and radial glial cells. Cells of the nervous system also include precursors of these cells such as oligodendrocyte precursor cells and cell lines derived from such cells.

DR6 Antagonist Polypeptides

DR6 antagonists to be used herein include those polypeptides which block, inhibit or interfere with the biological function of naturally occurring DR6. Specifically, soluble DR6 polypeptides include fragments, variants, or derivative thereof of a soluble DR6 polypeptide. Table 1 above describes the various domains of a human DR6 polypeptide. Similar domain structures can be deduced for DR6 polypeptides of other species, e.g., mouse or rat DR6. Soluble DR6 polypeptides typically lack the transmembrane domain of the DR6 polypeptide, and optionally lack the cytoplasmic domain of the DR6 polypeptide. For example, certain soluble human DR6 polypeptides lack amino acids 351-367 of SEQ ID NO:2, which comprises the transmembrane domain of human DR6. Another soluble human DR6 polypeptide lacks both the transmembrane domain and the intracellular domain (amino acids 350-655 of SEQ ID NO:2). Additionally, certain soluble DR6 polypeptides comprise one or more of the TNFR-like cysteine rich motifs and/or the entire extracellular domain (corresponding to amino acids 40 to 349 of SEQ ID NO:2, 40 to 350 of SEQ ID NO:2, 41 to 349 of SEQ ID NO:2 or 41 to 350 of SEQ ID NO:2) of the DR6 polypeptide. As one of skill in the art would appreciate, the entire extracellular domain of DR6 can comprise additional or fewer amino acids on either the C-terminal or N-terminal end of the extracellular domain polypeptide. The soluble antagonist DR6 polypeptide can or can not include the signal sequence.

Additional soluble DR6 polypeptides for use in the methods described herein include, but are not limited to, a soluble DR6 polypeptide comprising, consisting essentially of, or consisting of amino acids 1 to 40 of SEQ ID NO:2; 1 to 41 of SEQ ID NO:2; 65 to 105 of SEQ ID NO:2; 106 to 145 of SEQ ID NO:2; 146 to 185 of SEQ ID NO:2; and 186 to 212 of SEQ ID NO:2; or fragments, variants, or derivatives of such polypeptides.

Further soluble DR6 polypeptides for use in the methods described herein include, but are not limited to, a soluble DR6 polypeptide comprising, consisting essentially of, or consisting of amino acids 1 to 40 of SEQ ID NO:2; 1 to 41 of SEQ ID NO:2; 1 to 64 of SEQ ID NO:2; 1 to 105 of SEQ ID NO:2; 1 to 145 of SEQ ID NO:2; 1 to 185 of SEQ ID NO:2; 1 to 212 of SEQ ID NO:2; 1 to 349 of SEQ ID NO:2; or fragments, variants, or derivatives of such polypeptides.

Still further soluble DR6 polypeptides for use in the methods described herein include, but are not limited to, a DR6 polypeptide comprising, consisting essentially of, or consisting of amino acids 41 to 64 of SEQ ID NO:2; 41 to 105 of SEQ ID NO:2; 41 to 145 of SEQ ID NO:2; 41 to 185 of SEQ ID NO:2; 41 to 212 of SEQ ID NO:2; 41 to 349 of SEQ ID NO:2; 41 to 350 of SEQ ID NO:2; 42 to 64 of SEQ ID NO:2; 42 to 105 of SEQ ID NO:2; 42 to 145 of SEQ ID NO:2; 42 to 185 of SEQ ID NO:2; 42 to 212 of SEQ ID NO:2; 42 to 349 of SEQ ID NO:2; and 42 to 350 of SEQ ID NO:2; or fragments, variants, or derivatives of such polypeptides.

Additional soluble DR6 polypeptide for us in the methods described herein include, but are not limited to, a soluble DR6 polypeptide comprising, consisting essentially of, or consisting of amino acids 65 to 105 of SEQ ID NO:2; 65 to 212 of SEQ ID NO:2; 65 to 349 of SEQ ID NO:2; 106 to 145 of SEQ ID NO:2; 106 to 212 of SEQ ID NO:2; 106 to 349 of SEQ ID NO:2; 146 to 185 of SEQ ID NO:2; 146 to 212 of SEQ ID NO:2; 146 to 349 of SEQ ID NO:2; 186 to 212 of SEQ ID NO:2; 186 to 349 of SEQ ID NO:2; and 213 to 349 of SEQ ID NO:2; or fragments, variants, or derivatives of such polypeptides.

A variant DR6 polypeptide can also vary in sequence from the corresponding wild-type polypeptide. In particular, certain amino acid substitutions can be introduced into the DR6 sequence without appreciable loss of a DR6 biological activity. In exemplary embodiments, a variant DR6 polypeptide contains one or more amino acid substitutions, and/or comprises an amino acid sequence which is at least 70%, 80%, 85%, 90%, 95%, 98% or 99% identical to a reference amino acid sequence selected from the group consisting of: amino acids 41 to 349 of SEQ ID NO:2 or equivalent fragments of SEQ ID NO:4. A variant DR6 polypeptide differing in sequence from any given fragment of SEQ ID NO:2 or SEQ ID NO:4 can include one or more amino acid substitutions (conservative or non-conservative), one or more deletions, and/or one or more insertions. In certain embodiments, the soluble DR6 polypeptide promotes survival of cells of the neuronal system such as neurons and OPCs, e.g., in a mammal.

A soluble DR6 polypeptide can comprise a fragment of at least six, e.g., ten, fifteen, twenty, twenty-five, thirty, forty, fifty, sixty, seventy, one hundred, or more amino acids of SEQ ID NO:2 or SEQ ID NO:4. In addition, a soluble or dominant negative DR6 polypeptide can comprise at least one, e.g., five, ten, fifteen or twenty conservative amino acid substitutions. Corresponding fragments of soluble DR6 polypeptides at least 70%, 75%, 80%, 85%, 90%, or 95% identical to a reference DR6 polypeptide of SEQ ID NO:2 or SEQ ID NO:4 are also contemplated.

By "a DR6 reference amino acid sequence," or "reference amino acid sequence" is meant the specified sequence without the introduction of any amino acid substitutions. As one of ordinary skill in the art would understand, if there are no substitutions, the "isolated polypeptide" comprises an amino acid sequence which is identical to the reference amino acid sequence.

Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution.

Non-conservative substitutions include those in which (i) a residue having an electropositive side chain (e.g., Arg, His or Lys) is substituted for, or by, an electDR6egative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, Ile, Phe or Trp) is substituted for, or by, one having a smaller side chain (e.g., Ala, Ser) or no side chain (e.g., Gly).

As known in the art, "sequence identity" between two polypeptides is determined by comparing the amino acid sequence of one polypeptide to the sequence of a second polypeptide. When discussed herein, whether any particular polypeptide is at least about 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence described herein, the parameters are set, of course, such that the percentage of identity is calculated over the full length of the reference polypeptide sequence and that gaps in homology of up to 5% of the total number of amino acids in the reference sequence are allowed.

As would be well understood by a person of ordinary skill in the art, the DR6 fragments such as those listed above can vary in length, for example, by 1, 2, 3, 4, 5, 6, 7, 8, 9, or 10 amino acids at either end (either longer or shorter) based, for example, on alternate predictions of the DR6 domain regions. In addition, any of the fragments listed above can further include a secretory signal peptide at the N-terminus, e.g., amino acids 1 to 40 of SEQ ID NO:2 or amino acids 1 to 41 of SEQ ID NO:2. Other secretory signal peptides, such as those described elsewhere herein, can also be used. Corresponding fragments of soluble DR6 polypeptides at least 70%, 75%, 80%, 85%, 90%, or 95% identical to SEQ ID NO:2, SEQ ID NO:4, or fragments thereof described herein are also contemplated.

Soluble DR6 polypeptides for use in the methods described herein can include any combination of two or more soluble DR6 polypeptides. Accordingly, soluble DR6 polypeptide dimers, either homodimers or heterodimers, are contemplated. Two or more soluble DR6 polypeptides as described herein can be directly connected, or can be connected via a suitable peptide linker. Such peptide linkers are described elsewhere herein.

Soluble DR6 polypeptides for use in the methods described herein can be cyclic. Cyclization of the soluble DR6 polypetides reduces the conformational freedom of linear peptides and results in a more structurally constrained molecule. Many methods of peptide cyclization are known in the art. For example, "backbone to backbone" cyclization by the formation of an amide bond between the N-terminal and the C-terminal amino acid residues of the peptide. The "backbone to backbone" cyclization method includes the formation of disulfide bridges between two ω-thio amino acid residues (e.g. cysteine, homocysteine). Certain soluble DR6 peptides described herein include modifications on the N- and C-terminus of the peptide to form a cyclic DR6 polypeptide. Such modifications include, but are not limited, to cysteine residues, acetylated cysteine residues, cysteine residues with a NH2 moiety and biotin. Other methods of peptide cyclization are described in Li & Roller. Curr. Top. Med. Chem. 3:325-341 (2002), which is incorporated by reference herein in its entirety.

Cyclic DR6 polypeptides for use in the methods described herein include, but are not limited to, $C_1LSPX_9X_{10}X_{11}C_2$ (SEQ ID NO:5) where $X_1$ is lysine, arginine, histidine, glutamine, or asparagine, $X_2$ is lysine, arginine, histidine, glutamine, or asparagine, $X_3$ is lysine, arginine, histidine, glutamine, or asparagine, $C_1$ optionally has a moiety to promote cyclization (e.g. an acetyl group or biotin) attached and $C_2$ optionally has a moiety to promote cyclization (e.g. an $NH_2$ moiety) attached.

In some embodiments, the DR6 antagonist polypeptide inhibits binding of DR6 to p75. In some emeodiments, the DR6 antagonist polypeptide inhibis binding of DR6 to p75, but does not prevent DR6 binding to APP.

DR6 Antagonist Compounds

DR6 antagonists in the methods described herein include any chemical or synthetic compound which inhibits or decreases the activity of DR6 compared to the activity of DR6 in the absence of the antagonist compound. The DR6 antagonist compound can be one that inhibits binding of DR6 to p75. The DR6 antagonist compound can also be one that inhibits binding of DR6 to p75 but does not prevent binding of DR6 to APP.

One of ordinary skill in the art would know how to screen and test for DR6 antagonist compounds which would be useful in the methods described herein, for example by screening for compounds that modify nervous system cell survival using assays described elsewhere herein.

DR6 Antibodies or Immunospecific Fragments Thereof

DR6 antagonists for use in the methods described herein also include DR6-antigen binding molecules, DR-specific antibodies or antigen-binding fragments, variants, or derivatives which are antagonists of DR6 activity. For example, binding of certain DR6 antigen binding molecules or DR6 antibodies to DR6, as expressed in neurons inhibit apoptosis or promote cell survival.

In certain embodiments, the antibody is an antibody or antigen-binding fragment, variant or derivative of that specifically binds to DR6, wherein the antibody promotes survival of cells of the nervous system. In certain embodiments, the antibody is an antibody or antigen-binding fragment, variant or derivative of that specifically binds to DR6, wherein the antibody promotes proliferation, differentiation or survival of oligodendrocytes. In certain embodiments, the DR6 antibody is an antibody or antigen-binding fragment, variant or derivative thereof that specifically binds to DR6, wherein the antibody promotes myelination. In other embodiments, the DR6 antibody is an antibody or antigen-binding fragment, variant or derivative thereof that inhibits binding of DR6 to p75. In other embodiments, the DR6 antibody is an antibody or antigen-binding fragment, variant or derivative thereof that inhibits inding of DR6 to p75 but does not prevent binding of DR6 to APP.

DR6 antibodies include, but are not limited to, polyclonal, monoclonal, multispecific, human, humanized or chimeric antibodies, single chain antibodies, scFvs, diabodies, triabodies, tetrabodies, minibodies, domain-deleted antibodies, Fab fragments, F(ab')2 fragments, fragments produced by a Fab expression library, anti-idiotypic (anti-Id) antibodies (including, e.g., anti-Id antibodies to antibodies described herein) and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule.

Certain DR6 antagonist antibodies for use in the methods described herein specifically or preferentially binds to a particular DR6 polypeptide fragment or domain, for example, a DR6 polypeptide, fragment, variant, or derivative as described herein. Such DR6 polypeptide fragments include, but are not limited to, a DR6 polypeptide comprising, consisting essentially of, or consisting of one or more TNFR-like cysteine-rich motifs of DR6. Such fragments include for example, fragments comprising, consisting essentially of or consisting of amino acids 65 to 105 of SEQ ID NO:2; 106 to 145 of SEQ ID NO:2; 146 to 185 of SEQ ID NO:2; 186 to 212 of SEQ ID NO:2; 65 to 145 of SEQ ID NO:2; 65 to 185 of SEQ ID NO:2; 65 to 212 of SEQ ID NO:2; 106 to 185 of SEQ ID NO:2; 106 to 212 of SEQ ID NO:2; and 146 to 212 of SEQ ID NO:2. Such fragments also include amino acids 134-189 of SEQ ID NO:2; 168-189 of SEQ ID NO:2; and 134-168 of SEQ ID NO:2. Corresponding fragments of a variant DR6 polypeptide at least 70%, 75%, 80%, 85%, 90% or 95% identical to amino acids 65 to 105 of SEQ ID NO:2; 106 to 145 of SEQ ID NO:2; 146 to 185 of SEQ ID NO:2; 186 to 212 of SEQ ID NO:2; 65 to 145 of SEQ ID NO:2; 65 to 185 of SEQ ID NO:2; 65 to 212 of SEQ ID NO:2; 106 to 185 of SEQ ID NO:2; 106 to 212 of SEQ ID NO:2; 146 to 212 of SEQ ID NO:2; 134-189 of SEQ ID NO:2; 168-189 of SEQ ID NO:2; and 134-168 of SEQ ID NO:2 are also contemplated. In some embodiments, the DR6 antibody, antigen-binding fragment, variant, or derivative thereof requires both the Cys3 and Cys4 regions of DR6 to interact with DR6.

In other embodiments, the antibody is an antibody, or antigen-binding fragment, variant, or derivative thereof which specifically or preferentially binds to at least one epitope of DR6, where the epitope comprises, consists essentially of, or consists of at least about four to five amino acids of SEQ ID NO:2 or SEQ ID NO:4, at least seven, at least nine, or between at least about 15 to about 30 amino acids of SEQ ID NO:2 or SEQ ID NO:4. The amino acids of a given epitope of SEQ ID NO:2 or SEQ ID NO:4 as described can be, but need not be contiguous or linear. In certain embodiments, the at least one epitope of DR6 comprises, consists essentially of, or consists of a non-linear epitope formed by the extracellular domain of DR6 as expressed on the surface of a cell or as a soluble fragment, e.g., fused to an IgG Fc region. Thus, in certain embodiments the at least one epitope of DR6 comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NO:2, or SEQ ID NO:4. where non-contiguous amino acids form an epitope through protein folding.

In other embodiments, the antibody is an antibody, or antigen-binding fragment, variant, or derivative thereof which specifically or preferentially binds to at least one epitope of DR6, where the epitope comprises, consists essentially of, or consists of, in addition to one, two, three, four, five, six or more contiguous or non-contiguous amino acids of SEQ ID NO:2 or SEQ ID NO:4 as described above, and an additional moiety which modifies the protein, e.g., a carbohydrate moiety can be included such that the DR6 antibody binds with higher affinity to modified target protein than it does to an unmodified version of the protein. Alternatively, the DR6 antibody does not bind the unmodified version of the target protein at all.

In certain aspects, the antibody is an antibody, or antigen-binding fragment, variant, or derivative thereof which specifically binds to a DR6 polypeptide or fragment thereof, or a DR6 variant polypeptide, with an affinity characterized by a dissociation constant ($K_D$) which is less than the $K_D$ for a given reference monoclonal antibody.

In certain embodiments, an antibody, or antigen-binding fragment, variant, or derivative thereof binds specifically to at least one epitope of DR6 or fragment or variant described above, i.e., binds to such an epitope more readily than it would bind to an unrelated, or random epitope; binds preferentially to at least one epitope of DR6 or fragment or variant described above, i.e., binds to such an epitope more readily than it would bind to a related, similar, homologous, or analogous epitope; competitively inhibits binding of a reference antibody which itself binds specifically or preferentially to a certain epitope of DR6 or fragment or variant described above; or binds to at least one epitope of DR6 or fragment or variant described above with an affinity characterized by a dissociation constant $K_D$ of less than about $5\times10^{-2}$ M, about $10^{-2}$M, about $5\times10^{-3}$M, about $10^{-3}$M, about $5\times10^{-4}$M, about $10^{-4}$M, about $5\times10^{-5}$M, about $10^{-5}$M, about $5\times10^{-6}$ M, about $10^{-6}$M, about $5\times10^{-7}$M, about $10^{-7}$ M, about $5\times10^{-8}$M, about $10^{-8}$M, about $5\times10^{-9}$M, about $10^{-9}$ M, about $5\times10^{-10}$M, about $10^{-10}$ M, about $5\times10^{-11}$ M, about $10^{-11}$ M, about $5\times10^{-12}$M, about $10^{-12}$ M, about $5\times10^{-13}$ M, about $10^{-13}$ M, about $5\times10^{-14}$ M, about $10^{-14}$ M, about $5\times10^{-15}$ M, or about $10^{-15}$ M. In a particular aspect, the antibody or fragment thereof preferentially binds to a human DR6 polypeptide or fragment thereof, relative to a murine DR6 polypeptide or fragment thereof. In another particular aspect, the antibody or fragment thereof preferentially binds to one or more DR6 polypeptides or fragments thereof, e.g., one or more mammalian DR6 polypeptides.

As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M.

In specific embodiments, an antibody, or antigen-binding fragment, variant, or derivative thereof binds DR6 polypeptides or fragments or variants thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. Alternatively, an antibody, or antigen-binding fragment, variant, or derivative thereof binds DR6 polypeptides or fragments or variants thereof with an off rate (k(off)) of less than or equal to $5\times10^{-4}$ sec$^{-1}$, $10^{-4}$ sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10^{-17}$ sec$^{-1}$ or $10^{-7}$ sec$^{-1}$.

In other embodiments, an antibody, or antigen-binding fragment, variant, or derivative thereof binds DR6 polypeptides or fragments or variants thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$sec$^{-1}$. Alternatively, an antibody, or antigen-binding fragment, variant, or derivative thereof binds DR6 polypeptides or fragments or variants thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

In one embodiment, the DR6 antibody includes DR6 antibodies, or antigen-binding fragments, variants, or derivatives thereof which at least the antigen-binding domains of certain monoclonal antibodies, and fragments, variants, and derivatives thereof shown in Tables 3 and 4. Table 3 lists human anti-DR6 Fab regions identified from a phage display library. Table 4 lists mouse anti-DR6 antibodies derived from hybridomas.

TABLE 3

DR6-specific human Fabs.

| | Fab |
|---|---|
| 1 | M50-H01 |
| 2 | M51-H09 |
| 3 | M53-E04 |
| 4. | M53-F04 |
| 5 | M62-B02 |
| 6. | M63-E10 |
| 7. | M66-B03 |
| 8. | M67-G02 |
| 9. | M72-F03 |
| 10. | M73-C04 |

TABLE 4

DR6-specific Murine Monoclonal Antibodies.

| | Murine Antibody |
|---|---|
| 1 | 1P1D6.3 |
| 2 | 1P2F2.1 |
| 3 | 1P5D10.2 |

As used herein, the term "antigen binding domain" includes a site that specifically binds an epitope on an antigen (e.g., an epitope of DR6). The antigen binding domain of an antibody typically includes at least a portion of an immunoglobulin heavy chain variable region and at least a portion of an immunoglobulin light chain variable region. The binding site formed by these variable regions determines the specificity of the antibody.

In some embodiments, the DR6 antibody is a DR6 antibody, or antigen-binding fragment, variant or derivatives thereof, where the DR6 antibody specifically binds to the same DR6 epitope as a reference monoclonal Fab antibody fragment selected from the group consisting of M50-H01, M51-H09, M53-E04, M53-F04, M62-B02, M63-E10, M66-B03, M67-G02, M72-F03, and M73-C04 or a reference monoclonal antibody selected from the group consisting of 1P1D6.3, 1P2F2.1, and 1P5D10.2.

In some embodiments, the DR6 antibody is a DR6 antibody, or antigen-binding fragment, variant or derivatives thereof, where the DR6 antibody competitively inhibits a reference monoclonal Fab antibody fragment selected from the group consisting of M50-H01, M51-H09, M53-E04, M53-F04, M62-B02, M63-E10, M66-B03, M67-G02, M72-F03, and M73-C04 or a reference monoclonal antibody selected from the group consisting of 1P1D6.3, 1P2F2.1, and 1P5D10.2 from binding to DR6.

In some embodiments, the DR6 antibody is a DR6 antibody, or antigen-binding fragment, variant or derivatives thereof, where the DR6 antibody comprises an antigen binding domain identical to that of a monoclonal Fab antibody fragment selected from the group consisting of M50-H01, M51-H09, M53-E04, M53-F04, M62-B02, M63-E10, M66-B03, M67-G02, M72-F03, and M73-C04 or a reference monoclonal antibody selected from the group consisting of 1P1D6.3, 1P2F2.1, and 1P5D10.2.

In some embodiments, the DR6 antibody is not an antibody selected from the group consisting of 3F4.48, 4B6.9.7 or 1E5.57 as described in International Publication No. WO2008/080045, filed Dec. 21, 2007. In some embodiments, the DR6 antibody is not antibody selected from the group consisting of antibodies that competitively inhibit binding of 3F4.48, 4B6.9.7 or 1E5.57 to DR6.

In some embodiments, the DR6 antibody is an antagonist antibody.

Methods of making antibodies are well known in the art and described herein. Once antibodies to various fragments of, or to the full-length DR6 without the signal sequence, have been produced, determining which amino acids, or epitope, of DR6 to which the antibody or antigen binding fragment binds can be determined by epitope mapping protocols as described herein as well as methods known in the art (e.g. double antibody-sandwich ELISA as described in "Chapter 11—Immunology," *Current Protocols in Molecular Biology*, Ed. Ausubel et al., v.2, John Wiley & Sons, Inc. (1996)). Additional epitope mapping protocols can be found in Morris, G. *Epitope Mapping Protocols*, New Jersey: Humana Press (1996), which are both incorporated herein by reference in their entireties. Epitope mapping can also be performed by commercially available means (i.e. ProtoPROBE, Inc. (Milwaukee, Wis.)).

Additionally, antibodies produced which bind to any portion of DR6 can then be screened for their ability to act as an antagonist of DR6 for example, promoting survival of cells of the nervous system, treating a condition associated with death of cells of the nervous and preventing apoptosis of cells of the nervous system Antibodies can be screened for these and other properties according to methods described in detail in the Examples. Other functions of antibodies described herein can be tested using other assays as described in the Examples herein.

In one embodiment, a DR6 antagonist for use in the methods described herein is an antibody molecule, or immunospecific fragment thereof. Unless it is specifically noted, as used herein a "fragment thereof" in reference to an antibody refers to an immunospecific fragment, i.e., an antigen-specific fragment.

In one embodiment, a binding molecule or antigen binding molecule for use in the methods described herein comprises a synthetic constant region wherein one or more domains are partially or entirely deleted ("domain-deleted antibodies"). Certain methods described herein comprise administration of a DR6 antagonist antibody, or immunospecific fragment thereof, in which at least a fraction of one or more of the constant region domains has been deleted or otherwise altered so as to provide desired biochemical characteristics such as reduced effector functions, the ability to non-covalently dimerize, increased ability to localize at the site of action, reduced serum half-life, or increased serum half-life when compared with a whole, unaltered antibody of approximately the same immunogenicity. For example, certain antibodies for use in the treatment methods described herein are domain deleted antibodies which comprise a polypeptide chain similar to an immunoglobulin heavy chain, but which lack at least a portion of one or more heavy chain domains.

In certain embodiments compatible modified antibodies will comprise domain deleted constructs or variants wherein the entire $C_H2$ domain has been removed ($\Delta C_H2$ constructs). For other embodiments a short connecting peptide can be substituted for the deleted domain to provide flexibility and freedom of movement for the variable region. Those skilled in the art will appreciate that such constructs can be desirable under certain circumstances due to the regulatory properties of the $C_H2$ domain on the catabolic rate of the antibody. Domain deleted constructs can be derived using a vector (e.g., from Biogen DEC Incorporated) encoding an IgG$_1$ human constant domain (see, e.g., WO 02/060955A2 and WO02/096948A2). This exemplary vector was engineered to delete the $C_H2$ domain and provide a synthetic vector expressing a domain deleted IgG$_1$ constant region.

In certain embodiments, modified antibodies for use in the methods disclosed herein are minibodies. Minibodies can be made using methods described in the art (see, e.g., see e.g., U.S. Pat. No. 5,837,821 or WO 94/09817A1).

In one embodiment, a DR6 antagonist antibody or fragment thereof for use in the treatment methods disclosed herein comprises an immunoglobulin heavy chain having deletion or substitution of a few or even a single amino acid as long as it permits association between the monomeric subunits. For example, the mutation of a single amino acid in selected areas of the $C_H2$ domain can be enough to substantially reduce Fc binding and thereby increase localization to the intended site of action. Similarly, it can be desirable to simply delete that part of one or more constant region domains that control the effector function (e.g. complement binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be synthetic through the mutation or substitution of one or more amino acids that enhances the profile of the resulting construct. In this respect it can be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it can be desirable to insert or replicate specific sequences derived from selected constant region domains.

In certain DR6 antagonist antibodies or immunospecific fragments thereof for use in the therapeutic methods described herein, the Fc portion can be mutated to decrease effector function using techniques known in the art. For example, modifications of the constant region can be used to modify disulfide linkages or oligosaccharide moieties that allow for enhanced localization due to increased antigen specificity or antibody flexibility. The resulting physiological profile, bioavailability and other biochemical effects of the modifications can easily be measured and quantified using well know immunological techniques without undue experimentation.

The methods described herein also provide the use of antibodies that comprise, consist essentially of, or consist of, variants (including derivatives) of antibody molecules (e.g., the $V_H$ regions and/or $V_L$ regions) described herein, which antibodies or fragments thereof immunospecifically bind to a DR6 polypeptide. Standard techniques known to those of skill in the art can be used to introduce mutations in the nucleotide sequence encoding a binding molecule, including, but not limited to, site-directed mutagenesis and PCR-mediated mutagenesis which result in amino acid substitutions. In various embodiments, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$CDR1, $V_H$CDR2, $V_H$CDR3, $V_L$ region, $V_L$CDR1, $V_L$CDR2, or $V_L$CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity.

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations can alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein can routinely be expressed and the functional and/or biological activity of the encoded protein can be determined using techniques described herein or by routinely modifying techniques known in the art.

In one embodiment, an antibody is a bispecific binding molecule, binding polypeptide, or antibody, e.g., a bispecific antibody, minibody, domain deleted antibody, or fusion protein having binding specificity for more than one epitope, e.g., more than one antigen or more than one epitope on the same antigen. In one embodiment, a bispecific antibody has at least one binding domain specific for at least one epitope on DR6. A bispecific antibody can be a tetravalent antibody that has two target binding domains specific for an epitope of DR6 and two target binding domains specific for a second target. Thus, a tetravalent bispecific antibody can be bivalent for each specificity.

Modified forms of antibodies or immunospecific fragments thereof for use in the diagnostic and therapeutic methods disclosed herein can be made from whole precursor or parent antibodies using techniques known in the art. Exemplary techniques are discussed in more detail herein.

DR6 antagonist antibodies or immunospecific fragments thereof for use in the diagnostic and treatment methods disclosed herein can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

DR6 antagonist antibodies or fragments thereof for use in the methods described herein can be generated by any suitable method known in the art.

Polyclonal antibodies can be produced by various procedures well known in the art. For example, a DR6 immunospecific fragment can be administered to various host animals including, but not limited to, rabbits, mice, rats, etc. to induce the production of sera containing polyclonal antibodies specific for the antigen. Various adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, Cold Spring Harbor Laboratory Press, 2nd ed. (1988); Hammerling et al., in: *Monoclonal Antibodies and T-Cell Hybridomas* Elsevier, N.Y., 563-681 (1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using a wide variety of techniques known in the art including the use of hybridoma and recombinant and phage display technology.

Using art recognized protocols, in one example, antibodies are raised in mammals by multiple subcutaneous or intraperitoneal injections of the relevant antigen (e.g., purified DR6 antigens or cells or cellular extracts comprising such antigens) and an adjuvant. This immunization typically elicits an immune response that comprises production of antigen-reactive antibodies from activated splenocytes or lymphocytes. While the resulting antibodies can be harvested from the serum of the animal to provide polyclonal preparations, it is often desirable to isolate individual lymphocytes from the spleen, lymph nodes or peripheral blood to provide homogenous preparations of monoclonal antibodies (MAbs). In certain specific embodiments, the lymphocytes are obtained from the spleen.

In this well known process (Kohler et al., *Nature* 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Typically, hybridoma cells thus prepared are seeded and grown in a suitable culture medium that contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. In certain embodiments, the binding specificity of the monoclonal antibodies produced by hybridoma cells is determined by in vitro assays such as immunoprecipitation, radioimmunoassay (RIA) or enzyme-linked immunoabsorbent assay (ELISA). After hybridoma cells are identified that produce antibodies of the desired specificity, affinity and/or activity, the clones can be subcloned by limiting dilution procedures and grown by standard methods (Goding, Monoclonal Antibodies: Principles and Practice, Academic Press, pp. 59-103 (1986)). It will further be appreciated that the monoclonal antibodies secreted by the subclones can be separated from culture medium, ascites fluid or serum by conventional purification procedures such as, for example, protein-A, hydroxylapatite chromatography, gel electrophoresis, dialysis or affinity chromatography.

Antibody fragments that recognize specific epitopes can be generated by known techniques. For example, Fab and F(ab')$_2$ fragments can be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the $C_H1$ domain of the heavy chain.

Those skilled in the art will also appreciate that DNA encoding antibodies or antibody fragments (e.g., antigen binding sites) can also be derived from antibody phage libraries. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Exemplary methods are set forth, for example, in EP 368 684 B1; U.S. Pat. No. 5,969,108, Hoogenboom, H. R. and Chames, Immunol. Today 21:371 (2000); Nagy et al. Nat. Med. 8:801 (2002); Huie et al., Proc. Natl. Acad. Sci. USA 98:2682 (2001); Lui et al., J. Mol. Biol. 315:1063 (2002), each of which is incorporated herein by reference. Several publications (e.g., Marks et al., Bio/Technology 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al., Nat. Biotechnol. 18:1287 (2000); Wilson et al., Proc. Natl. Acad. Sci. USA 98:3750 (2001); or Irving et al., J. Immunol. Methods 248:31 (2001)). In yet another embodiment, cell surface libraries can be screened for antibodies (Boder et al., Proc. Natl. Acad. Sci. USA 97:10701 (2000); Daugherty et al., J. Immunol. Methods 243:211 (2000)). Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. In particular, DNA sequences encoding $V_H$ and $V_L$ regions are amplified from animal cDNA libraries (e.g., human or murine cDNA libraries of lymphoid tissues) or synthetic cDNA libraries. In certain embodiments, the DNA encoding the $V_H$ and $V_L$ regions are joined together by an scFv linker by PCR and cloned into a phagemid vector (e.g., p CANTAB 6 or pComb 3 HSS). The vector is electroporated in E. coli and the E. coli is infected with helper phage. Phage used in these methods are typically filamentous phage including fd and M13 and the $V_H$ or $V_L$ regions are usually recombinantly fused to either the phage gene III or gene VIII. Phage expressing an antigen binding domain that binds to an antigen of interest (i.e., a DR6 polypeptide or a fragment thereof) can be selected or identified with antigen, e.g., using labeled antigen or antigen bound or captured to a solid surface or bead.

Additional examples of phage display methods that can be used to make the antibodies include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187:9-18 (1997); Burton et al., Advances in Immunology 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

In another embodiment, DNA encoding desired monoclonal antibodies can be readily isolated and sequenced using conventional procedures (e.g., by using oligonucleotide probes that are capable of binding specifically to genes encoding the heavy and light chains of murine antibodies). In certain embodiments, isolated and subcloned hybridoma cells serve as a source of such DNA. Once isolated, the DNA can be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which can be synthetic as described herein) can be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody can be grown up in relatively large quantities to provide clinical and commercial supplies of the immunoglobulin.

In a specific embodiment, the amino acid sequence of the heavy and/or light chain variable domains can be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs can be inserted within framework regions, e.g., into human framework regions to humanize a non-human antibody. The framework regions can be naturally occurring or consensus framework regions, e.g., human framework regions (see, e.g., Chothia et al., J. Mol. Biol. 278:457-479 (1998) for a listing of human framework regions). In certain embodiments, the polynucleotide generated by the combination of the framework regions and CDRs encodes an antibody that specifically binds to at least one epitope of a desired polypeptide, e.g., DR6. In further embodiments, one or more amino acid substitutions can be made within the framework regions, for example, to improve binding of the antibody to its antigen. Additionally, such methods can be used to make amino acid substitutions or deletions of one or more variable region cysteine residues participating in an intrachain disulfide bond to generate antibody molecules lacking one or more intrachain disulfide bonds. Other alterations to the polynucleotide are contemplated and within the skill of the art.

In certain embodiments, a DR6 antagonist antibody or immunospecific fragment thereof for use in the treatment methods disclosed herein will not elicit a deleterious immune response in the animal to be treated, e.g., in a human. In one embodiment, DR6 antagonist antibodies or immunospecific fragments thereof for use in the treatment methods disclosed herein be modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This can be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., Proc. Natl. Acad. Sci. 81:6851-6855 (1984); Morrison et al., Adv. Immunol. 44:65-92 (1988); Verhoeyen et al., Science 239:1534-1536 (1988); Padlan, Molec. Immun. 28:489-498 (1991); Padlan, Molec. Immun. 31:169-217 (1994), and U.S. Pat. Nos. 5,585, 089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, $V_H$ and $V_L$ sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., DR6 antagonist antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, Science 229:1202 (1985); Oi et al., BioTechniques 4:214 (1986); Gillies et al., J. Immunol. Methods 125:191-202 (1989); Takeda et al., Nature 314:452-454 (1985), Neuberger et al., Nature 312:604-608 (1984); U.S. Pat. Nos. 5,807,715; 4,816,567; and 4,816397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, e.g., improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565, 332).

Yet another highly efficient means for generating recombinant antibodies is disclosed by Newman, Biotechnology 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. The human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Another means of generating human antibodies using SCID mice is disclosed in U.S. Pat. No. 5,811,524 which is incorporated herein by reference. It will be appreciated that the genetic material associated with these human antibodies can also be isolated and manipulated as described herein.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 12:899-903 (1988)). See also, U.S. Pat. No. 5,565,332, which discloses, for example, selection from random libraries where only $V_H$CDR3 is unvaried.

Alternatively, techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:544-554 (1989)) can be used. Single chain antibodies are formed by linking the heavy and light chain fragments of the Fv region via an amino acid bridge, resulting in a single chain antibody. Techniques for the assembly of functional Fv fragments in *E. coli* can also be used (Skerra et al., *Science* 242:1038-1041 (1988)). Examples of techniques which can be used to produce single-chain Fvs and antibodies include those described in U.S. Pat. Nos. 4,946,778 and 5,258,498; Huston et al., *Methods in Enzymology* 203:46-88 (1991); and Shu et al., *PNAS* 90:7995-7999 (1993).

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines can be selected and cultured using techniques well known to the skilled artisan. Such techniques are described in a variety of laboratory manuals and primary publications. In this respect, techniques suitable for use in the methods as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibodies for use in the therapeutic methods disclosed herein can be produced by any method known in the art for the synthesis of antibodies, in particular, by chemical synthesis or by recombinant expression techniques as described herein.

It will further be appreciated that the alleles, variants and mutations of antigen binding DNA sequences can be used in the methods described herein.

In one embodiment, cDNAs that encode the light and the heavy chains of the antibody can be made, either simultaneously or separately, using reverse transcriptase and DNA polymerase in accordance with well known methods. PCR can be initiated by consensus constant region primers or by more specific primers based on the published heavy and light chain DNA and amino acid sequences. As discussed above, PCR also can be used to isolate DNA clones encoding the antibody light and heavy chains. In this case the libraries can be screened by consensus primers or larger homologous probes, such as mouse constant region probes.

DNA, typically plasmid DNA, can be isolated from the cells using techniques known in the art, restriction mapped and sequenced in accordance with standard, well known techniques set forth in detail, e.g., in the foregoing references relating to recombinant DNA techniques. Of course, the DNA can be synthetic at any point during the isolation process or subsequent analysis.

Recombinant expression of an antibody, or fragment, derivative or analog thereof, e.g., a heavy or light chain of an antibody which is a DR6 antagonist, requires construction of an expression vector containing a polynucleotide that encodes the antibody. Once a polynucleotide encoding an antibody molecule or a heavy or light chain of an antibody, or portion thereof (e.g., containing the heavy or light chain variable domain), has been obtained, the vector for the production of the antibody molecule can be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Also considered herein are replicable vectors comprising a nucleotide sequence encoding an antibody molecule, or a heavy or light chain thereof, or a heavy or light chain variable domain, operably linked to a promoter. Such vectors can include the nucleotide sequence encoding the constant region of the antibody molecule (see, e.g., PCT Publication WO 86/05807; PCT Publication WO 89/01036; and U.S. Pat. No. 5,122,464) and the variable domain of the antibody can be cloned into such a vector for expression of the entire heavy or light chain.

The expression vector is transferred to a host cell by conventional techniques and the transfected cells are then cultured by conventional techniques to produce an antibody for use in the methods described herein. Thus, host cells containing a polynucleotide encoding an antibody, or a heavy or light chain thereof, operably linked to a heterologous promoter are also described herein. In certain embodiments for the expression of double-chained antibodies, vectors encoding both the heavy and light chains can be co-expressed in the host cell for expression of the entire immunoglobulin molecule, as detailed below.

A variety of host-expression vector systems can be utilized to express antibody molecules for use in the methods described elsewhere herein.

The host cell can be co-transfected with two expression vectors, the first vector encoding a heavy chain derived polypeptide and the second vector encoding a light chain derived polypeptide. The two vectors can contain identical selectable markers which enable equal expression of heavy and light chain polypeptides. Alternatively, a single vector can be used which encodes both heavy and light chain polypeptides. In such situations, the light chain is advantageously placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains can comprise cDNA or genomic DNA.

Once an antibody molecule has been recombinantly expressed, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a method for increasing the affinity of antibodies is disclosed in US 2002 0123057 A1.

Furthermore, as described in more detail below, any of the DR6 antibodies or antibody fragments as described herein can be conjugated (covalently linked) to one or more polymers. In one particular embodiment, an antibody fragment that recognizes a specific epitope, for example, a Fab, F(ab')$_2$, Fv fragment or single chain antibody can be conjugated to a polymer. Examples of polymers suitable for such conjugation include polypeptides, sugar polymers and polyalkylene glycol chains (as described in more detail below). The class of polymer generally used is a polyalkylene glycol. Polyethylene glycol (PEG) is most frequently used. PEG moieties, e.g., 1, 2, 3, 4 or 5 PEG polymers, can be conjugated to DR6 antibodies or fragments thereof to increase serum half life. PEG moieties are non-antigenic and essentially biologically inert. PEG moieties used can be branched or unbranched.

Polynucleotides Encoding DR6 Antibodies

The polynucleotides described herein include nucleic acid molecules encoding DR6 antibodies, or antigen-binding fragments, variants, or derivatives thereof.

In one embodiment, the polynucleotide an isolated polynucleotide comprising, consisting essentially of, or consisting of a nucleic acid encoding an immunoglobulin heavy chain variable region (VH), where at least one of the CDRs of the heavy chain variable region or at least two of the VH-CDRs of the heavy chain variable region are at least 80%, 85%, 90% or 95% identical to reference heavy chain VH-CDR1, VH-CDR2, or VH-CDR3 amino acid sequences from monoclonal DR6 antibodies disclosed herein. Alternatively, the VH-CDR1, VH-CDR2, and VH-CDR3 regions of the VH are at least 80%, 85%, 90% or 95% identical to reference heavy chain VH-CDR1, VH-CDR2, and VH-CDR3 amino acid sequences from monoclonal DR6 antibodies disclosed herein. Thus, according to this embodiment a heavy chain variable region has VH-CDR1, VH-CDR2, or VH-CDR3 polypeptide sequences related to the polypeptide sequences shown in Table 5.

In another embodiment, the polynucleotide is an isolated polynucleotide comprising, consisting essentially of, or consisting of a nucleic acid encoding an immunoglobulin light chain variable region (VL), where at least one of the VL-CDRs of the light chain variable region or at least two of the VL-CDRs of the light chain variable region are at least 80%, 85%, 90% or 95% identical to reference light chain VL-CDR1, VL-CDR2, or VL-CDR3 amino acid sequences from monoclonal DR6 antibodies disclosed herein. Alternatively, the VL-CDR1, VL-CDR2, and VL-CDR3 regions of the VL are at least 80%, 85%, 90% or 95% identical to reference light chain VL-CDR1, VL-CDR2, and VL-CDR3 amino acid sequences from monoclonal DR6 antibodies disclosed herein. Thus, according to this embodiment a light chain variable region has VL-CDR1, VL-CDR2, or VL-CDR3 polypeptide sequences related to the polypeptide sequences shown in Table 5.

TABLE 5

| | DR6 Antibody Sequence SEQ ID NOs | | | | | | | | |
|---|---|---|---|---|---|---|---|---|---|
| Antibody | VH PN | VH PP | VH CDR1 | VH CDR2 | VH CDR3 | VL PN | VL PP | VL CDR1 | VL CDR2 | VL CDR2 |
| M50-H01 | 6 | 7 | 8 | 9 | 10 | 11 | 12 | 13 | 14 | 15 |
| M51-H09 | 16 | 17 | 18 | 19 | 20 | 21 | 22 | 23 | 24 | 25 |
| M53-E04 | 26 | 27 | 28 | 29 | 30 | 31 | 32 | 33 | 34 | 35 |
| M53-F04 | 36 | 37 | 38 | 39 | 40 | 41 | 42 | 43 | 44 | 45 |
| M62-B02 | 46 | 47 | 48 | 49 | 50 | 51 | 52 | 53 | 54 | 55 |

TABLE 5-continued

DR6 Antibody Sequence SEQ ID NOs

| Antibody | VH PN | VH PP | VH CDR1 | VH CDR2 | VH CDR3 | VL PN | VL PP | VL CDR1 | VL CDR2 | VL CDR2 |
|---|---|---|---|---|---|---|---|---|---|---|
| M63-E10 | 56 | 57 | 58 | 59 | 60 | 61 | 62 | 63 | 64 | 65 |
| M66-B03 | 66 | 67 | 68 | 69 | 70 | 71 | 72 | 73 | 74 | 75 |
| M67-G02 | 76 | 77 | 78 | 79 | 80 | 81 | 82 | 83 | 84 | 85 |
| M72-F03 | 86 | 87 | 88 | 89 | 90 | 91 | 92 | 93 | 94 | 95 |
| M73-C04 | 96 | 97 | 98 | 99 | 100 | 101 | 102 | 103 | 104 | 105 |
| 1P1D6.3 | 106 | 107 | 108 | 109 | 110 | 111 | 112 | 113 | 114 | 115 |
| 1P2F2.1 | 116 | 117 | 118 | 119 | 120 | 121 | 122 | 123 | 124 | 125 |
| 1P5D10.2 | 126 | 127 | 128 | 129 | 130 | 131 | 132 | 133 | 134 | 135 |

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence, the parameters are set, of course, such that the percentage of identity is calculated over the full length of the reference polypeptide sequence and that gaps in homology of up to 5% of the total number of amino acids in the reference sequence are allowed.

In certain embodiments, an antibody or antigen-binding fragment comprising the VH encoded by the polynucleotide specifically or preferentially binds to DR6. In certain embodiments the nucleotide sequence encoding the VH polypeptide is altered without altering the amino acid sequence encoded thereby. For instance, the sequence can be altered for improved codon usage in a given species, to remove splice sites, or the remove restriction enzyme sites. Sequence optimizations such as these are described in the examples and are well known and routinely carried out by those of ordinary skill in the art.

In another embodiment, the polynucleotide is an isolated polynucleotide comprising, consisting essentially of, or consisting of a nucleic acid encoding an immunoglobulin heavy chain variable region (VH) in which the VH-CDR1, VH-CDR2, and VH-CDR3 regions have polypeptide sequences which are identical to the VH-CDR1, VH-CDR2, and VH-CDR3 groups shown in Table 5. In certain embodiments, an antibody or antigen-binding fragment comprising the VH encoded by the polynucleotide specifically or preferentially binds to DR6.

In some embodiments, the polynucleotide is an isolated polynucleotide comprising a nucleic acid which encodes an antibody VH polypeptide, where the VH polypeptide comprises VH-CDR1, VH-CDR2, and VH-CDR3 amino acid sequences selected from the group consisting of: SEQ ID NOs: 8, 9, and 10; SEQ ID NOs: 18, 19, and 20; SEQ ID NOs: 28, 29, and 30; SEQ ID NOs: 38, 39, and 40; SEQ ID NOs: 48, 49, and 50; SEQ ID NOs: 58, 59, and 60; SEQ ID NOs: 68, 69, and 70; SEQ ID NOs: 78, 79, and 80; SEQ ID NOs: 88, 89, and 90; SEQ ID NOs: 98, 99, and 100; SEQ ID NOs: 108, 109, and 110; SEQ ID NOs: 118, 119, and 120; and SEQ ID NOs: 128, 129, and 130; and where an antibody or antigen binding fragment thereof comprising the VH-CDR3 specifically binds to DR6.

In certain embodiments, an antibody or antigen-binding fragment thereof comprising, consisting essentially of, or consisting of a VH encoded by one or more of the polynucleotides described above specifically or preferentially binds to the same DR6 epitope as a reference monoclonal Fab antibody fragment selected from the group consisting of M50-H01, M51-H09, M53-E04, M53-F04, M62-B02, M63-E10, M66-B03, M67-G02, M72-F03, and M73-C04 or a reference monoclonal antibody selected from the group consisting of 1P1D6.3, 1P2F2.1, and 1P5D10.2, or will competitively inhibit such a monoclonal antibody or fragment from binding to DR6.

In certain embodiments, an antibody or antigen-binding fragment thereof comprising, consisting essentially of, or consisting of a VH encoded by one or more of the polynucleotides described above specifically or preferentially binds to a DR6 polypeptide or fragment thereof, or a DR6 variant polypeptide, with an affinity characterized by a dissociation constant (KD) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In certain embodiments, an antibody or antigen-binding fragment comprising the VL encoded by the polynucleotide specifically or preferentially binds to DR6.

In another embodiment, the polynucleotide is an isolated polynucleotide comprising, consisting essentially of, or consisting of a nucleic acid encoding an immunoglobulin light chain variable region (VL) in which the VL-CDR1, VL-CDR2, and VL-CDR3 regions have polypeptide sequences which are identical to the VL-CDR1, VL-CDR2, and VL-CDR3 groups shown in Table 5. In certain embodiments, an antibody or antigen-binding fragment comprising the VL encoded by the polynucleotide specifically or preferentially binds to DR6.

In a further aspect, the polynucleotide is an isolated polynucleotide comprising, consisting essentially of, or consisting of a nucleic acid encoding an immunoglobulin light chain variable region (VL) in which the VL-CDR1, VL-CDR2, and VL-CDR3 regions are encoded by nucleotide sequences which are identical to the nucleotide sequences which encode the VL-CDR1, VL-CDR2, and VL-CDR3 groups shown in Table 5. In certain embodiments, an antibody or antigen-binding fragment comprising the VL encoded by the polynucleotide specifically or preferentially binds to DR6.

In some embodiments, the polynucleotide is an isolated polynucleotide comprising a nucleic acid which encodes an antibody VL polypeptide, wherein said VL polypeptide comprises VL-CDR1, VL-CDR2, and VL-CDR3 amino acid sequences selected from the group consisting of: SEQ ID NOs: 13, 14, and 15; SEQ ID NOs: 23, 24, and 25; SEQ ID NOs: 33, 34, and 35; SEQ ID NOs: 43, 44, and 45; SEQ ID NOs: 53, 54, and 55; SEQ ID NOs: 63, 64, and 65; SEQ ID NOs: 73, 74, and 75; SEQ ID NOs: 83, 84, and 85; SEQ ID NOs: 93, 94, and 95; SEQ ID NOs: 103, 104, and 105; SEQ ID NOs: 113, 114, and 115; SEQ ID NOs: 123, 124, and 125; and SEQ ID NOs: 133, 134, and 135; and wherein an antibody or antigen binding fragment thereof comprising said VL-CDR3 specifically binds to DR6.

In certain embodiments, an antibody or antigen-binding fragment thereof comprising, consisting essentially of, or consisting of a VL encoded by one or more of the polynucleotides described above specifically or preferentially binds to the same DR6 epitope as a reference monoclonal Fab antibody fragment selected from the group consisting of M50-H01, M51-H09, M53-E04, M53-F04, M62-B02, M63-E10, M66-B03, M67-G02, M72-F03, and M73-C04 or a reference monoclonal antibody selected from the group consisting of 1P1D6.3, 1P2F2.1, and 1P5D10.2 or will competitively inhibit such a monoclonal antibody or fragment from binding to DR6.

In certain embodiments, an antibody or antigen-binding fragment thereof comprising, consisting essentially of, or consisting of a VL encoded by one or more of the polynucleotides described above specifically or preferentially binds to a DR6 polypeptide or fragment thereof, or a DR6 variant polypeptide, with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In a further embodiment, the polynucleotide can be an isolated polynucleotide comprising, consisting essentially of, or consisting of a nucleic acid encoding a VH at least 80%, 85%, 90% 95% or 100% identical to a reference VH polypeptide sequence selected from the group consisting of SEQ ID NOs: 7, 17, 27, 37, 47, 57, 67, 77, 87, 97, 107, 117 and 127. In certain embodiments, an antibody or antigen-binding fragment comprising the VH encoded by the polynucleotide specifically or preferentially binds to DR6.

In another aspect, the polynucleotide can be an isolated polynucleotide comprising, consisting essentially of, or consisting of a nucleic acid sequence encoding a VH having a polypeptide sequence selected from the group consisting of SEQ ID NOs: 7, 17, 27, 37, 47, 57, 67, 77, 87, 97, 107, 117 and 127. In certain embodiments, an antibody or antigen-binding fragment comprising the VH encoded by the polynucleotide specifically or preferentially binds to DR6.

In a further embodiment, the polynucleotide can be an isolated polynucleotide comprising, consisting essentially of, or consisting of a VH-encoding nucleic acid at least 80%, 85%, 90% 95% or 100% identical to a reference nucleic acid sequence selected from the group consisting of SEQ ID NOs: 6, 16, 26, 36, 46, 56, 66, 76, 86, 96, 106, 116, and 126. In certain embodiments, an antibody or antigen-binding fragment comprising the VH encoded by such polynucleotides specifically or preferentially binds to DR6.

In another aspect, the polynucleotide can be an isolated polynucleotide comprising, consisting essentially of, or consisting of a nucleic acid sequence encoding a VH, where the amino acid sequence of the VH is selected from the group consisting of SEQ ID NOs: 7, 17, 27, 37, 47, 57, 67, 77, 87, 97, 107, 117 and 127. The polynucleotide can also be an isolated polynucleotide comprising, consisting essentially of, or consisting of a nucleic acid sequence encoding a VH, where the sequence of the nucleic acid is selected from the group consisting of SEQ ID NOs: 6, 16, 26, 36, 46, 56, 66, 76, 86, 96, 106, 116, and 126. In certain embodiments, an antibody or antigen-binding fragment comprising the VH encoded by such polynucleotides specifically or preferentially binds to DR6.

In certain embodiments, an antibody or antigen-binding fragment thereof comprising, consisting essentially of, or consisting of a VH encoded by one or more of the polynucleotides described above specifically or preferentially binds to the same DR6 epitope as a reference monoclonal Fab antibody fragment selected from the group consisting of M50-H01, M51-H09, M53-E04, M53-F04, M62-B02, M63-E10, M66-B03, M67-G02, M72-F03, and M73-C04 or a reference monoclonal antibody selected from the group consisting of 1P1D6.3, 1P2F2.1, and 1P5D10.2, or will competitively inhibit such a monoclonal antibody or fragment from binding to DR6, or will competitively inhibit such a monoclonal antibody from binding to DR6.

In certain embodiments, an antibody or antigen-binding fragment thereof comprising, consisting essentially of, or consisting of a VH encoded by one or more of the polynucleotides described above specifically or preferentially binds to a DR6 polypeptide or fragment thereof, or a DR6 variant polypeptide, with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$M, or $10^{-15}$ M.

In a further embodiment, the polynucleotide can be an isolated polynucleotide comprising, consisting essentially of, or consisting of a nucleic acid encoding a VL at least 80%, 85%, 90% 95% or 100% identical to a reference VL polypeptide sequence having an amino acid sequence selected from the group consisting of SEQ ID NOs: 12, 22, 32, 42, 52, 62, 72, 82, 92, 102, 112, 122 and 132. In a further embodiment, the polynucleotide can be an isolated polynucleotide comprising, consisting essentially of, or consisting of a VL-encoding nucleic acid at least 80%, 85%, 90% 95% or 100% identical to a reference nucleic acid sequence selected from the group consisting of SEQ ID NOs: 11, 21, 31, 41, 51, 61, 71, 81, 91, 101, 111, 121, and 131. In certain embodiments, an antibody or antigen-binding fragment comprising the VL encoded by such polynucleotides specifically or preferentially binds to DR6.

In another aspect, the polynucleotide can be an isolated polynucleotide comprising, consisting essentially of, or consisting of a nucleic acid sequence encoding a VL having a polypeptide sequence selected from the group consisting of SEQ ID NOs: 12, 22, 32, 42, 52, 62, 72, 82, 92, 102, 112, 122 and 132. The polynucleotide can be an isolated polynucleotide comprising, consisting essentially of, or consisting of a nucleic acid sequence encoding a VL, where the sequence of the nucleic acid is selected from the group consisting of SEQ ID NOs: 11, 21, 31, 41, 51, 61, 71, 81, 91, 101, 111, 121, and 131. In certain embodiments, an antibody or antigen-binding fragment comprising the VL encoded by such polynucleotides specifically or preferentially binds to DR6.

In certain embodiments, an antibody or antigen-binding fragment thereof comprising, consisting essentially of, or consisting of a VL encoded by one or more of the polynucleotides described above specifically or preferentially binds to the same DR6 epitope as a reference monoclonal Fab antibody fragment selected from the group consisting of M50-H01, M51-H09, M53-E04, M53-F04, M62-B02, M63-E10, M66-B03, M67-G02, M72-F03, and M73-C04 or a reference monoclonal antibody selected from the group consisting of 1P1D6.3, 1P2F2.1, and 1P5D10.2, or will competitively inhibit such a monoclonal antibody or fragment from binding to DR6.

In certain embodiments, an antibody or antigen-binding fragment thereof comprising, consisting essentially of, or consisting of a VL encoded by one or more of the polynucleotides described above specifically or preferentially binds to a DR6 polypeptide or fragment thereof, or a DR6 variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

Any of the polynucleotides described above can further include additional nucleic acids, encoding, e.g., a signal peptide to direct secretion of the encoded polypeptide, antibody constant regions as described herein, or other heterologous polypeptides as described herein.

Also, as described in more detail elsewhere herein, the compositions include compositions comprising the polynucleotides comprising one or more of the polynucleotides described above. In one embodiment, the compositions includes compositions comprising a first polynucleotide and second polynucleotide wherein said first polynucleotide encodes a VH polypeptide as described herein and wherein said second polynucleotide encodes a VL polypeptide as described herein. Specifically a composition which comprises, consists essentially of, or consists of a VH polynucleotide, and a VL polynucleotide, wherein the VH polynucleotide and the VL polynucleotide encode polypeptides, respectively at least 80%, 85%, 90% 95% or 100% identical to reference VH and VL polypeptide amino acid sequences selected from the group consisting of SEQ ID NOs: 7 and 12, 17 and 22, 27 and 32, 37 and 42, 47 and 52, 57 and 62, 67 and 72, 77 and 82, 87 and 92, 97 and 102, 107 and 112, 117 and 122 and 127 and 132. Or alternatively, a composition which comprises, consists essentially of, or consists of a VH polynucleotide, and a VL polynucleotide at least 80%, 85%, 90% 95% or 100% identical, respectively, to reference VL and VL nucleic acid sequences selected from the group consisting of SEQ 1D NOs: 6 and 11, 16 and 21, 26 and 31, 36 and 41, 46 and 51, 56 and 61, 66 and 71, 76 and 81, 86 and 91, 96 and 101, 106 and 111, 116 and 121, and 126 and 131. In certain embodiments, an antibody or antigen-binding fragment comprising the VH and VL encoded by the polynucleotides in such compositions specifically or preferentially binds to DR6.

The polynucleotides described herein also include fragments of the polynucleotides, as described elsewhere. Additionally polynucleotides which encode fusion polynucleotides, Fab fragments, and other derivatives, as described herein, are also contemplated.

The polynucleotides can be produced or manufactured by any method known in the art. For example, if the nucleotide sequence of the antibody is known, a polynucleotide encoding the antibody can be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding a DR6 antibody, or antigen-binding fragment, variant, or derivative thereof can be generated from nucleic acid from a suitable source. If a clone containing a nucleic acid encoding a particular antibody is not available, but the sequence of the antibody molecule is known, a nucleic acid encoding the antibody can be chemically synthesized or obtained from a suitable source (e.g., an antibody cDNA library, or a cDNA library generated from, or nucleic acid, such as poly A+RNA, isolated from, any tissue or cells expressing the antibody or other DR6 antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other DR6 antibody. Amplified nucleic acids generated by PCR can then be cloned into replicable cloning vectors using any method well known in the art.

Once the nucleotide sequence and corresponding amino acid sequence of the DR6 antibody, or antigen-binding fragment, variant, or derivative thereof is determined, its nucleotide sequence can be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning, A Laboratory Manual,* 2d Ed., Cold Spring Harbor Laboratory, Cold Spring Harbor, N.Y. (1990) and Ausubel et al., eds., *Current Protocols in Molecular Biology,* John Wiley & Sons, NY (1998), which are both incorporated by reference herein in their entireties), to generate antibodies having a different amino acid sequence, for example to create amino acid substitutions, deletions, and/or insertions.

A polynucleotide encoding a DR6 antibody, or antigen-binding fragment, variant, or derivative thereof can be composed of any polyribonucleotide or polydeoxyribonucleotide, which can be unmodified RNA or DNA or modified RNA or DNA. For example, a polynucleotide encoding DR6 antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, a polynucleotide encoding a DR6 antibody, or antigen-binding fragment, variant, or derivative thereof can be composed of triple-stranded regions comprising RNA or DNA or both RNA and DNA. A polynucleotide encoding a DR6 antibody, or antigen-binding fragment, variant, or derivative thereof can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations can be introduced by standard techniques, such as site-directed mutagenesis and PCR-mediated mutagenesis. Conservative amino acid substitutions can be made at one or more non-essential amino acid residues.

DR6 Antibody Polypeptides

Isolated polypeptides which make up DR6 antibodies, and polynucleotides encoding such polypeptides are also described herein. DR6 antibodies comprise polypeptides, e.g., amino acid sequences encoding DR6-specific antigen binding regions derived from immunoglobulin molecules. A polypeptide or amino acid sequence "derived from" a designated protein refers to the origin of the polypeptide having a certain amino acid sequence. In certain cases, the polypeptide or amino acid sequence which is derived from a particular starting polypeptide or amino acid sequence has an amino acid sequence that is essentially identical to that of the starting sequence, or a portion thereof, wherein the portion consists of at least 10-20 amino acids, at least 20-30 amino acids, at least 30-50 amino acids, or which is otherwise identifiable to one of ordinary skill in the art as having its origin in the starting sequence.

In one embodiment, the polypeptide can be an isolated polypeptide comprising, consisting essentially of, or consisting of an immunoglobulin heavy chain variable region (VH), where at least one of VH-CDRs of the heavy chain variable region or at least two of the VH-CDRs of the heavy chain variable region are at least 80%, 85%, 90% or 95% identical to reference heavy chain VH-CDR1, VH-CDR2 or VH-CDR3 amino acid sequences from monoclonal DR6 antibodies disclosed herein. Alternatively, the VH-CDR1, VH-CDR2 and VH-CDR3 regions of the VH are at least 80%, 85%, 90% or 95% identical to reference heavy chain VH-CDR1, VH-CDR2 and VH-CDR3 amino acid sequences from monoclonal DR6 antibodies disclosed herein. Thus, according to this embodiment a heavy chain variable region has VH-CDR1, VH-CDR2 and VH-CDR3 polypeptide sequences related to the groups shown in Table 5, supra. While Table 5 shows VH-CDRs defined by the Kabat system, other CDR definitions, e.g., VH-CDRs defined by the Chothia system, are also described. In certain embodiments, an antibody or antigen-binding fragment comprising the VH specifically or preferentially binds to DR6.

In another embodiment, the polypeptide can be an isolated polypeptide comprising, consisting essentially of, or consisting of an immunoglobulin heavy chain variable region (VH) in which the VH-CDR1, VH-CDR2 and VH-CDR3 regions have polypeptide sequences which are identical to the VH-CDR1, VH-CDR2 and VH-CDR3 groups shown in Table 5. In certain embodiments, an antibody or antigen-binding fragment comprising the VH specifically or preferentially binds to DR6.

In another embodiment, the polypeptide can be an isolated polypeptide comprising, consisting essentially of, or consisting of an immunoglobulin heavy chain variable region (VH) in which the VH-CDR1, VH-CDR2 and VH-CDR3 regions have polypeptide sequences which are identical to the VH-CDR1, VH-CDR2 and VH-CDR3 groups shown in Table 5, except for one, two, three, four, five, or six amino acid substitutions in any one VH-CDR. In larger CDRs, e.g., VH-CDR-3, additional substitutions can be made in the CDR, as long as the a VH comprising the VH-CDR specifically or preferentially binds to DR6. In certain embodiments the amino acid substitutions are conservative. In certain embodiments, an antibody or antigen-binding fragment comprising the VH specifically or preferentially binds to DR6.

In some embodiments, the polypeptide can be an isolated polypeptide comprising, consisting essentially of, or consisting of an immunoglobulin heavy chain variable region (VH) in which the VH-CDR1, VH-CDR2 and VH-CDR3 regions have polypeptide sequences selected from the group consisting of: SEQ ID NOs: 8, 9, and 10; SEQ ID NOs: 18, 19, and 20; SEQ ID NOs: 28, 29, and 30; SEQ ID NOs: 38, 39, and 40; SEQ ID NOs: 48, 49, and 50; SEQ ID NOs: 58, 59, and 60; SEQ ID NOs: 68, 69, and 70; SEQ ID NOs: 78, 79, and 80; SEQ ID NOs: 88, 89, and 90; SEQ ID NOs: 98, 99, and 100; SEQ ID NOs: 108, 109, and 110; SEQ ID NOs: 118, 119, and 120; and SEQ ID NOs: 128, 129 and 130, except for one, two, three, four, five or six amino acid substitutions in at least one of said VH-CDRs.

In some embodiments, the polypeptide can be an isolated polypeptide comprising, consisting essentially of, or consisting of an immunoglobulin heavy chain variable region (VH) in which the VH-CDR1, VH-CDR2 and VH-CDR3 regions have polypeptide sequences selected from the group consisting of: SEQ ID NOs: 8, 9, and 10; SEQ ID NOs: 18, 19, and 20; SEQ ID NOs: 28, 29, and 30; SEQ ID NOs: 38, 39, and 40; SEQ ID NOs: 48, 49, and 50; SEQ ID NOs: 58, 59, and 60; SEQ ID NOs: 68, 69, and 70; SEQ ID NOs: 78, 79, and 80; SEQ ID NOs: 88, 89, and 90; SEQ ID NOs: 98, 99, and 100; SEQ ID NOs: 108, 109, and 110; SEQ ID NOs: 118, 119, and 120; and SEQ ID NOs: 128, 129 and 130.

In a further embodiment, the polypeptide can be an isolated polypeptide comprising, consisting essentially of, or consisting of a VH polypeptide at least 80%, 85%, 90% 95% or 100% identical to a reference VH polypeptide amino acid sequence selected from the group consisting of SEQ ID NOs: 7, 17, 27, 37, 47, 57, 67, 77, 87, 97, 107, 117, and 127. In certain embodiments, an antibody or antigen-binding fragment comprising the VH polypeptide specifically or preferentially binds to DR6.

In another aspect, the polypeptide can be an isolated polypeptide comprising, consisting essentially of, or consisting of a VH polypeptide selected from the group consisting of SEQ ID NOs: 7, 17, 27, 37, 47, 57, 67, 77, 87, 97, 107, 117, and 127. In certain embodiments, an antibody or antigen-binding fragment comprising the VH polypeptide specifically or preferentially binds to DR6.

In certain embodiments, an antibody or antigen-binding fragment thereof comprising, consisting essentially of, or consisting of a one or more of the VH polypeptides described above specifically or preferentially binds to the same DR6 epitope as a reference monoclonal Fab antibody fragment selected from the group consisting of M50-H01, M51-H09, M53-E04, M53-F04, M62-B02, M63-E10, M66-B03, M67-G02, M72-F03, and M73-C04 or a reference monoclonal antibody selected from the group consisting of 1P1D6.3, 1P2F2.1, and 1P5D10.2, or will competitively inhibit such a monoclonal antibody or fragment from binding to DR6.

In certain embodiments, an antibody or antigen-binding fragment thereof comprising, consisting essentially of, or consisting of one or more of the VH polypeptides described above specifically or preferentially binds to a DR6 polypeptide or fragment thereof; or a DR6 variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In another embodiment, the polypeptide can be an isolated polypeptide comprising, consisting essentially of, or consisting of an immunoglobulin light chain variable region (VL), where at least one of the VL-CDRs of the light chain variable region or at least two of the VL-CDRs of the light chain variable region are at least 80%, 85%, 90% or 95% identical to reference light chain VL-CDR1, VL-CDR2 or VL-CDR3 amino acid sequences from monoclonal DR6 antibodies disclosed herein. Alternatively, the VL-CDR1, VL-CDR2 and VL-CDR3 regions of the VL are at least 80%, 85%, 90% or 95% identical to reference light chain VL-CDR1, VL-CDR2 and VL-CDR3 amino acid sequences from monoclonal DR6 antibodies disclosed herein. Thus, according to this embodiment a light chain variable region has VL-CDR1, VL-CDR2 and VL-CDR3 polypeptide sequences related to the polypeptides shown in Table 5, supra. While Table 5 shows VL-CDRs defined by the Kabat system, other CDR definitions, e.g., VL-CDRs defined by the Chothia system, are also described. In certain embodiments, an antibody or antigen-binding fragment comprising the VL polypeptide specifically or preferentially binds to DR6.

In another embodiment, the polypeptide can be an isolated polypeptide comprising, consisting essentially of, or consisting of an immunoglobulin light chain variable region (VL) in which the VL-CDR1, VL-CDR2 and VL-CDR3 regions have polypeptide sequences which are identical to the VL-CDR1, VL-CDR2 and VL-CDR3 groups shown in Table 5. In certain embodiments, an antibody or antigen-binding fragment comprising the VL polypeptide specifically or preferentially binds to DR6.

In another embodiment, the polypeptide can be an isolated polypeptide comprising, consisting essentially of, or consisting of an immunoglobulin heavy chain variable region (VL) in which the VL-CDR1, VL-CDR2 and VL-CDR3 regions have polypeptide sequences which are identical to the VL-CDR1, VL-CDR2 and VL-CDR3 groups shown in Table 5, except for one, two, three, four, five, or six amino acid substitutions in any one VL-CDR. In larger CDRs, additional substitutions can be made in the VL-CDR, as long as the a VL comprising the VL-CDR specifically or preferentially binds to DR6. In certain embodiments the amino acid substitutions are conservative. In certain embodiments, an antibody or antigen-binding fragment comprising the VL specifically or preferentially binds to DR6.

In some embodiments, the polypeptide can be an isolated polypeptide comprising, consisting essentially of, or consisting of an immunoglobulin heavy chain variable region (VL) in which the VL-CDR1, VL-CDR2 and VL-CDR3 regions have polypeptide sequences selected from the group consisting of: SEQ ID NOs: 13, 14, and 15; SEQ ID NOs: 23, 24, and 25; SEQ ID NOs: 33, 34, and 35; SEQ ID NOs: 43, 44, and 45; SEQ ID NOs: 53, 54, and 55; SEQ ID NOs: 63, 64, and 65; SEQ ID NOs: 73, 74, and 75; SEQ ID NOs: 83, 84, and 85; SEQ ID NOs: 93, 94, and 95; SEQ ID NOs: 103, 104, and 105; SEQ ID NOs: 113, 114 and 115; SEQ ID NOs: 123, 124, and 125; and SEQ ID NOs: 133, 134 and 135, except for one, two, three, four, five or six amino acid substitutions in at least one of said VL-CDRs.

In some embodiments, the polypeptide can be an isolated polypeptide comprising, consisting essentially of, or consisting of an immunoglobulin heavy chain variable region (VL) in which the VL-CDR1, VL-CDR2 and VL-CDR3 regions have polypeptide sequences selected from the group consisting of: SEQ ID NOs: 13, 14, and 15; SEQ ID NOs: 23, 24, and 25; SEQ ID NOs: 33, 34, and 35; SEQ ID NOs: 43, 44, and 45; SEQ ID NOs: 53, 54, and 55; SEQ ID NOs: 63, 64, and 65; SEQ ID NOs: 73, 74, and 75; SEQ ID NOs: 83, 84, and 85; SEQ ID NOs: 93, 94, and 95; SEQ ID NOs: 103, 104, and 105; SEQ ID NOs: 113, 114 and 115; SEQ ID NOs: 123, 124, and 125; and SEQ ID NOs: 133, 134 and 135.

In a further embodiment, the polypeptide can be an isolated polypeptide comprising, consisting essentially of, or consisting of a VL polypeptide at least 80%, 85%, 90% 95% or 100% identical to a reference VL polypeptide sequence selected from the group consisting of SEQ ID NOs: 12, 22, 32, 42, 52, 62, 72, 82, 92, 102, 112, 122, and 132. In certain embodiments, an antibody or antigen-binding fragment comprising the VL polypeptide specifically or preferentially binds to DR6.

In another aspect, the polypeptide can be an isolated polypeptide comprising, consisting essentially of, or consisting of a VL polypeptide selected from the group consisting of SEQ ID NOs: 12, 22, 32, 42, 52, 62, 72, 82, 92, 102, 112, 122, and 132. In certain embodiments, an antibody or antigen-binding fragment comprising the VL polypeptide specifically or preferentially binds to DR6.

In certain embodiments, an antibody or antigen-binding fragment thereof comprising, consisting essentially of, one or more of the VL polypeptides described above specifically or preferentially binds to the same DR6 epitope as a reference monoclonal Fab antibody fragment selected from the group consisting of M50-H01, M51-H09, M53-E04, M53-F04, M62-B02, M63-E10, M66-B03, M67-G02, M72-F03, and M73-C04 or a reference monoclonal antibody selected from the group consisting of 1P1D6.3, 1P2F2.1, and 1P5D10.2, or will competitively inhibit such a monoclonal antibody or fragment from binding to DR6.

In certain embodiments, an antibody or antigen-binding fragment thereof comprising, consisting essentially of, or consisting of a one or more of the VL polypeptides described above specifically or preferentially binds to a DR6 polypeptide or fragment thereof, or a DR6 variant polypeptide, with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^6$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In other embodiments, an antibody or antigen-binding fragment thereof comprises, consists essentially of or consists of a VH polypeptide, and a VL polypeptide, where the VH polypeptide and the VL polypeptide, respectively are at least 80%, 85%, 90% 95% or 100% identical to reference VH and VL polypeptide amino acid sequences selected from the group consisting of SEQ ID NOs: 7 and 12, 17 and 22, 27 and 32, 37 and 42, 47 and 52, 57 and 62, 67 and 72, 77 and 82, 87 and 92, 97 and 102, 107 and 112, 117 and 122 and 127 and 132. In certain embodiments, an antibody or antigen-binding fragment comprising these VH and VL polypeptides specifically or preferentially binds to DR6.

Any of the polypeptides described above can further include additional polypeptides, e.g., a signal peptide to direct secretion of the encoded polypeptide, antibody constant regions as described herein, or other heterologous polypeptides as described herein. Additionally, polypeptides include polypeptide fragments as described elsewhere. Additionally polypeptides include fusion polypeptide, Fab fragments, and other derivatives, as described herein.

Also, as described in more detail elsewhere herein, the present compositions include compositions comprising the polypeptides described above.

It will also be understood by one of ordinary skill in the art that DR6 antibody polypeptides as disclosed herein can be modified such that they vary in amino acid sequence from the naturally occurring binding polypeptide from which they were derived. For example, a polypeptide or amino acid sequence derived from a designated protein can be similar, e.g., have a certain percent identity to the starting sequence, e.g., it can be 60%, 70%, 75%, 80%, 85%, 90%, or 95% identical to the starting sequence.

Furthermore, nucleotide or amino acid substitutions, deletions, or insertions leading to conservative substitutions or changes at "non-essential" amino acid regions can be made. For example, a polypeptide or amino acid sequence derived from a designated protein can be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. A polypeptide or amino acid sequence derived from a designated protein can be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In other embodiments, a polypeptide or amino acid sequence derived from a designated protein can be identical to the starting sequence except for two or fewer, three or fewer, four or fewer, five or fewer, six or fewer, seven or fewer, eight or fewer, nine or fewer, ten or fewer, fifteen or fewer, or twenty or fewer individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

Certain DR6 antibody polypeptides comprise, consist essentially of, or consist of an amino acid sequence derived from a human amino acid sequence. However, certain DR6 antibody polypeptides comprise one or more contiguous amino acids derived from another mammalian species. For example, a DR6 antibody can include a primate heavy chain portion, hinge portion, or antigen binding region. In another example, one or more murine-derived amino acids can be present in a non-murine antibody polypeptide, e.g., in an antigen binding site of a DR6 antibody. In another example, the antigen binding site of a DR6 antibody is fully murine. In certain therapeutic applications, DR6-specific antibodies, or antigen-binding fragments, variants, or analogs thereof are designed so as to not be immunogenic in the animal to which the antibody is administered.

In certain embodiments, a DR6 antibody polypeptide comprises an amino acid sequence or one or more moieties not normally associated with an antibody. Exemplary modifications are described in more detail below. For example, a single-chain fv antibody fragment can comprise a flexible linker sequence, or can be modified to add a functional moiety (e.g., PEG, a drug, a toxin, or a label).

An DR6 antibody polypeptide can comprise, consist essentially of, or consist of a fusion protein. Fusion proteins are chimeric molecules which comprise, for example, an immunoglobulin antigen-binding domain with at least one target binding site, and at least one heterologous portion, i.e., a portion with which it is not naturally linked in nature. The amino acid sequences can normally exist in separate proteins that are brought together in the fusion polypeptide or they can normally exist in the same protein but are placed in a new arrangement in the fusion polypeptide. Fusion proteins can be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to a DR6 antibody, or an antigen-binding fragment, variant, or analog thereof is derived from a non-immunoglobulin polypeptide of the same species, or an immunoglobulin or non-immunoglobulin polypeptide of a different species.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide can be replaced with another amino acid residue from the same side chain family. In another embodiment, a string of amino acids can be replaced with a structurally similar string that differs in order and/or composition of side chain family members.

Alternatively, in another embodiment, mutations can be introduced randomly along all or part of the immunoglobulin coding sequence, such as by saturation mutagenesis, and the resultant mutants can be incorporated into DR6 antibodies for use in the diagnostic and treatment methods disclosed herein and screened for their ability to bind to the desired antigen, e.g., DR6.

Fusion Polypeptides and Antibodies

DR6 polypeptides and antibodies for use in the treatment methods disclosed herein can further be recombinantly fused to a heterologous polypeptide at the N- or C-terminus. For example, DR6 antagonist polypeptides or antibodies can be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

DR6 antagonist polypeptides and antibodies for use in the treatment methods disclosed herein can be composed of amino acids joined to each other by peptide bonds or modified peptide bonds, i.e., peptide isosteres, and can contain amino acids other than the 20 gene-encoded amino acids.

DR6 antagonists include fusion proteins comprising, consisting essentially of, or consisting of a DR6 antagonist polypeptide or antibody fusion that inhibits DR6 function. In certain embodiments, the heterologous polypeptide to which the DR6 antagonist polypeptide or antibody is fused is useful for function or is useful to target the DR6 antagonist polypeptide or antibody. In certain embodiments, a soluble DR6 antagonist polypeptide, e.g., a DR6 polypeptide comprising the extracellular domain (corresponding to amino acids 1 to 349 or 41 to 349 of SEQ ID NO: 2), or any other soluble DR6 polypeptide fragment, variant or derivative described herein, is fused to a heterologous polypeptide moiety to form a DR6 antagonist fusion polypeptide. DR6 antagonist fusion proteins and antibodies can be used to accomplish various objectives, e.g., increased serum half-life, improved bioavailability, in vivo targeting to a specific organ or tissue type, improved recombinant expression efficiency, improved host cell secretion, ease of purification, and higher avidity. Depending on the objective(s) to be achieved, the heterologous moiety can be inert or biologically active. Also, it can be chosen to be stably fused to the DR6 antagonist polypeptide or antibody or to be cleavable, in vitro or in vivo. Heterologous moieties to accomplish these other objectives are known in the art.

As an alternative to expression of a DR6 antagonist fusion polypeptide or antibody, a chosen heterologous moiety can be preformed and chemically conjugated to the DR6 antagonist polypeptide or antibody. In most cases, a chosen heterologous moiety will function similarly, whether fused or conjugated to the DR6 antagonist polypeptide or antibody. Therefore, in the following discussion of heterologous amino acid sequences, unless otherwise noted, it is to be understood that the heterologous sequence can be joined to the DR6 antagonist polypeptide or antibody in the form of a fusion protein or as a chemical conjugate.

Pharmacologically active polypeptides such as DR6 antagonist polypeptides or antibodies often exhibit rapid in vivo clearance, necessitating large doses to achieve therapeutically effective concentrations in the body. In addition, polypeptides smaller than about 60 kDa potentially undergo glomerular filtration, which sometimes leads to nephrotoxicity. Fusion or conjugation of relatively small polypeptides such as DR6 antagonist polypeptides or antibodies can be employed to reduce or avoid the risk of such nephrotoxicity. Various heterologous amino acid sequences, i.e., polypeptide moieties or "carriers," for increasing the in vivo stability, i.e., serum half-life, of therapeutic polypeptides are known.

Due to its long half-life, wide in vivo distribution, and lack of enzymatic or immunological function, essentially full-length human serum albumin (HSA), or an HSA fragment, is commonly used as a heterologous moiety. Through application of methods and materials such as those taught in Yeh et al., *Proc. Natl. Acad. Sci. USA* 89:1904-08 (1992) and Syed et al., *Blood* 89:3243-52 (1997), HSA can be used to form a DR6 antagonist fusion polypeptide or antibody or polypeptide/antibody conjugate that displays pharmacological activity by virtue of the DR6 moiety while displaying significantly increased in vivo stability, e.g., 10-fold to 100-fold higher. The C-terminus of the HSA can be fused to the N-terminus of the DR6 polypeptide. Since HSA is a naturally secreted protein, the HSA signal sequence can be exploited to obtain secretion of a soluble DR6 fusion protein into the cell culture medium when the fusion protein is produced in a eukaryotic, e.g., mammalian, expression system.

In certain embodiments, DR6 antagonist polypeptides or antibodies for use in the methods described herein further comprise a targeting moiety. Targeting moieties include a protein or a peptide which directs localization to a certain part of the body, for example, to the brain or compartments therein. In certain embodiments, DR6 antagonist polypeptides or antibody for use in the methods described herein are attached or fused to a brain targeting moiety. The brain targeting moieties are attached covalently (e.g., direct, translational fusion, or by chemical linkage either directly or through a spacer molecule, which can be optionally cleavable) or non-covalently attached (e.g., through reversible interactions such as avidin, biotin, protein A, IgG, etc.). In other embodiments, a DR6 antagonist polypeptide or antibody for use in the methods described herein is attached to one more brain targeting moieties. In additional embodiments, the brain targeting moiety is attached to a plurality of DR6 antagonist polypeptides or antibodies for use in the methods described herein.

A brain targeting moiety associated with a DR6 antagonist polypeptide or antibody enhances brain delivery of such a DR6 antagonist polypeptide or antibody. A number of polypeptides have been described which, when fused to a protein or therapeutic agent, delivers the protein or therapeutic agent through the blood brain barrier (BBB). Non-limiting examples include the single domain antibody FC5 (Abulrob et al. (2005) *J. Neurochem.* 95, 1201-1214); mAB 83-14, a monoclonal antibody to the human insulin receptor (Pardridge et al. (1995) *Pharmacol. Res.* 12, 807-816); the B2, B6 and B8 peptides binding to the human transferrin receptor (hTfR) (Xia et al. (2000) *J. Virol.* 74, 11359-11366); the OX26 monoclonal antibody to the transferrin receptor (Pardridge et al. (1991) *J. Pharmacol. Exp. Ther.* 259, 66-70); and SEQ ID NOs: 1-18 of U.S. Pat. No. 6,306,365. The contents of the above references are incorporated herein by reference in their entirety.

Enhanced brain delivery of a DR6 antagonist composition is determined by a number of means well established in the art. For example, administering to an animal a radioactively, enzymatically or fluorescently labeled DR6 antagonist polypeptide or antibody linked to a brain targeting moiety; determining brain localization; and comparing localization with an equivalent radioactively labeled DR6 antagonist polypeptide o antibody that is not associated with a brain targeting moiety. Other means of determining enhanced targeting are described in the above references.

The signal sequence is a polynucleotide that encodes an amino acid sequence that initiates transport of a protein across the membrane of the endoplasmic reticulum. Signal sequences useful for constructing an immunofusin include antibody light chain signal sequences, e.g., antibody 14.18 (Gillies et al., *J. Immunol. Meth.* 125:191-202 (1989)), antibody heavy chain signal sequences, e.g., the MOPC141 antibody heavy chain signal sequence (Sakano et al., *Nature* 286:5774 (1980)). Alternatively, other signal sequences can be used. See, e.g., Watson, *Nucl. Acids Res.* 12:5145 (1984). The signal peptide is usually cleaved in the lumen of the endoplasmic reticulum by signal peptidases. This results in the secretion of an immunofusin protein containing the Fc region and the DR6 polpeptide.

In some embodiments, the DNA sequence can encode a proteolytic cleavage site between the secretion cassette and the DR6 polypeptide. Such a cleavage site can provide, e.g., for the proteolytic cleavage of the encoded fusion protein, thus separating the Fc domain from the target protein. Useful proteolytic cleavage sites include amino acid sequences recognized by proteolytic enzymes such as trypsin, plasmin, thrombin, factor Xa, or enterokinase K.

The secretion cassette can be incorporated into a replicable expression vector. Useful vectors include linear nucleic acids, plasmids, phagemids, cosmids and the like. An exemplary expression vector is pdC, in which the transcription of the immunofusin DNA is placed under the control of the enhancer and promoter of the human cytomegalovirus. See, e.g., Lo et al., *Biochim. Biophys. Acta* 1088:712 (1991); and Lo et al., *Protein Engineering* 11:495-500 (1998). An appropriate host cell can be transformed or transfected with a DNA that encodes a DR6 polypeptide and used for the expression and secretion of the DR6 polypeptide. Host cells that are typically used include immortal hybridoma cells, myeloma cells, 293 cells, Chinese hamster ovary (CHO) cells, Hela cells, and COS cells.

In one embodiment, a DR6 polypeptide is fused to a hinge and Fc region, i.e., the C-terminal portion of an Ig heavy chain constant region. Potential advantages of a DR6-Fc fusion include solubility, in vivo stability, and multivalency, e.g., dimerization. The Fc region used can be an IgA, IgD, or IgG Fc region (hinge-$C_H2$-$C_H3$). Alternatively, it can be an IgE or IgM Fc region (hinge-$C_H2$-$C_H3$-$C_H4$). An IgG Fc region is generally used, e.g., an $IgG_1$ Fc region or $IgG_4$ Fc region. In one embodiment, a sequence beginning in the hinge region just upstream of the papain cleavage site which defines IgG Fc chemically (i.e. residue 216, taking the first residue of heavy chain constant region to be 114 according to the Kabat system), or analogous sites of other immunoglobulins is used in the fusion. The precise site at which the fusion is made is not critical; particular sites are well known and can be selected in order to optimize the biological activity, secretion, or binding characteristics of the molecule. Materials and methods for constructing and expressing DNA encoding Fc fusions are known in the art and can be applied to obtain DR6 fusions without undue experimentation. Some methods described herein employ a DR6 fusion protein such as those described in Capon et al., U.S. Pat. Nos. 5,428,130 and 5,565,335.

In some embodiments, fully intact, wild-type Fc regions display effector functions that can be unnecessary and undesired in an Fc fusion protein used in the methods described herein. Therefore, certain binding sites can be deleted from the Fc region during the construction of the secretion cassette. For example, since coexpression with the light chain is unnecessary, the binding site for the heavy chain binding protein, Bip (Hendershot et al., *Immunol. Today* 8:111-14 (1987)), is deleted from the $C_H2$ domain of the Fc region of IgE, such that this site does not interfere with the efficient secretion of the immunofusin. Transmembrane domain sequences, such as those present in IgM, also are generally deleted.

In certain embodiments, the $IgG_1$ Fc region is used. Alternatively, the Fc region of the other subclasses of immunoglobulin gamma (gamma-2, gamma-3 and gamma-4) can be used in the secretion cassette. The $IgG_1$ Fc region of immunoglobulin gamma-1 includes at least part of the hinge region, the $C_H2$ region, and the $C_H3$ region. In some embodiments, the Fc region of immunoglobulin gamma-1 is a $C_H2$-deleted-Fc, which includes part of the hinge region and the $C_H3$ region, but not the $C_H2$ region. A $C_H2$-deleted-Fc has been described by Gillies et al., *Hum. Antibod. Hybridomas* 1:47 (1990). In some embodiments, the Fc region of one of IgA, IgD, IgE, or IgM, is used.

DR6-Fc fusion proteins can be constructed in several different configurations. In one configuration the C-terminus of the DR6 polypeptide is fused directly to the N-terminus of the Fc hinge moiety. In a slightly different configuration, a short polypeptide, e.g., 2-10 amino acids, is incorporated into the fusion between the N-terminus of the DR6 moiety and the C-terminus of the Fc moiety. Such a linker provides conformational flexibility, which can improve biological activity in some circumstances. If a sufficient portion of the hinge region is retained in the Fc moiety, the DR6-Fc fusion will dimerize, thus forming a divalent molecule. A homogeneous population of monomeric Fc fusions will yield monospecific, bivalent dimers. A mixture of two monomeric Fc fusions each having a different specificity will yield bispecific, bivalent dimers.

Soluble DR6 polypeptides can be fused to heterologous peptides to facilitate purification or identification of the soluble DR6 moiety. For example, a histidine tag can be fused to a soluble DR6 polypeptide to facilitate purification using commercially available chromatography media.

A "linker" sequence is a series of one or more amino acids separating two polypeptide coding regions in a fusion protein. A typical linker comprises at least 5 amino acids. Additional linkers comprise at least 10 or at least 15 amino acids. In certain embodiments, the amino acids of a peptide linker are selected so that the linker is hydrophilic. The linker (Gly-Gly-Gly-Gly-Ser)$_3$ ($G_4S$)$_3$ (SEQ ID NO:136) is a useful linker that is widely applicable to many antibodies as it provides sufficient flexibility. Other linkers include (Gly-Gly-Gly-Gly-Ser)$_2$ ($G_4S$)$_2$ (SEQ ID NO:137), Glu Ser Gly Arg Ser Gly Gly Gly Gly Ser Gly Gly Gly Gly Gly Gly Ser (SEQ ID NO:138), Glu Gly Lys Ser Ser Gly Ser Gly Ser Glu Ser Lys Ser Thr (SEQ ID NO:139), Glu Gly Lys Ser Ser Gly Ser Gly Ser Glu Ser Lys Ser Thr Gln (SEQ ID NO:140), Glu Gly Lys Ser Ser Gly Ser Gly Ser Glu Ser Lys Val Asp (SEQ ID NO:141), Gly Ser Thr Ser Gly Ser Gly Lys Ser Ser Glu Gly Lys Gly (SEQ ID NO:142), Lys Glu Ser Gly Ser Val Ser Ser Glu Gln Leu Ala Gln Phe Arg Ser Leu Asp (SEQ ID NO:143), and Glu Ser Gly Ser Val Ser Ser Glu Glu Leu Ala Phe Arg Ser Leu Asp (SEQ ID NO:144). Examples of shorter linkers include fragments of the above linkers, and examples of longer linkers include combinations of the linkers above, combinations of fragments of the linkers above, and combinations of the linkers above with fragments of the linkers above.

DR6 polypeptides can be fused to a polypeptide tag. The term "polypeptide tag," as used herein, is intended to mean any sequence of amino acids that can be attached to, connected to, or linked to a DR6 polypeptide and that can be used to identify, purify, concentrate or isolate the DR6 polypeptide. The attachment of the polypeptide tag to the DR6 polypeptide can occur, e.g., by constructing a nucleic acid molecule that comprises: (a) a nucleic acid sequence that encodes the polypeptide tag, and (b) a nucleic acid sequence that encodes a DR6 polypeptide. Exemplary polypeptide tags include, e.g., amino acid sequences that are capable of being post-translationally modified, e.g., amino acid sequences that are biotinylated. Other exemplary polypeptide tags include, e.g., amino acid sequences that are capable of being recognized and/or bound by an antibody (or fragment thereof) or other specific binding reagent. Polypeptide tags that are capable of being recognized by an antibody (or fragment thereof) or other specific binding reagent include, e.g., those that are known in the art as "epitope tags." An epitope tag can be a natural or an artificial epitope tag. Natural and artificial epitope tags are known in the art, including, e.g., artificial epitopes such as FLAG, Strep, or poly-histidine peptides. FLAG peptides include the sequence Asp-Tyr-Lys-Asp-Asp-Asp-Asp-Lys (SEQ ID NO:145) or Asp-Tyr-Lys-Asp-Glu-Asp-Asp-Lys (SEQ ID NO:146) (Einhauer, A. and Jungbauer, A., J. Biochem. Biophys. Methods 49:1-3:455-465 (2001)). The Strep epitope has the sequence Ala-Trp-Arg-His-Pro-Gln-Phe-Gly-Gly (SEQ ID NO:147). The VSV-G epitope can also be used and has the sequence Tyr-Thr-Asp-Ile-Glu-Met-Asn-Arg-Leu-Gly-Lys (SEQ ID NO:148). Another artificial epitope is a poly-His sequence having six histidine residues (His-His-His-His-His-His) (SEQ ID NO:149). Naturally-occurring epitopes include the influenza virus hemagglutinin (HA) sequence Tyr-Pro-Tyr-Asp-Val-Pro-Asp-Tyr-Ala-Ile-Glu-Gly-Arg (SEQ ID NO:150) recognized by the monoclonal antibody 12CA5 (Murray et al., *Anal. Biochem.* 229:170-179 (1995)) and the eleven amino acid sequence from human c-myc (Myc) recognized by the monoclonal antibody 9E10 (Glu-Gln-Lys-Leu-Leu-Ser-Glu-Glu-Asp-Leu-Asn) (SEQ ID NO:151) (Manstein et al., *Gene* 162:129-134 (1995)). Another useful epitope is the tripeptide Glu-Glu-Phe which is recognized by the monoclonal antibody YL 1/2. (Stammers et al. *FEBS Lett.* 283:298-302 (1991)).

In certain embodiments, the DR6 polypeptide and the polypeptide tag can be connected via a linking amino acid sequence. As used herein, a "linking amino acid sequence" can be an amino acid sequence that is capable of being recognized and/or cleaved by one or more proteases. Amino acid sequences that can be recognized and/or cleaved by one or more proteases are known in the art. Exemplary amino acid sequences are those that are recognized by the following proteases: factor VIIa, factor IXa, factor Xa, APC, t-PA, u-PA, trypsin, chymotrypsin, enterokinase, pepsin, cathepsin B, H, L, S, D, cathepsin G, renin, angiotensin converting enzyme, matrix metalloproteases (collagenases, stromelysins, gelatinases), macrophage elastase, Cir, and Cis. The amino acid sequences that are recognized by the aforementioned proteases are known in the art. Exemplary sequences recognized by certain proteases can be found, e.g., in U.S. Pat. No. 5,811,252.

In some methods, a soluble DR6 fusion construct is used to enhance the production of a soluble DR6 moiety in bacteria. In such constructs a bacterial protein normally expressed and/or secreted at a high level is employed as the N-terminal fusion partner of a soluble DR6 polypeptide. See, e.g., Smith et al., Gene 67:31 (1988); Hopp et al., Biotechnology 6:1204 (1988); La Vallie et al., Biotechnology 11:187 (1993).

By fusing a soluble DR6 moiety at the amino and carboxy termini of a suitable fusion partner, bivalent or tetravalent forms of a soluble DR6 polypeptide can be obtained. For example, a soluble DR6 moiety can be fused to the amino and carboxy termini of an Ig moiety to produce a bivalent monomeric polypeptide containing two soluble DR6 moieties. Upon dimerization of two of these monomers, by virtue of the Ig moiety, a tetravalent form of a soluble DR6 protein is obtained. Such multivalent forms can be used to achieve increased binding affinity for the target. Multivalent forms of soluble DR6 also can be obtained by placing soluble DR6 moieties in tandem to form concatamers, which can be employed alone or fused to a fusion partner such as Ig or HSA.

DR6 Antagonist Conjugates

DR6 antagonist polypeptides and antibodies for use in the treatment methods disclosed herein include derivatives that are modified, i.e., by the covalent attachment of any type of molecule such that covalent attachment does not prevent the DR6 antagonist polypeptide or antibody from inhibiting the biological function of DR6. For example, but not by way of limitation, the DR6 antagonist polypeptides and antibodies can be modified e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc. Additionally, the derivative can contain one or more non-classical amino acids.

DR6 antagonist polypeptides and antibodies can be modified by natural processes, such as posttranslational processing, or by chemical modification techniques which are well known in the art. Such modifications are well described in basic texts and in more detailed monographs, as well as in a voluminous research literature. Modifications can occur anywhere in the DR6 antagonist polypeptide or antibody, including the peptide backbone, the amino acid side-chains and the amino or carboxyl termini, or on moieties such as carbohydrates. It will be appreciated that the same type of modification can be present in the same or varying degrees at several sites in a given DR6 antagonist polypeptide or antibody. Also, a given DR6 antagonist polypeptide or antibody can contain many types of modifications. DR6 antagonist polypeptides or antibodies can be branched, for example, as a result of ubiquitination, and they can be cyclic, with or without branching. Cyclic, branched, and branched cyclic DR6 antagonist polypeptides and antibodies can result from posttranslation natural processes or can be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties*, T. E. Creighton, W.H. Freeman and Company, New York 2nd Ed., (1993); *Posttranslational Covalent Modification Of Proteins*, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

Any of a number of cross-linkers that contain a corresponding amino-reactive group and thiol-reactive group can be used to link DR6 antagonist polypeptides to a heterologous fusion partner. Examples of suitable linkers include amine reactive cross-linkers that insert a thiol-reactive maleimide, e.g., SMCC, AMAS, BMPS, MBS, EMCS, SMPB, SMPH, KMUS, and GMBS. Other suitable linkers insert a thiol-reactive haloacetate group, e.g., SBAP, SIA, STAB. Linkers that provide a protected or non-protected thiol for reaction with sulfhydryl groups to product a reducible linkage include SPDP, SMPT, SATA, and SATP. Such reagents are commercially available (e.g., Pierce Chemicals).

Conjugation does not have to involve the N-terminus of a soluble DR6 polypeptide or the thiol moiety on serum albumin. For example, soluble DR6-albumin fusions can be obtained using genetic engineering techniques, wherein the soluble DR6 moiety is fused to the serum albumin gene at its N-terminus, C-terminus, or both.

Soluble DR6 polypeptides or DR6 antibodies can be polypeptides or antibodies wherein one or more polymers are conjugated (covalently linked) to the DR6 polypeptide or antibody. Examples of polymers suitable for such conjugation include polypeptides (discussed above), sugar polymers and polyalkylene glycol chains. Typically, but not necessarily, a polymer is conjugated to the soluble DR6 polypeptide or DR6 antibody for the purpose of improving one or more of the following: solubility, stability, or bioavailability.

The class of polymer generally used for conjugation to a DR6 antagonist polypeptide or antibody is a polyalkylene glycol. Polyethylene glycol (PEG) is most frequently used. PEG moieties, e.g., 1, 2, 3, 4 or 5 PEG polymers, can be conjugated to each DR6 antagonist polypeptide or antibody to increase serum half life, as compared to the DR6 antagonist polypeptide or antibody alone. PEG moieties are non-antigenic and essentially biologically inert. PEG moieties can be branched or unbranched.

The number of PEG moieties attached to the DR6 antagonist polypeptide or antibody and the molecular weight of the individual PEG chains can vary. In general, the higher the molecular weight of the polymer, the fewer polymer chains attached to the polypeptide. Usually, the total polymer mass attached to the DR6 antagonist polypeptide or antibody is from 20 kDa to 40 kDa. Thus, if one polymer chain is attached, the molecular weight of the chain is generally 20-40 kDa. If two chains are attached, the molecular weight of each chain is generally 10-20 kDa. If three chains are attached, the molecular weight is generally 7-14 kDa.

The polymer, e.g., PEG, can be linked to the DR6 antagonist polypeptide or antibody through any suitable, exposed reactive group on the polypeptide. The exposed reactive group(s) can be, e.g., an N-terminal amino group or the epsilon amino group of an internal lysine residue, or both. An activated polymer can react and covalently link at any free amino group on the DR6 antagonist polypeptide or antibody. Free carboxylic groups, suitably activated carbonyl groups, hydroxyl, guanidyl, imidazole, oxidized carbohydrate moieties and mercapto groups of the DR6 antagonist polypeptide or antibody (if available) also can be used as reactive groups for polymer attachment.

In a conjugation reaction, from about 1.0 to about 10 moles of activated polymer per mole of polypeptide, depending on polypeptide concentration, is typically employed. Usually, the ratio chosen represents a balance between maximizing the reaction while minimizing side reactions (often non-specific) that can impair the desired pharmacological activity of the DR6 antagonist polypeptide or antibody. In certain embodiments, at least 50% of the biological activity (as demonstrated, e.g., in any of the assays described herein or known in the art) of the DR6 antagonist polypeptide or antibody is retained. In further embodiments, nearly 100% is retained.

The polymer can be conjugated to the DR6 antagonist polypeptide or antibody using conventional chemistry. For example, a polyalkylene glycol moiety can be coupled to a lysine epsilon amino group of the DR6 antagonist polypeptide or antibody. Linkage to the lysine side chain can be performed with an N-hydroxylsuccinimide (NHS) active ester such as PEG succinimidyl succinate (SS-PEG) and succinimidyl propionate (SPA-PEG). Suitable polyalkylene glycol moieties include, e.g., carboxymethyl-NHS and norleucine-NHS, SC. These reagents are commercially available. Additional amine-reactive PEG linkers can be substituted for the succinimidyl moiety. These include, e.g., isothiocyanates, nitrophenylcarbonates (PNP), epoxides, benzotriazole carbonates, SC-PEG, tresylate, aldehyde, epoxide, carbonylimidazole and PNP carbonate. Conditions are usually optimized to maximize the selectivity and extent of reaction. Such optimization of reaction conditions is within ordinary skill in the art.

PEGylation can be carried out by any of the PEGylation reactions known in the art. See, e.g., *Focus on Growth Factors* 3:4-10 (1992), and European patent applications EP0154316 and EP0401384. PEGylation can be carried out using an acylation reaction or an alkylation reaction with a reactive polyethylene glycol molecule (or an analogous reactive water-soluble polymer).

PEGylation by acylation generally involves reacting an active ester derivative of polyethylene glycol. Any reactive PEG molecule can be employed in the PEGylation. PEG esterified to N-hydroxysuccinimide (NHS) is a frequently used activated PEG ester. As used herein, "acylation" includes without limitation the following types of linkages between the therapeutic protein and a water-soluble polymer such as PEG: amide, carbamate, urethane, and the like. See, e.g., *Bioconjugate Chem.* 5:133-140, 1994. Reaction parameters are generally selected to avoid temperature, solvent, and pH conditions that would damage or inactivate the soluble DR6 polypeptide.

Generally, the connecting linkage is an amide and typically at least 95% of the resulting product is mono-, di- or tri-PEGylated. However, some species with higher degrees of PEGylation can be formed in amounts depending on the specific reaction conditions used. Optionally, purified PEGylated species are separated from the mixture, particularly unreacted species, by conventional purification methods, including, e.g., dialysis, salting-out, ultrafiltration, ion-exchange chromatography, gel filtration chromatography, hydrophobic exchange chromatography, and electrophoresis.

PEGylation by alkylation generally involves reacting a terminal aldehyde derivative of PEG with DR6 antagonist polypeptide or antibody in the presence of a reducing agent. In addition, one can manipulate the reaction conditions to favor PEGylation substantially only at the N-terminal amino group of a DR6 antagonist polypeptide or antibody, i.e. a mono-PEGylated protein. In either case of mono-PEGylation or poly-PEGylation, the PEG groups are typically attached to the protein via a —$C_H2$-NH— group. With particular reference to the —$C_H2$-group, this type of linkage is known as an "alkyl" linkage.

Derivatization via reductive alkylation to produce an N-terminally targeted mono-PEGylated product exploits differential reactivity of different types of primary amino groups (lysine versus the N-terminal) available for derivatization. The reaction is performed at a pH that allows one to take advantage of the pKa differences between the epsilon-amino groups of the lysine residues and that of the N-terminal amino group of the protein. By such selective derivatization, attachment of a water-soluble polymer that contains a reactive group, such as an aldehyde, to a protein is controlled: the conjugation with the polymer takes place predominantly at the N-terminus of the protein and no significant modification of other reactive groups, such as the lysine side chain amino groups, occurs.

The polymer molecules used in both the acylation and alkylation approaches are selected from among water-soluble polymers. The polymer selected is typically modified to have a single reactive group, such as an active ester for acylation or an aldehyde for alkylation, so that the degree of polymerization can be controlled as provided for in the present methods. An exemplary reactive PEG aldehyde is polyethylene glycol propionaldehyde, which is water stable, or mono C1-C10 alkoxy or aryloxy derivatives thereof (see, e.g., Harris et al., U.S. Pat. No. 5,252,714). The polymer can be branched or unbranched. For the acylation reactions, the polymer(s) selected typically have a single reactive ester group. For reductive alkylation, the polymer(s) selected typically have a single reactive aldehyde group. Generally, the water-soluble polymer will not be selected from naturally occurring glycosyl residues, because these are usually made more conveniently by mammalian recombinant expression systems.

Methods for preparing a PEGylated soluble DR6 polypeptide or antibody generally includes the steps of (a) reacting a DR6 antagonist polypeptide or antibody with polyethylene glycol (such as a reactive ester or aldehyde derivative of PEG) under conditions whereby the molecule becomes attached to one or more PEG groups, and (b) obtaining the reaction product(s). In general, the optimal reaction conditions for the acylation reactions will be determined case-by-case based on known parameters and the desired result. For example, a larger the ratio of PEG to protein, generally leads to a greater the percentage of poly-PEGylated product.

Reductive alkylation to produce a substantially homogeneous population of mono-polymer/soluble DR6 polypeptide or DR6 antibody generally includes the steps of: (a) reacting a soluble DR6 protein or polypeptide with a reactive PEG molecule under reductive alkylation conditions, at a pH suitable to permit selective modification of the N-terminal amino group of the polypeptide or antibody; and (b) obtaining the reaction product(s).

For a substantially homogeneous population of monopolymer/soluble DR6 polypeptide or DR6 antibody, the reductive alkylation reaction conditions are those that permit the selective attachment of the water-soluble polymer moiety to the N-terminus of the polypeptide or antibody. Such reaction conditions generally provide for pKa differences between the lysine side chain amino groups and the N-terminal amino group. For purposes described herein, the pH is generally in the range of 3-9, typically 3-6.

Soluble DR6 polypeptides or antibodies can include a tag, e.g., a moiety that can be subsequently released by proteolysis. Thus, the lysine moiety can be selectively modified by first reacting a His-tag modified with a low-molecular-weight linker such as Traut's reagent (Pierce) which will react with both the lysine and N-terminus, and then releasing the His tag. The polypeptide will then contain a free SH group that can be selectively modified with a PEG containing a thiol-reactive head group such as a maleimide group, a vinylsulfone group, a haloacetate group, or a free or protected SH.

Traut's reagent can be replaced with any linker that will set up a specific site for PEG attachment. For example, Traut's reagent can be replaced with SPDP, SMPT, SATA, or SATP (Pierce). Similarly one could react the protein with an amine-reactive linker that inserts a maleimide (for example SMCC, AMAS, BMPS, MBS, EMCS, SMPB, SMPH, KMUS, or GMBS), a haloacetate group (SBAP, SIA, SIAB), or a vinylsulfone group and react the resulting product with a PEG that contains a free SH.

In some embodiments, the polyalkylene glycol moiety is coupled to a cysteine group of the DR6 antagonist polypeptide or antibody. Coupling can be effected using, e.g., a maleimide group, a vinylsulfone group, a haloacetate group, or a thiol group.

Optionally, the soluble DR6 polypeptide or antibody is conjugated to the polyethylene-glycol moiety through a labile bond. The labile bond can be cleaved in, e.g., biochemical hydrolysis, proteolysis, or sulfhydryl cleavage. For example, the bond can be cleaved under in vivo (physiological) conditions.

The reactions can take place by any suitable method used for reacting biologically active materials with inert polymers, generally at about pH 5-8, e.g., pH 5, 6, 7, or 8, if the reactive groups are on the alpha amino group at the N-terminus. Generally the process involves preparing an activated polymer and thereafter reacting the protein with the activated polymer to produce the soluble protein suitable for formulation.

In some embodiments, the antibodies or polypeptides are fusion proteins comprising a DR6 antibody, or antigen-binding fragment, variant, or derivative thereof, and a heterologous polypeptide. The heterologous polypeptide to which the antibody is fused can be useful for function or is useful to target the DR6 polypeptide expressing cells. In one embodiment, a fusion protein comprises, consists essentially of, or consists of, a polypeptide having the amino acid sequence of any one or more of the VH regions of an antibody or the amino acid sequence of any one or more of the VL regions of an antibody or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the VH-CDRs of a DR6-specific antibody, or fragments, variants, or derivatives thereof; or the amino acid sequence of any one, two, three of the VL-CDRs of a DR6-specific antibody, or fragments, variants, or derivatives thereof, and a heterologous polypeptide sequence. In one embodiment, the fusion protein comprises a polypeptide having the amino acid sequence of a VH-CDR3 of a DR6-specific antibody, or fragment, derivative, or variant thereof, and a heterologous polypeptide sequence, which fusion protein specifically binds to at least one epitope of DR6. In another embodiment, a fusion protein comprises a polypeptide having the amino acid sequence of at least one VH region of a DR6-specific antibody and the amino acid sequence of at least one VL region of a DR6-specific antibody or fragments, derivatives or variants thereof, and a heterologous polypeptide sequence. In one embodiment, the VH and VL regions of the fusion protein correspond to a single source antibody (or scFv or Fab fragment) which specifically binds at least one epitope of DR6. In yet another embodiment, a fusion protein for use in the diagnostic and treatment methods disclosed herein comprises a polypeptide having the amino acid sequence of any one, two, three or more of the VH CDRs of a DR6-specific antibody and the amino acid sequence of any one, two, three or more of the VL CDRs of a DR6-specific antibody, or fragments or variants thereof, and a heterologous polypeptide sequence. In some embodiments, two, three, four, five, six, or more of the VH-CDR(s) or VL-CDR(s) correspond to single source antibody (or scFv or Fab fragment). Nucleic acid molecules encoding these fusion proteins are also encompassed.

DR6 Polynucleotide Antagonists

Specific embodiments comprise a method of promoting nervous system cell survival by contacting the cells with a DR6 polynucleotide antagonist. The polynucleotide antagonist can be any polynucleotide that encodes a DR6-antagonist polypeptide. The polynuceotide antagonist can also be a nucleic acid molecule which specifically binds to a polynucleotide which encodes DR6. The DR6 polynucleotide antagonist prevents expression of DR6 (knockdown). In certain embodiments, the DR6 polynucleotide antagonist promotes nervous system cell survival or inhibits nervous system cell apoptosis. DR6 polynucleotide antagonists include, but are not limited to antisense molecules, ribozymes, siRNA, shRNA and RNAi. Typically, such binding molecules are separately administered to the animal (see, for example, O'Connor, *J. Neurochem.* 56:560 (1991), but such binding molecules can also be expressed in vivo from polynucleotides taken up by a host cell and expressed in vivo. See also Oligodeoxynucleotides as Antisense Inhibitors of Gene Expression, CRC Press, Boca Raton, Fla. (1988).

RNAi refers to the expression of an RNA which interferes with the expression of the targeted mRNA. Specifically, the RNAi silences a targeted gene via interacting with the specific mRNA (e.g. DR6) through a siRNA (short interfering RNA). The ds RNA complex is then targeted for degradation by the cell. Additional RNAi molecules include Short hairpin RNA (shRNA); also short interfering hairpin. The shRNA molecule contains sense and antisense sequences from a target gene connected by a loop. The shRNA is transported from the nucleus into the cytoplasm, it is degraded along with the mRNA. Pol III or U6 promoters can be used to express RNAs for RNAi.

RNAi is mediated by double stranded RNA (dsRNA) molecules that have sequence-specific homology to their "target" mRNAs (Caplen et al., *Proc Natl Acad Sci USA* 98:9742-9747, 2001). Biochemical studies in *Drosophila* cell-free lysates indicates that the mediators of RNA-dependent gene silencing are 21-25 nucleotide "small interfering" RNA duplexes (siRNAs). Accordingly, siRNA molecules are advantageously used in the methods described herein. The siRNAs are derived from the processing of dsRNA by an RNase known as DICER (Bernstein et al., *Nature* 409:363-366, 2001). It appears that siRNA duplex products are recruited into a multi-protein siRNA complex termed RISC (RNA Induced Silencing Complex). Without wishing to be bound by any particular theory, it is believed that a RISC is guided to a target mRNA, where the siRNA duplex interacts sequence-specifically to mediate cleavage in a catalytic fashion (Bernstein et al., *Nature* 409:363-366, 2001; Boutla et al., *Curr Biol* 11:1776-1780, 2001).

RNAi has been used to analyze gene function and to identify essential genes in mammalian cells (Elbashir et al., *Methods* 26:199-213, 2002; Harborth et al., *J Cell Sci* 114:4557-4565, 2001), including by way of non-limiting example neurons (Krichevsky et al., *Proc Natl Acad Sci USA* 99:11926-11929, 2002). RNAi is also being evaluated for therapeutic modalities, such as inhibiting or blocking the infection, replication and/or growth of viruses, including without limitation poliovirus (Gitlin et al., *Nature* 418:379-380, 2002) and HIV (Capodici et al., *J Immunol* 169:5196-5201, 2002), and reducing expression of oncogenes (e.g., the bcr-abl gene; Scherr et al., *Blood* Sep. 26 epub ahead of print, 2002). RNAi has been used to modulate gene expression in mammalian (mouse) and amphibian (*Xenopus*) embryos (respectively, Calegari et al., *Proc Natl Acad Sci USA* 99:14236-14240, 2002; and Zhou, et al., *Nucleic Acids Res* 30:1664-1669, 2002), and in postnatal mice (Lewis et al., *Nat Genet* 32:107-108, 2002), and to reduce trangsene expression in adult transgenic mice (McCaffrey et al., *Nature* 418:38-39, 2002). Methods have been described for determining the efficacy and specificity of siRNAs in cell culture and in vivo (see, e.g., Bertrand et al., *Biochem Biophys Res Commun* 296:1000-1004, 2002; Lassus et al., *Sci STKE* 2002(147):PL13, 2002; and Leirdal et al., *Biochem Biophys Res Commun* 295:744-748, 2002).

Molecules that mediate RNAi, including without limitation siRNA, can be produced in vitro by chemical synthesis (Hohjoh, *FEBS Lett* 521:195-199, 2002), hydrolysis of dsRNA (Yang et al., *Proc Natl Acad Sci USA* 99:9942-9947, 2002), by in vitro transcription with T7 RNA polymerase (Donzeet et al., *Nucleic Acids Res* 30:e46, 2002; Yu et al., *Proc Natl Acad Sci USA* 99:6047-6052, 2002), and by hydrolysis of double-stranded RNA using a nuclease such as *E. coli* RNase III (Yang et al., *Proc Natl Acad Sci USA* 99:9942-9947, 2002).

siRNA molecules can also be formed by annealing two oligonucleotides to each other, typically have the following general structure, which includes both double-stranded and single-stranded portions:

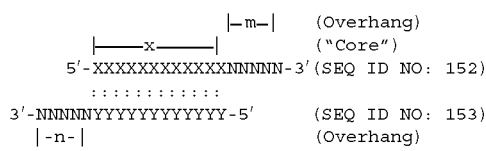

Wherein N, X and Y are nucleotides; X hydrogen bonds to Y; ":" signifies a hydrogen bond between two bases; x is a natural integer having a value between 1 and about 100; and m and n are whole integers having, independently, values between 0 and about 100. In some embodiments, N, X and Y are independently A, G, C and T or U. Non-naturally occurring bases and nucleotides can be present, particularly in the case of synthetic siRNA (i.e., the product of annealing two oligonucleotides). The double-stranded central section is called the "core" and has base pairs (bp) as units of measurement; the single-stranded portions are overhangs, having nucleotides (nt) as units of measurement. The overhangs shown are 3' overhangs, but molecules with 5' overhangs are also contemplated. Also contemplated are siRNA molecules with no overhangs (i.e., m=0 and n=0), and those having an overhang on one side of the core but not the other (e.g., m=0 and n≧1, or vice-versa).

Initially, RNAi technology did not appear to be readily applicable to mammalian systems. This is because, in mammals, dsRNA activates dsRNA-activated protein kinase (PKR) resulting in an apoptotic cascade and cell death (Der et al, *Proc. Natl. Acad. Sci. USA* 94:3279-3283, 1997). In addition, it has long been known that dsRNA activates the interfeDR6 cascade in mammalian cells, which can also lead to altered cell physiology (Colby et al, *Annu. Rev. Microbiol.* 25:333, 1971; Kleinschmidt et al., *Annu. Rev. Biochem.* 41:517, 1972; Lampson et al., *Proc. Natl. Acad. Sci. USA* 58L782, 1967; Lomniczi et al., *J. Gen. Virol.* 8:55, 1970; and Younger et al., *J. Bacteriol.* 92:862, 1966). However, dsRNA-mediated activation of the PKR and interfeDR6 cascades requires dsRNA longer than about 30 base pairs. In contrast, dsRNA less than 30 base pairs in length has been demonstrated to cause RNAi in mammalian cells (Caplen et al., *Proc. Natl. Acad. Sci. USA* 98:9742-9747, 2001). Thus, it is expected that undesirable, non-specific effects associated with longer dsRNA molecules can be avoided by preparing short RNA that is substantially free from longer dsRNAs.

References regarding siRNA: Bernstein et al., *Nature* 409:363-366, 2001; Boutla et al., *Curr Biol* 11:1776-1780, 2001; Cullen, *Nat Immunol.* 3:597-599, 2002; Caplen et al., *Proc Natl Acad Sci USA* 98:9742-9747, 2001; Hamilton et al., *Science* 286:950-952, 1999; Nagase et al., *DNA Res.* 6:63-70, 1999; Napoli et al., *Plant Cell* 2:279-289, 1990; Nicholson et al., *Mamm. Genome* 13:67-73, 2002; Parrish et al., *Mol Cell* 6:1077-1087, 2000; Romano et al., *Mol Microbiol* 6:3343-3353, 1992; Tabara et al., *Cell* 99:123-132, 1999; and Tuschl, *Chembiochem.* 2:239-245, 2001.

Paddison et al. (*Genes & Dev.* 16:948-958, 2002) have used small RNA molecules folded into hairpins as a means to effect RNAi. Accordingly, such short hairpin RNA (shRNA) molecules are also advantageously used in the methods described herein. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the dsRNA products of the DICER RNase and, in any event, have the same capacity for inhibiting expression of a specific gene. The shRNA can be expressed from a lentiviral vector (e.g., pLL3.7).

Antisense technology can be used to control gene expression through antisense DNA or RNA, or through triple-helix formation. Antisense techniques are discussed for example, in Okano, *J. Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the 5' coding portion of a polynucleotide that encodes DR6 can be used to design an antisense RNA oligonucleotide of from about 10 to 40 base pairs in length. A DNA oligonucleotide is designed to be complementary to a region of the gene involved in transcription thereby preventing transcription and the production of the target protein. The antisense RNA oligonucleotide hybridizes to the mRNA in vivo and blocks translation of the mRNA molecule into the target polypeptide.

In one embodiment, antisense nucleic acids specific for the DR6 gene are produced intracellularly by transcription from an exogenous sequence. For example, a vector or a portion thereof, is transcribed, producing an antisense nucleic acid (RNA). Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the antisense molecule can be by any promoter known in the art to act in vertebrate, e.g., human cells, such as those described elsewhere herein.

Absolute complementarity of an antisense molecule is not required. A sequence complementary to at least a portion of an RNA encoding DR6, means a sequence having sufficient complementarity to be able to hybridize with the RNA, forming a stable duplex; or triplex. The ability to hybridize will depend on both the degree of complementarity and the length of the antisense nucleic acid. Generally, the larger the hybridizing nucleic acid, the more base mismatches it can contain and still form a stable duplex (or triplex as the case can be). One skilled in the art can ascertain a tolerable degree of mismatch by use of standard procedures to determine the melting point of the hybridized complex.

Oligonucleotides that are complementary to the 5' end of a messenger RNA, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature* 372:333-335 (1994). Thus, oligonucleotides complementary to either the 5'- or 3'-non-translated, non-coding regions could be used in an antisense approach to inhibit translation of DR6. Oligonucleotides complementary to the 5' untranslated region of the mRNA should include the complement of the AUG start codon. Antisense oligonucleotides complementary to mRNA coding regions are less efficient inhibitors of translation but could be used in accordance with the methods described herein. Antisense nucleic acids are typically at least six nucleotides in length and include, for example, oligonucleotides ranging from 6 to about 50 nucleotides in length. In specific aspects the oligonucleotide is at least 10 nucleotides, at least 17 nucleotides, at least 25 nucleotides or at least 50 nucleotides.

Polynucleotides for use the therapeutic methods disclosed herein can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide can include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553-6556 (1989); Lemaitre et al., *Proc. Natl. Acad. Sci.* 84:648-652 (1987)); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., *BioTechniques* 6:958-976 (1988)) or intercalating agents. (See, e.g., Zon, *Pharm. Res.* 5:539-549 (1988)). To this end, the oligonucleotide can be conjugated to another molecule, e.g., a peptide, hybridization triggered cross-linking agent, transport agent, hybridization-triggered cleavage agent, etc.

An antisense oligonucleotide for use in the therapeutic methods disclosed herein can comprise at least one modified base moiety such as, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methylcytosine, N-6-adenine, 7-methylguanine, 5-methylaminomethyluracil, 5-methoxyaminomethyl-2-thiouracil, beta-D-mannosylqueosine, 5' methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3(3-amino-3-N2-carboxypropyl)uracil, (acp3)w, and 2,6-diaminopurine.

An antisense oligonucleotide for use in the therapeutic methods disclosed herein can also comprise at least one modified sugar moiety selected from the group including, but not limited to, arabinose, 2-fluoroarabinose, xylulose, and hexose.

In yet another embodiment, an antisense oligonucleotide for use in the therapeutic methods disclosed herein comprises at least one modified phosphate backbone such as, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, an antisense oligonucleotide for use in the therapeutic methods disclosed herein is an α-anomeric oligonucleotide. An α-anomeric oligonucleotide forms specific double-stranded hybrids with complementary RNA in which, contrary to the usual situation, the strands run parallel to each other (Gautier et al., *Nucl. Acids Res.* 15:6625-6641 (1987)). The oligonucleotide is a 2'-0-methylribonucleotide (Inoue et al., *Nucl. Acids Res.* 15:6131-6148 (1987)), or a chimeric RNA-DNA analogue (Inoue et al., *FEBS Lett.* 215:327-330 (1987)).

Polynucleotides can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al., *Nucl. Acids Res.* 16:3209 (1988), methylphosphonate oligonucleotides can be prepared by use of controlled pore glass polymer supports (Sarin et al., *Proc. Natl. Acad. Sci. U.S.A.* 85:7448-7451 (1988)), etc.

Polynucleotide compositions for use in the therapeutic methods disclosed herein further include catalytic RNA, or a ribozyme (See, e.g., PCT International Publication WO 90/11364, published Oct. 4, 1990; Sarver et al., *Science* 247: 1222-1225 (1990). Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585-591 (1988). In certain embodiments, the ribozyme is engineered so that the cleavage recognition site is located near the 5' end of the target mRNA; i.e., to increase efficiency and minimize the intracellular accumulation of non-functional mRNA transcripts.

As in the antisense approach, ribozymes for use in the diagnostic and therapeutic methods disclosed herein can be composed of modified oligonucleotides (e.g. for improved stability, targeting, etc.) and can be delivered to cells which express DR6 in vivo. DNA constructs encoding the ribozyme can be introduced into the cell in the same manner as described above for the introduction of antisense encoding DNA. One method of delivery involves using a DNA construct "encoding" the ribozyme under the control of a stDR6g constitutive or inducible promoter, such as, for example, pol III or pol II promoter, so that transfected cells will produce sufficient quantities of the ribozyme to destroy endogenous DR6 messages and inhibit translation. Since ribozymes unlike antisense molecules, are catalytic, a lower intracellular concentration is required for efficiency.

DR6 Aptamer Antagonists

In another embodiment, the DR6 antagonist for use in the methods described herein is an aptamer. An aptamer can be a nucleotide or a polypeptide which has a unique sequence, has the property of binding specifically to a desired target (e.g., a polypeptide), and is a specific ligand of a given target. Nucleotide aptamers include double stranded DNA and single stranded RNA molecules that bind to DR6. In certain embodiments, the DR6 aptamer antagonist promotes proliferation, differentiation, or survival of oligodendrocytes; promotes, oligodendrocyte-mediated myelination of neurons, or prevents demyelination, e.g., in a mammal.

Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in e.g. U.S. Pat. Nos. 5,475,096, 5,580,737, 5,567, 588, 5,707,796, 5,763,177, 6,011,577, and 6,699,843, incorporated herein by reference in their entirety. Another screening method to identify aptamers is described in U.S. Pat. No. 5,270,163 (also incorporated herein by reference). The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets.

The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, which can comprise a segment of randomized sequence, the SELEX method includes steps of contacting the mixture with the target under conditions favorable for binding; partitioning unbound nucleic acids from those nucleic acids which have bound specifically to target molecules; dissociating the nucleic acid-target complexes; amplifying the nucleic acids dissociated from the nucleic acid-target complexes to yield a ligand enriched mixture of nucleic acids. The steps of binding, partitioning, dissociating and amplifying are repeated through as many cycles as desired to yield highly specific high affinity nucleic acid ligands to the target molecule.

Nucleotide aptamers can be used, for example, as diagnostic tools or as specific inhibitors to dissect intracellular signaling and transport pathways (James, *Curr. Opin. Pharmacol.* 1:540-546 (2001)). The high affinity and specificity of nucleotide aptamers makes them good candidates for drug discovery. For example, aptamer antagonists to the toxin ricin have been isolated and have IC50 values in the nanomolar range (Hesselberth J R et al., *J Biol Chem* 275:4937-4942 (2000)). Nucleotide aptamers can also be used against infectious disease, malignancy and viral surface proteins to reduce cellular infectivity.

Nucleotide aptamers for use in the methods described herein can be modified (e.g., by modifying the backbone or bases or conjugated to peptides) as described herein for other polynucleotides.

Using the protein structure of DR6, screening for aptamers that act on DR6 using the SELEX process would allow for the identification of aptamers that inhibit DR6-mediated processes.

Polypeptide aptamers for use in the methods described herein are random peptides selected for their ability to bind to and thereby block the action of DR6. Polypeptide aptamers can include a short variable peptide domain attached at both ends to a protein scaffold. This double structural constraint greatly increases the binding affinity of the peptide aptamer to levels comparable to an antibody's (nanomolar range). See, e.g., Hoppe-Seyler F et al., *J Mol Med* 78(8):426-430 (2000). The length of the short variable peptide is typically about 10 to 20 amino acids, and the scaffold can be any protein which has good solubility and compacity properties. One non-limiting example of a scaffold protein is the bacterial protein Thioredoxin-A. See, e.g., Cohen B A et al., *PNAS* 95(24): 14272-14277 (1998).

Polypeptide aptamers are peptides or small polypeptides that act as dominant inhibitors of protein function. Peptide aptamers specifically bind to target proteins, blocking their functional ability (Kolonin et al. (1998) *Proc. Natl. Acad. Sci.* 95: 14,266-14,271). Peptide aptamers that bind with high affinity and specificity to a target protein can be isolated by a variety of techniques known in the art. Peptide aptamers can be isolated from random peptide libraries by yeast two-hybrid screens (Xu, C. W., et al. (1997) *Proc. Natl. Acad. Sci.* 94:12, 473-12,478) or by ribosome display (Hanes et al. (1997) *Proc. Natl. Acad. Sci.* 94:4937-4942). They can also be isolated from phage libraries (Hoogenboom, H. R., et al. (1998) Immunotechnology 4:1-20) or chemically generated peptide libraries. Additionally, polypeptide aptamers can be selected using the selection of Ligand Regulated Peptide Aptamers (LiRPAs). See, e.g., Binkowski B F et al., (2005) *Chem & Biol* 12(7): 847-855, incorporated herein by reference. Although the difficult means by which peptide aptamers are synthesized makes their use more complex than polynucleotide aptamers, they have unlimited chemical diversity. Polynucleotide aptamers are limited because they utilize only the four nucleotide bases, while peptide aptamers would have a much-expanded repertoire (i.e., 20 amino acids).

Peptide aptamers for use in the methods described herein can be modified (e.g., conjugated to polymers or fused to proteins) as described for other polypeptides elsewhere herein.

P75 Antagonists

Antagonists of p75 to be used in accordance with the methods described herein include, for example, (i) p75 antagonists compounds; (ii) p75 antagonist polypeptides; (iii) p75 antagonist antibodies or fragments thereof; (iv) −75 antagonist polynucleotides; (v) p75 aptamers; and (vi) combinations of two or more of said p75 antagonists. In some embodiments, the p75 antagonist inhibits interaction of p75 with DR6.

P75 antagonists are known in the art, and one of ordinary skill in the art would know how to screen for and test p75 antagonists which would inhibit the interaction of p75 and DR6. For example, a cyclic decapeptide antagonist of p75 is described in Turner et al. *J. Neuroscience Research* 78: 193-199 (2004), which is herein incorporated by reference in its entirety.

Vectors and Host Cells

Host-expression systems represent vehicles by which the coding sequences of interest can be produced and subsequently purified, but also represent cells which can, when transformed or transfected with the appropriate nucleotide coding sequences, express a DR6 and/or p75 antagonist polypeptide or antibody in situ. These include but are not limited to microorganisms such as bacteria (e.g., *E. coli, B. subtilis*) transformed with recombinant bacteriophage DNA, plasmid DNA or cosmid DNA expression vectors containing DR6 and/or p75 antagonist polypeptide or antibody coding sequences; yeast (e.g., *Saccharomyces, Pichia*) transformed with recombinant yeast expression vectors containing DR6 and/or p75 antagonist polypeptide or antibody coding sequences; insect cell systems infected with recombinant virus expression vectors (e.g., baculovirus) containing DR6 and/or p75 antagonist polypeptide or antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing DR6 and/or p75 antagonist polypeptide or antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or eukaryotic cells, e.g., for the expression of DR6 and/or p75 antagonist polypeptide or whole recombinant antibody molecules, are used for the expression of a recombinant DR6 and/or p75 antagonist polypeptide or antibody molecule. For example, mammalian cells such as Chinese hamster ovary cells (CHO), in conjunction with a vector such as the major intermediate early gene promoter element from human cytomegalovirus is an effective expression system for DR6 and/or p75 antagonist polypeptide or antibodies (Foecking et al., *Gene* 45:101 (1986); Cockett et al., *Bio/Technology* 8:2 (1990)).

In bacterial systems, a number of expression vectors can be advantageously selected depending upon the use intended for the DR6 and/or p75 antagonist polypeptide or antibody molecule being expressed. For example, when a large quantity of such a protein is to be produced, for the generation of pharmaceutical compositions of the DR6 and/or p75 antagonist polypeptide or antibody molecule, vectors which direct the expression of high levels of fusion protein products that are readily purified can be desirable. Such vectors include, but are not limited, to the *E. coli* expression vector pUR278 (Ruther et al., *EMBO J.* 2:1791 (1983)), in which the DR6 and/or p75 antagonist polypeptide or antibody coding sequence can be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors can also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is typically used as a vector to express foreign genes. The virus grows in *Spodoptera frugiperda* cells. The DR6 and/or p75 antagonist polypeptide or antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the DR6 and/or p75 antagonist polypeptide or antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the DR6 and/or p75 antagonist polypeptide or antibody molecule in infected hosts. (e.g., see Logan & Shenk, *Proc. Natl. Acad. Sci. USA* 81:355-359 (1984)). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see Bittner et al., *Methods in Enzymol.* 153:51-544 (1987)).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERY, BHK, HeLa, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is typically used. For example, cell lines which stably express the DR6 and/or p75 antagonist polypeptide or antibody molecule can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which stably express the DR6 and/or p75 antagonist polypeptide or antibody molecule.

A number of selection systems can be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 1980) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 *Clinical Pharmacy* 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); *TIB TECH* 11(5):155-215 (May, 1993); and hygro, which confers resistance to hygromycin (Santerre et al., *Gene* 30:147 (1984). Methods commonly known in the art of recombinant DNA technology which can be used are described in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds), *Current Prolocols in Human Genetics*, John Wiley & Sons, NY (1994); Colberre-Garapin et al., *J. Mol. Biol.* 150:1 (1981), which are incorporated by reference herein in their entireties.

The expression levels of a DR6 and/or p75 antagonist polypeptide or antibody can be increased by vector amplification (for a review, see Bebbington and Hentschel, *The use of vectors based on gene amplification for the expression of cloned genes in mammalian cells in DNA cloning*, Academic Press, New York, Vol. 3. (1987)). When a marker in the vector system expressing a DR6 and/or p75 antagonist polypeptide or antibody is amplifiable, increase in the level of inhibitor present in culture of host cell will increase the number of copies of the marker gene. Since the amplified region is associated with the antibody or other polypeptide gene, production of the antibody or other polypeptide will also increase (Crouse et al., *Mol. Cell. Biol.* 3:257 (1983)).

Vectors comprising nucleic acids encoding DR6 and/or p75 antagonists, e.g., soluble polypeptides, antibodies, antagonist polynucleotides, or aptamers, can be used to produce antagonists for use in the methods described herein. The choice of vector and expression control sequences to which such nucleic acids are operably linked depends on the functional properties desired, e.g., protein expression, and the host cell to be transformed.

Expression control elements useful for regulating the expression of an operably linked coding sequence are known in the art. Examples include, but are not limited to, inducible promoters, constitutive promoters, secretion signals, and other regulatory elements. When an inducible promoter is used, it can be controlled, e.g., by a change in nutrient status, or a change in temperature, in the host cell medium.

The vector can include a prokaryotic replicon, i.e., a DNA sequence having the ability to direct autonomous replication and maintenance of the recombinant DNA molecule extrachromosomally in a bacterial host cell. Such replicons are well known in the art. In addition, vectors that include a prokaryotic replicon can also include a gene whose expression confers a detectable marker such as a drug resistance. Examples of bacterial drug-resistance genes are those that confer resistance to ampicillin or tetracycline.

Vectors that include a prokaryotic replicon can also include a prokaryotic or bacteriophage promoter for directing expression of the coding gene sequences in a bacterial host cell. Promoter sequences compatible with bacterial hosts are typically provided in plasmid vectors containing convenient restriction sites for insertion of a DNA segment to be expressed. Examples of such plasmid vectors are pUC8, pUC9, pBR322 and pBR329 (BioRad), pPL and pKK223 (Pharmacia). Any suitable prokaryotic host can be used to express a recombinant DNA molecule encoding a protein used in the methods described herein.

For the purposes described herein, numerous expression vector systems can be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. The neomycin phosphotransferase (neo) gene is an example of a selectable marker gene (Southern et al., *J. Mol. Anal. Genet.* 1:327-341 (1982)). Additional elements can also be needed for optimal synthesis of mRNA. These elements can include signal sequences, splice signals, as well as transcriptional promoters, enhancers, and termination signals.

In one embodiment, a proprietary expression vector of Biogen MEC, Inc., referred to as NEOSPLA (U.S. Pat. No. 6,159,730) can be used. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression upon transfection in CHO cells, followed by selection in G418 containing medium and methotrexate amplification. Of course, any expression vector which is capable of eliciting expression in eukaryotic cells can be used. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). Additional eukaryotic cell expression vectors are known in the art and are commercially available. Typically, such vectors contain convenient restriction sites for insertion of the desired DNA segment. Exemplary vectors include pSVL and pKSV-10 (Pharmacia), pBPV-1, pml2d (International Biotechnologies), pTDT1 (ATCC 31255), retroviral expression vector pMIG and pLL3.7, adenovirus shuttle vector pDC315, and AAV vectors. Other exemplary vector systems are disclosed e.g., in U.S. Pat. No. 6,413,777.

In general, screening large numbers of transformed cells for those which express suitably high levels of the antagonist is routine experimentation which can be carried out, for example, by robotic systems.

Frequently used regulatory sequences for mammalian host cell expression include viral elements that direct high levels of protein expression in mammalian cells, such as promoters and enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdmlP)), polyoma and strong mammalian promoters such as native immunoglobulin and actin promoters. For further description of viral regulatory elements, and sequences thereof; see e.g., Stinski, U.S. Pat. No. 5,168,062; Bell, U.S. Pat. No. 4,510,245; and Schaffner, U.S. Pat. No. 4,968,615.

The recombinant expression vectors can carry sequences that regulate replication of the vector in host cells (e.g., origins of replication) and selectable marker genes. The selectable marker gene facilitates selection of host cells into which the vector has been introduced (see, e.g., Axel, U.S. Pat. Nos. 4,399,216; 4,634,665 and 5,179,017). For example, typically the selectable marker gene confers resistance to a drug, such as G418, hygromycin or methotrexate, on a host cell into which the vector has been introduced. Frequently used selectable marker genes include the dihydrofolate reductase (DHFR) gene (for use in dhfr-host cells with methotrexate selection/amplification) and the neo gene (for G418 selection).

Vectors encoding DR6 and/or p75 antagonists can be used for transformation of a suitable host cell. Transformation can be by any suitable method. Methods for introduction of exogenous DNA into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules can be introduced into mammalian cells by viral vectors.

Host cells for expression of a DR6 and/or p75 antagonist for use in a method described herein can be prokaryotic or eukaryotic. Exemplary eukaryotic host cells include, but are not limited to, yeast and mammalian cells, e.g., Chinese hamster ovary (CHO) cells (ATCC Accession No. CCL61), NIH Swiss mouse embryo cells NIH-3T3 (ATCC Accession No. CRL1658), and baby hamster kidney cells (BHK). Other useful eukaryotic host cells include insect cells and plant cells. Exemplary prokaryotic host cells are *E. coli* and *Streptomyces*.

Transformation of host cells can be accomplished by conventional methods suited to the vector and host cell employed. For transformation of prokaryotic host cells, electroporation and salt treatment methods can be employed (Cohen et al., *Proc. Natl. Acad. Sci. USA* 69:2110-14 (1972)). For transformation of vertebrate cells, electroporation, cationic lipid or salt treatment methods can be employed. See, e.g., Graham et al., *Virology* 52:456-467 (1973); Wigler et al., *Proc. Natl. Acad. Sci. USA* 76:1373-76 (1979).

In certain embodiments, the host cell line used for protein expression is of mammalian origin; those skilled in the art are credited with ability to determine particular host cell lines which are best suited for the desired gene product to be expressed therein. Exemplary host cell lines include, but are not limited to NSO, SP2 cells, baby hamster kidney (BHK) cells, monkey kidney cells (COS), human hepatocellular carcinoma cells (e.g., Hep G2), A549 cells DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3×63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

Expression of polypeptides from production cell lines can be enhanced using known techniques. For example, the glutamine synthetase (GS) system is commonly used for enhancing expression under certain conditions. See, e.g., European Patent Nos. 0 216 846, 0 256 055, and 0 323 997 and European Patent Application No. 89303964.4.

Gene Therapy

A DR6 and/or p75 antagonist can be produced in vivo in a mammal, e.g., a human patient, using a gene-therapy approach to treatment of a nervous-system disease, disorder or injury in which promoting survival, proliferation and differentiation of oligodendrocytes or promoting myelination of neurons would be therapeutically beneficial. This involves administration of a suitable DR6 and/or p75 antagonist-encoding nucleic acid operably linked to suitable expression control sequences. Generally, these sequences are incorporated into a viral vector. Suitable viral vectors for such gene therapy include an adenoviral vector, an alphavirus vector, an enterovirus vector, a pestivirus vector, a lentiviral vector, a baculoviral vector, a herpesvirus vector, an Epstein Barr viral vector, a papovaviral vector, a poxvirus vector, a vaccinia viral vector, adeno-associated viral vector and a herpes simplex viral vector. The viral vector can be a replication-defective viral vector. Adenoviral vectors that have a deletion in its E1 gene or E3 gene are typically used. When an adenoviral vector is used, the vector usually does not have a selectable marker gene.

Pharmaceutical Compositions

The DR6 and/or p75 antagonists used in the methods described herein can be formulated into pharmaceutical compositions for administration to mammals, including humans. The pharmaceutical compositions used in the methods described herein comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions used in the methods described herein can be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. As described previously, DR6 and/or p75 antagonists used in the methods described herein act in the nervous system to promote survival and prevent apoptosis of nervous system cells. Accordingly, in certain methods described herein, the DR6 and/or p75 antagonists are administered in such a way that they cross the blood-brain barrier. This crossing can result from the physico-chemical properties inherent in the DR6 and/or p75 antagonist molecule itself, from other components in a pharmaceutical formulation, or from the use of a mechanical device such as a needle, cannula or surgical instruments to breach the blood-brain barrier. Where the DR6 and/or p75 antagonist is a molecule that does not inherently cross the blood-brain barrier, e.g., a fusion to a moiety that facilitates the crossing, suitable routes of administration are, e.g., intrathecal or intracranial, e.g., directly into a chronic lesion of MS. Where the DR6 and/or p75 antagonist is a molecule that inherently crosses the blood-brain barrier, the route of administration can be by one or more of the various routes described below.

Sterile injectable forms of the compositions described herein can be aqueous or oleaginous suspension. These suspensions can be formulated according to techniques known in the art using suitable dispersing or wetting agents and suspending agents. The sterile, injectable preparation can also be a sterile, injectable solution or suspension in a non-toxic parenterally acceptable diluent or solvent, for example as a suspension in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms can also be used for the purposes of formulation.

Parenteral formulations can be a single bolus dose, an infusion or a loading bolus dose followed with a maintenance dose. These compositions can be administered at specific fixed or variable intervals, e.g., once a day, or on an "as needed" basis.

Certain pharmaceutical compositions used in the methods described herein can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of a DR6 and/or p75 antagonist that can be combined with the carrier materials to produce a single dosage form will vary depending upon the host treated, the type of antagonist used and the particular mode of administration. The composition can be administered as a single dose, multiple doses or over an established period of time in an infusion. Dosage regimens also can be adjusted to provide the optimum desired response (e.g., a therapeutic or prophylactic response).

In some cases, the methods described herein use a "therapeutically effective amount" or a "prophylactically effective amount" of a DR6 and/or p75 antagonist. Such a therapeutically or prophylactically effective amount can vary according to factors such as the disease state, age, sex, and weight of the individual. A therapeutically or prophylactically effective amount is also one in which any toxic or detrimental effects are outweighed by the therapeutically beneficial effects.

A specific dosage and treatment regimen for any particular patient will depend upon a variety of factors, including the particular DR6 and/or p75 antagonist used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

In the methods described herein the DR6 and/or p75 antagonists are generally administered directly to the nervous system, intracerebroventricularly, or intrathecally, e.g. into a chronic lesion. Compositions for administration according to the methods described herein can be formulated so that a dosage of 0.001-10 mg/kg body weight per day of the DR6 and/or p75 antagonist is administered. In some embodiments, the dosage is 0.01-1.0 mg/kg body weight per day. In some embodiments, the dosage is 0.001-0.5 mg/kg body weight per day.

For treatment with a DR6 and/or p75 antagonist antibody, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, for example, at least 1 mg/kg. Doses intermediate in the above ranges can also be used. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

In certain embodiments, a subject can be treated with a nucleic acid molecule encoding a DR6 and/or p75 antagonist polynucleotide. Doses for nucleic acids range from about 10 ng to 1 g, 100 ng to 100 mg, 1 μg to 10 mg, or 30-300 μg DNA per patient. Doses for infectious viral vectors vary from 10-100, or more, virions per dose.

Supplementary active compounds also can be incorporated into the compositions used in the methods described herein. For example, a soluble polypeptide or a fusion protein can be coformulated with and/or coadministered with one or more additional therapeutic agents.

The delivery methods encompass any suitable delivery method for a DR6 and/or p75 antagonist to a selected target tissue, including bolus injection of an aqueous solution or implantation of a controlled-release system. Use of a controlled-release implant reduces the need for repeat injections.

The DR6 and/or p75 antagonists described herein can be directly infused into the brain. Various implants for direct brain infusion of compounds are known and are effective in the delivery of therapeutic compounds to human patients suffering from neurological disorders. These include chronic infusion into the brain using a pump, stereotactically implanted, temporary interstitial catheters, permanent intracranial catheter implants, and surgically implanted biodegradable implants. See, e.g., Gill et al., supra; Scharfen et al., "High Activity Iodine-125 Interstitial Implant For Gliomas," *Int. J. Radiation Oncology Biol. Phys.* 24(4):583-591 (1992); Gaspar et al., "Permanent 125I Implants for Recurrent Malignant Gliomas," *Int. J. Radiation Oncology Biol. Phys.* 43(5): 977-982 (1999); chapter 66, pages 577-580, Bellezza et al., "Stereotactic Interstitial Brachytherapy," in Gildenberg et al., Textbook of Stereotactic and Functional Neurosurgery, McGraw-Hill (1998); and Brem et al., "The Safety of Interstitial Chemotherapy with BCNU-Loaded Polymer Followed by Radiation Therapy in the Treatment of Newly Diagnosed Malignant Gliomas: Phase I Trial," *J. Neuro-Oncology* 26:111-23 (1995).

The compositions can also comprise a DR6 and/or p75 antagonist dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., *Biopolymers* 22:547-56 (1985)); poly(2-hydroxyethyl-methacrylate), ethylene vinyl acetate (Langer et al., *J. Biomed. Mater. Res.* 15:167-277 (1981); Langer, *Chem. Tech.* 12:98-105 (1982)) or poly-D-(−)-3hydroxybutyric acid (EP 133,988).

In some embodiments of the methods described herein, a DR6 and/or p75 antagonist is administered to a patient by direct infusion into an appropriate region of the brain. See, e.g., Gill et al., *Nature Med.* 9: 589-95 (2003). Alternative techniques are available and can be applied to administer a DR6 and/or p75 antagonist. For example, stereotactic placement of a catheter or implant can be accomplished using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three-dimensional multiplanar treatment planning (STP, Fischer, Freiburg, Germany). This equipment permits planning on the basis of magnetic resonance imaging studies, merging the CT and MRI target information for clear target confirmation.

The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

The methods of treatment of nervous system disorders associated with increased cell death as described herein are typically tested in vitro, and then in vivo in an acceptable animal model, for the desired therapeutic or prophylactic activity, prior to use in humans. Suitable animal models, including transgenic animals, are will known to those of ordinary skill in the art. For example, in vitro assays to demonstrate the survival effect of the DR6 and/or p75 antagonists are described herein. The effect of the DR6 and/or p75 antagonists on apoptosis can be tested in vitro as described in the Examples. Finally, in vivo tests can be performed by creating transgenic mice which express the DR6 and/or p75 antagonist or by administering the DR6 and/or p75 antagonist to mice or rats in models as described herein.

The practices described herein will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning: A Laboratory Manual (3-Volume Set), J. Sambrook, D. W. Russell, Cold Spring Harbor Laboratory Press (2001); Genes VIII, B. Lewin, Prentice Hall (2003); PCR Primer, C. W. Dieffenbach and G. S. Dveksler, CSHL Press (2003); DNA Cloning, D. N. Glover ed., Volumes I and II (1985); Oligonucleotide Synthesis Methods and Applications (Methods in Molecular Biology), P. Herdewijn (Ed.), Humana Press (2004); Culture of Animal Cells: A Manual of Basic Technique, 4th edition, R. I. Freshney, Wiley-Liss (2000); Oligonucleotide Synthesis, M. J. Gait (Ed.), (1984); Mullis et al. U.S. Pat. No. 4,683,195; Nucleic Acid Hybridization, B. D. Hames & S. J. Higgins eds. (1984); Nucleic Acid Hybridization, M. L. M. Anderson, Springer (1999); Animal Cell Culture and Technology, 2nd edition, M. Butler, BIOS Scientific Publishers (2004); Immobilized Cells and Enzymes: A Practical Approach (Practical Approach Series), J. Woodward, Irl Pr (1992); Transcription And Translation, B. D. Hames & S. J. Higgins (Eds.) (1984); Culture Of Animal Cells, R. I. Freshney, Alan R. Liss, Inc., (1987); Immobilized Cells And Enzymes, IRL Press, (1986); A Practical Guide To Molecular Cloning, 3rd edition, B. Perbal, John Wiley & Sons Inc. (1988); the treatise, Methods In Enzymology, Academic Press, Inc., N.Y.; Gene Transfer Vectors For Mammalian Cells, J. H. Miller and M. P. Calos eds., Cold Spring Harbor Laboratory (1987); Methods In Enzymology, Vols. 154 and 155, Wu et al. (Eds.); Immunochemical Methods In Cell And Molecular Biology, Mayer and Walker, (Eds.), Academic Press, London (1987); Handbook Of Experimental Immunology, Volumes I-IV, D. M. Weir and C. C. Blackwell (Eds.), (1986); Immunology Methods Manual: The Comprehensive Sourcebook of Techniques (4 Volume Set), 1st edition, I. Lefkovits, Academic Press (1997); Manipulating the Mouse Embryo: A Laboratory Manual, 3rd edition, Cold Spring Harbor Laboratory Press (2002); and in Ausubel et al., Current Protocols in Molecular Biology, John Wiley and Sons, Baltimore, Md. (1989).

General principles of antibody engineering are set forth in Antibody Engineering: Methods and Protocols (Methods in Molecular Biology), B. L. Lo (Ed.), Humana Press (2003); Antibody engineering, R. Kontermann and S. Dubel (Eds.), Springer Verlag (2001); Antibody Engineering, 2nd edition, C. A. K. Borrebaeck (Ed.), Oxford Univ. Press (1995). General principles of protein engineering are set forth in Protein Engineering, A Practical Approach, Rickwood, D., et al. (Eds.), IRL Press at Oxford Univ. Press, Oxford, Eng. (1995). General principles of antibodies and antibody-hapten binding are set forth in: Antibodies: A Laboratory Manual, E. Harlow and D. Lane, Cold Spring Harbor Laboratory Press (1988); Nisonoff, A., Molecular Immunology, 2nd edition, Sinauer Associates, Sunderland, Mass. (1984); and Steward, M. W., Antibodies, Their Structure and Function, Chapman and Hall, New York, N.Y. (1984). Additionally, standard methods in immunology known in the art and not specifically described are generally followed as in Current Protocols in Immunology, John Wiley & Sons, New York; Stites et al. (Eds.), Immunochemical Protocols (Methods in Molecular Biology), 2nd edition, J. D. Pound (Ed.), Humana Press (1998), Weir's Handbook of Experimental Immunology, 5th edition, D. M. Weir (Ed.), Blackwell Publishers (1996), Methods in Cellular Immunology, 2nd edition, R. Fernandez-Botran, CRC Press (2001); Basic and Clinical Immunology, 8th edition, Appleton & Lange, Norwalk, Conn. (1994) and Mishell and Shiigi (Eds.), Selected Methods in Cellular Immunology, W.H. Freeman and Co., New York (1980).

Standard reference works setting forth general principles of immunology include Current Protocols in Immunology, John Wiley & Sons, New York; Klein, J.; Kuby Immunology, 4th edition, R. A. Goldsby, et al., H. Freeman & Co. (2000); Basic and Clinical Immunology, M. Peakman, et al., Churchill Livingstone (1997); Immunology, 6th edition, I. Roitt, et al., Mosby, London (2001); Cellular and Molecular Immunology, 5th edition; A. K. Abbas, A. H. Lichtman, Elsevier—Health Sciences Division (2005); Immunology Methods Manual: The Comprehensive Sourcebook of Techniques (4 Volume Set), 1st edition, I. Lefkovits, Academic Press (1997) Immunology, 5th edition, R. A. Goldsby, et al., W.H. Freeman (2002); Monoclonal Antibodies: Principles and Practice, 3rd Edition, J. W. Goding, Academic Press (1996); Immunology: The Science of Self-Nonself Discrimination, John Wiley & Sons, New York (1982); Kennett, R., et al. (Eds.), Monoclonal Antibodies, Hybridoma: A New Dimension in Biological Analyses, Plenum Press, New York (1980); Campbell, A., "Monoclonal Antibody Technology" in Burden, R., et al. (Eds.), Laboratory Techniques in Biochemistry and Molecular Biology, Vol. 13, Elsevere, Amsterdam (1984).

All of the references cited above, as well as all references cited herein, are incorporated herein by reference in their entireties.

EXAMPLES

Example 1

DR6 is Expressed in the Nervous System

Tissue sections from adult mouse cerebral cortex and rat spinal cord were examined for expression of DR6 protein. Tissue sections were first penetrated with PBS containing 1% Triton X-100 (Sigma) for 30 minutes followed by incubation in blocking solution (PBS containing 0.1% Triton X-100 and 10% normal goat serum (NGS)) for 1 hour at room temperature. For primary antibody labeling, sections were incubated in blocking medium containing rabbit anti-DR6 (Santa Cruz, sc-13106, 1:200) and mouse anti-neuronal class III β-tubulin (Covance, MMS-435P, 1:500) at 4° C. overnight. After three PBS rinses, sections were incubated in 5% NGS-PBS containing Alexa 594 anti-rabbit antibody (Invitrogen) (1:500) at room temperature for 1 hour. The results show that the colocalization of DR6 and neuronal class III β-tubulin, which indicates that DR6 is expressed in neurons (data not shown).

To understand the role of DR6 in the nervous system, DR6 mRNA expression levels were evaluated to determine if they were developmentally regulated across rat brain tissues using quantitative real-time polymerase chain reaction after reverse transcription (RT-PCR). mRNA was extracted from whole brain and spinal cord homogenates taken at embryonic day 18 (E18), postnatal days 1 (P1), 7 (P7), 14 (P14), and 21 (P21) and from adults. All mRNA were extracted using Absolutely RNA miniprep kit following the manufacturer's instructions (Stratagene). Purified RNA (High Capacity cDNA Archive Kit, Applied Biosystems) was then used to generate cDNA of DR6. The cDNAs served as the template for quantitative real-time PCR (Q-PCR), and TaqMan Gene Expression system (Mx3000P) was used to quantify the DR6 using Mm00446361_ml premixed primer set with MGB probes (Applied Biosystems). As seen in FIGS. 1A-B, DR6 expression level is low at E18, peaks at postnatal day 7 or 14, then reaches lower levels in both brain and spinal cord after maturation. The developmental transcription profile agreed with protein expression profile based on Western blot using anti-DR6 antibody (FIG. 1C). Immunohistochemical staining of human and rat brain tissues section revealed that DR6 is expressed in both human and rat neurons based on colocalization with the βIII-tubulin neuron marker (data not shown).

In addition, several other cell types were examined for expression of DR6 mRNA. mRNA was extracted from purified cultures of P2 oligodendrocyte progenitor cells (OPCs), E18 cortical neurons, P2 microglias and P42 cerebral cortex astrocytes. All mRNA were extracted using Absolutely RNA miniprep kit following the manufacturer's instructions (Stratagene). Purified RNA (High Capacity cDNA Archive Kit, Applied Biosystems) was then used to generate cDNA of DR6 and of glyceraldehyde 3-phosphate dehydrogenase (GAPDH) as a control. FIG. 1D shows that DR6 is expressed in all four cell types examined.

The expression of DR6 is temporally regulated in the oligodendrocyte lineage. Three different approaches were used to examine the DR6 expression in oligodendrocytes. First, semi-quantitive RT-PCR was performed to determine the mRNA level from three different stages of purified populations of oligodendrocyte (A2B5, O4 and MBP). As shown in the FIG. 2A, DR6 mRNA was detected through all stage of the oligodendrocyte lineage with equivalent mRNA levels found in A2B5$^+$, O4$^+$ and MBP$^+$ oligodendrocytes. Second, Western blot was performed to determine the DR6 protein level in the three different stage of oligodendrocytes. As shown in the FIG. 2B, DR6 protein is detectable in all three stages of oligodendrocyte. Interestingly, it is 5-fold higher in pre-myelinating (O4$^+$) oligodendrocytes stage than earlier progenitor A2B5 and 10 fold higher than mature oligodendrocyte (MBP positive) suggesting that premyelinaitng oligodendrocytes are the predominant DR6 expressing cells. Third, the presence of DR6 protein in oligodendrocytes was confirmed using immunohistochemistry to show that A2B5$^+$, O4$^+$ and MBP$^+$ oligodendrocytes were labeled by an anti-DR6 antibody (data not shown). Again, O4 positive cells show much more intensive fluorescence staining than MBP positive cells suggesting more DR6 expression in the premyelinating stage (O4 positive) than the mature oligodendrocytes. Pre-adsorption of the anti-DR6 antibody by addition of competing DR6-Fc completely ablated the signal.

Example 2

DR6 is Overexpressed in Brains of Patients with Alzheimer's Disease

Levels of DR6 mRNA in the brains of Alzhemier's disease patients were also examined. Quantitative real-time PCR was performed using six snap-frozen brain tissue blocks from four different donors with Alzhemier's disease. These results were compared to those obtained using three brain tissue blocks from 2 donors without neurological disease.

As shown in FIG. 3, DR6 is expressed 1.2- to 1.8-fold higher in Alzheimer's samples (2 frontal lobes, 1 temporal lobe, 1 basal ganglion and 2 unspecified regions collected from 4 individual donors) when compared to 3 normal brain samples (FIG. 3). To determine if the up-regulated DR6 is neurons specific, immunohistochemistry staining was performed. Cells in the center of αβ amyloid plaque are DR6 positive. The cells near the plaque have significantly brighter DR6 staining, suggesting higher levels of DR6 expression. The mRNA extraction, cDNA production and Q-PCR were performed as described in Example 1.

Example 3

DR6 is Upregulated after Axotomy

The effect of axotomy on DR6 mRNA and protein levels was also examined. For these experiments, embryonic DRG neurons were prepared as previously described (Mi et al., *Nat. Neurosci.* 8:745-51 (2005)). Briefly, DRGs were first dissected out from 2-week-old E16 Sprague Dawley rats (Charles River) and incubated in 0.25% Trypsin/EDTA (Invitrogen) at 37° C. for 30 minutes. An equal volume of DMEM (Invitrogen) containing 20% fetal bovine serum (Invitrogen) was then added to the digestion mixture to stop the reaction. Cell pellets that were collected after spinning down at 1,000 rpm at room temperature for 5 minutes were mechanically dissociated by gently passing through a plastic pipette until no large fragments were visible. About $1 \times 10^5$ DRG neurons were spotted in the center of each well of 4 well chamber-slides (LabTek) that were coated with 100 μg/ml Poly-D-lysine (Sigma). Cells were allowed to attach in growth medium (Neurobasal medium containing B27 supplement (Invitrogen) and 100 ng/ml nerve growth factor (BD Biosciences) at 37° C. in humidified air with 5% $CO_2$. The next morning, the medium was replaced with fresh growth medium and cells were treated with 20 μM of fluorodeoxyuridine for 3 days to remove proliferating glial cells. Cultures were then maintained in growth medium at 37° C. in humidified air with 5% $CO_2$ with fresh medium change every 3-4 days.

These cultured axons were severed by blade, and then at 0, 24 and 48 hours after injury, mRNAs were extracted using the Absolutely RNA miniprep kit following manufacturer's instructions (Stratagene). Quantitation, as shown in FIG. 4, revealed that DR6 mRNA levels were high at both 24 and 48 hours after axotomy compared to control uninjured axon cultures.

The mRNA extraction, cDNA production and Q-PCR were performed as described in Example 1.

Example 4

DR6 is Upregulated in Motor Neurons at the Lesion Site after Spinal Cord Injury

To create a model of spinal cord injury, dorsal hemisection of rat spinal cords were performed as described by Ji et al. (*Mol Cell Neurosci.* 33: 311-20 (2006)). The spinal cord tissues were fixed and stained using an anti-DR6 antibody. A significantly higher level of DR6 positive motor neurons was detected in rats with spinal cord injuries than in uninjured rats.

Example 5

Overexpression of DR6 Induces Neuronal Death

Cell Culture

Cerebral cortical neurons grown in cell cultures were infected with lentivirus expressing DR6, and the effects on cell death were examined. Cerebral cortical neurons were prepared from E18 Sprague Dawley rats (Charles River). Briefly, cerebral cortices from E18 rat embryos were dissected out, minced and incubated in 0.25% Trypsin/EDTA (Invitrogen) at 37° C. for 10 minutes. The cells were triturated after adding 60 μg/ml DNase I (Sigma) and 10% fetal bovine serum (Invitrogen) to stop the reaction. Cell pellets collected after spinning down at 1,000 rpm at room temperature for 5 minutes were then mechanically dissociated by gently passing through a plastic pipette until no large fragments were visible. All surfaces of tissue culture plates (Costar) were coated with 100 μg/ml Poly-D-lysine (Sigma) prior to cell seeding. The plating densities for different experimental set-ups were as follows: $1 \times 10^6$/well of a 12 well plate for western blots, $1 \times 10^5$/well of a 24 well plate for time-lapse imaging and $2 \times 10^4$/well of a 96 well plate for LDH assay, homogeneous caspase assay and Q-PCR analysis. Cells were maintained in Neurobasal medium containing B27 supplement (Invitrogen) at 37° C. in humidified air with 5% $CO_2$ with fresh medium change every 3-4 days.

Protein Expression Constructs

DNA encoding full-length DR6 (amino acids 1-655) was inserted into the Not I sites of HRST-IRESeGFP lentivirus vector. The sequence of full-length human DR6 in lentivirus was obtained and is the sequence of SEQ ID NO:154. Nucleotides 124-153 of SEQ ID NO:154 encode a Myc tag that is used to check protein expression. The nucleotide sequence encodes a full-length Myc-tagged human DR6 polypeptide of the sequence of SEQ ID NO:155. Amino acids 42-51 of SEQ ID NO:155 are the Myc tag.

DNA encoding dominant negative DR6 (amino acids 1-370) was inserted into the Not I sites of HRST-IRESeGFP lentivirus vector. The sequence of dominant negative DR6 in lentivirus is provided as SEQ ID NO: 156. Nucleotides 124-153 of SEQ ID NO:156 encode a Myc tag that is used to check protein expression. The polyeptide sequence of dominant negative human DR6 polypeptide is provided as SEQ ID NO: 157. Amino acids 42-51 of SEQ ID NO:157 are the Myc tag.

Infections

The resulting plasmids and a GFP control plasmid were transfected into 293 cells to produce lentivirus as previously described (Rubinson et al. *Nat. Genet.* 33:401-6 (2003)), and the cortical neurons were infected with lentivirus at a mutiplicity of infection (MOI) of 1. Ectopic expression of FL-DR6 induced cortical neurons apoptosis as visualized by cell morphology and cell count (FIG. 5A) compared to control infected cells after 92 hours.

DR6 induced cell death was further verified by XTT assay in parallel cultures that monitors mitochondrial activities of all living cells. The XTT assay is a colorimetric way to determine cell number by measuring mitochondrial activity. FL-DR6 infected cortical neurons exhibited a 2 fold reduction in XTT reading reflecting a significant decrease in cell number caused by DR6 overexpression-induced neuronal death (FIG. 5B). To determine if the Death domain (DD) is required for the cell death, a dominant-negative DR6 lentivirus (DN-DR6) which does not contain the DD, was introduced into cortical neurons by infection. As shown in FIG. 5B, DN-DR6 failed to induce apoptosis in cultured neurons suggesting that DR6 death domain is essential for its neuronal death induction.

The effect of DR6 on caspase-3, a key mediator of apoptosis, was also analyzed. Cortical neurons were infected as described above, and cell lysates were collected 48 hours after infection. A fluorometric homogenous caspase assay kit (Roche, 03005372001) was used to measure caspase-3 activity. Cells were assayed 48 hours after infection. As shown in FIG. 5C, free Rhodamine levels increased 2 fold after infection with the full-length DR6 lentivirus compared to uninfected cells, cells infected with the GFP control lentivirus or cells infected with the dominant negative DR6 lentivirus. This indicates that DR6, but not dominant negative DR6, increases the activity of caspase-3.

These results were confirmed by western blot. Cell lysates were subjected to PAGE, and the separated proteins were probed with anti-DR6 antibody (Santa Cruz). As shown in FIG. 5D, active caspase-3 levels were higher in cells infected with the full-length DR6 lentivirus than with cells infected with the dominant negative DR6 lentivirus or the GFP control lentivirus. In contrast, levels of a control protein (βIII-tubulin) were similar in all three infections. Efficacy of each of the infections was comparable as demonstrated by similar levels of GFP produced by the lentivirus vector in each of the infections. (See FIG. 5D).

Each of these results suggests that DR6 is able to induce cell death in cortical neurons.

Example 6

DR6-FL Overexpression Induces Death of OPCs

The effect of DR6 on the viability of oligodendrocyte precursor cells (OPCs) was also examined. In these experiments, cultures of enriched oligodendrocytes were prepared as previously described (Mi et al., *Nat. Neurosci.* 8:745-51 (2005)). Briefly, forebrains from P2 Sprague Dawley rats (Charles River) were dissected out, minced and incubated in 0.01% Trypsin (Sigma) and 10 μg/ml DNase (Sigma) at 37° C. for 15 minutes. Dissociated cells were plated into 100 μg/ml poly-D-lysine T75 tissue culture flasks and were grown at 37° C. for 10 days in Dulbecco's modified Eagle's medium (DMEM) containing 20% fetal bovine serum (Invitrogen). To get enriched oligodendrocyte progenitors, flasks were shaken at 200 rpm at 37° C. overnight, resulting in a population of 95% purity. Oligodendrocyte progenitor cells were then plated at $2 \times 10^4$/well of a 96 well plate and maintained in DMEM (Invitrogen) containing 10 ng/ml platelet-derived growth factor ($PDGF_{AA}$) and 10 ng/ml fibroblast growth factor (FGF) at 37° C. in humidified air with 5% $CO_2$.

OPCs were then infected with GFP, full-length DR6 and dominant negative DR6 lentivirus as described in Example 5, and 48 hours after infection, the number of dying cells was assessed. Untreated cells and cells treated with 2% Triton X-100 were also examined as negative and positive controls, respectively. First, cells were visualized using phase contrast microscopy and the total number of cells, as well as the number of dying cells, was counted. The percentage of dying cells is represented graphically in FIG. 6A. Infection with full-length DR6 lentivirus led to a significant increase in the percentage of dying cells as compared to cells infected with dominant negative DR6 lentivirus or GFP lentivirus.

The effect of DR6 on the viability of OPCs was also evaluated using XTT and LDH assays. The XTT assay was performed as described in Example 5. Cells were treated with rotenone, an NADH inhibitor, as a positive control. As shown in FIG. 6B, cells that were infected with either dominant negative DR6 lentivirus or GFP lentivirus showed similar levels of cell viability. In contrast, cells treated with rotenone or infected with full-length DR6 lentivirus showed significantly lower levels of cell viability.

Similar results were obtained using an LDH assay. LDH is an enzyme that is released upon cell lysis, so colorimetric assays for LDH activity can be used to measure cell damage. The LDH assay was performed using a cytotoxicity detection kit (LDH, Roche, 11644793001) by following the manufacture's instruction. The results are displayed graphically in FIG. 6C and demonstrate that infection of OPCs with full-length DR6 lentivirus result in significantly greater cytotoxicity as compared to infection with either dominant negative DR6 lentivirus or GFP lentivirus.

Each of these experiments suggest that full-length DR6 is able to induce cell death in OPCs, in addition to cortical neurons.

Example 7

Blocking DR6 Signaling Pathway Promotes Oligodendrocyte Survival and Differentiation Since oligodendrocyte survival is critical for their terminal differentiation, the ability of DR6 antagonists to promote oligodendrocyte survival, differentiation and myelination was evaluated. To address this issue, DR6-DN (deletion of death domain) was used to block DR6 function in oligodendrocytes. As shown in the FIG. 7A, cells infected with DR6 DN exhibited 5-fold higher levels of $MBP^+$ cells and higher MBP and MOG protein determined by Western blot analysis using mouse anti-MBP antibody (SMI 94 and SMI 99, 1:4000, Convance), mouse anti-MOG antibody (1:500) and rabbit anti-beta actin antibody (1:2000, Sigma) (FIG. 7A). Cell infection by lentivirus was confirmed by Western blot detection of the GFP protein co-expression marker (FIG. 7A). In addition, a CNPase assay (FIG. 7B) was performed to measure the level of CNPase, a marker for both immature and mature oligodendrocytes, in an ELISA format. As shown in FIG. 7B, the culture of DR6 FL infected oligodendrocytes expressed decreased CNPase activity compared to the control. In contrast, blocking the DR6 signaling pathwasy with DR6 DN increased CNPase activity (FIG. 7B). These data support the notion that endogenous DR6 negatively regulates oligodendrocyte survival and differentiation.

Example 8

DR6-Induced Neuronal Death is Reversed by DR6-Fc

Cortical neurons were infected with full-length DR6 lentivirus as described in Example 5. However, these cells were incubated in media that was supplemented with increasing amounts of recombinant soluble DR6. Recombinant soluble DR6 was produced by fusing amino acids 1-349 of DR6 to an Fc sequence. The nucleotide sequence of SEQ ID NO: 158 was used in these experiments. Nucleotides 1-1047 of SEQ ID NO: 158 encode DR6 amino acids, and nucleotides 1051-1731 of SEQ ID NO: 158 encode Fc amino acids. Nucleotides 1048-1050 of SEQ ID NO: 158 were inserted due to cloning procedures.

The sequence of the soluble DR6 polypeptide is provided as SEQ ID NO: 159. Amino acids 1-349 of SEQ ID NO: 159 are DR6 amino acids. Amino acids 351-576 of SEQ ID NO:159 are Fc amino acids, and amino acid 350 is an amino acid that was inserted due to cloning procedures.

The soluble DR6 coding sequence was inserted into a lenti viral vector and then used to produce and purify recombinant soluble DR6 from 293 cells. To directly monitor the survival effects of DR6-Fc on FL-DR6 expressing neurons, time-lapse images were obtained. In the presence of DR6-Fc, FL-DR6 failed to induce cortical neuron death (FIG. 8A-B).

The effect of soluble DR6 on DRG neurons was also examined. DRG neurons were first dissected out from adult Sprague Dawley rats (Charles River) and incubated in 0.25% Trypsin/EDTA (Invitrogen) at 37° C. for 30 minutes. An equal volume of DMEM (Invitrogen) containing 20% fetal bovine serum (Invitrogen) was then added to the digestion mixture to stop the reaction. Cell pellets were collected after spinning down at 1,000 rpm at room temperature for 5 minutes and were mechanically dissociated by gently passing through a plastic pipette until no large fragments were visible. About $1 \times 10^5$ DRG neurons were spotted in the center of each well of 4 well chamber-slides (LabTek) that were coated with 100 µg/ml Poly-D-lysine (Sigma). Cells were allowed to attach in growth medium (Neurobasal medium containing B27 supplement (Invitrogen) and 100 ng/ml nerve growth factor (BD Biosciences)) at 37° C. in humidified air with 5% $CO_2$. The next morning, fresh growth medium was replaced, and cells were treated with 20 µM of fluorodeoxyuridine for 3 days to remove proliferating glial cells. Cultures were then maintained in growth medium at 37° C. in humidified air with 5% $CO_2$ with fresh medium change every 3-4 days. After 7 days of culture, DRGs were treated with either control Fc or soluble DR6-Fc for 3 days. DRGs were fixed with 4% paraformaldehyde, and then stained with mouse anti-neuronal class III β-tubulin (Covance, MMS-435P, 1:500). Soluble DR6-Fc increased the total number of neurons bearing processes. In addition, the number of neurons with large and complex processes increased when treated with soluble DR6-Fc (FIG. 9A-B).

In another experiment, cortical neurons were incubated in media containing 0, 1, 3, 10 or 30 µg/ml soluble DR6 protein. After 48 hours, cell lysates were collected and levels of activated caspase-3 protein were measured using rabbit anti-cleaved caspase-3 antibody (91:1000; Cell Signaling). As shown in FIG. 10A, activated caspase-3 was not detectable in uninfected cells, but cells infected with full-length DR6 lentivirus showed high levels of activated caspase-3. However, levels of activated caspase-3 decreased when infected cells were incubated in media containing soluble DR6 (FIG. 10 A-B). Cell lysates were also probed with anti-GFP and anti-β-actin antibodies to control for efficacy of infection and quantity and quality of cell lysates, respectively. These data support the notion that blocking DR6 expression promotes neuronal survival and axon integrity.

Example 9

The Effect of DR6-Fc on Cell Death in Animal Model of Alzheimer's Disease

The effect of DR6-Fc in vivo can be studied using a mouse model of Alzheimer's disease, for example, APPswe/PS-1ΔE9 mice (Park et al., *J. Neurosci* 26:1386-1395 (2006)) from Jackson laboratories (Bar Harbor, Me.) (Stock #04462).

Mice are divided into several treatment groups. The first groups serves as a normal control. Each additional group is treated with DR6-Fc, for example, by intracranial injection or by systemic administration. The amount administered varies for each treatment group. For example, a group can receive 1, 10, 25, 50, 75, 100, 200, 300, 400 or 500 µg/kg per day. Administration can be a one time administration or can occur repeatedly for a specified period of time. Administration can occur before the onset of Alzheimer's symptoms, such that a delay or lack of development of symptoms is indicative of successful prevention and/or treatment. Alternatively, administration can begin after the onset of symptoms (i.e. at 7 months of age), such that a decrease or lack of increase in symptoms is indicative of successful treatment.

Efficacy of treatment can be evaluated symptomatically in live mice, for example by comparison of treated and untreated mice in a water mice. Efficacy can also be evaluated by molecular, biochemical and histological analysis of tissues, such as brain tissue, from sacrificed mice. For example, the number of apoptotic cells, e.g. cortical neurons, in a predetermined size and region of the brain can be compared in treated and untreated mice. The number of apoptotic cells can be determined using any known method in the art including for example, the TUNEL (TdT-mediated dUTP Nick-End Labeling) assay or anti-PARP (poly(ADP-ribose) polymerase) staining. In addition, the total number of surviving cortical neurons in a predetermined size and region of the brain can be compared in treated and untreated mice.

Example 10

The Effect of DR6-Fc on Cell Death in Animal Model of ALS

The effect of DR6-Fc in vivo can also be studied using an animal model of Amyotrophic Lateral Sclerosis (ALS), for example, mice, rats, flies, or worms expressing a mutant superoxide dismutase (SOD1).

For example, mice expressing mutant SOD1 (G37R) are treated with DR6-Fc by any mode of administration such as parenteral administration, subcutaneous administration etc. The amounts and times of administration can be varied. Administration can occur before the onset of ALS symptoms (i.e. at 7 to 9 months of age), such that a delay or lack of development of symptoms is indicative of successful prevention and/or treatment. In addition, administration can begin after the onset of symptoms, such that a decrease or lack of increase in symptoms is indicative of successful treatment.

Efficacy of treatment can be evaluated symptomatically, for example by comparison of muscle strength or longevity of treated and untreated mice. Efficacy can also be evaluated by molecular, biochemical and histological analysis of tissues, such as sections of motor neurons, from sacrificed mice. For example, the number of apoptotic cells, e.g. motor neurons, from a predetermined location, for example, along the spinal cord, can be compared in treated and untreated mice. The number of apoptotic cells can be determined using any known method in the art including for example, the TUNEL (TdT-mediated dUTP Nick-End Labeling) assay or anti-PARP (poly(ADP-ribose) polymerase) staining. In addition, the total number of surviving motor neurons in a predetermined size and region of the spinal cord can be compared in treated and untreated mice.

Example 11

DR6 RNAi Promotes Neuron Survival

Neocortical neurons were removed from embryonic 18 rats, and three million cells were transfected with either 200 nM DR6 siRNAs or scramble control siRNAs using Rat Neuron Nucleofector Kit (Amaxa Inc.). The DR6 siRNAs were a mixture of 4 siRNAs obtained from Dharmacon. The sequences of the 4 siRNAs were: AGAAACGGCUCCU-UUAUUA (SEQ ID NO:160), GGAAGGACAUCUAU-CAGUU (SEQ ID NO:161), GGCCGAUGA- UUGAGAGAUU (SEQ ID NO:162), GCAGUUGGA-AACAGACAAA (SEQ ID NO:163). The sequence of the control siRNA was: GGUGACAUGAUCGACAGCCAU (SEQ ID NO:164).

Transfected cells were plated in one 96-well plate and cultured for 6 days. At day 7, half of the culture media (100 µl) was removed and replaced with 100 µl fresh Neurobasal media containing different concentrations of glutamate, Aβ42 or TNFα. Triplicate cultures were set up for each treatment condition. Cultures were treated for 24 hours. 100 µl of supernatant was removed from each well, and LDH assays were performed using a cytotoxicity kit (LDH Cytotoxicity Detection Kit, Clontech Laboratories, Inc.) according to the manufacturer's instruction. As shown in FIG. 11, knocking down DR6 using RNAi promotes neocortical neuronal survival. Moreover, reducing DR6 expression attenuates Aβ42, glutamate, and TNFα-induced neuronal cytotoxicity. The data also suggests that blocking DR6 expression using RNAi promotes neuronal survival and prevents neuronal death.

Example 12

Blocking DR6 Signaling Pathway by siRNA Promotes Oligodendrocte Differentiation

The effect of DR6 antagonism by DR6 RNAi on oligodendrocyte survival, differentiation and myelination was also evaluated. In these experiments, A2B5 cells were transfected with DR6 RNAi or control RNAi. The cells were harvested and half of the lysis was used for RT-PCR and analyzed by 15% agarose gel. The rest of the cell lysis was used for MBP and MOG western. As shown in FIGS. 12A-B, cells exposed to DR6 RNAi exhibited 2 fold higher levels of MBP+ cells, and higher MBP and MOG protein levels were shown by Western blot analysis (FIG. 12B). Cell infection by lentivirus was confirmed by Western blot detection of the GFP protein co-expression marker. These data further support the notion that endogenous DR6 negatively regulates oligodendrocyte survival and differentiation.

Example 13

Generation of Phage-Display-Derived Fab Antibodies

Recombinant human DR6 ectodomain was used to screen a human naïve phagemid Fab library containing $3.5 \times 10^{10}$ unique clones (Nat Biotechnol. 2005 March; 23(3):344-8.) Biotinylated AP-DR6 protein was captured on steptavidin-coated magnetic beads prior to incubation with the phage library. Selections were performed as described previously, with depletion on a AP-p75 to eliminate AP specific binders (Nat Biotechnol. 2005 March; 23(3):344-8.). After 3 rounds of panning, the 479 bp gene III stump was removed by MluI digestion, and the vector was religated for soluble Fab expression in TG1 cells. ELISA analysis of 2496 clones yielded 212 positive clones, containing 49 unique sequences. Unique clones were purified and binding was reconfirmed at a single concentration to recombinant human DR6 ectodomain by ELISA as well as by FACS on 293E cells transiently transfected with full-length human DR6. Twenty-four unique clones were selected from this analysis for further characterization. The 24 Fabs were tested at multiple concentrations by ELISA on human DR6-Fc to confirm specificity for the DR6 ectodomain versus the AP-DR6 fusion protein, as well as by FACS on full-length human DR6-293E cells, full-length rat DR6-293E cells, and untransfected 293E cells to check for species cross-reactivity. Based on specificity and cross-reactivity data, ten Fabs were selected.

Example 14

Cloning of Murine Anti-Human DR6 Monoclonal Antibody Variable Domains

Total cellular RNA from murine hybridoma cells was prepared using a Qiagen RNeasy mini kit following the manufacturer's recommended protocol. cDNAs encoding the variable regions of the heavy and light chains were cloned by RT-PCR from total cellular RNA, using random hexamers for priming of first strand cDNA. For PCR amplification of the murine immunoglobulin variable domains with intact signal sequences, a cocktail of degenerate forward primers hybridizing to multiple murine immunoglobulin gene family signal sequences and a single back primer specific for the 5' end of the murine constant domain were used. The PCR products were gel-purified and subcloned into Invitrogen's pCR2.1TOPO vector using their TOPO cloning kit following the manufacturer's recommended protocol. Inserts from multiple independent subclones were sequenced to establish a consensus sequence. Deduced mature immunoglobulin N-termini were identical to those determined by Edman degradation of the purified immunoglobulins from the hybridomas. Assignment to specific subgroups is based upon BLAST analysis using consensus immunoglobulin variable domain sequences from the Kabat database. CDRs are designated using the Kabat definitions.

Shown below as SEQ ID NO:107 is the 1P1D6.3 mature heavy chain variable domain protein sequence, with CDRs (Kabat definitions) underlined:

```
  1    QVQLQQSGTE LARPGASVKL SCKASGYTFT DYYLNWMKQG

TGQGLEWIGE

51    IYPGGDHTYY NEKFKGKATL TADKSSNTAF MQLSSLTSED

SAVYFCTRGV

101    IKWGQGTLVT VSL
```

This is a murine subgroup II(A) heavy chain. The DNA sequence of the 1P1D6.3 heavy chain variable domain (from pYL466) is provided as SEQ ID NO:106.

Shown below as SEQ ID NO:112 is the 1P1D6.3 mature light chain variable domain protein sequence, with CDRs underlined:

```
  1    DILMTQSPPS MSVSLGDTVS ITCHASQGIS SNIGWLQQKP

GKSFKGLIYH

51    GSTLEDGVPS RFSGSGSGAE FSLTISSLES EDFADYYCVQ

YAQFPYTFGG

101    GTKLEIK
```

This is a murine subgroup V kappa light chain. The DNA sequence of the mature light chain variable domain (from pYL469) is provided as SEQ ID NO:111.

Shown below as SEQ ID NO:117 is the mature 1P2F2.1 heavy chain variable domain protein sequence, with CDRs underlined:
  1 QVQLQQSGPE VARPGASVKL SCKASGYTFT DYYLNWVKQR TGQGLEWIGE

```
 51 IYPGNNETYY NEKFKGKATL TADNSSSTAY
LQFSSLTSED SAVYFCTRGV
101 IKWGQGTLVT VSV
```

This is a murine subgroup II(A) heavy chain. Note the potential N-linked glycosylation site in CDR2 indicated as double underlined above. The DNA sequence of the 1P2F2.1 heavy chain variable domain (from pYL467) is provided as SEQ ID NO:116.

The heavy chains of 1P1D6.3 and 1P2F2.1 are related, sharing 89.4% identity at the protein level, with identical CDR1 and CDR3 sequences. IgBLAST analyses suggest that they were derived from the same recombinational event. Shown below is the alignment of the heavy chains of 1P1D6.3 (top) and 1P2F2.1 (bottom):

```
  1 QVQLQQSGTELARPGASVKLSCKASGYTFTDYYLNWMKQGTGQGLEWIGE    50
    ||||||||  |•||||||||||||||||||||||||||| •|| ||||||||||
  1 QVQLQQSGPEVARPGASVKLSCKASGYTFTDYYLNWVKQRTGQGLEWIGE    50

•         •         •         •         •
 51 IYPGGDHTYYNEKFKGKATLTADKSSNTAFMQLSSLTSEDSAVYFCTRGV   100
    ||||  •||||||||||||||||||| ||•||::| ||||||||||||||||||||
 51 IYPGNNHTYYNEKFKGKATLTADNSSTAYLQFSSLTSEDSAVYFCTRGV   100

•
101 IKWGQGTLVTVSL 113    (SEQ ID NO: 107)
    |||||||||||•
101 IKWGQGTLVTVSV 113    (SEQ ID NO: 117)
```

Shown below as SEQ ID NO:122 is the 1P2F2.1 mature light chain variable domain protein sequence, with CDRs underlined:

```
  1   DILMTQSPSS MSVSLGDTVS ITCHASQGIR NSIGWLQQKP
      GKSFKGLIYH
 51   ATTLEDGVPS RFTGSGSGAD FSLTISSLES EDFADYYCVQ
      YAQFPYTFGG
101   GTKLEIK
```

This is a murine subgroup V kappa light chain. The DNA sequence of the mature light chain variable domain (from pYL470) is provided as SEQ ID NO:121.

The light chains of 1P1D6.3 and 1P2F2.1 are related, sharing 92.5% identity at the protein level, with identical CDR3 sequences. IgBLAST analyses suggest that they were derived from the same recombinational event. Shown below is the alignment of the light chains of 1P1D6.3 (top) and 1P2F2.1 (bottom):

```
  1 DILMTQSPPSMSVSLGDTVSITCHASQGISSNIGWLQQKPGKSFKGLIYH    50
    ||||||||  ||||||||||||||||||||||||||  ••|||||||||||||||||||
  1 DILMTQSPSSMSVSLGDTVSITCHASQGIRNSIGWLQQKPGKSFKGLIYH    50

•         •         •         •         •
 51 GSTLEDGVPSRFSGSGSGAEFSLTISSLESEDFADYYCVQYAQFPYTFGG   100
    •|||||||||•||||||:|||||||||||||||||||||||||||||||||
 51 ATTLEDGVPSRFTGSGSGADFSLTISSLESEDFADYYCVQYAQFPYTFGG   100

101 GTKLEIK 107    (SEQ ID NO: 112)
    |||||||
101 GTKLEIK 107    (SEQ ID NO: 122)
```

Shown below as SEQ ID NO:127 is the mature 1P5D10.2 heavy chain variable domain protein sequence, with CDRs underlined:

```
  1   EVQLVESGGG LVKPGGSLKL SCAASGFTFS DYYMYWVRQT
      PEKRLEWVAT
 51   ISDGGLYTYY QDSVKGRFTI SRDNAKNNLY LQMSSLKSED
      TAMYYCARED
101   DYDGDFYTMD YWGQGTSVTV SS
```

This is a murine subgroup III(D) heavy chain. The DNA sequence of the 1P5D10.2 heavy chain variable domain (from pYL468) is provided as SEQ ID NO:126.

Shown below as SEQ ID NO:132 is the 1P5D10.2 mature light chain variable domain protein sequence, with CDRs underlined:

```
  1   QIVLTQSPAI MSASPGEKVT ITCSASSSVS YMHWFQQKPG
      TSPKLWIYST
 51   SNLASGVPAR FSGSGSGTSY SLTISRMEAE DAATYYCQQR
      SSYPLTFGAG
101   TKLELK
```

This is a murine subgroup VI kappa light chain. The DNA sequence of the mature 1P5D10.2 light chain variable domain (from pYL471) is provided as SEQ ID NO:131.

Example 15

Anti-DR6 Antibodies Bind to Rat, Mouse and Human DR6

Six million HEK293 cells were transfected with 10 ug of plasmid DNA, which encoded full length human, rat, or mouse DR6. Three days after transfection, approximately 50,000 cells in 200 μL of PBS, 1% BSA, 0.1% NaN3 (FACS buffer) were analyzed. Cells were pelleted and resuspended in 150 μl of serial dilutions of anti-DR6 antibodies in FACS buffer. Samples were incubated for 1 hour on ice with occasional agitation and then washed three times. Bound DR6 antibody was visualized with PE-labeled goat F(ab)$_2$ anti-human Fab (for Dyax Fabs) or anti-mouse IgG specific antibody (for monoclonal antibodies) (Jackson Labs). The results, shown in FIG. 13, demonstrate that 5D10 and 1E6 antibodies each bind to human, rat, and mouse DR6. The results of binding assays using 5D10 and M53E04 are shown in FIG. 30.

Example 16

Blocking DR6 by Anti-DR6 Antibodies Promotes Oligodendrocyte Differentiation and Inhibit Apoptosis To further validate the role of DR6 function in oligodendrocyte survival, anti-DR6 antibodies were used to block DR6 function in the oligodendrocytes culture. As shown in FIGS. 14A-B, anti-DR6 antibody treatment reduced caspase 3$^+$ cells about 3 fold (FIG. 14A) and increased MBP$^+$ cells by 10 fold (FIG. 14B). These results were confirmed by the Western blot analysis (FIG. 14C) where the anti-DR6 antibody reduced the caspase 3 production about 3 fold. In contrast, a 10 fold increase of MBP protein production was seen in the cell cultures treated with the anti-DR6 antibody (FIG. 14C). The results of an oligodendrocyte-DRG co-culture assay using DR6 antibodies M53E04 and 5D10 are shown in FIG. 31 and compared to the results obtained using anti-LINGO-1 antibody Li81 as a positive control.

Example 17

Blocking DR6 by Anti-DR6 Antibodies Promotes Oligodendrocyte/DRG Myelination in Co-Culture To test the hypothesis that blocking DR6 promotes myelination, co-cultures of rat primary oligodendrocytes and DRG neurons were used to ascertain the effects of anti-DR6 antibody on myelination. Such co-cultures normally exhibit low basal levels of myelination which was profoundly enhanced by the addition of anti-DR6 antibody. The cocultures were infected with lentivirus at a multiplicity of infection of two per cell (2 MOI). Treatment with anti-DR6 antibody for 10 days resulted in robust axonal myelination as evident by the presence of MBP myelinated axons, 10 fold higher than control Ig treated cells culture. Western blot analysis using mouse anti-MBP antibody (SMI 94 and SMI 99, 1:4000, Convance), mouse anti-MOG antibody (1:500), and rabbit anti-beta actin antibody (1:2000, Sigma) demonstrates that anti-DR6 antibody promotes myelination in a dosage dependent manner, the higher concentration of anti-DR6 antibody added to the co-culture, the higher level of MBP and MOG protein was produce (FIG. 15). These studies demonstrate that blocking DR6 function promotes oligodendrocyte survival, differentiation and myelination.

Example 18

Blocking DR6 by Anti-DR6 Antibodies Promote Remyelination in Rat Brain Slice Culture The brain slice culture system provides a powerful in vitro model for the analyses of the pathology of demyelination and mechanisms of remyelination. Three day treatment of P17 brain slices with the bioactive lipid, lysophosphatidylcholine (LPC), results in a rapid and near-complete demyelination as visualized by the absence of black gold staining for myelination (FIG. 16A). Exposure to anti-DR6 antibody for 4 days after LPC removal resulted in 15-fold more black gold staining, whereas the control antibody treatment had no effect (FIGS. 16A-B). We next determined whether remyelination could be achieved in vivo in the adult LPC induced demyelination model. LPC was injected into the dorsal columns of the 9 week old young adult (250 gms) rat spinal cords at day 0, followed by anti-DR6 antibody administration 3 days later. The extent of the LPC induced lesion and remyelination was next determined by black gold staining. Myelinated white matter appears dark red in the black gold stained sections and demyelinated lesions appear as pale red or white. Sections from control antibody-treated animals (n=3) showed large lesions with extensive areas of demyelination, whereas substantially smaller lesions were apparent in the anti-DR6 treated group (n=3) 7 days after LPC injection. The black gold staining pattern of anti-DR6-treated and control lesions differed. In anti-DR6 treated lesions, lace-like structures were present throughout the lesion indicative of remyelination. Both brain slice culture and in vivo lysolecithin studies demonstrated that blocking DR6 function by anti-DR6 antibody promote remyelination.

Example 19

Anti-DR6 Antibodies Promote Functional Recovery in Rat EAE Model

Adult 9-week old Brown Norway rats (150 g) were anaesthetized with isoflourine, followed by an injection at the base of the tail with 200 μl of cocktail solution containing: 100 μl of CFA (complete Freund's adjuvant from Chondrex Inc.) and 100 μl of 100 μg recombinant rat MOG corresponding to the N-terminal sequence of rat MOG (amino acids 1-125) in DPBS (MP Biomedicals, LCC). Animals developed signs of EAE 10-15 days after injections. After MOG induction, each animal was assessed by a behavioral test based on motor functions. EAE scores were used as a surrogate clinical metric for demyelination. Rats were scored for clinical signs of EAE daily. The signs were scored as follows: grade 0.5, distal paresis of the tail; grade 1, complete tail paralysis; grade 1.5, paresis of the tail and mild hind leg paresis; grade 2.0, unilateral severe hind leg paresis; grade 2.5, bilateral severe hind limb paresis; grade 3.0, complete bilateral hind limb paralysis; grade 3.5, complete bilateral hind limb paralysis and paresis of one front limb; and grade 4, complete paralysis (tetraplegia), moribund state, or death. After 15 day immunization, rats were randomly assigned to one of two groups. One group of rats (n=10) was injected with isotype control antibodies, and another group (n=10) was injected with DR6 antibodies. The rats were injected twice a week at 6 mg/kg for a total of 5 treatments. EAE scores were measured daily, and the statistical significance was assessed using an unpaired t-test (two-tailed). As shown in FIG. 17A, the EAE scores in DR6 antibody treated rats were significantly lower compared with control animals. For electrophysiological recordings, after 40 day immunization, motor potentials (MEPs) were induced by magnetic cortical stimulation (Magstim) and recorded from the gatrocnemius muscles (Cadwell). The onset of the first, usually negative, deflection was taken as the cortical MEP latency. As shown in FIG. 17B, the DR6-treated rats showed faster nerve conduction velocity.

Example 20

Lymphocyte Number is not Affected in EAE Rats Treated by Anti-DR6 Antibodies

EAE is a complex model for demyelination, as it involves both immune and neurological components. To determine whether treatment with anti-DR6 antibodies affects lymphocytes, after 40 day MOG immunization, peripheral blood was drawn from the facial vein of EAE rats treated with anti-DR6 antibody or control antibody. The total whole blood cells and subset numbers were measured using Hemavet. As shown in FIG. 18, the total lymphocyte numbers and the percentage of lymphocytes in total white blood cells did not show significant differences between the control and anti-DR6 antibody treated animals.

Example 21

Anti-DR6 Antibodies Inhibit T-Cell Infiltration into Spinal Cord in EAE Rats

To determine whether anti-DR6 antibodies affect T cell infiltration into the CNS, EAE rats were euthanized with $CO_2$, then perfused with 0.1 M phosphate buffer after six weeks of MOG immunizations. The lumbar region of spinal cords were dissected out and fixed in 4% paraformaldehyde overnight at 4° C. followed by incubation in 25% sucrose in 0.1 M PBS. 15 transverse and longitude frozen sections (Leica microtome) were cut and standard fluoresce immunohistochemistry was performed using anti-CD4 antibodies (BD Pharmingen). Images were taken under Leica fluorescence microscopy and analyzed using Openlab. As shown in FIG. 19, systemic administration of anti-DR6 antibodies significantly reduced the infiltration of T cells into the spinal cord of the EAE rats, suggesting that the decreased T cell infiltration at least partially explains the decreased severity of the EAE symptoms (lower EAE scores) in anti-DR6 treated animals.

Example 22

TNFalpha Promotes Neuron Death Through NFκb

TNF has been reported to induce DR6 expression in tumor cells to activate apoptosis by activating the NF-κB, Caspase-3 pathway and down regulating Iκb protein level. In order to determine if TNFalpha induces DR6 expression in cortical neurons, neurons were exposed to 24 hour treatment with TNFalpha, and immunohistochemistry staining was performed. The results demonstrated that DR6 expression was increased significantly. TNFalpha induced neuronal death and was well correlated with DR6 positive cells (FIG. 20A-C). The study was confirmed by Western blot (FIG. 21A). Treatment with TNFalpha induced a 2 fold increase in DR6 expression after a 24 hour treatment, which also correlated with a 10 fold NF-κB increase and a 2 fold Iκb protein down regulation (FIGS. 21A-D). DR6 RNAi transfected neurons showed a 2 fold reduction of DR6 and NFκB level (FIGS. 22B and C). In contrast, DR6 RNAi tranfected neurons showed increased (2 fold) Iκb protein expression (FIGS. 22A-D). (Control and DR6 siRNAs used were as described in Example 11). These data suggest that DR6 up-regulation correlated with NFκb expression and inversely correlated with Iκb expression.

Example 23

DR6 Antagonists Promote Schwann Cell Myelination of DRG Axons

In order to determine if DR6 antagonists affect schwann cells, the effect of anti-DR6 antibodies on schwann cell and DR6 neuron co-cultures was examined. In these experiments, DRG neurons from E16 rats were plated (50,000/well) in 4 well slides with Neurobasal medium plus B27 and NGF. The cultures were treated by FDUR for 4-6 days to removed the dividing cells. After day 7, the DRG cells were treated with Neurobasal medium plus B27 and NGF (100 ng/ml) for an additional 7-10 days. Then, purified schwann cells (50,000/well) were added to the DRG neurons (50,000/well) in Neurobasal medium with B27 and 100 ng/ml NGF. The medium was changed weekly. The co-cultures were harvested and assayed by IHC or Western blot for MBP protein after 10 days. IHC staining and Western blots (FIG. 23) both showed increased levels of MBP protein in cultures treated with anti-DR6 antibodies compared to cultures treated with a control antibody. These data indicate that DR6 antagonists promote schwann cell myelination of neurons.

Example 24

DR6 is Upregulated in Apoptotic Cortical Neurons

In order to examine DR6 expression in neocortical neurons, neurons were first separated from E18 Sprague Dawley rats (Charles River). Briefly, cerebral cortices from E18 rat embryos were dissected out, minced, and incubated in 0.25% Trypsin/EDTA (Invitrogen) at 37° C. for 10 minutes. The cells were then triturated after adding 20 ug/ml DNase I (Sigma) and 10% fetal bovine serum (Invitrogen) to stop the reaction. Cell pellets were collected and then mechanically dissociated by gently passing through a plastic pipette until no large fragments were visible. Cells were plated in 8-well slide chambers (NUNC) that were pre-coated with 100 ug/ml Poly-D-Lysine (Sigma) at $4 \times 10^4$ cells per well. Cells were maintained in Neurobasal medium containing B27 supplement (Invitrogen) at 37° C. in humidified air with 5% $CO_2$ with fresh medium changed every 3-4 days. Cells were cultured for 3 weeks and fixed with 4% paraformaldehyde in PBS for 30 minutes. After three washes with PBS, cells were penetrated with PBS containing 1% Triton X-100 (PBST, Sigma) for 30 minutes followed by incubation in blocking solution (PBS containing 0.1% Triton X-100 and 10% normal goat serum (NGS)) for 30 minutes at room temperature. For primary labeling, cells were then incubated in blocking medium containing rabbit anti-DR6 (Santa Cruz, sc-13106, 1:200) and mouse anti-neuronal class III β-tubulin (Covance, MMS-435P, 1:500) at 4° C. overnight. After three PBST rinses, cells were incubated in 5% NGS-PBS containing Alexa 594 anti-rabbit IgG (1:500) and Alexa 488 anti-mouse IgG (1:500) secondary antibodies at room temperature for 1 hour in the dark. After three PBST washes, cells were mounted with antifade with DAPI reagents (Invitrogen) and observed under fluorescence microscope. Apoptosis, shown by nuclear condensation, was visible in neocortical neurons after 3 weeks in culture. Levels of DR6 were compared in apoptotic and non-apoptotic neurons. The expression level of DR6 was up-regulated in the apoptotic neurons compared to non-apoptotic neurons. These results suggest than an increase in DR6 expression can contribute to aged neuron apoptosis.

Example 25

DR6 Antagonists Promote Axon Integrity

In order to examine the effect of DR6 antagonists on the axonal integrity of neocortical neurons, neurons were separated from E18 Sprague Dawley rats (Charles River) and cultured in neurobasal medium containing B27 supplement (Invitrogen) at 37° C. in humidified air with 5% $CO_2$ as described in Example 24. After 7 days of culture, cells were treated with β-amyloid (aggregated Aβ-42) at a concentration of (50 μg/ml) and either 10 μg/ml soluble DR6-Fc or 10 μg/ml soluble control antibody. After 48 hours, neurons were fixed with 4% paraformaldehyde and then stained with mouse anti-neuronal class III β-tubulin (Covance, MMS-435P, 1:500) as described in Example 24. Treatment with β-amyloid induced neuronal cell death and axon degeneration as compared to untreated controls. However, soluble DR6-Fc treatment significantly attenuated β-amyloid induced axonal degeneration and neuronal cell death. Soluble DR6-Fc treatment also led to increased survival of neurons and decreased axon beading, which is typical of axon degeneration morphology. These results suggest that DR6 antagonists diminish the negative effects of β-amyloid on neocortical neurons.

Example 26

DR6 and AKT Expression are Inversely Correlated

Phosphorylated AKT (phospho-AKT) is a well-known survival signal. Therefore, the relationship of DR6 and phospho-AKT levels was examined in neocortical neurons. In these experiments, neocortical neurons were separated as described above. After 3, 7, 14, and 20 days of culture, neocortical neurons were lysed in 80 μl lysis buffer (50 mM HEPES, pH 7.5, 150 mM NaCl, 1.5 mM $MgCl_2$, 1 mM EGTA, 1% Triton X-100, and 10% glycerol) for 30 minutes at 4° C. After centrifugation at 14,000×g for 15 minutes, the supernatants were boiled in Laemmli sample buffer, subjected to 4-20% SDS-PAGE, and analyzed by Western blotting with rabbit anti-phospho-AKT antibody (1:500, cell signaling), rabbit anti-AKT antibody (1:1000, cell signaling), goat anti-DR6 antibody (1:1000, Santa Cruz), and rabbit anti-beta actin antibody (1:2000, Sigma). Primary antibodies were visualized using anti-rabbit IgG-HRP (1:5000) and anti-goat IgG-HRP (1:5000, Bio-Rad) accordingly. The expression levels of DR6 were high in day 7 cultures and low in day 20 cultures (FIG. 24). In contrast, the levels of phospho-AKT were low at day 7 and high at day 20 (FIG. 24). The inverse correlation of DR6 and phospho-AKT levels suggests that DR6 could induce cell death through the AKT signaling pathway.

Example 27

DR6 and p75 Form a Complex

In order to determine if p75 could interact with DR6, recombinant cell lines expressing (i) DR6, p75, and TrkA, (ii) DR6 and TrkA, (iii) p75 and TrkA, and (iv) DR6 and p75 were created. In these experiments, human TrkA was expressed with a Flag tag fused to the N-terminal of the mature TrkA protein (amino acids 34-796). Rat p75 was expressed with a His tag fused to the N-terminus of the mature p75 protein (amino acids 30-431), and human DR6 was expressed with a Myc tag fused to the N-terminus of the mature DR6 protein (amino acids 32-655). DR6 was immunoprecipitated from cell lysates using a Myc antibody, and the levels of DR6 and p75 in the samples was assessed. Western blots (FIG. 25 A) show that p75 co-immunoprecipitated with DR6 in the presence or absence of TrkA.

In addition, cells containing a vector encoding DR6 or a negative control vector (pV90) were assayed for binding to p75. Alkaline phosphatase-p75 protein was added to the cells and cell surface binding was measured. The results are shown in FIG. 25B.

Similar results were obtained using samples obtained from human fetal spinal cords obtained from BioChain®. Immunoprepitation experiments demonstrated that p75 co-immunoprecipiates with DR6 (FIG. 25 C).

These data demonstrate that DR6 and p75 form a complex both in cell culture assays and in human samples.

Example 28

The Expression Patterns of DR6 and p75 Overlap

The expression levels of DR6 and p75 mRNA were obtained from the publically available database mouse.brain-map.org, made available by the Allen Institute for Brain Science. Both DR6 and p75 were highly expressed in various regions of the brain, and expression levels were well correlated (FIG. 26). These results suggest that DR6 and p75 co-localize, and therefore can interact and function together in vivo.

Example 29

DR6 Antibodies can Block Interaction of DR6 with p75

In order to determine if DR6 antibodies block the interaction of DR6 with p75, recombinant DR6 was immunoprepitated from cells using either the 2A9 anti-DR6 antibody or the 5D10 anti-DR6 antibody. Western analysis demonstrated that while both anti-DR6 antibodies were able to pull down DR6 protein, p75 only co-immunoprecipitated with DR6 when the 2A9 antibody was used (FIG. 27A). Thus, the 5D10 DR6 antibody disrupted interaction of DR6 with p75.

The ability of 5D10 to disrupt the interaction of DR6 and p75 was also confirmed by a functional assay. In this assay cells CHO cells containing either a control vector or a vector encoding p75 were incubated with alkaline phosphatase-DR6 and assayed for binding. High levels of cell surface binding were observed when the p75-expressing cells were incubated with DR6. However, the addition of 5D10 prevented DR6 from binding to p75-expressing cells (FIG. 27B). These results indicate that the DR6 antibody 5D10 can disrupt binding of DR6 to p75 and promote cell survival.

Example 30

The TNFR-Cys Repeats 3 and 4 of DR6 Bind to Antibodies that Disrupt the DR6-p75 Interaction In order to identify domains of DR6 that bind to DR6 antibodies that disrupt the DR6-p75 interaction, cells expressing DR6 deletion constructs were created. The deletion constructs were tagged with Myc. The constructs tested included deletions of amino acids 168-189 of SEQ ID NO:2 (#123); amino acids 134-168 of SEQ ID NO:2 (#124); amino acids 109-131 of SEQ ID NO:2 (#134); amino acids 49-108 of SEQ ID NO:2 (#234); amino acids 133-189 of SEQ ID NO:2 (#12); amino acids 49-131 of SEQ ID NO:2 (#34); and amino acids 49-108 and 168-189 of SEQ ID NO:2 (#23).

FACS analysis was used to demonstrate that each of the deletion constructs expressed in cells (FIG. 28A). Then, samples obtained from the recombinant cells were immunoprecipiated with an anti-Myc antibody or an anti-DR6 antibody. The immunoprecipitates were assayed for p75 protein by Western, and the results showed that antibody 5D10 binds to the Cys3 and Cys4 domain of DR6 (amino acids 133-189) (FIG. 28B). Antibody 2A9 binds to the Cys1 domain of DR6 (amino acids 49-131) (FIG. 28B). The binding of a panel of DR6 antibodies to DR6 deletion constructs was also assayed (FIG. 28C). The results demonstrated that 5D10 and 4A4 bind to the Cys3 and Cys4 domains of DR6, and 2A9, 1D6, and 2F2 bind to the Cys1 domain of DR6.

Example 31

The TNFR-Cys Repeats 3 and 4 of DR6 Bind to p75

In order to indentify the domains of DR6 that bind to p'75, cells expressing the DR6 deletion constructs described in Example 30 were assayed for binding to p75. Recombinant cells were incubated with p75, and then cell lysates were immunoprecipitated using an anti-Myc antibody. Levels of p75 were assessed by Western, and the results demonstrated that deletion of the Cys3 and Cys4 domain of DR6 (amino acids 133-189) resulted in a decreased ability of DR6 to interact with p75.

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

It is to be appreciated that the Detailed Description section, and not the Summary and Abstract sections, is intended to be used to interpret the claims. The Summary and Abstract sections can set forth one or more but not all exemplary embodiments of the present invention as contemplated by the inventor(s), and thus, are not intended to limit the present invention and the appended claims in any way.

What is claimed is:

1. An isolated antibody or antigen-binding fragment thereof that can specifically bind to DR6 and that inhibits binding of DR6 to p75.

2. The antibody or fragment thereof of claim 1 that does not prevent binding of DR6 to APP.

3. A method of promoting oligodendrocyte differentiation or survival comprising contacting an oligodendrocyte cell or oligodendrocyte precursor cell with the antibody or fragment thereof of claim 1.

4. The method of claim 3, wherein said cell is in a mammal and said contacting comprises administering an effective amount of the antibody or fragment thereof to a mammal in need thereof.

5. The method of claim 3, wherein said contacting occurs in vitro.

6. The isolated antibody or fragment thereof of claim 1, wherein the antibody or fragment can bind to the same DR6 epitope as an antibody comprising a heavy chain variable region (VH) comprising the amino acids of SEQ ID NO: 127 and a light chain variable region (VL) comprising the amino acids of SEQ ID NO: 132.

7. The isolated antibody or fragment there of claim 1, wherein the antibody or fragment comprises a heavy chain variable region (VH) comprising the amino acids of SEQ ID NO: 127.

8. The isolated antibody or fragment there of claim 1, wherein the antibody or fragment comprises a light chain variable region (VL) comprising the amino acids of SEQ ID NO: 132.

9. The isolated antibody or fragment there of claim 7, wherein the antibody or fragment further comprises a light chain variable region (VL) comprising the amino acids of SEQ ID NO: 132.

10. The isolated antibody or fragment there of claim 1, wherein the antibody or fragment comprises
a heavy chain variable region (VH) comprising VH-CDR1, VH-CDR2, and VH-CDR3 regions comprising the amino acid sequences of SEQ ID NOs: 128, 129, and 130 and
a light chain variable region (VL) comprising VL-CDR1, VL-CDR2, and VL-CDR3 regions comprising the amino acid sequences of SEQ ID NOs: 133, 134, and 135.

11. The isolated antibody or antigen-binding fragment thereof of claim 1, wherein the antibody binds to an epitope in amino acids 133-189 of SEQ ID NO:2.

12. An isolated antibody or antigen-binding fragment thereof that can specifically bind to the same DR6 epitope as a reference monoclonal Fab antibody fragment selected from the group consisting of M50-H01, M51-H09, M53-E04, M53-F04, M62-B02, M63-E10, M66-B03, M67-G02, M72-F03, and M73-C04 or a reference monoclonal antibody selected from the group consisting of 1P1D6.3, 1P2F2.1, and 1P5D10.2.

13. The isolated antibody or fragment thereof of claim 12, wherein said antibody or fragment thereof comprises an antigen binding domain identical to that of a monoclonal Fab antibody fragment selected from the group consisting of M50-H01, M51-H09, M53-E04, M53-F04, M62-B02, M63-E10, M66-B03, M67-G02, M72-F03, and M73-004 or a reference monoclonal antibody selected from the group consisting of 1P1D6.3, 1P2F2.1, and 1P5D10.2.

14. The isolated antibody or fragment thereof of claim 12, wherein the VH of said antibody or fragment thereof comprises VH-CDR1, VH-CDR2, and VH-CDR3 amino acid sequences selected from the group consisting of: SEQ ID NOs: 8, 9, and 10; SEQ ID NOs: 18, 19, and 20;

SEQ ID NOs: 28, 29, and 30; SEQ ID NOs: 38, 39, and 40; SEQ ID NOs: 48, 49, and 50; SEQ ID NOs: 58, 59, and 60; SEQ ID NOs: 68, 69, and 70; SEQ ID NOs: 78, 79, and 80; SEQ ID NOs: 88, 89, and 90; SEQ ID NOs: 98, 99, and 100; SEQ ID NOs: 108, 109, and 110; SEQ ID NOs: 118, 119, and 120; and SEQ ID NOs: 128, 129, and 130; and wherein the VL of said antibody or fragment thereof comprises VL-CDR1, VL-CDR2, and VL-CDR3 amino acid sequences selected from the group consisting of: SEQ ID NOs: 13, 14, and 15; SEQ ID NOs: 23, 24, and 25; SEQ ID NOs: 33, 34, and 35; SEQ ID NOs: 43, 44, and 45; SEQ ID NOs: 53, 54, and 55; SEQ ID NOs: 63, 64, and 65; SEQ ID NOs: 73, 74, and 75; SEQ ID NOs: 83, 84, and 85; SEQ ID NOs: 93, 94, and 95; SEQ ID NOs: 103, 104, and 105; SEQ ID NOs: 113, 114, and 115; SEQ ID NOs: 123, 124, and 125; and SEQ ID NOs: 133, 134, and 135.

15. An isolated polynucleotide comprising a nucleic acid encoding an immunoglobulin heavy chain variable region (VH), wherein the VH-CDR1, VH-CDR2, and VH-CDR3 of said VH comprise amino acid sequences selected from the group consisting of: SEQ ID NOs: 8, 9, and 10; SEQ ID NOs: 18, 19, and 20; SEQ ID NOs: 28, 29, and 30; SEQ ID NOs: 38, 39, and 40; SEQ ID NOs: 48, 49, and 50; SEQ ID NOs: 58, 59, and 60; SEQ ID NOs: 68, 69, and 70; SEQ ID NOs: 78, 79, and 80; SEQ ID NOs: 88, 89, and 90; SEQ ID NOs: 98, 99, and 100; SEQ ID NOs: 108, 109, and 110; SEQ ID NOs: 118, 119, and 120; and SEQ ID NOs: 128, 129, and 130.

16. A polypeptide encoded by the polynucleotide of claim 15.

17. A composition comprising the polynucleotide of claim 15 and further comprising an isolated polynucleotide comprising a nucleic acid encoding an immunoglobulin light chain variable region (VL), wherein the VL-CDR1, VL-CDR2, and VL-CDR3 of said VL comprise amino acid sequences selected from the group consisting of: SEQ ID NOs: 13, 14, and 15; SEQ ID NOs: 23, 24, and 25; SEQ ID NOs: 33, 34, and 35; SEQ ID NOs: 43, 44, and 45; SEQ ID NOs: 53, 54, and 55; SEQ ID NOs: 63, 64, and 65; SEQ ID NOs: 73, 74, and 75; SEQ ID NOs: 83, 84, and 85; SEQ ID NOs: 93, 94, and 95; SEQ ID NOs: 103, 104, and 105; SEQ ID NOs: 113, 114, and 115; SEQ ID NOs: 123, 124, and 125; and SEQ ID NOs: 133, 134, and 135; and wherein the nucleic acid encoding the VH and the nucleic acid encoding the VL are in a single vector or in a first and second vector.

18. A polypeptide encoded by the polynucleotide of claim 17.

* * * * *

SEQUENCE LISTING

```
<160> NUMBER OF SEQ ID NOS: 166

<210> SEQ ID NO 1
<211> LENGTH: 3660
<212> TYPE: DNA
<213> ORGANISM: Homo sapiens

<400> SEQUENCE: 1
gccaccacgt gtgtccctgc gcccggtggc caccgactca gtccctcgcc gaccagtctg      60
ggcagcggag gagggtggtt ggcagtggct ggaagcttcg ctatgggaag ttgttccttt     120
gctctctcgc gcccagtcct cctccctggt tctcctcagc cgctgtcgga ggagagcacc     180
cggagacgcg ggctgcagtc gcggcggctt ctccccgcct gggcggccgc gccgctgggc     240
aggtgctgag cgcccctaga gcctcccttg ccgcctccct cctctgcccg gccgcagcag     300
tgcacatggg gtgttggagg tagatgggct cccggcccgg gaggcggcgg tggatgcggc     360
gctgggcaga agcagccgcc gattccagct gccccgcgcg ccccgggcgc ccctgcgagt     420
ccccggttca gccatgggga cctctccgag cagcagcacc gccctcgcct cctgcagccg     480
catcgcccgc cgagccacag ccacgatgat cgcgggctcc cttctcctgc ttggattcct     540
tagcaccacc acagctcagc cagaacagaa ggcctcgaat ctcattggca cataccgcca     600
tgttgaccgt gccaccggcc aggtgctaac ctgtgacaag tgtccagcag gaacctatgt     660
ctctgagcat tgtaccaaca caagcctgcg cgtctgcagc agttgccctg tggggacctt     720
taccaggcat gagaatggca tagagaaatg ccatgactgt agtcagccat gcccatggcc     780
aatgattgag aaattacctt gtgctgcctt gactgaccga gaatgcactt gcccacctgg     840
catgttccag tctaacgcta cctgtgcccc ccatacggtg tgtcctgtgg gttggggtgt     900
gcggaagaaa gggacagaga ctgaggatgt gcggtgtaag cagtgtgctc ggggtacctt     960
```

-continued

```
ctcagatgtg ccttctagtg tgatgaaatg caaagcatac acagactgtc tgagtcagaa      1020
cctggtggtg atcaagccgg ggaccaagga gacagacaac gtctgtggca cactcccgtc      1080
cttctccagc tccacctcac cttccctgg cacagccatc tttccacgcc ctgagcacat       1140
ggaaacccat gaagtccctt cctccactta tgttcccaaa ggcatgaact caacagaatc      1200
caactcttct gcctctgtta gaccaaaggt actgagtagc atccaggaag gacagtccc       1260 tgacaacaca agctcagcaa gggggaagga agacgtgaac aagaccctcc caaaccttca     1320
ggtagtcaac caccagcaag gcccccacca cagacacatc ctgaagctgc tgccgtccat     1380
ggaggccact gggggcgaga agtccagcac gcccatcaag ggccccaaga ggggacatcc     1440
tagacagaac ctacacaagc attttgacat caatgagcat ttgccctgga tgattgtgct     1500
tttcctgctg ctggtgcttg tggtgattgt ggtgtgcagt atccggaaaa gctcgaggac     1560
tctgaaaaag gggccccggc aggatcccag tgccattgtg aaaaggcag gctgaagaa      1620 atccatgact ccaacccaga accgggagaa atggatctac tactgcaatg ccatggtat     1680 cgatatcctg aagcttgtag cagcccaagt gggaagccag tggaaagata tctatcagtt     1740
tctttgcaat gccagtgaga gggaggttgc tgctttctcc aatgggtaca cagccgacca     1800
cgagcgggcc tacgcagctc tgcagcactg gaccatccgg ggccccgagg ccagcctcgc     1860
ccagctaatt agcgccctgc gccagcaccg gagaaacgat gttgtggaga agattcgtgg     1920
gctgatggaa gacaccaccc agctggaaac tgacaaacta gctctcccga tgagcccag      1980 cccgcttagc ccgagcccca tccccagccc aacgcgaaa cttgagaatt ccgctctcct     2040
gacggtggag ccttccccac aggacaagaa caagggcttc ttcgtggatg agtcggagcc     2100
ccttctccgc tgtgactcta catccagcgg ctccctccgcg ctgagcagga acggttcctt    2160
tattaccaaa gaaaagaagg acacagtgtt gcggcaggta cgcctggacc cctgtgactt    2220
gcagcctatc tttgatgaca tgctccactt tctaaatcct gaggagctgc gggtgattga    2280
agagattccc caggctgagg acaaactaga ccggctattc gaaattattg gagtcaagag    2340
ccaggaagcc agccagaccc tcctggactc tgtttatagc catcttcctg acctgctgta    2400
gaacataggg atactgcatt ctggaaatta ctcaatttag tggcagggtg gttttttaat    2460
tttcttctgt ttctgatttt tgttgtttgg ggtgtgtgtg tgtgtttgtg tgtgtgtgtg    2520
tgtgtgtgtg tgtgtgtgtg tttaacagag aatatggcca gtgcttgagt tctttctcct    2580
tctctctctc tctttttttt ttaaataact cttctgggaa gttggtttat aagcctttgc    2640
caggtgtaac tgttgtgaaa tacccaccac taaagttttt taagttccat attttctcca    2700
ttttgccttc ttatgtattt tcaagattat tctgtgcact ttaaatttac ttaacttacc    2760
ataaatgcag tgtgactttt cccacacact ggattgtgag gctcttaact tcttaaaagt    2820
ataatggcat cttgtgaatc ctataagcag tctttatgtc tcttaacatt cacacctact    2880
ttttaaaaac aaatattatt actattttta ttattgtttg tcctttataa attttcttaa    2940
agattaagaa aatttaagac cccattgagt tactgtaatg caattcaact ttgagttatc    3000
ttttaaatat gtcttgtata gttcatattc atggctgaaa cttgaccaca ctattgctga    3060
ttgtatggtt ttcacctgga caccgtgtag aatgcttgat tacttgtact cttcttatgc    3120
taatatgctc tgggctggag aaatgaaatc ctcaagccat caggatttgc tatttaagtg    3180
gcttgacaac tgggccacca agaacttga acttcacctt ttaggatttg agctgttctg     3240
gaacacattg ctgcactttg gaaagtcaaa atcaagtgcc agtggcgccc tttccataga    3300
gaatttgccc agctttgctt taaaagatgt cttgtttttt atatacacat aatcaatagg    3360
```

-continued

```
tccaatctgc tctcaaggcc ttggtcctgg tgggattcct tcaccaatta ctttaattaa    3420
aaatggctgc aactgtaaga acccttgtct gatatatttg caactatgct cccatttaca    3480
aatgtacctt ctaatgctca gttgccaggt tccaatgcaa aggtggcgtg gactcccttt    3540
gtgtgggtgg ggtttgtggg tagtggtgaa ggaccgatat cagaaaaatg ccttcaagtg    3600
tactaattta ttaataaaca ttaggtgttt gttaaaaaaa aaaaaaaaaa aaaaaaaaa     3660
```

<210> SEQ ID NO 2
<211> LENGTH: 655
<212> TYPE: PRT
<213> ORGANISM: Homo sapiens

<400> SEQUENCE: 2

```
Met Gly Thr Ser Pro Ser Ser Thr Ala Leu Ala Ser Cys Ser Arg
1               5                   10                  15

Ile Ala Arg Arg Ala Thr Ala Thr Met Ile Ala Gly Ser Leu Leu
                20                  25                  30

Leu Gly Phe Leu Ser Thr Thr Thr Ala Gln Pro Glu Gln Lys Ala Ser
            35                  40                  45

Asn Leu Ile Gly Thr Tyr Arg His Val Asp Arg Ala Thr Gly Gln Val
        50                  55                  60

Leu Thr Cys Asp Lys Cys Pro Ala Gly Thr Tyr Val Ser Glu His Cys
65                  70                  75                  80

Thr Asn Thr Ser Leu Arg Val Cys Ser Ser Cys Pro Val Gly Thr Phe
                85                  90                  95

Thr Arg His Glu Asn Gly Ile Glu Lys Cys His Asp Cys Ser Gln Pro
            100                 105                 110

Cys Pro Trp Pro Met Ile Glu Lys Leu Pro Cys Ala Ala Leu Thr Asp
        115                 120                 125

Arg Glu Cys Thr Cys Pro Pro Gly Met Phe Gln Ser Asn Ala Thr Cys
    130                 135                 140

Ala Pro His Thr Val Cys Pro Val Gly Trp Gly Val Arg Lys Lys Gly
145                 150                 155                 160

Thr Glu Thr Glu Asp Val Arg Cys Lys Gln Cys Ala Arg Gly Thr Phe
                165                 170                 175

Ser Asp Val Pro Ser Ser Val Met Lys Cys Lys Ala Tyr Thr Asp Cys
            180                 185                 190

Leu Ser Gln Asn Leu Val Val Ile Lys Pro Gly Thr Lys Glu Thr Asp
        195                 200                 205

Asn Val Cys Gly Thr Leu Pro Ser Phe Ser Ser Thr Ser Pro Ser
    210                 215                 220

Pro Gly Thr Ala Ile Phe Pro Arg Pro Glu His Met Glu Thr His Glu
225                 230                 235                 240

Val Pro Ser Ser Thr Tyr Val Pro Lys Gly Met Asn Ser Thr Glu Ser
                245                 250                 255

Asn Ser Ser Ala Ser Val Arg Pro Lys Val Leu Ser Ser Ile Gln Glu
            260                 265                 270

Gly Thr Val Pro Asp Asn Thr Ser Ala Arg Gly Lys Glu Asp Val
        275                 280                 285

Asn Lys Thr Leu Pro Asn Leu Gln Val Val Asn His Gln Gln Gly Pro
    290                 295                 300

His His Arg His Ile Leu Lys Leu Leu Pro Ser Met Glu Ala Thr Gly
305                 310                 315                 320

Gly Glu Lys Ser Ser Thr Pro Ile Lys Gly Pro Lys Arg Gly His Pro
                325                 330                 335
```

Arg Gln Asn Leu His Lys His Phe Asp Ile Asn Glu His Leu Pro Trp
                340                 345                 350

Met Ile Val Leu Phe Leu Leu Val Leu Val Ile Val Val Cys
            355                 360                 365

Ser Ile Arg Lys Ser Ser Arg Thr Leu Lys Lys Gly Pro Arg Gln Asp
            370                 375                 380

Pro Ser Ala Ile Val Glu Lys Ala Gly Leu Lys Lys Ser Met Thr Pro
385                 390                 395                 400

Thr Gln Asn Arg Glu Lys Trp Ile Tyr Tyr Cys Asn Gly His Gly Ile
            405                 410                 415

Asp Ile Leu Lys Leu Val Ala Ala Gln Val Gly Ser Gln Trp Lys Asp
            420                 425                 430

Ile Tyr Gln Phe Leu Cys Asn Ala Ser Glu Arg Glu Val Ala Ala Phe
            435                 440                 445

Ser Asn Gly Tyr Thr Ala Asp His Glu Arg Ala Tyr Ala Ala Leu Gln
            450                 455                 460

His Trp Thr Ile Arg Gly Pro Glu Ala Ser Leu Ala Gln Leu Ile Ser
465                 470                 475                 480

Ala Leu Arg Gln His Arg Arg Asn Asp Val Val Glu Lys Ile Arg Gly
            485                 490                 495

Leu Met Glu Asp Thr Thr Gln Leu Glu Thr Asp Lys Leu Ala Leu Pro
            500                 505                 510

Met Ser Pro Ser Pro Leu Ser Pro Ser Pro Ile Pro Ser Pro Asn Ala
            515                 520                 525

Lys Leu Glu Asn Ser Ala Leu Leu Thr Val Glu Pro Ser Pro Gln Asp
            530                 535                 540

Lys Asn Lys Gly Phe Phe Val Asp Glu Ser Glu Pro Leu Leu Arg Cys
545                 550                 555                 560

Asp Ser Thr Ser Ser Gly Ser Ser Ala Leu Ser Arg Asn Gly Ser Phe
            565                 570                 575

Ile Thr Lys Glu Lys Lys Asp Thr Val Leu Arg Gln Val Arg Leu Asp
            580                 585                 590

Pro Cys Asp Leu Gln Pro Ile Phe Asp Asp Met Leu His Phe Leu Asn
            595                 600                 605

Pro Glu Glu Leu Arg Val Ile Glu Glu Ile Pro Gln Ala Glu Asp Lys
            610                 615                 620

Leu Asp Arg Leu Phe Glu Ile Ile Gly Val Lys Ser Gln Glu Ala Ser
625                 630                 635                 640

Gln Thr Leu Leu Asp Ser Val Tyr Ser His Leu Pro Asp Leu Leu
            645                 650                 655

<210> SEQ ID NO 3
<211> LENGTH: 3626
<212> TYPE: DNA
<213> ORGANISM: Mus musculus

<400> SEQUENCE: 3
gtgtccccga gctgagtggc catccgactc agtccctcgc cggccggtct aggcagcgga      60
ggaggcgagt gcttgatagt ggctggaagc ttcgctatgg gaagtcgctc tttagcactg     120
tcgcggctag ccctgctctc tggttctccg cagccgctgt cgttggagag caccggggag     180
cgcgggttgc gagcgcgcct gcttctcacc gcccgggcgc cagcgcccct gggcaggtgc     240
tgagcgcctt tcggagcctc ccctgctgcc tccctcttcc gctgggtgc  ctggctgctg      300 cagtgcacat gggctgctgg aggtagatgg gctcaccgcc cgtgaggcgg cggtggatgc     360

```
ggcgctgggc agaaacagcc accaattcca gctgccgtgg ggccgagcgc cccgggcgcc    420
gctgcgagcc ccgagctcgg ccatggggac ccgggcaagc agcatcaccg ccctcgcctc    480
ttgcagccgc accgccggcc aagtcggagc cacgatggtc gccggctctc ttctcctgct    540
tggattcctc agcaccatca cagctcaacc agaacaaaag actctgagtc tccctggcac    600
ctaccgccat gttgaccgta ccactggcca ggtgctaacc tgcgacaagt gcccagcagg    660
aacgtacgtc tccgagcact gtaccaacat gagcctgcga gtctgcagca gctgcccgc     720
ggggaccttt accaggcacg agaacggcat agagagatgc catgactgta gtcagccatg    780
tccatggccg atgattgaga gattaccttg tgctgccttg actgaccgag agtgcatctg    840
cccacctgga atgtatcagt ctaatggtac ctgcgctccc catacagtgt gccccgtggg    900
ctggggtgtg cggaagaaag ggacagagaa tgaagatgtg cgctgtaagc agtgcgctcg    960
gggtaccttc tctgacgtgc cttccagtgt gatgaagtgt aaagctcaca cggactgtct   1020
gggtcagaac ctggaggtgg tcaagccagg gaccaaggag acagacaacg tctgtggcat   1080
gcgcctgttc ttctccagca caaacccacc ttcctctggc acagttacct tttctcaccc   1140
tgagcatatg gaatcccacg atgtcccttc ctccacctat gagccccaag gcatgaactc   1200
aacagattcc aactctactg cctctgttag aactaaggta ccaagtggca tcgaggaagg   1260
gacagtgcct gacaatacga gctcaaccag tgggaaggaa ggcactaata ggaccctgcc   1320
aaacccacca caagttaccc accagcaagc cccccaccac agacacattc tgaagctgct   1380
gccatcgtcc atggaggcca cgggtgagaa gtccagcaca gccatcaagg cccccaagag   1440
gggtcacccc agacagaacg ctcacaagca tttcgacatc aacgagcact gccttggat    1500
gatcgtcctc ttccttctgc tggtcctggt gctgatagtg gtgtgcagta tccgaaagag   1560
ctccaggact ctcaaaaagg ggccccggca ggatcccagc gccatagtgg aaaaggcggg   1620
gctgaagaag tccctgactc ccacccagaa ccgggagaaa tggatctact accgcaacgg   1680
ccatggtatt gacatcttga agcttgtagc agcccaggtg ggaagccagt ggaaggacat   1740
ctatcagttt ctttgcaacg ccagcgagag ggaggtggcg gccttctcca atggatacac   1800
tgcagatcat gaacgggcct acgcggctct gcagcactgg accatccgtg gccctgaggc   1860
cagccttgcc cagctcatta gcgccttgcg ccagcaccga cgcaatgatg ttgtggagaa   1920
gattcgtggg ctgatggaag acaccacgca gttggaaaca gacaaactgg ctctccccat   1980
gagccccagt ccgcttagcc cgagcccat gcccagtcct aacgtgaaac ttgagaattc    2040
cactctcctg acagtggagc cctcaccgct ggacaagaac aagtgcttct tcgtggacga   2100
gtcagagccc cttctgcgat gcgactccac atccagtggc tcttcagcac tgagcagaaa   2160
cggctccttt attaccaaag aaaagaagga cacagtgttg cggcaggtcc gcctggaccc   2220
ctgtgacttg cagcccatct ttgatgacat gctgcatatc ctgaacccg aggagctgcg    2280
ggtgattgaa gagattcccc aggctgagga caaactggac cgcctcttcg agatcattgg   2340
ggtcaagagc caagaagcca gccagaccct cttggactct gtgtacagtc atcttcctga   2400
cctattgtag aacacagggg cactgcattc tgggaatcaa cctactggcg gggtgatttc   2460
atttcgtttc tgacttttgt gttttggtgt gtatgtatgt gtttaacaga gtgtatggcc   2520
ggtgagtttg ggttctttct ttctttcttt ttctttcttt ctttctttct ttctttctt    2580
ttctttcttt ctttctttct tccttcctga aagtgaatgt ataaagcctt tacaatgtat   2640
aactgttgga aaatgcccac cactaaattt ttttttaagt tccacatatt ctccatttt    2700
gccttcttat atatatcttc aacactattc tgtgcacttt aaaaacttaa cataaacgca   2760
```

```
gtgtgacttc tcccatatgc tgggtcccga gactctcaac ttcttaaaaa cctaatggca    2820
tcttgtgact cctagaagta gacataagtc tttcaacctt cacacctact ctttctgttt    2880
taattattat tgctatttgt cttattgttt gtgctttaca agcgttcttg aggacggagg    2940
gaatctacga ccctgttgat gactgtaact ctattcgact ttgagttgtc ttcttcatgt    3000
cttgttatat agttcatatt catggctgaa acttgaccat actccctagc gctgattgta    3060
tggttttcgt ctggacaccg tacactgcct gataacttgt gcacctctta acgctactat    3120
gctctgggct ggagaatgaa atctttaagt caccaggact tgctgtttca gtggcttgac    3180
acctgggcca ccaaagaact cgatcttcat cttttaggga cacctctgct gcaccttgga    3240
aagccaacct taagtgccag tgcacttta tgcccagctt tgctttgaaa gatatctttc    3300
ttgttttttt tatccttctc tttctctctt ttttttaaaa atacacatag tcaataggtc    3360
cagtctgccc tcaaggcctt gctgggtttt cttcatcatc caatcacttt cattaaaaat    3420
ggctgcagct gtaagaactc ttgtctgata aattttcaac tatgctctca tttatctacc    3480
tgccctctga tgctcagtcg tcagactcta atgcaaaggt ggacgtcggc tgcctttgcg    3540
tgggcgggct tagtggtgag gaactgatat cagaaaaaaa atgccttcaa gtatactaat    3600
ttattaataa atattaggtg tttgtt                                         3626

<210> SEQ ID NO 4
<211> LENGTH: 655
<212> TYPE: PRT
<213> ORGANISM: Mus musculus

<400> SEQUENCE: 4

Met Gly Thr Arg Ala Ser Ser Ile Thr Ala Leu Ala Ser Cys Ser Arg
 1               5                  10                  15

Thr Ala Gly Gln Val Gly Ala Thr Met Val Ala Gly Ser Leu Leu Leu
                20                  25                  30

Leu Gly Phe Leu Ser Thr Ile Thr Ala Gln Pro Glu Gln Lys Thr Leu
            35                  40                  45

Ser Leu Pro Gly Thr Tyr Arg His Val Asp Arg Thr Thr Gly Gln Val
        50                  55                  60

Leu Thr Cys Asp Lys Cys Pro Ala Gly Thr Tyr Val Ser Glu His Cys
65                  70                  75                  80

Thr Asn Met Ser Leu Arg Val Cys Ser Ser Cys Pro Ala Gly Thr Phe
                85                  90                  95

Thr Arg His Glu Asn Gly Ile Glu Arg Cys His Asp Cys Ser Gln Pro
            100                 105                 110

Cys Pro Trp Pro Met Ile Glu Arg Leu Pro Cys Ala Ala Leu Thr Asp
        115                 120                 125

Arg Glu Cys Ile Cys Pro Pro Gly Met Tyr Gln Ser Asn Gly Thr Cys
    130                 135                 140

Ala Pro His Thr Val Cys Pro Val Gly Trp Gly Val Arg Lys Lys Gly
145                 150                 155                 160

Thr Glu Asn Glu Asp Val Arg Cys Lys Gln Cys Ala Arg Gly Thr Phe
                165                 170                 175

Ser Asp Val Pro Ser Ser Val Met Lys Cys Lys Ala His Thr Asp Cys
            180                 185                 190

Leu Gly Gln Asn Leu Glu Val Val Lys Pro Gly Thr Lys Glu Thr Asp
        195                 200                 205

Asn Val Cys Gly Met Arg Leu Phe Phe Ser Ser Thr Asn Pro Pro Ser
    210                 215                 220
```

-continued

```
Ser Gly Thr Val Thr Phe Ser His Pro Glu His Met Glu Ser His Asp
225                 230                 235                 240

Val Pro Ser Ser Thr Tyr Glu Pro Gln Gly Met Asn Ser Thr Asp Ser
            245                 250                 255

Asn Ser Thr Ala Ser Val Arg Thr Lys Val Pro Ser Gly Ile Glu Glu
                260                 265                 270

Gly Thr Val Pro Asp Asn Thr Ser Ser Thr Ser Gly Lys Glu Gly Thr
        275                 280                 285

Asn Arg Thr Leu Pro Asn Pro Pro Gln Val Thr His Gln Gln Ala Pro
290                 295                 300

His His Arg His Ile Leu Lys Leu Leu Pro Ser Ser Met Glu Ala Thr
305                 310                 315                 320

Gly Glu Lys Ser Ser Thr Ala Ile Lys Ala Pro Lys Arg Gly His Pro
                325                 330                 335

Arg Gln Asn Ala His Lys His Phe Asp Ile Asn Glu His Leu Pro Trp
                340                 345                 350

Met Ile Val Leu Phe Leu Leu Val Leu Val Leu Ile Val Val Cys
                355                 360                 365

Ser Ile Arg Lys Ser Ser Arg Thr Leu Lys Lys Gly Pro Arg Gln Asp
370                 375                 380

Pro Ser Ala Ile Val Glu Lys Ala Gly Leu Lys Lys Ser Leu Thr Pro
385                 390                 395                 400

Thr Gln Asn Arg Glu Lys Trp Ile Tyr Tyr Arg Asn Gly His Gly Ile
                405                 410                 415

Asp Ile Leu Lys Leu Val Ala Ala Gln Val Gly Ser Gln Trp Lys Asp
                420                 425                 430

Ile Tyr Gln Phe Leu Cys Asn Ala Ser Glu Arg Glu Val Ala Ala Phe
                435                 440                 445

Ser Asn Gly Tyr Thr Ala Asp His Glu Arg Ala Tyr Ala Ala Leu Gln
450                 455                 460

His Trp Thr Ile Arg Gly Pro Glu Ala Ser Leu Ala Gln Leu Ile Ser
465                 470                 475                 480

Ala Leu Arg Gln His Arg Arg Asn Asp Val Val Glu Lys Ile Arg Gly
                485                 490                 495

Leu Met Glu Asp Thr Thr Gln Leu Glu Thr Asp Lys Leu Ala Leu Pro
                500                 505                 510

Met Ser Pro Ser Pro Leu Ser Pro Ser Pro Met Pro Ser Pro Asn Val
                515                 520                 525

Lys Leu Glu Asn Ser Thr Leu Leu Thr Val Glu Pro Ser Pro Leu Asp
530                 535                 540

Lys Asn Lys Cys Phe Phe Val Asp Glu Ser Glu Pro Leu Leu Arg Cys
545                 550                 555                 560

Asp Ser Thr Ser Ser Gly Ser Ser Ala Leu Ser Arg Asn Gly Ser Phe
                565                 570                 575

Ile Thr Lys Glu Lys Lys Asp Thr Val Leu Arg Gln Val Arg Leu Asp
                580                 585                 590

Pro Cys Asp Leu Gln Pro Ile Phe Asp Asp Met Leu His Ile Leu Asn
                595                 600                 605

Pro Glu Glu Leu Arg Val Ile Glu Glu Ile Pro Gln Ala Glu Asp Lys
                610                 615                 620

Leu Asp Arg Leu Phe Glu Ile Ile Gly Val Lys Ser Gln Glu Ala Ser
625                 630                 635                 640

Gln Thr Leu Leu Asp Ser Val Tyr Ser His Leu Pro Asp Leu Leu
```

645                 650                 655

<210> SEQ ID NO 5
<211> LENGTH: 8
<212> TYPE: PRT
<213> ORGANISM: Artificial sequence
<220> FEATURE:
<223> OTHER INFORMATION: Cyclic DR6 polypeptides
<220> FEATURE:
<221> NAME/KEY: misc_feature
<222> LOCATION: (5)..(7)
<223> OTHER INFORMATION: Xaa can be lysine, arginine, histidine,
      glutamine or asparagine

<400> SEQUENCE: 5

Cys Leu Ser Pro Xaa Xaa Xaa Cys
1               5

<210> SEQ ID NO 6
<211> LENGTH: 357
<212> TYPE: DNA
<213> ORGANISM: Artificial Sequence
<220> FEATURE:
<223> OTHER INFORMATION: M50-H01 variable heavy chain

<400> SEQUENCE: 6
gaagttcaat tgttagagtc tggtggcggt cttgttcagc ctggtggttc tttacgtctt    60
tcttgcgctg cttccggatt cactttctct gattacccta tgatgtgggt tcgccaagct   120
cctggtaaag gtttggagtg gtttctcgt atctctcctt ctggtggcca tactatttat    180
gctgactccg ttaaaggtcg cttcactatc tctagagaca actctaagaa tactctctac   240
ttgcagatga acagcttaag ggctgaggac acggccgtgt attactgtgc gaaagattgg   300
cacggtggtg gtgctttga tatctggggc caagggacaa tggtcaccgt ctcaagc      357

<210> SEQ ID NO 7
<211> LENGTH: 119
<212> TYPE: PRT
<213> ORGANISM: Artificial sequence
<220> FEATURE:
<223> OTHER INFORMATION: M50-H01 variable heavy chain

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Pro Met Met Trp Val Arg Gln Ala Pro Gly Lys Gly Leu Glu Trp Val
        35                  40                  45

Ser Arg Ile Ser Pro Ser Gly Gly His Thr Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Trp His Gly Gly Gly Ala Phe Asp Ile Trp Gly Gln Gly
            100                 105                 110

Thr Met Val Thr Val Ser Ser
        115

<210> SEQ ID NO 8
<211> LENGTH: 5
<212> TYPE: PRT

```
<213> ORGANISM: Artificial Sequence
<220> FEATURE:
<223> OTHER INFORMATION: M50-H01 VH CDR1

<400> SEQUENCE: 8

Asp Tyr Pro Met Met
1               5

<210> SEQ ID NO 9
<211> LENGTH: 17
<212> TYPE: PRT
<213> ORGANISM: Artificial sequence
<220> FEATURE:
<223> OTHER INFORMATION: M50-H01 VH CDR2

<400> SEQUENCE: 9

Arg Ile Ser Pro Ser Gly Gly His Thr Ile Tyr Ala Asp Ser Val Lys
1               5                   10                  15

Gly

<210> SEQ ID NO 10
<211> LENGTH: 10
<212> TYPE: PRT
<213> ORGANISM: Artificial Sequence
<220> FEATURE:
<223> OTHER INFORMATION: M50-H01  VH CDR3

<400> SEQUENCE: 10

Asp Trp His Gly Gly Gly Ala Phe Asp Ile
1               5                   10

<210> SEQ ID NO 11
<211> LENGTH: 321
<212> TYPE: DNA
<213> ORGANISM: Artificial Sequence
<220> FEATURE:
<223> OTHER INFORMATION: M50-H01 variable light chain

<400> SEQUENCE: 11
gacatccaga tgacccagtc tccatcctct gtgtctgcat ctgtaggaga cagagtcacc      60
atcacttgtc gggcgagtca gggtattaga agctggttag cctggtatca gcagaaacca     120
gggaaagccc ctaaactcct gatctatgat gcatccactt tgcaaagtgg ggtcccatca     180
aggttcaggg gcggtggctc tgggacagat ttcactctca ctatcagcag cctgcagcct     240
gaagattttg caacttacta ctgtcaacag agttacagta ccccgctcac tttcggcgga     300
gggaccaagg tggagatcaa a                                               321

<210> SEQ ID NO 12
<211> LENGTH: 107
<212> TYPE: PRT
<213> ORGANISM: Artificial sequence
<220> FEATURE:
<223> OTHER INFORMATION: M50-H01 variable light chain

<400> SEQUENCE: 12

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Ser Trp
            20                  25                  30

Leu Ala Trp Tyr Gln Gln Lys Pro Gly Lys Ala Pro Lys Leu Leu Ile
        35                  40                  45

Tyr Asp Ala Ser Thr Leu Gln Ser Gly Val Pro Ser Arg Phe Arg Gly
    50                  55                  60
```

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 13
<211> LENGTH: 11
<212> TYPE: PRT
<213> ORGANISM: Artificial Sequence
<220> FEATURE:
<223> OTHER INFORMATION: M50-H01 VL CDR1

<400> SEQUENCE: 13

Arg Ala Ser Gln Gly Ile Arg Ser Trp Leu Ala
1               5                   10

<210> SEQ ID NO 14
<211> LENGTH: 7
<212> TYPE: PRT
<213> ORGANISM: Artificial sequence
<220> FEATURE:
<223> OTHER INFORMATION: M50-H01 VL CDR2

<400> SEQUENCE: 14

Asp Ala Ser Thr Leu Gln Ser
1               5

<210> SEQ ID NO 15
<211> LENGTH: 9
<212> TYPE: PRT
<213> ORGANISM: Artificial Sequence
<220> FEATURE:
<223> OTHER INFORMATION: M50-H01 VL CDR3

<400> SEQUENCE: 15

Gln Gln Ser Tyr Ser Thr Pro Leu Thr
1               5

<210> SEQ ID NO 16
<211> LENGTH: 351
<212> TYPE: DNA
<213> ORGANISM: Artificial sequence
<220> FEATURE:
<223> OTHER INFORMATION: M51-H09 variable heavy chain

<400> SEQUENCE: 16
gaagttcaat tgttagagtc tggtggcggt cttgttcagc ctggtggttc tttacgtctt      60
tcttgcgctg cttccggatt cactttctct ccttactcta tgacttgggt tcgccaagct     120
cctggtaaag gtttgagtg gtttcttct atcgttcctt ctggtggcaa gacttggtat      180
gctgactccg ttaaaggtcg cttcactatc tctagagaca actctaagaa tactctctac     240
ttgcagatga acagcttaag ggctgaggac acggccgtgt attactgtgc gaggaccaat     300
cttagctact tgactactg gggccagggc accctggtca ccgtctcaag c              351

<210> SEQ ID NO 17
<211> LENGTH: 117
<212> TYPE: PRT
<213> ORGANISM: Artificial sequence
<220> FEATURE:
<223> OTHER INFORMATION: M51-H09 variable heavy chain

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Ser Met Thr Trp Val Arg Gln Ala Pro Gly Lys Gly Leu Glu Trp Val
        35                  40                  45

Ser Ser Ile Val Pro Ser Gly Gly Lys Thr Trp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Asn Leu Ser Tyr Phe Asp Tyr Trp Gly Gln Gly Thr Leu
            100                 105                 110

Val Thr Val Ser Ser
        115

<210> SEQ ID NO 18
<211> LENGTH: 5
<212> TYPE: PRT
<213> ORGANISM: Artificial Sequence
<220> FEATURE:
<223> OTHER INFORMATION: M51-H09 VH CDR1

<400> SEQUENCE: 18

Pro Tyr Ser Met Thr
1               5

<210> SEQ ID NO 19
<211> LENGTH: 17
<212> TYPE: PRT
<213> ORGANISM: Artificial Sequence
<220> FEATURE:
<223> OTHER INFORMATION: M51-H09 VH CDR2

<400> SEQUENCE: 19

Ser Ile Val Pro Ser Gly Gly Lys Thr Trp Tyr Ala Asp Ser Val Lys
1               5                   10                  15

Gly

<210> SEQ ID NO 20
<211> LENGTH: 8
<212> TYPE: PRT
<213> ORGANISM: Artificial Sequence
<220> FEATURE:
<223> OTHER INFORMATION: M51-H09 VH CDR3

<400> SEQUENCE: 20

Thr Asn Leu Ser Tyr Phe Asp Tyr
1               5

<210> SEQ ID NO 21
<211> LENGTH: 330
<212> TYPE: DNA
<213> ORGANISM: Artificial Sequence
<220> FEATURE:
<223> OTHER INFORMATION: M51-H09 variable light chain

<400> SEQUENCE: 21
cagagcgaat tgactcagcc tccctccgcg tccgggtctc ctggacagtc agtcaccatc      60
tcctgcactg gaaccagcaa tgacgttggt agttataact atatctcctg gttccaacag     120

```
cacccaggca aagcccccaa actcatgatt tatgaggtca ataagcggcc ctcaggggtc    180
cctgatcgct tctctggctc caagtctgac aacacggcct ccctgaccgt ctctgggctc    240
caggctgaag atgaggctga ttattactgc acctcatatg caggcagcca caagtgggtg    300
ttcggcggag ggaccaagct gaccgtccta                                     330
```

<210> SEQ ID NO 22
<211> LENGTH: 110
<212> TYPE: PRT
<213> ORGANISM: Artificial Sequence
<220> FEATURE:
<223> OTHER INFORMATION: M51-H09 variable light chain

<400> SEQUENCE: 22

```
Gln Ser Glu Leu Thr Gln Pro Pro Ser Ala Ser Gly Ser Pro Gly Gln
1               5                   10                  15

Ser Val Thr Ile Ser Cys Thr Gly Thr Ser Asn Asp Val Gly Ser Tyr
            20                  25                  30

Asn Tyr Ile Ser Trp Phe Gln Gln His Pro Gly Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Asp Asn Thr Ala Ser Leu Thr Val Ser Gly Leu
65                  70                  75                  80

Gln Ala Glu Asp Glu Ala Asp Tyr Tyr Cys Thr Ser Tyr Ala Gly Ser
                85                  90                  95

His Lys Trp Val Phe Gly Gly Gly Thr Lys Leu Thr Val Leu
            100                 105                 110
```

<210> SEQ ID NO 23
<211> LENGTH: 14
<212> TYPE: PRT
<213> ORGANISM: Artificial Sequence
<220> FEATURE:
<223> OTHER INFORMATION: M51-H09 VL CDR1

<400> SEQUENCE: 23

```
Thr Gly Thr Ser Asn Asp Val Gly Ser Tyr Asn Tyr Ile Ser
1               5                   10
```

<210> SEQ ID NO 24
<211> LENGTH: 7
<212> TYPE: PRT
<213> ORGANISM: Artificial Sequence
<220> FEATURE:
<223> OTHER INFORMATION: M51-H09 VL CDR2

<400> SEQUENCE: 24

```
Glu Val Asn Lys Arg Pro Ser
1               5
```

<210> SEQ ID NO 25
<211> LENGTH: 10
<212> TYPE: PRT
<213> ORGANISM: Artificial Sequence
<220> FEATURE:
<223> OTHER INFORMATION: M51-H09 VL CDR3

<400> SEQUENCE: 25

```
Thr Ser Tyr Ala Gly Ser His Lys Trp Val
1               5                   10
```

<210> SEQ ID NO 26

<211> LENGTH: 345
<212> TYPE: DNA
<213> ORGANISM: Artificial Sequence
<220> FEATURE:
<223> OTHER INFORMATION: M53-E04 variable heavy chain

<400> SEQUENCE: 26

```
gaagttcaat tgttagagtc tggtggcggt cttgttcagc ctggtggttc tttacgtctt      60
tcttgcgctg cttccggatt cactttctct aattacgaga tgtcttgggt tcgccaagct     120
cctggtaaag gtttggagtg ggtttcttct atctattctt ctggtggcga gactctttat     180
gctgactccg ttaaaggtcg cttcactatc tctagagaca actctaagaa tactctctac     240
ttgcagatga acagcttaag ggctgaggac acggccgtgt attactgtgc gagagatgga     300
gcagctgact actggggcca gggcaccctg gtcaccgtct caagc                     345
```

<210> SEQ ID NO 27
<211> LENGTH: 115
<212> TYPE: PRT
<213> ORGANISM: Artificial Sequence
<220> FEATURE:
<223> OTHER INFORMATION: M53-E04 variable heavy chain

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Glu Met Ser Trp Val Arg Gln Ala Pro Gly Lys Gly Leu Glu Trp Val
        35                  40                  45

Ser Ser Ile Tyr Ser Ser Gly Gly Glu Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Ala Asp Tyr Trp Gly Gln Gly Thr Leu Val Thr
            100                 105                 110

Val Ser Ser
        115

<210> SEQ ID NO 28
<211> LENGTH: 5
<212> TYPE: PRT
<213> ORGANISM: Artificial Sequence
<220> FEATURE:
<223> OTHER INFORMATION: M53-E04 VH CDR1

<400> SEQUENCE: 28

Asn Tyr Glu Met Ser
1               5

<210> SEQ ID NO 29
<211> LENGTH: 17
<212> TYPE: PRT
<213> ORGANISM: Artificial Sequence
<220> FEATURE:
<223> OTHER INFORMATION: M53-E04 VH CDR2

<400> SEQUENCE: 29

Ser Ile Tyr Ser Ser Gly Gly Glu Thr Leu Tyr Ala Asp Ser Val Lys
1               5                   10                  15

<210> SEQ ID NO 30
<211> LENGTH: 6
<212> TYPE: PRT
<213> ORGANISM: Artificial Sequence
<220> FEATURE:
<223> OTHER INFORMATION: M53-E04 VH CDR3

<400> SEQUENCE: 30

Asp Gly Ala Ala Asp Tyr
1               5

<210> SEQ ID NO 31
<211> LENGTH: 330
<212> TYPE: DNA
<213> ORGANISM: Artificial Sequence
<220> FEATURE:
<223> OTHER INFORMATION: M53-E04 variable light chain

<400> SEQUENCE: 31
cagagcgaat tgactcagcc accctcggcg tctgggaccc ccgggcagtg ggtcaccatc      60
tcttgttctg gaagcacctc caacatcgga ataattatg tatactgta ccagcagctc      120 ccaggaacgg cccccaagct cctcatctat acgaataatc agcggccctc aggggtccct      180
gaccgattct ctggctccaa gtctggcacg tccgcctccc tggccatcag tgggctccgg      240
tccgaggatg aggctgatta ttactgtgcg acatgggatg acagtttgta tgctccggta      300
ttcggcggag ggaccaaggt gaccgtccta                                       330

<210> SEQ ID NO 32
<211> LENGTH: 110
<212> TYPE: PRT
<213> ORGANISM: Artificial Sequence
<220> FEATURE:
<223> OTHER INFORMATION: M53-E04 variable light chain

<400> SEQUENCE: 32

Gln Ser Glu Leu Thr Gln Pro Pro Ser Ala Ser Gly Thr Pro Gly Gln
1               5                   10                  15

Trp Val Thr Ile Ser Cys Ser Gly Ser Thr Ser Asn Ile Gly Asn Asn
            20                  25                  30

Tyr Val Tyr Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Tyr Ala Pro Val Phe Gly Gly Gly Thr Lys Val Thr Val Leu
            100                 105                 110

<210> SEQ ID NO 33
<211> LENGTH: 13
<212> TYPE: PRT
<213> ORGANISM: Artificial Sequence
<220> FEATURE:
<223> OTHER INFORMATION: M53-E04 VL CDR1

<400> SEQUENCE: 33

Ser Gly Ser Thr Ser Asn Ile Gly Asn Asn Tyr Val Tyr
1               5                   10

<210> SEQ ID NO 34
<211> LENGTH: 7
<212> TYPE: PRT
<213> ORGANISM: Artificial Sequence
<220> FEATURE:
<223> OTHER INFORMATION: M53-E04 VL CDR2

<400> SEQUENCE: 34

Thr Asn Asn Gln Arg Pro Ser
1               5

<210> SEQ ID NO 35
<211> LENGTH: 11
<212> TYPE: PRT
<213> ORGANISM: Artificial Sequence
<220> FEATURE:
<223> OTHER INFORMATION: M53-E04 VL CDR3

<400> SEQUENCE: 35

Ala Thr Trp Asp Asp Ser Leu Tyr Ala Pro Val
1               5                   10

<210> SEQ ID NO 36
<211> LENGTH: 351
<212> TYPE: DNA
<213> ORGANISM: Artificial Sequence
<220> FEATURE:
<223> OTHER INFORMATION: M53-F04 variable heavy chain

<400> SEQUENCE: 36
gaagttcaat tgttagagtc tggtggcggt cttgttcagc ctggtggttc tttacgtctt      60
tcttgcgctg cttccggatt cactttctct gagtacacta tgcattgggt tcgccaagct     120
cctggtaaag gtttggagtg ggtttctgtt atctcttctt ctggtggccg tactgtttat     180
gctgactccg ttaaaggtcg cttcactatc tctagagaca actctaagaa tactctctac     240
ttgcagatga acagcttaag ggctgaggac acggccgtgt attactgtgc gagagatctg     300
agtaactaca tggactactg gggccagggc accctggtca ccgtctcaag c              351

<210> SEQ ID NO 37
<211> LENGTH: 117
<212> TYPE: PRT
<213> ORGANISM: Artificial Sequence
<220> FEATURE:
<223> OTHER INFORMATION: M53-F04 variable heavy chain

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Thr Met His Trp Val Arg Gln Ala Pro Gly Lys Gly Leu Glu Trp Val
        35                  40                  45

Ser Val Ile Ser Ser Ser Gly Gly Arg Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Asn Tyr Met Asp Tyr Trp Gly Gln Gly Thr Leu
            100                 105                 110

Val Thr Val Ser Ser
        115

<210> SEQ ID NO 38
<211> LENGTH: 5
<212> TYPE: PRT
<213> ORGANISM: Artificial Sequence
<220> FEATURE:
<223> OTHER INFORMATION: M53-F04 VH CDR1

<400> SEQUENCE: 38

Glu Tyr Thr Met His
1               5

<210> SEQ ID NO 39
<211> LENGTH: 17
<212> TYPE: PRT
<213> ORGANISM: Artificial Sequence
<220> FEATURE:
<223> OTHER INFORMATION: M53-F04 VH CDR2

<400> SEQUENCE: 39

Val Ile Ser Ser Ser Gly Gly Arg Thr Val Tyr Ala Asp Ser Val Lys
1               5                   10                  15

Gly

<210> SEQ ID NO 40
<211> LENGTH: 8
<212> TYPE: PRT
<213> ORGANISM: Artificial Sequence
<220> FEATURE:
<223> OTHER INFORMATION: M53-F04 VH CDR3

<400> SEQUENCE: 40

Asp Leu Ser Asn Tyr Met Asp Tyr
1               5

<210> SEQ ID NO 41
<211> LENGTH: 318
<212> TYPE: DNA
<213> ORGANISM: Artificial Sequence
<220> FEATURE:
<223> OTHER INFORMATION: M53-F04 variable light chain

<400> SEQUENCE: 41
gacatccaga tgacccagtc tccagccacc ctgtctttgt ctccagggga aagagccacc      60
ctctcctgca gggccagtca gactgttagc aactacttag cctggtacca acagaaacct     120
ggccaggctc ccaggctcct catctatgat gcctccaaca gggccactgg catcccagcc     180
aggttcagtg gcagtgggtc tgggacagac ttcactctca ccatcagcag cctagagcct     240
gaagattttg cagtttatta ctgtcagcag cgtagcaagt ggctctcttt cggcggaggg     300
accaaggtgg agatcaaa                                                   318

<210> SEQ ID NO 42
<211> LENGTH: 106
<212> TYPE: PRT
<213> ORGANISM: Artificial Sequence
<220> FEATURE:
<223> OTHER INFORMATION: M53-F04 variable light chain

<400> SEQUENCE: 42

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Thr Val Ser Asn Tyr

```
                    20                  25                  30
Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Leu Ser
                85                  90                  95

Phe Gly Gly Gly Thr Lys Val Glu Ile Lys
            100                 105

<210> SEQ ID NO 43
<211> LENGTH: 11
<212> TYPE: PRT
<213> ORGANISM: Artificial Sequence
<220> FEATURE:
<223> OTHER INFORMATION: M53-F04 VL CDR1

<400> SEQUENCE: 43

Arg Ala Ser Gln Thr Val Ser Asn Tyr Leu Ala
1               5                   10

<210> SEQ ID NO 44
<211> LENGTH: 7
<212> TYPE: PRT
<213> ORGANISM: Artificial Sequence
<220> FEATURE:
<223> OTHER INFORMATION: M53-F04 VL CDR2

<400> SEQUENCE: 44

Asp Ala Ser Asn Arg Ala Thr
1               5

<210> SEQ ID NO 45
<211> LENGTH: 8
<212> TYPE: PRT
<213> ORGANISM: Artificial Sequence
<220> FEATURE:
<223> OTHER INFORMATION: M53-F04 VL CDR3

<400> SEQUENCE: 45

Gln Gln Arg Ser Lys Trp Leu Ser
1               5

<210> SEQ ID NO 46
<211> LENGTH: 348
<212> TYPE: DNA
<213> ORGANISM: Artificial Sequence
<220> FEATURE:
<223> OTHER INFORMATION: M62-B02 variable heavy chain

<400> SEQUENCE: 46
gaagttcaat tgttagagtc tggtggcggt cttgttcagc ctggtggttc tttacgtctt      60
tcttgcgctg cttccggatt cactttctct atgtacatta tgaattgggt tcgccaagct     120
cctggtaaag gtttggagtg ggtttcttct atcgtttctt ctggtggctg gacttttat     180
gctgactccg ttaaaggtcg cttcactatc tctagagaca actctaagaa tactctctac     240
ttgcagatga acagcttaag ggctgaggac acggccgtgt attactgtgc gagggggccac     300
tacggtatgg acgtctgggg ccaagggacc acggtcaccg tctcaagc                  348

<210> SEQ ID NO 47
```

```
<211> LENGTH: 116
<212> TYPE: PRT
<213> ORGANISM: Artificial Sequence
<220> FEATURE:
<223> OTHER INFORMATION: M62-B02 variable heavy chain

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Ile Met Asn Trp Val Arg Gln Ala Pro Gly Lys Gly Leu Glu Trp Val
        35                  40                  45

Ser Ser Ile Val Ser Ser Gly Gly Trp Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Gly Met Asp Val Trp Gly Gln Gly Thr Thr Val
            100                 105                 110

Thr Val Ser Ser
        115

<210> SEQ ID NO 48
<211> LENGTH: 5
<212> TYPE: PRT
<213> ORGANISM: Artificial Sequence
<220> FEATURE:
<223> OTHER INFORMATION: M62-B02 VH CDR1

<400> SEQUENCE: 48

Met Tyr Ile Met Asn
1               5

<210> SEQ ID NO 49
<211> LENGTH: 17
<212> TYPE: PRT
<213> ORGANISM: Artificial Sequence
<220> FEATURE:
<223> OTHER INFORMATION: M62-B02 VH CDR2

<400> SEQUENCE: 49

Ser Ile Val Ser Ser Gly Gly Trp Thr Phe Tyr Ala Asp Ser Val Lys
1               5                   10                  15

Gly

<210> SEQ ID NO 50
<211> LENGTH: 7
<212> TYPE: PRT
<213> ORGANISM: Artificial Sequence
<220> FEATURE:
<223> OTHER INFORMATION: M62-B02 VH CDR3

<400> SEQUENCE: 50

Gly His Tyr Gly Met Asp Val
1               5

<210> SEQ ID NO 51
<211> LENGTH: 339
<212> TYPE: DNA
<213> ORGANISM: Artificial Sequence
<220> FEATURE:
<223> OTHER INFORMATION: M62-B02 variable light chain
```

<400> SEQUENCE: 51

```
gacatccaga tgacccagtc tccagactcc ctggctgtgt ctctgggcga gagggccacc    60
atcaactgca agtccagccg gagtgtttta tacagctcca acaataagaa ctacttagct   120
tggtaccagc agaaaccagg acagcctcct aagctgctca tttactgggc ttctacccgg   180
gaatccgggg tccctgaccg attcagtggc agcgggtctg ggacagattt cactctcacc   240
atcagcagcc tgcaggctga agatgtggca gtttattact gtcagcaata ttatagtact   300
cctctcactt tcggcggagg gaccaaggtg gagatcaaa                          339
```

<210> SEQ ID NO 52
<211> LENGTH: 113
<212> TYPE: PRT
<213> ORGANISM: Artificial Sequence
<220> FEATURE:
<223> OTHER INFORMATION: M62-B02 variable light chain

<400> SEQUENCE: 52

```
Asp Ile Gln Met Thr Gln Ser Pro Asp Ser Leu Ala Val Ser Leu Gly
1               5                   10                  15
Glu Arg Ala Thr Ile Asn Cys Lys Ser Ser Arg Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Ser Thr Pro Leu Thr Phe Gly Gly Gly Thr Lys Val Glu Ile
            100                 105                 110
Lys
```

<210> SEQ ID NO 53
<211> LENGTH: 17
<212> TYPE: PRT
<213> ORGANISM: Artificial Sequence
<220> FEATURE:
<223> OTHER INFORMATION: M62-B02 VL CDR1

<400> SEQUENCE: 53

```
Lys Ser Ser Arg Ser Val Leu Tyr Ser Asn Asn Lys Asn Tyr Leu
1               5                   10                  15
Ala
```

<210> SEQ ID NO 54
<211> LENGTH: 7
<212> TYPE: PRT
<213> ORGANISM: Artificial Sequence
<220> FEATURE:
<223> OTHER INFORMATION: M62-B02 VL CDR2

<400> SEQUENCE: 54

```
Trp Ala Ser Thr Arg Glu Ser
1               5
```

<210> SEQ ID NO 55
<211> LENGTH: 9
<212> TYPE: PRT

<213> ORGANISM: Artificial Sequence
<220> FEATURE:
<223> OTHER INFORMATION: M62-B02 VL CDR3

<400> SEQUENCE: 55

Gln Gln Tyr Tyr Ser Thr Pro Leu Thr
1               5

<210> SEQ ID NO 56
<211> LENGTH: 363
<212> TYPE: DNA
<213> ORGANISM: Artificial Sequence
<220> FEATURE:
<223> OTHER INFORMATION: M63-E10 variable heavy chain

<400> SEQUENCE: 56

```
gaagttcaat tgttagagtc tggtggcggt cttgttcagc ctggtggttc tttacgtctt    60
tcttgcgctg cttccggatt cactttctct cagtacaaga tgtcttgggt tcgccaagct   120
cctggtaaag ttggagtg gtttcttct atctcttctt ctggtggcac taattatgct   180
gactccgtta aggtcgctt cactatctct agagacaact ctaagaatac tctctacttg   240
cagatgaaca gcttaagggc tgaggacacc gccatgtatt actgtgcgag acggaactac   300
ggtgacagac cttactggta cttcgatctc tggggccgtg gcaccctggt caccgtctca   360
agc                                                                 363
```

<210> SEQ ID NO 57
<211> LENGTH: 121
<212> TYPE: PRT
<213> ORGANISM: Artificial Sequence
<220> FEATURE:
<223> OTHER INFORMATION: M63-E10 variable heavy chain

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Lys Met Ser Trp Val Arg Gln Ala Pro Gly Lys Gly Leu Glu Trp Val
        35                  40                  45

Ser Ser Ile Ser Ser Ser Gly Gly Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Arg Arg Asn Tyr Gly Asp Arg Pro Tyr Trp Tyr Phe Asp Leu Trp Gly
            100                 105                 110

Arg Gly Thr Leu Val Thr Val Ser Ser
        115                 120

<210> SEQ ID NO 58
<211> LENGTH: 5
<212> TYPE: PRT
<213> ORGANISM: Artificial Sequence
<220> FEATURE:
<223> OTHER INFORMATION: M63-E10 VH CDR1

<400> SEQUENCE: 58

Gln Tyr Lys Met Ser
1               5

```
<210> SEQ ID NO 59
<211> LENGTH: 16
<212> TYPE: PRT
<213> ORGANISM: Artificial Sequence
<220> FEATURE:
<223> OTHER INFORMATION: M63-E10 VH CDR2

<400> SEQUENCE: 59

Ser Ile Ser Ser Ser Gly Gly Thr Asn Tyr Ala Asp Ser Val Lys Gly
1               5                   10                  15

<210> SEQ ID NO 60
<211> LENGTH: 13
<212> TYPE: PRT
<213> ORGANISM: Artificial Sequence
<220> FEATURE:
<223> OTHER INFORMATION: M63-E10 VH CDR3

<400> SEQUENCE: 60

Arg Asn Tyr Gly Asp Arg Pro Tyr Trp Tyr Phe Asp Leu
1               5                   10

<210> SEQ ID NO 61
<211> LENGTH: 321
<212> TYPE: DNA
<213> ORGANISM: Artificial Sequence
<220> FEATURE:
<223> OTHER INFORMATION: M63-E10 variable light chain

<400> SEQUENCE: 61
gacatccaga tgacccagtc tccttccacc ctgtctgcat ctgtaggaga cagagtcacc      60
atcacttgcc gggccagtca gactattagt agatggttgg cctggtatca gcacaaacca     120
gggaaagccc ctaaactcct gatctacaag acgtctaatt tagaaagtgg ggtcccatca     180
aggttcagcg gcagtggatc tgggacagaa ttcactctca ccatcagtag cctgcagcct     240
gatgattttg ccacttatta ctgccaacag tataaaagtt attcgatcac cttcggccct     300
gggaccaaag tggatatcaa a                                                321

<210> SEQ ID NO 62
<211> LENGTH: 107
<212> TYPE: PRT
<213> ORGANISM: Artificial Sequence
<220> FEATURE:
<223> OTHER INFORMATION: M63-E10 variable light chain

<400> SEQUENCE: 62

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Ser Arg Trp
            20                  25                  30

Leu Ala Trp Tyr Gln His Lys Pro Gly Lys Ala Pro Lys Leu Leu Ile
        35                  40                  45

Tyr Lys Thr Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Ser Tyr Ser Ile
                85                  90                  95

Thr Phe Gly Pro Gly Thr Lys Val Asp Ile Lys
            100                 105
```

-continued

<210> SEQ ID NO 63
<211> LENGTH: 11
<212> TYPE: PRT
<213> ORGANISM: Artificial Sequence
<220> FEATURE:
<223> OTHER INFORMATION: M63-E10 VL CDR1

<400> SEQUENCE: 63

Arg Ala Ser Gln Thr Ile Ser Arg Trp Leu Ala
1               5                   10

<210> SEQ ID NO 64
<211> LENGTH: 7
<212> TYPE: PRT
<213> ORGANISM: Artificial Sequence
<220> FEATURE:
<223> OTHER INFORMATION: M63-E10 VL CDR2

<400> SEQUENCE: 64

Lys Thr Ser Asn Leu Glu Ser
1               5

<210> SEQ ID NO 65
<211> LENGTH: 9
<212> TYPE: PRT
<213> ORGANISM: Artificial Sequence
<220> FEATURE:
<223> OTHER INFORMATION: M63-E10 VL CDR3

<400> SEQUENCE: 65

Gln Gln Tyr Lys Ser Tyr Ser Ile Thr
1               5

<210> SEQ ID NO 66
<211> LENGTH: 354
<212> TYPE: DNA
<213> ORGANISM: Artificial Sequence
<220> FEATURE:
<223> OTHER INFORMATION: M66-B03 variable heavy chain

<400> SEQUENCE: 66
gaagttcaat tgttagagtc tggtggcggt cttgttcagc ctggtggttc tttacgtctt      60
tcttgcgctg cttccggatt cacttctct ccttactgga tgtcttgggt tcgccaagct     120
cctggtaaag gtttggagtg ggtttctgtt atctatcctt ctggtggcca tacttattat     180
gctgactccg ttaaaggtcg cttcactatc tctagagaca actctaagaa tactctctac     240
ttgcagatga acagcttaag ggctgaggac acggccgtgt attactgtgc gaggccaggg     300
ttcggggcgg ctttgacta ctggggcccg ggaaccctgg tcaccgtctc aagc            354

<210> SEQ ID NO 67
<211> LENGTH: 118
<212> TYPE: PRT
<213> ORGANISM: Artificial Sequence
<220> FEATURE:
<223> OTHER INFORMATION: M66-B03 variable heavy chain

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Trp Met Ser Trp Val Arg Gln Ala Pro Gly Lys Gly Leu Glu Trp Val
        35                  40                  45

Ser Val Ile Tyr Pro Ser Gly Gly His Thr Tyr Tyr Ala Asp Ser Val

```
                50                  55                  60
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Phe Gly Ala Ala Phe Asp Tyr Trp Gly Pro Gly Thr
            100                 105                 110

Leu Val Thr Val Ser Ser
        115

<210> SEQ ID NO 68
<211> LENGTH: 5
<212> TYPE: PRT
<213> ORGANISM: Artificial Sequence
<220> FEATURE:
<223> OTHER INFORMATION: M66-B03 VH CDR1

<400> SEQUENCE: 68

Pro Tyr Trp Met Ser
1               5

<210> SEQ ID NO 69
<211> LENGTH: 17
<212> TYPE: PRT
<213> ORGANISM: Artificial Sequence
<220> FEATURE:
<223> OTHER INFORMATION: M66-B03 VH CDR2

<400> SEQUENCE: 69

Val Ile Tyr Pro Ser Gly Gly His Thr Tyr Tyr Ala Asp Ser Val Lys
1               5                   10                  15

Gly

<210> SEQ ID NO 70
<211> LENGTH: 9
<212> TYPE: PRT
<213> ORGANISM: Artificial Sequence
<220> FEATURE:
<223> OTHER INFORMATION: M66-B03 VH CDR3

<400> SEQUENCE: 70

Pro Gly Phe Gly Ala Ala Phe Asp Tyr
1               5

<210> SEQ ID NO 71
<211> LENGTH: 321
<212> TYPE: DNA
<213> ORGANISM: Artificial Sequence
<220> FEATURE:
<223> OTHER INFORMATION: M66-B03 variable light chain

<400> SEQUENCE: 71
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaagtgg ggtcccatca     180
aggttcagcg gcagtggatc tgggacagat tcactctca ccatcagcag cctgcagcct      240
gaagattttg caacttacta ttgtcaacag gctaacagtt tccccctcac tttcggcgga     300
gggaccaagg tggagatcaa a                                                321

<210> SEQ ID NO 72
<211> LENGTH: 107
```

<212> TYPE: PRT
<213> ORGANIZM: Artificial Sequence
<220> FEATURE:
<223> OTHER INFORMATION: M66-B03 variable light chain

<400> SEQUENCE: 72

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105
```

<210> SEQ ID NO 73
<211> LENGTH: 11
<212> TYPE: PRT
<213> ORGANISM: Artificial Sequence
<220> FEATURE:
<223> OTHER INFORMATION: M66-B03 VL CDR1

<400> SEQUENCE: 73

```
Arg Ala Ser Gln Gly Ile Ser Ser Trp Leu Ala
1               5                   10
```

<210> SEQ ID NO 74
<211> LENGTH: 7
<212> TYPE: PRT
<213> ORGANISM: Artificial Sequence
<220> FEATURE:
<223> OTHER INFORMATION: M66-B03 VL CDR2

<400> SEQUENCE: 74

```
Ala Ala Ser Ser Leu Gln Ser
1               5
```

<210> SEQ ID NO 75
<211> LENGTH: 9
<212> TYPE: PRT
<213> ORGANISM: Artificial Sequence
<220> FEATURE:
<223> OTHER INFORMATION: M66-B03 VL CDR3

<400> SEQUENCE: 75

```
Gln Gln Ala Asn Ser Phe Pro Leu Thr
1               5
```

<210> SEQ ID NO 76
<211> LENGTH: 384
<212> TYPE: DNA
<213> ORGANISM: Artificial Sequence
<220> FEATURE:
<223> OTHER INFORMATION: M67-G02 variable heavy chain

<400> SEQUENCE: 76

```
gaagttcaat tgttagagtc tggtggcggt cttgttcagc ctggtggttc tttacgtctt    60
tcttgcgctg cttccggatt cactttctct cgttactcta tgcagtgggt tcgccaagct   120
```

```
cctggtaaag gtttggagtg ggtttctgtt atctctcctt ctggtggctc tactatgtat      180
gctgactccg ttaaaggtcg cttcactatc tctagagaca actctaagaa tactctctac      240
ttgcagatga acagcttaag ggctgaggac acggccgtgt attactgtgc gagagaatca      300
tatagcagca gctggtattc tgggtactac tactactacg gtatggacgt ctggggccaa      360
gggaccacgg tcaccgtctc aagc                                             384
```

```
<210> SEQ ID NO 77
<211> LENGTH: 128
<212> TYPE: PRT
<213> ORGANISM: Artificial Sequence
<220> FEATURE:
<223> OTHER INFORMATION: M67-G02 variable heavy chain

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Gln Trp Val Arg Gln Ala Pro Gly Lys Gly Leu Glu Trp Val
        35                  40                  45

Ser Val Ile Ser Pro Ser Gly Gly Ser Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Tyr Ser Ser Ser Trp Tyr Ser Gly Tyr Tyr Tyr Tyr
            100                 105                 110

Tyr Gly Met Asp Val Trp Gly Gln Gly Thr Thr Val Thr Val Ser Ser
        115                 120                 125

<210> SEQ ID NO 78
<211> LENGTH: 5
<212> TYPE: PRT
<213> ORGANISM: Artificial Sequence
<220> FEATURE:
<223> OTHER INFORMATION: M67-G02 VH CDR1

<400> SEQUENCE: 78

Arg Tyr Ser Met Gln
1               5

<210> SEQ ID NO 79
<211> LENGTH: 17
<212> TYPE: PRT
<213> ORGANISM: Artificial Sequence
<220> FEATURE:
<223> OTHER INFORMATION: M67-G02 VH CDR2

<400> SEQUENCE: 79

Val Ile Ser Pro Ser Gly Gly Ser Thr Met Tyr Ala Asp Ser Val Lys
1               5                   10                  15

Gly

<210> SEQ ID NO 80
<211> LENGTH: 19
<212> TYPE: PRT
<213> ORGANISM: Artificial Sequence
<220> FEATURE:
<223> OTHER INFORMATION: M67-G02 VH CDR3
```

-continued

<400> SEQUENCE: 80

Glu Ser Tyr Ser Ser Ser Trp Tyr Ser Gly Tyr Tyr Tyr Tyr Gly
1               5                   10                  15

Met Asp Val

<210> SEQ ID NO 81
<211> LENGTH: 321
<212> TYPE: DNA
<213> ORGANISM: Artificial Sequence
<220> FEATURE:
<223> OTHER INFORMATION: M67-G02 variable light chain

<400> SEQUENCE: 81
gacatccaga tgacccagtc tccagcctcc ctgtctgcat ctgttggaga cagagtcacc      60
atcacttgcc gggcaagtca gaccattgcc ggctatttaa attggtatca gcagacacca     120
gggaaagccc ctaatctcct gatctatgat gcatcccgtt tgcaaagtgg ggtcccatca     180
cggttcagtg gcagtggatc tgggacagat ttcactctca gcatcagcgg tctgcaacct     240
gaagattttg gaacttacta ctgtcaacag agttacacca tcccgctcac tttcggcgga     300
gggaccaagg tggagatcaa a                                                321

<210> SEQ ID NO 82
<211> LENGTH: 107
<212> TYPE: PRT
<213> ORGANISM: Artificial Sequence
<220> FEATURE:
<223> OTHER INFORMATION: M67-G02 variable light chain

<400> SEQUENCE: 82

Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Thr Ile Ala Gly Tyr
            20                  25                  30

Leu Asn Trp Tyr Gln Gln Thr Pro Gly Lys Ala Pro Asn Leu Leu Ile
        35                  40                  45

Tyr Asp Ala Ser Arg Leu Gln Ser Gly Val Pro Ser Arg Phe Ser Gly
    50                  55                  60

Ser Gly Ser Gly Thr Asp Phe Thr Leu Ser Ile Ser Gly Leu Gln Pro
65                  70                  75                  80

Glu Asp Phe Gly Thr Tyr Tyr Cys Gln Gln Ser Tyr Thr Ile Pro Leu
                85                  90                  95

Thr Phe Gly Gly Gly Thr Lys Val Glu Ile Lys
            100                 105

<210> SEQ ID NO 83
<211> LENGTH: 11
<212> TYPE: PRT
<213> ORGANISM: Artificial Sequence
<220> FEATURE:
<223> OTHER INFORMATION: M67-G02 VL CDR1

<400> SEQUENCE: 83

Arg Ala Ser Gln Thr Ile Ala Gly Tyr Leu Asn
1               5                   10

<210> SEQ ID NO 84
<211> LENGTH: 7
<212> TYPE: PRT
<213> ORGANISM: Artificial Sequence
<220> FEATURE:

<223> OTHER INFORMATION: M67-G02 VL CDR2

<400> SEQUENCE: 84

Asp Ala Ser Arg Leu Gln Ser
1               5

<210> SEQ ID NO 85
<211> LENGTH: 9
<212> TYPE: PRT
<213> ORGANISM: Artificial Sequence
<220> FEATURE:
<223> OTHER INFORMATION: M67-G02 VL CDR3

<400> SEQUENCE: 85

Gln Gln Ser Tyr Thr Ile Pro Leu Thr
1               5

<210> SEQ ID NO 86
<211> LENGTH: 348
<212> TYPE: DNA
<213> ORGANISM: Artificial Sequence
<220> FEATURE:
<223> OTHER INFORMATION: M72-F03 variable heavy chain

<400> SEQUENCE: 86
gaagttcaat tgttagagtc tggtggcggt cttgttcagc ctggtggttc tttacgtctt    60
tcttgcgctg cttccggatt cactttctct cagtacatga tgtcttgggt tcgccaagct   120
cctggtaaag tttggagtg gtttctgtt atctatcctt ctggtggctc tactcattat    180
gctgactccg ttaaaggtcg cttcactatc tctagagaca actctaagaa tactctctac   240
ttgcagatga acagcttaag ggctgaggac acggccgtgt attactgtgc gagaggccac   300
tacggtatgg acgtctgggg ccaggggacc acggtcaccg tctcaagc               348

<210> SEQ ID NO 87
<211> LENGTH: 116
<212> TYPE: PRT
<213> ORGANISM: Artificial Sequence
<220> FEATURE:
<223> OTHER INFORMATION: M72-F03 variable heavy chain

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Met Met Ser Trp Val Arg Gln Ala Pro Gly Lys Gly Leu Glu Trp Val
        35                  40                  45

Ser Val Ile Tyr Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Gly Met Asp Val Trp Gly Gln Gly Thr Thr Val
            100                 105                 110

Thr Val Ser Ser
        115

<210> SEQ ID NO 88
<211> LENGTH: 5
<212> TYPE: PRT

```
<213> ORGANISM: Artificial Sequence
<220> FEATURE:
<223> OTHER INFORMATION: M72-F03 VH CDR1

<400> SEQUENCE: 88

Gln Tyr Met Met Ser
1               5

<210> SEQ ID NO 89
<211> LENGTH: 18
<212> TYPE: PRT
<213> ORGANISM: Artificial Sequence
<220> FEATURE:
<223> OTHER INFORMATION: M72-F03 VH CDR2

<400> SEQUENCE: 89

Val Ile Tyr Pro Ser Gly Gly Ser Thr His Tyr Ala Asp Ser Val Lys
1               5                   10                  15

Gly Arg

<210> SEQ ID NO 90
<211> LENGTH: 7
<212> TYPE: PRT
<213> ORGANISM: Artificial Sequence
<220> FEATURE:
<223> OTHER INFORMATION: M72-F03 VH CDR3

<400> SEQUENCE: 90

Gly His Tyr Gly Met Asp Val
1               5

<210> SEQ ID NO 91
<211> LENGTH: 339
<212> TYPE: DNA
<213> ORGANISM: Artificial Sequence
<220> FEATURE:
<223> OTHER INFORMATION: M72-F03 variable light chain

<400> SEQUENCE: 91
gacatccaga tgacccagtc tccagactcc ctggctgtgt ctctgggcga gagggccacc      60
atcaactgca agtccagcca gagtgtttta tacagctcca acaataagaa ctacttagct     120
tggtatcagc ataaagcagg acagcctcct aagctgctca ttcactgggc atcttcccgg     180
gcatccgggg tccctgaccg attcagtggc agcgggtctg ggacagattt cactctcacc     240
atcagcagcc tgcaggctga ggatgtggcc gtctattact gtcagcaatt ttacagtctt     300
cctctcactt tcggcggagg gaccaaggtg gagatcaga                            339

<210> SEQ ID NO 92
<211> LENGTH: 113
<212> TYPE: PRT
<213> ORGANISM: Artificial Sequence
<220> FEATURE:
<223> OTHER INFORMATION: M72-F03 variable light chain

<400> SEQUENCE: 92

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln His Lys Ala Gly Gln
        35                  40                  45

Pro Pro Lys Leu Leu Ile His Trp Ala Ser Ser Arg Ala Ser Gly Val
    50                  55                  60
```

```
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ser Leu Pro Leu Thr Phe Gly Gly Gly Thr Lys Val Glu Ile
            100                 105                 110

Arg

<210> SEQ ID NO 93
<211> LENGTH: 17
<212> TYPE: PRT
<213> ORGANISM: Artificial Sequence
<220> FEATURE:
<223> OTHER INFORMATION: M72-F03 VL CDR1

<400> SEQUENCE: 93

Lys Ser Ser Gln Ser Val Leu Tyr Ser Ser Asn Asn Lys Asn Tyr Leu
1               5                   10                  15

Ala

<210> SEQ ID NO 94
<211> LENGTH: 7
<212> TYPE: PRT
<213> ORGANISM: Artificial Sequence
<220> FEATURE:
<223> OTHER INFORMATION: M72-F03 VL CDR2

<400> SEQUENCE: 94

Trp Ala Ser Ser Arg Ala Ser
1               5

<210> SEQ ID NO 95
<211> LENGTH: 9
<212> TYPE: PRT
<213> ORGANISM: Artificial Sequence
<220> FEATURE:
<223> OTHER INFORMATION: M72-F03 VL CDR3

<400> SEQUENCE: 95

Gln Gln Phe Tyr Ser Leu Pro Leu Thr
1               5

<210> SEQ ID NO 96
<211> LENGTH: 360
<212> TYPE: DNA
<213> ORGANISM: Artificial Sequence
<220> FEATURE:
<223> OTHER INFORMATION: M73-C04 variable heavy chain

<400> SEQUENCE: 96
gaagttcaat tgttagagtc tggtggcggt cttgttcagc ctggtggttc tttacgtctt      60
tcttgcgctg cttccggatt cactttctct ccttacgcta tggtttgggt tcgccaagct     120
cctggtaaag gtttggagtg gtttcttct atctctcctt ctggtggcgg tactggttat      180
gctgactccg ttaaaggtcg cttcactatc tctagagaca actctaagaa tactctctac     240
ttgcagatga acagcttaag ggctgaggac acggccgtgt attactgtgc gagagagggg     300
tggaactact actacggtat ggacgtctgg ggccaaggga ccacggtcac cgtctcaagc     360

<210> SEQ ID NO 97
<211> LENGTH: 120
<212> TYPE: PRT
<213> ORGANISM: Artificial Sequence
```

<220> FEATURE:
<223> OTHER INFORMATION: M73-C04 variable heavy chain

<400> SEQUENCE: 97

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Ala Met Val Trp Val Arg Gln Ala Pro Gly Lys Gly Leu Glu Trp Val
        35                  40                  45

Ser Ser Ile Ser Pro Ser Gly Gly Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Trp Asn Tyr Tyr Tyr Gly Met Asp Val Trp Gly Gln
            100                 105                 110

Gly Thr Thr Val Thr Val Ser Ser
        115                 120
```

<210> SEQ ID NO 98
<211> LENGTH: 5
<212> TYPE: PRT
<213> ORGANISM: Artificial Sequence
<220> FEATURE:
<223> OTHER INFORMATION: M73-C04 VH CDR1

<400> SEQUENCE: 98

```
Pro Tyr Ala Met Val
1               5
```

<210> SEQ ID NO 99
<211> LENGTH: 17
<212> TYPE: PRT
<213> ORGANISM: Artificial Sequence
<220> FEATURE:
<223> OTHER INFORMATION: M73-C04 VH CDR2

<400> SEQUENCE: 99

```
Ser Ile Ser Pro Ser Gly Gly Thr Gly Tyr Ala Asp Ser Val Lys
1               5                   10                  15

Gly
```

<210> SEQ ID NO 100
<211> LENGTH: 11
<212> TYPE: PRT
<213> ORGANISM: Artificial Sequence
<220> FEATURE:
<223> OTHER INFORMATION: M73-C04 VH CDR3

<400> SEQUENCE: 100

```
Glu Gly Trp Asn Tyr Tyr Tyr Gly Met Asp Val
1               5                   10
```

<210> SEQ ID NO 101
<211> LENGTH: 321
<212> TYPE: DNA
<213> ORGANISM: Artificial Sequence
<220> FEATURE:
<223> OTHER INFORMATION: M73-C04 variable light chain

<400> SEQUENCE: 101

```
gacatccaga tgacccagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tggcacagat ttcactctcg ccatcagcag cctgcagcct     240
gaagattctg caacttatta ctgtctacaa gatttcattt acccgtacac ttttggccag     300
gggaccaagc tggagatcag a                                               321
```

```
<210> SEQ ID NO 102
<211> LENGTH: 107
<212> TYPE: PRT
<213> ORGANISM: Artificial Sequence
<220> FEATURE:
<223> OTHER INFORMATION: M73-C04 variable light chain

<400> SEQUENCE: 102
```

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Ala Ile Ser Ser Leu Gln Pro
65                  70                  75                  80

Glu Asp Ser Ala Thr Tyr Tyr Cys Leu Gln Asp Phe Ile Tyr Pro Tyr
                85                  90                  95

Thr Phe Gly Gln Gly Thr Lys Leu Glu Ile Arg
            100                 105

```
<210> SEQ ID NO 103
<211> LENGTH: 11
<212> TYPE: PRT
<213> ORGANISM: Artificial Sequence
<220> FEATURE:
<223> OTHER INFORMATION: M73-C04 VL CDR1

<400> SEQUENCE: 103
```

Arg Ala Ser Gln Ser Val Ser Ser Tyr Leu Ala
1               5                   10

```
<210> SEQ ID NO 104
<211> LENGTH: 7
<212> TYPE: PRT
<213> ORGANISM: Artificial Sequence
<220> FEATURE:
<223> OTHER INFORMATION: M73-C04 VL CDR2

<400> SEQUENCE: 104
```

Asp Ala Ser Asn Arg Ala Thr
1               5

```
<210> SEQ ID NO 105
<211> LENGTH: 9
<212> TYPE: PRT
<213> ORGANISM: Artificial Sequence
<220> FEATURE:
<223> OTHER INFORMATION: M73-C04 VL CDR3

<400> SEQUENCE: 105
```

Leu Gln Asp Phe Ile Tyr Pro Tyr Thr

<210> SEQ ID NO 106
<211> LENGTH: 339
<212> TYPE: DNA
<213> ORGANISM: Artificial Sequence
<220> FEATURE:
<223> OTHER INFORMATION: 1P1D6.3 variable heavy chain

<400> SEQUENCE: 106

```
caggttcagc tgcagcagtc tggaactgag ctggcgaggc ccggggcttc agtgaagctg      60
tcctgcaagg cttctggcta caccttcact gactactatc taaactggat gaaacagggg     120
actggacagg gccttgagtg gattggagag atttatcctg gaggtgatca cacttactac     180
aatgagaaat tcaagggcaa ggccacactg actgcagaca atcctccaa cacagccttc      240 atgcagctca gcagcctgac atctgaggac tctgcagtct atttctgtac aagagggtg      300 attaagtggg gccaagggac tctggtcact gtctcttta                             339
```

<210> SEQ ID NO 107
<211> LENGTH: 113
<212> TYPE: PRT
<213> ORGANISM: Artificial Sequence
<220> FEATURE:
<223> OTHER INFORMATION: 1P1D6.3 variable heavy chain

<400> SEQUENCE: 107

```
Gln Val Gln Leu Gln Gln Ser Gly Thr Glu Leu Ala Arg Pro Gly Ala
1               5                   10                  15

Ser Val Lys Leu Ser Cys Lys Ala Ser Gly Tyr Thr Phe Thr Asp Tyr
            20                  25                  30

Tyr Leu Asn Trp Met Lys Gln Gly Thr Gly Gln Gly Leu Glu Trp Ile
        35                  40                  45

Gly Glu Ile Tyr Pro Gly Gly Asp His Thr Tyr Tyr Asn Glu Lys Phe
    50                  55                  60

Lys Gly Lys Ala Thr Leu Thr Ala Asp Lys Ser Ser Asn Thr Ala Phe
65                  70                  75                  80

Met Gln Leu Ser Ser Leu Thr Ser Glu Asp Ser Ala Val Tyr Phe Cys
                85                  90                  95

Thr Arg Gly Val Ile Lys Trp Gly Gln Gly Thr Leu Val Thr Val Ser
            100                 105                 110

Leu
```

<210> SEQ ID NO 108
<211> LENGTH: 5
<212> TYPE: PRT
<213> ORGANISM: Artificial Sequence
<220> FEATURE:
<223> OTHER INFORMATION: 1P1D6.3 VH CDR1

<400> SEQUENCE: 108

```
Asp Tyr Tyr Leu Asn
1               5
```

<210> SEQ ID NO 109
<211> LENGTH: 17
<212> TYPE: PRT
<213> ORGANISM: Artificial Sequence
<220> FEATURE:
<223> OTHER INFORMATION: 1P1D6.3 VH CDR2

<400> SEQUENCE: 109

```
Glu Ile Tyr Pro Gly Gly Asp His Thr Tyr Tyr Asn Glu Lys Phe Lys
1               5                   10                  15

Gly

<210> SEQ ID NO 110
<211> LENGTH: 4
<212> TYPE: PRT
<213> ORGANISM: Artificial Sequence
<220> FEATURE:
<223> OTHER INFORMATION: 1P1D6.3 VH CDR3

<400> SEQUENCE: 110

Gly Val Ile Lys
1

<210> SEQ ID NO 111
<211> LENGTH: 321
<212> TYPE: DNA
<213> ORGANISM: Artificial Sequence
<220> FEATURE:
<223> OTHER INFORMATION: 1P1D6.3 variable light chain

<400> SEQUENCE: 111
gacatcctga tgacccaatc tccaccctcc atgtctgtct ctctgggaga cacagtcagc      60
atcacttgcc atgcaagtca gggcattagc agtaatatag gtggttgca gcagaaacca     120 gggaaatcat ttaagggcct gatctatcat ggatccacct tggaggatgg agttccatca     180
agattcagtg gcagtggatc tggagcagaa tttctctca ccatcagcag cctggaatct     240
gaagattttg cagactatta ctgtgttcaa tatgctcagt ttccttacac gttcggaggg     300
gggaccaagc tagaaataaa a                                               321

<210> SEQ ID NO 112
<211> LENGTH: 107
<212> TYPE: PRT
<213> ORGANISM: Artificial Sequence
<220> FEATURE:
<223> OTHER INFORMATION: 1P1D6.3 variable light chain

<400> SEQUENCE: 112

Asp Ile Leu Met Thr Gln Ser Pro Pro Ser Met Ser Val Ser Leu Gly
1               5                   10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Lys Gly Leu Ile
        35                  40                  45

Tyr His Gly Ser Thr Leu Glu Asp Gly Val Pro Ser Arg Phe Ser Gly
    50                  55                  60

Ser Gly Ser Gly Ala Glu Phe Ser Leu Thr Ile Ser Ser Leu Glu Ser
65                  70                  75                  80

Glu Asp Phe Ala Asp Tyr Tyr Cys Val Gln Tyr Ala Gln Phe Pro Tyr
                85                  90                  95

Thr Phe Gly Gly Gly Thr Lys Leu Glu Ile Lys
            100                 105

<210> SEQ ID NO 113
<211> LENGTH: 11
<212> TYPE: PRT
<213> ORGANISM: Artificial Sequence
<220> FEATURE:
<223> OTHER INFORMATION: 1P1D6.3 VL CDR1

<400> SEQUENCE: 113
```

His Ala Ser Gln Gly Ile Ser Ser Asn Ile Gly
1               5                   10

<210> SEQ ID NO 114
<211> LENGTH: 7
<212> TYPE: PRT
<213> ORGANISM: Artificial Sequence
<220> FEATURE:
<223> OTHER INFORMATION: 1P1D6.3 VL CDR2

<400> SEQUENCE: 114

His Gly Ser Thr Leu Glu Asp
1               5

<210> SEQ ID NO 115
<211> LENGTH: 9
<212> TYPE: PRT
<213> ORGANISM: Artificial Sequence
<220> FEATURE:
<223> OTHER INFORMATION: 1P1D6.3 VL CDR3

<400> SEQUENCE: 115

Val Gln Tyr Ala Gln Phe Pro Tyr Thr
1               5

<210> SEQ ID NO 116
<211> LENGTH: 339
<212> TYPE: DNA
<213> ORGANISM: Artificial Sequence
<220> FEATURE:
<223> OTHER INFORMATION: 1P2F2.1 variable heavy chain

<400> SEQUENCE: 116
caggttcagc tgcagcagtc tggacctgag gtggcgaggc ccggggcttc agtgaagctg      60
tcctgcaagg cttctggcta caccttcact gactactatt taaactgggt gaagcagagg     120
actggacagg gccttgagtg gattggagag atttatcctg gaaataatca tacttactac     180
aatgagaagt tcaagggcaa ggccacactg actgcagaca attcctccag cacagcctac     240
ttgcagttca gcagcctgac atctgaggac tctgctgtct atttctgtac aagagggggtg     300 attaagtggg gccaagggac tctggtcact gtctctgta                             339

<210> SEQ ID NO 117
<211> LENGTH: 113
<212> TYPE: PRT
<213> ORGANISM: Artificial Sequence
<220> FEATURE:
<223> OTHER INFORMATION: 1P2F2.1 variable heavy chain

<400> SEQUENCE: 117

Gln Val Gln Leu Gln Gln Ser Gly Pro Glu Val Ala Arg Pro Gly Ala
1               5                   10                  15

Ser Val Lys Leu Ser Cys Lys Ala Ser Gly Tyr Thr Phe Thr Asp Tyr
                20                  25                  30

Tyr Leu Asn Trp Val Lys Gln Arg Thr Gly Gln Gly Leu Glu Trp Ile
            35                  40                  45

Gly Glu Ile Tyr Pro Gly Asn Asn His Thr Tyr Tyr Asn Glu Lys Phe
        50                  55                  60

Lys Gly Lys Ala Thr Leu Thr Ala Asp Asn Ser Ser Ser Thr Ala Tyr
65                  70                  75                  80

Leu Gln Phe Ser Ser Leu Thr Ser Glu Asp Ser Ala Val Tyr Phe Cys
                85                  90                  95

Thr Arg Gly Val Ile Lys Trp Gly Gln Gly Thr Leu Val Thr Val Ser
            100                 105                 110
Val

<210> SEQ ID NO 118
<211> LENGTH: 5
<212> TYPE: PRT
<213> ORGANISM: Artificial Sequence
<220> FEATURE:
<223> OTHER INFORMATION: 1P2F2.1 VH CDR1

<400> SEQUENCE: 118

Asp Tyr Tyr Leu Asn
1               5

<210> SEQ ID NO 119
<211> LENGTH: 17
<212> TYPE: PRT
<213> ORGANISM: Artificial Sequence
<220> FEATURE:
<223> OTHER INFORMATION: 1P2F2.1 VH CDR2

<400> SEQUENCE: 119

Glu Ile Tyr Pro Gly Asn Asn His Thr Tyr Tyr Asn Glu Lys Phe Lys
1               5                   10                  15
Gly

<210> SEQ ID NO 120
<211> LENGTH: 4
<212> TYPE: PRT
<213> ORGANISM: Artificial Sequence
<220> FEATURE:
<223> OTHER INFORMATION: 1P2F2.1 VH CDR3

<400> SEQUENCE: 120

Gly Val Ile Lys
1

<210> SEQ ID NO 121
<211> LENGTH: 321
<212> TYPE: DNA
<213> ORGANISM: Artificial Sequence
<220> FEATURE:
<223> OTHER INFORMATION: 1P2F2.1 variable light chain

<400> SEQUENCE: 121
gacatcctga tgacccaatc tccatcctcc atgtctgtat ctctgggaga cacagtcagc      60
atcacttgcc atgccagtca gggcattagg aatagtatag ggtggttgca gcagaaacca     120
gggaaatcat ttaagggcct gatctatcat gcaaccacct tggaagatgg agttccatca     180
aggttcactg gcagtggatc tggagcagat tttctctca ccatcagcag cctggaatct     240
gaagattttg cagactatta ctgtgtacag tacgctcagt ttccttacac gttcggaggg     300
gggaccaagc tggaaataaa a                                               321

<210> SEQ ID NO 122
<211> LENGTH: 107
<212> TYPE: PRT
<213> ORGANISM: Artificial Sequence
<220> FEATURE:
<223> OTHER INFORMATION: 1P2F2.1 variable light chain

<400> SEQUENCE: 122

Asp Ile Leu Met Thr Gln Ser Pro Ser Ser Met Ser Val Ser Leu Gly
1               5                   10                  15

```
Asp Thr Val Ser Ile Thr Cys His Ala Ser Gln Gly Ile Arg Asn Ser
                 20                  25                  30

Ile Gly Trp Leu Gln Gln Lys Pro Gly Lys Ser Phe Lys Gly Leu Ile
             35                  40                  45

Tyr His Ala Thr Thr Leu Glu Asp Gly Val Pro Ser Arg Phe Thr Gly
         50                  55                  60

Ser Gly Ser Gly Ala Asp Phe Ser Leu Thr Ile Ser Ser Leu Glu Ser
 65                  70                  75                  80

Glu Asp Phe Ala Asp Tyr Tyr Cys Val Gln Tyr Ala Gln Phe Pro Tyr
                 85                  90                  95

Thr Phe Gly Gly Gly Thr Lys Leu Glu Ile Lys
            100                 105

<210> SEQ ID NO 123
<211> LENGTH: 11
<212> TYPE: PRT
<213> ORGANISM: Artificial Sequence
<220> FEATURE:
<223> OTHER INFORMATION: 1P2F2.1 VL CDR1

<400> SEQUENCE: 123

His Ala Ser Gln Gly Ile Arg Asn Ser Ile Gly
1               5                   10

<210> SEQ ID NO 124
<211> LENGTH: 7
<212> TYPE: PRT
<213> ORGANISM: Artificial Sequence
<220> FEATURE:
<223> OTHER INFORMATION: 1P2F2.1 VL CDR2

<400> SEQUENCE: 124

His Ala Thr Thr Leu Glu Asp
1               5

<210> SEQ ID NO 125
<211> LENGTH: 9
<212> TYPE: PRT
<213> ORGANISM: Artificial Sequence
<220> FEATURE:
<223> OTHER INFORMATION: 1P2F2.1 VL CDR3

<400> SEQUENCE: 125

Val Gln Tyr Ala Gln Phe Pro Tyr Thr
1               5

<210> SEQ ID NO 126
<211> LENGTH: 366
<212> TYPE: DNA
<213> ORGANISM: Artificial Sequence
<220> FEATURE:
<223> OTHER INFORMATION: 1P5D10.2 variable heavy chain

<400> SEQUENCE: 126
gaagtgcagc tggtggagtc ggggggaggc ttagtgaagc ctggagggtc cctgaaactc      60
tcctgtgcag cctctggatt cactttcagt gactattaca tgtattgggt tcgccagact     120
ccggaaaaga ggctggagtg ggtcgcaacc attagtgatg gtggtcttta cacctactat     180
caagacagtg tgaaggggcg attcaccatc tccagagaca tgccaagaa caacctgtac      240 ctgcaaatga gcagtctgaa gtctgaggac acagccatgt attactgtgc aagagaagat     300
gattacgacg gggatttcta ctactatgga ctactgggtc aaggaacctc agtcaccgtc     360
``` tcctca 366

```
<210> SEQ ID NO 127
<211> LENGTH: 122
<212> TYPE: PRT
<213> ORGANISM: Artificial Sequence
<220> FEATURE:
<223> OTHER INFORMATION: 1P5D10.2 variable heavy chain

<400> SEQUENCE: 127
```

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Gly Gly Leu Tyr Thr Tyr Tyr Gln Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Glu Asp Asp Tyr Asp Gly Asp Phe Tyr Thr Met Asp Tyr Trp
            100                 105                 110

Gly Gln Gly Thr Ser Val Thr Val Ser Ser
        115                 120

```
<210> SEQ ID NO 128
<211> LENGTH: 5
<212> TYPE: PRT
<213> ORGANISM: Artificial Sequence
<220> FEATURE:
<223> OTHER INFORMATION: 1P5D10.2 VH CDR1

<400> SEQUENCE: 128
```

Asp Tyr Tyr Met Tyr
1               5

```
<210> SEQ ID NO 129
<211> LENGTH: 17
<212> TYPE: PRT
<213> ORGANISM: Artificial Sequence
<220> FEATURE:
<223> OTHER INFORMATION: 1P5D10.2 VH CDR2

<400> SEQUENCE: 129
```

Thr Ile Ser Asp Gly Gly Leu Tyr Thr Tyr Tyr Gln Asp Ser Val Lys
1               5                   10                  15

Gly

```
<210> SEQ ID NO 130
<211> LENGTH: 13
<212> TYPE: PRT
<213> ORGANISM: Artificial Sequence
<220> FEATURE:
<223> OTHER INFORMATION: 1P5D10.2 VH CDR3

<400> SEQUENCE: 130
```

Glu Asp Asp Tyr Asp Gly Asp Phe Tyr Thr Met Asp Tyr
1               5                   10

```
<210> SEQ ID NO 131
<211> LENGTH: 318
```

<212> TYPE: DNA
<213> ORGANISM: Artificial Sequence
<220> FEATURE:
<223> OTHER INFORMATION: 1P5D10.2 variable light chain

<400> SEQUENCE: 131

```
caaattgttc tcacccagtc tccagcaatc atgtctgcat ctccagggga gaaggtcacc    60
ataacctgca gtgccagctc aagtgtaagt tacatgcact ggttccagca agagccaggc   120
acttctccca aactctggat ttatagcaca tccaacctgg cttctggagt ccctgctcgc   180
ttcagtggca gtggatctgg gacctcttac tctctcacaa tcagccgaat ggaggctgaa   240
gatgctgcca cttattactg ccagcaaagg agtagttacc cactcacgtt cggtgctggg   300
accaagctgg agctgaaa                                                 318
```

<210> SEQ ID NO 132
<211> LENGTH: 106
<212> TYPE: PRT
<213> ORGANISM: Artificial Sequence
<220> FEATURE:
<223> OTHER INFORMATION: 1P5D10.2 variable light chain

<400> SEQUENCE: 132

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys
            100                 105
```

<210> SEQ ID NO 133
<211> LENGTH: 10
<212> TYPE: PRT
<213> ORGANISM: Artificial Sequence
<220> FEATURE:
<223> OTHER INFORMATION: 1P5D10.2 VL CDR1

<400> SEQUENCE: 133

```
Ser Ala Ser Ser Ser Val Ser Tyr Met His
1               5                   10
```

<210> SEQ ID NO 134
<211> LENGTH: 7
<212> TYPE: PRT
<213> ORGANISM: Artificial Sequence
<220> FEATURE:
<223> OTHER INFORMATION: 1P5D10.2 VL CDR2

<400> SEQUENCE: 134

```
Ser Thr Ser Asn Leu Ala Ser
1               5
```

<210> SEQ ID NO 135
<211> LENGTH: 9
<212> TYPE: PRT

<213> ORGANISM: Artificial Sequence
<220> FEATURE:
<223> OTHER INFORMATION: 1P5D10.2 VL CDR3

<400> SEQUENCE: 135

Gln Gln Arg Ser Ser Tyr Pro Leu Thr
1               5

<210> SEQ ID NO 136
<211> LENGTH: 15
<212> TYPE: PRT
<213> ORGANISM: Artificial Sequence
<220> FEATURE:
<223> OTHER INFORMATION: flexible sequence linker

<400> SEQUENCE: 136

Gly Gly Gly Gly Ser Gly Gly Gly Gly Ser Gly Gly Gly Gly Ser
1               5                   10                  15

<210> SEQ ID NO 137
<211> LENGTH: 12
<212> TYPE: PRT
<213> ORGANISM: Artificial Sequence
<220> FEATURE:
<223> OTHER INFORMATION: flexible linker sequence

<400> SEQUENCE: 137

Gly Gly Gly Gly Gly Ser Gly Gly Gly Gly Gly Ser
1               5                   10

<210> SEQ ID NO 138
<211> LENGTH: 15
<212> TYPE: PRT
<213> ORGANISM: Artificial Sequence
<220> FEATURE:
<223> OTHER INFORMATION: flexible linker sequence

<400> SEQUENCE: 138

Glu Ser Gly Arg Ser Gly Gly Gly Ser Gly Gly Gly Gly Ser
1               5                   10                  15

<210> SEQ ID NO 139
<211> LENGTH: 14
<212> TYPE: PRT
<213> ORGANISM: Artificial Sequence
<220> FEATURE:
<223> OTHER INFORMATION: flexible linker sequence

<400> SEQUENCE: 139

Glu Gly Lys Ser Ser Gly Ser Gly Ser Glu Ser Lys Ser Thr
1               5                   10

<210> SEQ ID NO 140
<211> LENGTH: 15
<212> TYPE: PRT
<213> ORGANISM: Artificial Sequence
<220> FEATURE:
<223> OTHER INFORMATION: flexible linker sequence

<400> SEQUENCE: 140

Glu Gly Lys Ser Ser Gly Ser Gly Ser Glu Ser Lys Ser Thr Gln
1               5                   10                  15

<210> SEQ ID NO 141
<211> LENGTH: 14
<212> TYPE: PRT
<213> ORGANISM: Artificial Sequence
<220> FEATURE:

<223> OTHER INFORMATION: flexible linker sequence

<400> SEQUENCE: 141

Glu Gly Lys Ser Ser Gly Ser Gly Ser Glu Ser Lys Val Asp
1               5                   10

<210> SEQ ID NO 142
<211> LENGTH: 14
<212> TYPE: PRT
<213> ORGANISM: Artificial Sequence
<220> FEATURE:
<223> OTHER INFORMATION: flexible linker sequence

<400> SEQUENCE: 142

Gly Ser Thr Ser Gly Ser Gly Lys Ser Ser Glu Gly Lys Gly
1               5                   10

<210> SEQ ID NO 143
<211> LENGTH: 18
<212> TYPE: PRT
<213> ORGANISM: Artificial Sequence
<220> FEATURE:
<223> OTHER INFORMATION: flexible linker sequence

<400> SEQUENCE: 143

Lys Glu Ser Gly Ser Val Ser Ser Glu Gln Leu Ala Gln Phe Arg Ser
1               5                   10                  15

Leu Asp

<210> SEQ ID NO 144
<211> LENGTH: 16
<212> TYPE: PRT
<213> ORGANISM: Artificial Sequence
<220> FEATURE:
<223> OTHER INFORMATION: flexible linker sequence

<400> SEQUENCE: 144

Glu Ser Gly Ser Val Ser Ser Glu Glu Leu Ala Phe Arg Ser Leu Asp
1               5                   10                  15

<210> SEQ ID NO 145
<211> LENGTH: 8
<212> TYPE: PRT
<213> ORGANISM: Artificial Sequence
<220> FEATURE:
<223> OTHER INFORMATION: flag peptide

<400> SEQUENCE: 145

Asp Tyr Lys Asp Asp Asp Asp Lys
1               5

<210> SEQ ID NO 146
<211> LENGTH: 8
<212> TYPE: PRT
<213> ORGANISM: Artificial Sequence
<220> FEATURE:
<223> OTHER INFORMATION: flag peptide

<400> SEQUENCE: 146

Asp Tyr Lys Asp Glu Asp Asp Lys
1               5

<210> SEQ ID NO 147
<211> LENGTH: 9
<212> TYPE: PRT
<213> ORGANISM: Artificial Sequence
<220> FEATURE:

```
<223> OTHER INFORMATION: strep epitope

<400> SEQUENCE: 147

Ala Trp Arg His Pro Gln Phe Gly Gly
1               5

<210> SEQ ID NO 148
<211> LENGTH: 11
<212> TYPE: PRT
<213> ORGANISM: Artificial Sequence
<220> FEATURE:
<223> OTHER INFORMATION: VSV-G epitope

<400> SEQUENCE: 148

Tyr Thr Asp Ile Glu Met Asn Arg Leu Gly Lys
1               5                   10

<210> SEQ ID NO 149
<211> LENGTH: 6
<212> TYPE: PRT
<213> ORGANISM: Artificial Sequence
<220> FEATURE:
<223> OTHER INFORMATION: Poly-His tag

<400> SEQUENCE: 149

His His His His His His
1               5

<210> SEQ ID NO 150
<211> LENGTH: 13
<212> TYPE: PRT
<213> ORGANISM: Artificial Sequence
<220> FEATURE:
<223> OTHER INFORMATION: HA epitope

<400> SEQUENCE: 150

Tyr Pro Tyr Asp Val Pro Asp Tyr Ala Ile Glu Gly Arg
1               5                   10

<210> SEQ ID NO 151
<211> LENGTH: 11
<212> TYPE: PRT
<213> ORGANISM: Artificial Sequence
<220> FEATURE:
<223> OTHER INFORMATION: C-MYC epitope

<400> SEQUENCE: 151

Glu Gln Lys Leu Leu Ser Glu Glu Asp Leu Asn
1               5                   10

<210> SEQ ID NO 152
<211> LENGTH: 200
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(200)
<223> OTHER INFORMATION: n is a, c, g, or u
<220> FEATURE:
<221> NAME/KEY: misc_feature
<222> LOCATION: (2)..(200)
<223> OTHER INFORMATION: nucleotide may be missing

<400> SEQUENCE: 152
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
```

-continued

```
nnnnnnnnnn nnnnnnnnnn nnnnnnnnnn nnnnnnnnnn nnnnnnnnnn nnnnnnnnnn    180
nnnnnnnnnn nnnnnnnnnn                                                 200
```

<210> SEQ ID NO 153
<211> LENGTH: 200
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(200)
<223> OTHER INFORMATION: n is a, c, g, or u
<220> FEATURE:
<221> NAME/KEY: misc_feature
<222> LOCATION: (2)..(200)
<223> OTHER INFORMATION: nucleotide may be missing

<400> SEQUENCE: 153

```
nnnnnnnnnn nnnnnnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn                                                200
```

<210> SEQ ID NO 154
<211> LENGTH: 1998
<212> TYPE: DNA
<213> ORGANISM: Artificial Sequence
<220> FEATURE:
<223> OTHER INFORMATION: human DR6 with Myc tag

<400> SEQUENCE: 154

```
atggggacct ctccgagcag cagcaccgcc ctcgcctcct gcagccgcat cgcccgccga     60
gccacagcca cgatgatcgc gggctccctt ctcctgcttg gattccttag caccaccaca    120
gctgagcaga agctgatctc agaggaggac ctgcagccag aacagaaggc ctcgaatctc    180
attggcacat accgccatgt tgaccgtgcc accggccagg tgctaacctg tgacaagtgt    240
ccagcaggaa cctatgtctc tgagcattgt accaacacaa gcctgcgcgt ctgcagcagt    300
tgccctgtgg ggacctttac caggcatgag aatggcatag agaaatgcca tgactgtagt    360
cagccatgcc catggccaat gattgagaaa ttaccttgtg ctgccttgac tgaccgagaa    420
tgcacttgcc cacctggcat gttccagtct aacgctacct gtgccccca tacggtgtgt    480 cctgtgggtt ggggtgtgcg gaagaaaggg acagagactg aggatgtgcg gtgtaagcag    540
tgtgctcggg gtaccttctc agatgtgcct tctagtgtga tgaaatgcaa agcatacaca    600
gactgtctga gtcagaacct ggtggtgatc aagccgggga ccaaggagac agacaacgtc    660
tgtggcacac tcccgtcctt ctccagctcc acctcacctt ccctggcac agccatcttt    720 ccacgccctg agcacatgga aacccatgaa gtcccttcct ccacttatgt tcccaaaggc    780
atgaactcaa cagaatccaa ctcttctgcc tctgttagac caaaggtact gagtagcatc    840
caggaaggga cagtccctga caacacaagc tcagcaaggg ggaaggaaga cgtgaacaag    900
accctcccaa accttcaggt agtcaaccac cagcaaggcc cccaccacag acacatcctg    960
aagctgctgc cgtccatgga ggccactggg gcgagaagt ccagcacgcc catcaaggc    1020 cccaagaggg gacatcctag acagaaccta cacaagcatt ttgacatcaa tgagcatttg    1080
ccctggatga ttgtgcttt cctgctgctg gtgcttgtgg tgattgtggt gtgcagtatc    1140
cggaaaagct cgaggactct gaaaaagggg ccccggcagg atcccagtgc cattgtggaa    1200
```

```
aaggcagggc tgaagaaatc catgactcca acccagaacc gggagaaatg gatctactac    1260
tgcaatggcc atggtatcga tatcctgaag cttgtagcag cccaagtggg aagccagtgg    1320
aaagatatct atcagtttct ttgcaatgcc agtgagaggg aggttgctgc tttctccaat    1380
gggtacacag ccgaccacga gcgggcctac gcagctctgc agcactggac catccggggc    1440
cccgaggcca gcctcgccca gctaattagc gccctgcgcc agcaccggag aaacgatgtt    1500
gtggagaaga ttcgtgggct gatggaagac accacccagc tggaaactga caaactagct    1560
ctcccgatga gccccagccc gcttagcccg agccccatcc ccagcccaa cgcgaaactt     1620 gagaattccg ctctcctgac ggtggagcct tccccacagg acaagaacaa gggcttcttc    1680
gtggatgagt cggagcccct tctccgctgt gactctacat ccagcggctc ctccgcgctg    1740
agcaggaacg gttcctttat taccaaagaa aagaaggaca cagtgttgcg gcaggtacgc    1800
ctggacccct gtgacttgca gcctatcttt gatgacatgc tccactttct aaatcctgag    1860
gagctgcggg tgattgaaga gattccccag gctgaggaca aactagaccg gctattcgaa    1920
attattggag tcaagagcca ggaagccagc cagaccctcc tggactctgt ttatagccat    1980
cttcctgacc tgctgtag                                                  1998
```

<210> SEQ ID NO 155
<211> LENGTH: 665
<212> TYPE: PRT
<213> ORGANISM: Artificial Sequence
<220> FEATURE:
<223> OTHER INFORMATION: human DR6 with Myc tag

<400> SEQUENCE: 155

```
Met Gly Thr Ser Pro Ser Ser Thr Ala Leu Ala Ser Cys Ser Arg
1               5                   10                  15

Ile Ala Arg Arg Ala Thr Ala Thr Met Ile Ala Gly Ser Leu Leu Leu
                20                  25                  30

Leu Gly Phe Leu Ser Thr Thr Thr Ala Glu Gln Lys Leu Ile Ser Glu
            35                  40                  45

Glu Asp Leu Gln Pro Glu Gln Lys Ala Ser Asn Leu Ile Gly Thr Tyr
        50                  55                  60

Arg His Val Asp Arg Ala Thr Gly Gln Val Leu Thr Cys Asp Lys Cys
65                  70                  75                  80

Pro Ala Gly Thr Tyr Val Ser Glu His Cys Thr Asn Thr Ser Leu Arg
                85                  90                  95

Val Cys Ser Ser Cys Pro Val Gly Thr Phe Thr Arg His Glu Asn Gly
            100                 105                 110

Ile Glu Lys Cys His Asp Cys Ser Gln Pro Cys Pro Trp Pro Met Ile
        115                 120                 125

Glu Lys Leu Pro Cys Ala Ala Leu Thr Asp Arg Glu Cys Thr Cys Pro
    130                 135                 140

Pro Gly Met Phe Gln Ser Asn Ala Thr Cys Ala Pro His Thr Val Cys
145                 150                 155                 160

Pro Val Gly Trp Gly Val Arg Lys Lys Gly Thr Glu Thr Glu Asp Val
                165                 170                 175

Arg Cys Lys Gln Cys Ala Arg Gly Thr Phe Ser Asp Val Pro Ser Ser
            180                 185                 190

Val Met Lys Cys Lys Ala Tyr Thr Asp Cys Leu Ser Gln Asn Leu Val
        195                 200                 205

Val Ile Lys Pro Gly Thr Lys Glu Thr Asp Asn Val Cys Gly Thr Leu
    210                 215                 220
```

```
Pro Ser Phe Ser Ser Ser Thr Ser Pro Ser Pro Gly Thr Ala Ile Phe
225                 230                 235                 240

Pro Arg Pro Glu His Met Glu Thr His Glu Val Pro Ser Ser Thr Tyr
                245                 250                 255

Val Pro Lys Gly Met Asn Ser Thr Glu Ser Asn Ser Ser Ala Ser Val
            260                 265                 270

Arg Pro Lys Val Leu Ser Ser Ile Gln Glu Gly Thr Val Pro Asp Asn
            275                 280                 285

Thr Ser Ser Ala Arg Gly Lys Glu Asp Val Asn Lys Thr Leu Pro Asn
        290                 295                 300

Leu Gln Val Val Asn His Gln Gln Gly Pro His His Arg His Ile Leu
305                 310                 315                 320

Lys Leu Leu Pro Ser Met Glu Ala Thr Gly Gly Glu Lys Ser Ser Thr
                325                 330                 335

Pro Ile Lys Gly Pro Lys Arg Gly His Pro Arg Gln Asn Leu His Lys
                340                 345                 350

His Phe Asp Ile Asn Glu His Leu Pro Trp Met Ile Val Leu Phe Leu
        355                 360                 365

Leu Leu Val Leu Val Val Ile Val Val Cys Ser Ile Arg Lys Ser Ser
        370                 375                 380

Arg Thr Leu Lys Lys Gly Pro Arg Gln Asp Pro Ser Ala Ile Val Glu
385                 390                 395                 400

Lys Ala Gly Leu Lys Lys Ser Met Thr Pro Thr Gln Asn Arg Glu Lys
                405                 410                 415

Trp Ile Tyr Tyr Cys Asn Gly His Gly Ile Asp Ile Leu Lys Leu Val
                420                 425                 430

Ala Ala Gln Val Gly Ser Gln Trp Lys Asp Ile Tyr Gln Phe Leu Cys
        435                 440                 445

Asn Ala Ser Glu Arg Glu Val Ala Ala Phe Ser Asn Gly Tyr Thr Ala
        450                 455                 460

Asp His Glu Arg Ala Tyr Ala Ala Leu Gln His Trp Thr Ile Arg Gly
465                 470                 475                 480

Pro Glu Ala Ser Leu Ala Gln Leu Ile Ser Ala Leu Arg Gln His Arg
                485                 490                 495

Arg Asn Asp Val Val Glu Lys Ile Arg Gly Leu Met Glu Asp Thr Thr
            500                 505                 510

Gln Leu Glu Thr Asp Lys Leu Ala Leu Pro Met Ser Pro Ser Pro Leu
        515                 520                 525

Ser Pro Ser Pro Ile Pro Ser Pro Asn Ala Lys Leu Glu Asn Ser Ala
        530                 535                 540

Leu Leu Thr Val Glu Pro Ser Pro Gln Asp Lys Asn Lys Gly Phe Phe
545                 550                 555                 560

Val Asp Glu Ser Glu Pro Leu Leu Arg Cys Asp Ser Thr Ser Ser Gly
                565                 570                 575

Ser Ser Ala Leu Ser Arg Asn Gly Ser Phe Ile Thr Lys Glu Lys Lys
            580                 585                 590

Asp Thr Val Leu Arg Gln Val Arg Leu Asp Pro Cys Asp Leu Gln Pro
        595                 600                 605

Ile Phe Asp Asp Met Leu His Phe Leu Asn Pro Glu Glu Leu Arg Val
        610                 615                 620

Ile Glu Glu Ile Pro Gln Ala Glu Asp Lys Leu Asp Arg Leu Phe Glu
625                 630                 635                 640

Ile Ile Gly Val Lys Ser Gln Glu Ala Ser Gln Thr Leu Leu Asp Ser
```

```
                    645                 650                 655
Val Tyr Ser His Leu Pro Asp Leu Leu
            660                 665

<210> SEQ ID NO 156
<211> LENGTH: 1143
<212> TYPE: DNA
<213> ORGANISM: Artificial Sequence
<220> FEATURE:
<223> OTHER INFORMATION: dominant negative DR6 with Myc tag

<400> SEQUENCE: 156
atggggacct ctccgagcag cagcaccgcc ctcgcctcct gcagccgcat cgcccgccga     60
gccacagcca cgatgatcgc gggctcccct ctcctgcttg gattccttag caccaccaca    120
gctgagcaga agctgatctc agaggaggac ctgcagccag aacagaaggc ctcgaatctc    180
attggcacat accgccatgt tgaccgtgcc accggccagg tgctaacctg tgacaagtgt    240
ccagcaggaa cctatgtctc tgagcattgt accaacacaa gcctgcgcgt ctgcagcagt    300
tgccctgtgg ggaccttt ac caggcatgag aatggcatag agaaatgcca tgactgtagt    360
cagccatgcc catggccaat gattgagaaa ttaccttgtg ctgccttgac tgaccgagaa    420
tgcacttgcc cacctggcat gttccagtct aacgctacct gtgcccccca tacggtgtgt    480
cctgtgggtt ggggtgtgcg gaagaaaggg acagagactg aggatgtgcg gtgtaagcag    540
tgtgctcggg gtaccttctc agatgtgcct tctagtgtga tgaaatgcaa gcatacaca    600 gactgtctga gtcagaacct ggtggtgatc aagccgggga ccaaggagac agacaacgtc    660
tgtggcacac tcccgtcctt ctccagctcc acctcaccct cccctggcac agccatcttt    720
ccacgccctg agcacatgga aacccatgaa gtcccttcct ccacttatgt tcccaaaggc    780
atgaactcaa cagaatccaa ctcttctgcc tctgttagac aaaggtact gagtagcatc    840 caggaaggga cagtccctga caacacaagc tcagcaaggg ggaaggaaga cgtgaacaag    900
accctcccaa accttcaggt agtcaaccac cagcaaggcc cccaccacag acacatcctg    960
aagctgctgc cgtccatgga ggccactggg ggcgagaagt ccagcacgcc catcaagggc   1020
cccaagaggg gacatcctag acagaaccta cacaagcatt ttgacatcaa tgagcatttg   1080
ccctggatga ttgtgctttt cctgctgctg gtgcttgtgg tgattgtggt gtgcagtatc   1140
tag                                                                1143

<210> SEQ ID NO 157
<211> LENGTH: 380
<212> TYPE: PRT
<213> ORGANISM: Artificial Sequence
<220> FEATURE:
<223> OTHER INFORMATION: dominant negative DR6 with Myc tag

<400> SEQUENCE: 157

Met Gly Thr Ser Pro Ser Ser Ser Thr Ala Leu Ala Ser Cys Ser Arg
1               5                   10                  15

Ile Ala Arg Arg Ala Thr Ala Thr Met Ile Ala Gly Ser Leu Leu Leu
            20                  25                  30

Leu Gly Phe Leu Ser Thr Thr Thr Ala Glu Gln Lys Leu Ile Ser Glu
        35                  40                  45

Glu Asp Leu Gln Pro Glu Gln Lys Ala Ser Asn Leu Ile Gly Thr Tyr
    50                  55                  60

Arg His Val Asp Arg Ala Thr Gly Gln Val Leu Thr Cys Asp Lys Cys
65                  70                  75                  80
```

```
Pro Ala Gly Thr Tyr Val Ser Glu His Cys Thr Asn Thr Ser Leu Arg
                85                  90                  95
Val Cys Ser Ser Cys Pro Val Gly Thr Phe Thr Arg His Glu Asn Gly
            100                 105                 110
Ile Glu Lys Cys His Asp Cys Ser Gln Pro Cys Pro Trp Pro Met Ile
        115                 120                 125
Glu Lys Leu Pro Cys Ala Ala Leu Thr Asp Arg Glu Cys Thr Cys Pro
    130                 135                 140
Pro Gly Met Phe Gln Ser Asn Ala Thr Cys Ala Pro His Thr Val Cys
145                 150                 155                 160
Pro Val Gly Trp Gly Val Arg Lys Lys Gly Thr Glu Thr Glu Asp Val
                165                 170                 175
Arg Cys Lys Gln Cys Ala Arg Gly Thr Phe Ser Asp Val Pro Ser Ser
            180                 185                 190
Val Met Lys Cys Lys Ala Tyr Thr Asp Cys Leu Ser Gln Asn Leu Val
        195                 200                 205
Val Ile Lys Pro Gly Thr Lys Glu Thr Asp Asn Val Cys Gly Thr Leu
    210                 215                 220
Pro Ser Phe Ser Ser Thr Ser Pro Ser Pro Gly Thr Ala Ile Phe
225                 230                 235                 240
Pro Arg Pro Glu His Met Glu Thr His Glu Val Pro Ser Ser Thr Tyr
                245                 250                 255
Val Pro Lys Gly Met Asn Ser Thr Glu Ser Asn Ser Ser Ala Ser Val
            260                 265                 270
Arg Pro Lys Val Leu Ser Ser Ile Gln Glu Gly Thr Val Pro Asp Asn
        275                 280                 285
Thr Ser Ser Ala Arg Gly Lys Glu Asp Val Asn Lys Thr Leu Pro Asn
    290                 295                 300
Leu Gln Val Val Asn His Gln Gln Gly Pro His His Arg His Ile Leu
305                 310                 315                 320
Lys Leu Leu Pro Ser Met Glu Ala Thr Gly Gly Glu Lys Ser Ser Thr
                325                 330                 335
Pro Ile Lys Gly Pro Lys Arg Gly His Pro Arg Gln Asn Leu His Lys
            340                 345                 350
His Phe Asp Ile Asn Glu His Leu Pro Trp Met Ile Val Leu Phe Leu
        355                 360                 365
Leu Leu Val Leu Val Val Ile Val Val Cys Ser Ile
    370                 375                 380

<210> SEQ ID NO 158
<211> LENGTH: 1731
<212> TYPE: DNA
<213> ORGANISM: Artificial Sequence
<220> FEATURE:
<223> OTHER INFORMATION: soluble DR6: Fc

<400> SEQUENCE: 158
atggggacct ctccgagcag cagcaccgcc ctcgcctcct gcagccgcat cgcccgccga      60
gccacagcca cgatgatcgc gggctccctt ctcctgcttg gattccttag caccaccaca     120
gctcagccag aacagaaggc ctcgaatctc attggcacat accgccatgt tgaccgtgcc     180
accggccagg tgctaacctg tgacaagtgt ccagcaggaa cctatgtctc tgagcattgt     240
accaacacaa gcctgcgcgt ctgcagcagt tgccctgtgg ggacctttac caggcatgag     300
aatggcatag agaaatgcca tgactgtagt cagcctatgcc catggccaat gattgagaaa     360
ttaccttgtg ctgccttgac tgaccgagaa tgcacttgcc cacctggcat gttccagtct     420
```

```
aacgctacct gtgcccccca tacggtgtgt cctgtgggtt ggggtgtgcg aagaaaggg        480 acagagactg aggatgtgcg gtgtaagcag tgtgctcggg gtaccttctc agatgtgcct      540
tctagtgtga tgaaatgcaa agcatacaca gactgtctga gtcagaacct ggtggtgatc     600
aagccgggga ccaaggagac agacaacgtc tgtggcacac tcccgtcctt ctccagctcc      660
acctcacctt ccctggcac agccatcttt ccacgccctg agcacatgga aacccatgaa      720
gtcccttcct ccacttatgt tcccaaaggc atgaactcaa cagaatccaa ctcttctgcc      780
tctgttagac caaggtact gagtagcatc caggaaggga cagtccctga caacacaagc      840
tcagcaaggg ggaaggaaga cgtgaacaag accctcccaa accttcaggt agtcaaccac      900
cagcaaggcc cccaccacag acacatcctg aagctgctgc cgtccatgga ggccactggg      960
ggcgagaagt ccagcacgcc catcaagggc cccaagaggg gacatcctag acagaaccta     1020
cacaagcatt ttgacatcaa tgagcatgtc gacaaaactc acacatgccc accgtgccca     1080
gcacctgaac tcctgggggg accgtcagtc ttcctcttcc ccccaaaacc caaggacacc     1140
ctcatgatct cccggacccc tgaggtcaca tgcgtggtgg tggacgtgag ccacgaagac     1200
cctgaggtca agttcaactg gtacgtggac ggcgtggagg tgcataatgc caagacaaag     1260
ccgcgggagg agcagtacaa cagcacgtac cgtgtggtca gcgtcctcac cgtcctgcac     1320
caggactggc tgaatggcaa ggagtacaag tgcaaggtct ccaacaaagc cctcccagcc     1380
cccatcgaga aaaccatctc caaagccaaa gggcagcccc gagaaccaca ggtgtacacc     1440
ctgcccccat cccgggatga gctgaccaag aaccaggtca gcctgacctg cctggtcaaa     1500
ggcttctatc ccagcgacat cgccgtggag tgggagagca atgggcagcc ggagaacaac     1560
tacaagacca cgcctcccgt gttggactcc gacggctcct tcttcctcta cagcaagctc     1620
accgtggaca agagcaggtg gcagcagggg aacgtcttct catgctccgt gatgcatgag     1680
gctctgcaca accactacac gcagaagagc ctctccctgt ctcccgggtg a              1731
```

<210> SEQ ID NO 159
<211> LENGTH: 576
<212> TYPE: PRT
<213> ORGANISM: Artificial Sequence
<220> FEATURE:
<223> OTHER INFORMATION: soluble DR6: Fc

<400> SEQUENCE: 159

```
Met Gly Thr Ser Pro Ser Ser Thr Ala Leu Ala Ser Cys Ser Arg
1               5                   10                  15

Ile Ala Arg Arg Ala Thr Ala Thr Met Ile Ala Gly Ser Leu Leu Leu
            20                  25                  30

Leu Gly Phe Leu Ser Thr Thr Thr Ala Gln Pro Glu Gln Lys Ala Ser
        35                  40                  45

Asn Leu Ile Gly Thr Tyr Arg His Val Asp Arg Ala Thr Gly Gln Val
    50                  55                  60

Leu Thr Cys Asp Lys Cys Pro Ala Gly Thr Tyr Val Ser Glu His Cys
65                  70                  75                  80

Thr Asn Thr Ser Leu Arg Val Cys Ser Ser Cys Pro Val Gly Thr Phe
                85                  90                  95

Thr Arg His Glu Asn Gly Ile Glu Lys Cys His Asp Cys Ser Gln Pro
            100                 105                 110

Cys Pro Trp Pro Met Ile Glu Lys Leu Pro Cys Ala Ala Leu Thr Asp
        115                 120                 125

Arg Glu Cys Thr Cys Pro Pro Gly Met Phe Gln Ser Asn Ala Thr Cys
```

```
          130                 135                 140
Ala Pro His Thr Val Cys Pro Val Gly Trp Gly Val Arg Lys Lys Gly
145                 150                 155                 160

Thr Glu Thr Glu Asp Val Arg Cys Lys Gln Cys Ala Arg Gly Thr Phe
                165                 170                 175

Ser Asp Val Pro Ser Ser Val Met Lys Cys Lys Ala Tyr Thr Asp Cys
            180                 185                 190

Leu Ser Gln Asn Leu Val Val Ile Lys Pro Gly Thr Lys Glu Thr Asp
        195                 200                 205

Asn Val Cys Gly Thr Leu Pro Ser Phe Ser Ser Thr Ser Pro Ser
210                 215                 220

Pro Gly Thr Ala Ile Phe Pro Arg Pro Glu His Met Glu Thr His Glu
225                 230                 235                 240

Val Pro Ser Ser Thr Tyr Val Pro Lys Gly Met Asn Ser Thr Glu Ser
                245                 250                 255

Asn Ser Ser Ala Ser Val Arg Pro Lys Val Leu Ser Ser Ile Gln Glu
            260                 265                 270

Gly Thr Val Pro Asp Asn Thr Ser Ser Ala Arg Gly Lys Glu Asp Val
        275                 280                 285

Asn Lys Thr Leu Pro Asn Leu Gln Val Val Asn His Gln Gln Gly Pro
290                 295                 300

His His Arg His Ile Leu Lys Leu Leu Pro Ser Met Glu Ala Thr Gly
305                 310                 315                 320

Gly Glu Lys Ser Ser Thr Pro Ile Lys Gly Pro Lys Arg Gly His Pro
                325                 330                 335

Arg Gln Asn Leu His Lys His Phe Asp Ile Asn Glu His Val Asp Lys
            340                 345                 350

Thr His Thr Cys Pro Pro Cys Pro Ala Pro Glu Leu Leu Gly Gly Pro
        355                 360                 365

Ser Val Phe Leu Phe Pro Pro Lys Pro Lys Asp Thr Leu Met Ile Ser
370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
450                 455                 460

Thr Ile Ser Lys Ala Lys Gly Gln Pro Arg Glu Pro Gln Val Tyr Thr
465                 470                 475                 480

Leu Pro Pro Ser Arg Asp Glu Leu Thr Lys Asn Gln Val Ser Leu Thr
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Lys Leu Thr Val Asp Lys
530                 535                 540

Ser Arg Trp Gln Gln Gly Asn Val Phe Ser Cys Ser Val Met His Glu
545                 550                 555                 560
```

Ala Leu His Asn His Tyr Thr Gln Lys Ser Leu Ser Leu Ser Pro Gly
                565                 570                 575

<210> SEQ ID NO 160
<211> LENGTH: 19
<212> TYPE: RNA
<213> ORGANISM: Artificial Sequence
<220> FEATURE:
<223> OTHER INFORMATION: DR6 siRNA

<400> SEQUENCE: 160
agaaacggcu ccuuuauua                                                19

<210> SEQ ID NO 161
<211> LENGTH: 19
<212> TYPE: RNA
<213> ORGANISM: Artificial Sequence
<220> FEATURE:
<223> OTHER INFORMATION: DR6 siRNA

<400> SEQUENCE: 161
ggaaggacau cuaucaguu                                                19

<210> SEQ ID NO 162
<211> LENGTH: 19
<212> TYPE: RNA
<213> ORGANISM: Artificial Sequence
<220> FEATURE:
<223> OTHER INFORMATION: DR6 siRNA

<400> SEQUENCE: 162
ggccgaugau ugagagauu                                                19

<210> SEQ ID NO 163
<211> LENGTH: 19
<212> TYPE: RNA
<213> ORGANISM: Artificial Sequence
<220> FEATURE:
<223> OTHER INFORMATION: DR6 siRNA

<400> SEQUENCE: 163
gcaguuggaa acagacaaa                                                19

<210> SEQ ID NO 164
<211> LENGTH: 21
<212> TYPE: RNA
<213> ORGANISM: Artificial Sequence
<220> FEATURE:
<223> OTHER INFORMATION: control siRNA

<400> SEQUENCE: 164
ggugacauga ucgacagcca u                                             21

<210> SEQ ID NO 165
<211> LENGTH: 427
<212> TYPE: PRT
<213> ORGANISM: Homo sapiens

<400> SEQUENCE: 165

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
        35                  40                  45

```
Leu Gly Glu Gly Val Ala Gln Pro Cys Gly Ala Asn Gln Thr Val Cys
 50                  55                  60

Glu Pro Cys Leu Asp Ser Val Thr Phe Ser Asp Val Val Ser Ala Thr
 65                  70                  75                  80

Glu Pro Cys Lys Pro Cys Thr Glu Cys Val Gly Leu Gln Ser Met Ser
             85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
                180                 185                 190

Gly Arg Trp Ile Thr Arg Ser Thr Pro Pro Glu Gly Ser Asp Ser Thr
            195                 200                 205

Ala Pro Ser Thr Gln Glu Pro Glu Ala Pro Pro Glu Gln Asp Leu Ile
210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg Trp Asn Ser Cys Lys Gln Asn Lys Gln Gly Ala Asn Ser Arg
            275                 280                 285

Pro Val Asn Gln Thr Pro Pro Pro Glu Gly Glu Lys Leu His Ser Asp
290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
                340                 345                 350

Gly Ser Ala Gly Asp Thr Trp Arg His Leu Ala Gly Glu Leu Gly Tyr
            355                 360                 365

Gln Pro Glu His Ile Asp Ser Phe Thr His Glu Ala Cys Pro Val Arg
370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
                420                 425

<210> SEQ ID NO 166
<211> LENGTH: 3421
<212> TYPE: DNA
<213> ORGANISM: Homo sapiens

<400> SEQUENCE: 166
```

```
agagcgagcc gagccgcggc cagctccggc gggcaggggg ggcgctggag cgcagcgcag    60
cgcagcccca tcagtccgca aagcggaccg agctggaagt cgagcgctgc cgcgggaggc   120
gggcgatggg ggcaggtgcc accggccgcg ccatggacgg gccgcgcctg ctgctgttgc   180
tgcttctggg ggtgtccctt ggaggtgcca aggaggcatg ccccacaggc ctgtacacac   240
acagcggtga gtgctgcaaa gcctgcaacc tgggcgaggg tgtggcccag ccttgtggag   300
ccaaccagac cgtgtgtgag ccctgcctgg acagcgtgac gttctccgac gtggtgagcg   360
cgaccgagcc gtgcaagccg tgcaccgagt gcgtggggct ccagagcatg tcggcgccgt   420
gcgtggaggc cgacgacgcc gtgtgccgct gcgcctacgg ctactaccag gatgagacga   480
ctgggcgctg cgaggcgtgc cgcgtgtgcg aggcgggctc gggcctcgtg ttctcctgcc   540
aggacaagca gaacaccgtg tgcgaggagt gccccgacgg cacgtattcc gacgaggcca   600
accacgtgga cccgtgcctg ccctgcaccg tgtgcgagga caccgagcgc agctccgcg    660
agtgcacacg ctgggccgac gccgagtgcg aggagatccc tggccgttgg attacacggt   720
ccacaccccc agagggctcg gacagcacag cccccagcac caggagcct gaggcacctc    780
cagaacaaga cctcatagcc agcacggtgg caggtgtggt gaccacagtg atgggcagct   840
cccagcccgt ggtgacccga ggcaccaccg acaacctcat ccctgtctat tgctccatcc   900
tggctgctgt ggttgtgggc cttgtggcct acatagcctt caagaggtgg aacagctgca   960
agcagaacaa gcaaggagcc aacagccggc cagtgaacca gacgcccca ccagagggag   1020
aaaaactcca cagcgacagt ggcatctccg tggacagcca gagcctgcat gaccagcagc   1080
cccacacgca gacagcctcg ggccaggccc tcaagggtga cggaggcctc tacagcagcc   1140
tgccccagc caagcgggag gaggtggaga agcttctcaa cggctctgcg ggggacacct   1200
ggcggcacct ggcgggcgag ctgggctacc agcccgagca catagactcc tttacccatg   1260
aggcctgccc cgttcgcgcc ctgcttcaa gctgggccac ccaggacagc gccacactgg    1320
acgccctcct ggccgcctg cgccgcatcc agcgagccga cctcgtggag agtctgtgca   1380
gtgagtccac tgccacatcc ccggtgtgag cccaaccggg gagccccgc cccgccccac   1440
attccgacaa ccgatgctcc agccaaccc tgtggagccc gcaccccac cctttggggg   1500
gggcccgcct ggcagaactg agctcctctg gcaggacct cagagtccag gccccaaaac   1560
cacagccctg tcagtgcagc ccgtgtggcc ccttcacttc tgaccacact tcctgtccag   1620
agagagaagt gccctgctg cctccccaac cctgcccctg cccgtcacc atctcaggcc   1680
acctgccccc ttctcccaca ctgctaggtg gccagcccc tcccaccaca gcaggtgtca   1740
tatatggggg gccaacacca gggatggtac taggggaag tgacaaggcc ccagagactc   1800
agagggagga atcgaggaac cagagccatg gactctacac tgtgaacttg gggaacaagg   1860
gtggcatccc agtggcctca accctccctc agcccctctt gcccccacc ccagcctaag   1920
atgaagagga tcggaggctt gtcagagctg ggaggggttt tcgaagctca gcccaccccc   1980
ctcattttgg atataggtca gtgaggccca gggagaggcc atgattcgcc caaagccaga   2040
cagcaacggg gaggccaagt gcaggctggc accgccttct ctaaatgagg ggcctcaggt   2100
ttgcctgagg gcgaggggag ggtggcaggt gaccttctgg gaaatggctt gaagccaagt   2160
cagctttgcc ttccacgctg tctccagacc cccaccccctt ccccactgcc tgcccacccg   2220
tggagatggg atgcttgcct agggcctggt ccatgatgga gtcaggtttg ggttcgtgg   2280
aaagggtgct gcttccctct gcctgtccct ctcaggcatg cctgtgtgac atcagtggca   2340
tggctccagt ctgctgccct ccatcccgac atggacccgg agctaacact ggccccctaga  2400
```

```
atcagcctag gggtcaggga ccaaggaccc ctcaccttgc aacacacaga cacacgcaca   2460
cacacacaca ggaggagaaa tctcactttt ctccatgagt tttttctctt gggctgagac   2520
tggatactgc ccggggcagc tgccagagaa gcatcggagg gaattgaggt ctgctcggcc   2580
gtcttcactc gccccccgggt ttggcgggcc aaggactgcc gaccgaggct ggagctggcg   2640
tctgtcttca agggcttaca cgtggaggaa tgctccccca tcctcccctt ccctgcaaac   2700
atggggttgg ctgggcccag aaggttgtga tgaagaaaag tgggccagtg tgggaatgcg   2760
gcaagaagga attgacttcg actgtgacct gtggggattt ctcccagctc tagacaaccc   2820
tgcaaaggac tgtttttttcc tgagcttggc cagaaggggg ccatgaggcc tcagtggact   2880
ttccaccccc tccctggcct gttctgtttt gcctgaagtt ggagtgagtg tggctcccct   2940
ctatttagca tgacaagccc caggcaggct gtgcgctgac aaccaccgct ccccagccca   3000
gggttccccc agccctgtgg aagggactag gagcactgta gtaaatggca attctttgac   3060
ctcaacctgt gatgagggga ggaaactcac ctgctggccc ctcacctggg cacctgggga   3120
gtgggacaga gtctgggtgt atttattttc ctccccagca ggtggggagg gggtttgggg   3180
gcttgcaagt atgttttagc atgtgtttgg ttctggggcc ccttttttact ccccttgagc   3240 tgagatggaa ccctttttggc ccccgagctg ggggccatga gctccagacc cccagcaacc   3300
ctcctatcac ctcccctcct tgcctcctgt gtaatcattt cttgggccct cctgaaactt   3360
acacacaaaa cgttaagtga tgaacattaa atagcaaaga aagaaaaata aaaaaaaaaa   3420
a                                                                  3421
```